(12) United States Patent
Bunting et al.

(10) Patent No.: US 10,512,675 B2
(45) Date of Patent: Dec. 24, 2019

(54) ADENO-ASSOCIATED VIRUS FACTOR VIII VECTORS, ASSOCIATED VIRAL PARTICLES AND THERAPEUTIC FORMULATIONS COMPRISING THE SAME

(71) Applicant: BioMarin Pharmaceutical Inc., Novato, CA (US)

(72) Inventors: Stuart Bunting, Novato, CA (US); Peter Cameron Colosi, Novato, CA (US); Erno Pungor, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 199 days.

(21) Appl. No.: 15/274,046

(22) Filed: Sep. 23, 2016

(65) Prior Publication Data

US 2017/0087219 A1    Mar. 30, 2017

Related U.S. Application Data

(60) Provisional application No. 62/365,544, filed on Jul. 22, 2016, provisional application No. 62/323,182, filed on Apr. 15, 2016, provisional application No. 62/232,242, filed on Sep. 24, 2015.

(51) Int. Cl.

| | | |
|---|---|---|
| *A61K 38/37* | (2006.01) | |
| *A61K 48/00* | (2006.01) | |
| *C07K 14/755* | (2006.01) | |
| *C12N 7/00* | (2006.01) | |
| *C12N 15/867* | (2006.01) | |
| *C12N 15/00* | (2006.01) | |
| *A61K 47/02* | (2006.01) | |
| *A61K 47/10* | (2017.01) | |
| *A61K 47/26* | (2006.01) | |
| *G01N 33/68* | (2006.01) | |
| *A61K 39/12* | (2006.01) | |

(52) U.S. Cl.
CPC ............. *A61K 38/37* (2013.01); *A61K 39/12* (2013.01); *A61K 47/02* (2013.01); *A61K 47/10* (2013.01); *A61K 47/26* (2013.01); *A61K 48/0008* (2013.01); *A61K 48/0075* (2013.01); *C07K 14/755* (2013.01); *C12N 7/00* (2013.01); *G01N 33/6854* (2013.01); *C12N 2710/16044* (2013.01); *C12N 2750/14121* (2013.01); *C12N 2750/14141* (2013.01); *C12N 2750/14143* (2013.01); *G01N 2333/015* (2013.01)

(58) Field of Classification Search
None
See application file for complete search history.

(56) References Cited

U.S. PATENT DOCUMENTS

| | | |
|---|---|---|
| 4,745,051 A | 5/1988 | Smith et al. |
| 6,200,560 B1 | 3/2001 | Couto et al. |
| 6,204,059 B1 | 3/2001 | Samulski et al. |
| 6,221,349 B1 | 4/2001 | Couto et al. |
| 6,521,225 B1 | 2/2003 | Srivastava et al. |
| 7,351,577 B2 | 4/2008 | Couto et al. |
| 8,030,065 B2 | 10/2011 | Gray |
| 2003/0148506 A1 | 8/2003 | Kotin et al. |
| 2007/0042462 A1 | 2/2007 | Hildinger |
| 2009/0118184 A1 | 5/2009 | Fay et al. |
| 2011/0201088 A1 | 8/2011 | Beall et al. |
| 2015/0071883 A1 | 3/2015 | Colosi |

FOREIGN PATENT DOCUMENTS

| | | |
|---|---|---|
| EP | 0127839 A2 | 12/1984 |
| EP | 0155476 A1 | 9/1985 |
| RU | 2531493 C2 | 10/2014 |
| WO | WO-99/61595 A2 | 12/1999 |
| WO | WO-03/074714 A1 | 9/2003 |
| WO | WO-2011/005968 A1 | 1/2011 |
| WO | WO-2013/186563 A2 | 12/2013 |
| WO | WO 2014064277 * | 5/2014 |
| WO | WO-2015/038625 A1 | 3/2015 |

OTHER PUBLICATIONS

Bunting et al. Human Factor VIII Expression and Normalization of Bleeding Following AAV Gene Therapy in a Double Knockout Mouse Model of Hemophilia, Blood, 2015, 126:3239, pp. 1-2.*
Chen et al, Enhanced Factor VIII Heavy Chain for Gene Therapy of Hemophilia A, 2009, Molecular Therapy vol. 17 No. 3, 417-424.*
UK-MHRA, EU Clinical Trials Register, EudraCT# 2014-003880-38, 2015, pp. 1-5.*
Shanks et al, Are animal models predictive for humans? Philosophy, Ethics, and Humanities in Medicine, 2009, pp. 1-20.*
Arruda et al, Novel approaches to hemophilia therapy: successes and challenges, Blood, 2017, pp. 2251-2256.*
Fumoto et al, Targeted Gene Delivery: Importance of Administration Routes, Chapter 1, Intech, 2013, pp. 3-31.*
Boutin et al., Prevalence of serum IgG and neutralizing factors against adeno-associated virus (AAV) types 1, 2, 5, 6, 8, and 9 in the healthy population: implications for gene therapy using AAV vectors, Hum. Gene Ther., 21(6):704-12 (2010).
Chiorini et al., Cloning and characterization of adeno-associated virus type 5, J. Virol., 73(2):1309-19 (1999).
Chiorini et al., Cloning of adeno-associated virus type 4 (AAV4) and generation of recombinant AAV4 particles, J. Virol., 71(9):6823-33 (1997).
De Simone et al., Cis- and trans-acting elements responsible for the cell-specific expression of the human alpha 1-antitrypsin gene, EMBO J., 6(9):2759-66 (1987).

(Continued)

*Primary Examiner* — Maria Marvich
(74) *Attorney, Agent, or Firm* — Marshall, Gerstein & Borun LLP

(57) ABSTRACT

The invention provides adeno-associated virus (AAV) Factor VIII (FVIII)-encoding/expressing vectors and virus, including AAV FVIII vectors with high expression activity and AAV FVIII vectors that express full-length or truncated functional FVIII protein. The invention also relates to methods of making the herein described AAV FVIII vectors, recombinant AAV FVIII virus particles comprising or expressing such vectors, associated pharmaceutical formulations comprising the same and therapeutic uses thereof.

25 Claims, 18 Drawing Sheets

Specification includes a Sequence Listing.

(56) References Cited

OTHER PUBLICATIONS

GenBank Accession No. AF043303.1, Adeno-associated virus 2, complete genome, May 20, 2010.
GenBank Accession No. AF085716.1, Adeno-associated virus 5 DNA binding trs helicase (Rep22) and capsid protein (VP1) genes, complete cds, Feb. 9, 1999.
GenBank Accession No. J01901.1, Adeno-associated virus 2, complete genome, Apr. 27, 1993.
GenBank Accession No. U89790.1, Adeno-associated virus 4, complete genome, Aug. 21, 1997.
Ghosh et al., Expanding adeno-associated viral vector capacity: a tale of two vectors, Biotechnol. Genet. Eng. Rev., 24:165-177 (2007).
Hirsch et al., Little vector, big gene transduction: fragmented genome reassembly of adeno-associated virus, Mol. Ther., 18(1):6-8 (2010).
Kajigaya et al., Self-assembled B19 parvovirus capsids, produced in a baculovirus system, are antigenically and immunogenically similar to native virions, Proc. Natl. Acad. Sci. USA, 88(11):4646-50 (1991).
Kirnbauer et al., Virus-like particles of bovine papillomavirus type 4 in prophylactic and therapeutic immunization, Virology, 219(1):37-44 (1996).
Masat et al., Humoral immunity to AAV vectors in gene therapy: challenges and potential solutions, Discov. Med., 15(85):379-89 (2013).
McIntosh et al., Therapeutic levels of FVIII following a single peripheral vein administration of rAAV vector encoding a novel human factor VIII variant, Blood, 121(17):3335-44 (2013).
Mingozzi et al., Immune responses to AAV vectors: overcoming barriers to successful gene therapy, Blood, 122(1):23-36 (2013).
Nathwani et al., Adenovirus-associated virus vector-mediated gene transfer in hemophilia B, N. Engl. J. Med., 365(25):2357-65 (2011).
Ruffing et al., Assembly of viruslike particles by recombinant structural proteins of adeno-associated virus type 2 in insect cells, J. Virol., 66(12):6922-30 (1992).
Rutledge et al., Infectious clones and vectors derived from adeno-associated virus (AAV) serotypes other than AAV type 2, J. Virol., 72(1):309-19 (1998).
Samulski et al., Helper-free stocks of recombinant adeno-associated viruses: normal integration does not require viral gene expression, J. Virol., 63(9):3822-8 (1989).
Vlak et al., Functional studies on the p10 gene of Autographa californica nuclear polyhedrosis virus using a recombinant expressing a p10-beta-galactosidase fusion gene, J. Gen. Virol., 69 (Pt. 4):765-76 (1988).
Wang et al., Adeno-associated virus type 2 DNA replication in vivo: mutation analyses of the D sequence in viral inverted terminal repeats, J. Virol., 71(4):3077-82 (1997).
Wang et al., Rescue and replication of adeno-associated virus type 2 as well as vector DNA sequences from recombinant plasmids containing deletions in the viral inverted terminal repeats: selective encapsidation of viral genomes in progeny virions, J. Virol., 70(3):1668-77 (1996).
Ward et al., Codon optimization of human factor VIII cDNAs leads to high-level expression, Blood, 117(3):798-807 (2011).
Wu et al., Mutational analysis of the adeno-associated virus type 2 (AAV2) capsid gene and construction of AAV2 vectors with altered tropism, J. Virol., 74(18):8635-47 (2000).
Yan et al., Inverted terminal repeat sequences are important for intermolecular recombination and circularization of adeno-associated virus genomes, J. Virol., 79(1):364-79 (2005).
Zhao et al., BPV1 E2 protein enhances packaging of full-length plasmid DNA in BPV1 pseudovirions, Virology, 272(2):382-93 (2000).
EU Clinical Trials Register, EudraCT No. 2014-003880-38, A Phase 1/2, Dose-Escalation Safety, Tolerability and Efficacy Study of BMN 270, an Adenovirus-Associated Virus Vector-Mediated Gene Transfer of Human Factor VIII in Patients with Severe Haemophilia A. Accessed From the Internet at: <https://www.clinicaltrialsregister.eu/ctrsearch/trial/2014-003880-38/GB> (Jun. 9, 2015).
Canale et al., Effect of corticosteroids on factor 8 level, J. Pediatr., 71(6):878-80 (Dec. 1967).

* cited by examiner

Schematic of Proto 1

Schematic of Proto 1S

Schematic of Proto 2S

Schematic of Proto 3S

Schematic of Proto 4

Schematic of Proto 5

Schematic of Proto 6

Insert ApoE/C1 enhancer (forward orientation) into FVIII intron

Schematic of Proto 7

Insert ApoE/C1 enhancer (reverse orientation) into FVIII intron

SEQUENCE LISTING

<160> NUMBER OF SEQ ID NOS: 44

<210> SEQ ID NO 1
<211> LENGTH: 4970
<212> TYPE: DNA
<213> ORGANISM: Adeno-Associated Virus

<400> SEQUENCE: 1

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240
gcccctgttt gctcctccga taactggggt gaccttggtt aatattcacc agcagcctcc     300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgaggttc tgcttctctg ccaccaggag atactacctg     480
ggggctgtgg agctgagctg ggactacatg cagtctgacc tggggagct gcctgtggat     540 gccaggttcc cccccagagt gcccaagagc ttcccttca acacctctgt ggtgtacaag     600
aagaccctgt ttgtggagtt cactgaccac ctgttcaaca ttgccaagcc caggccccc     660 tggatgggcc tgctgggccc caccatccag ctgaggtgt atgacactgt ggtgatcacc     720
ctgaagaaca tggccagcca ccctgtgagc ctgcatgctg tgggggtgag ctactggaag     780
gcctctgagg gggctgagta tgatgaccag accagccaga gggagaagga ggatgacaag     840
gtgttccctg ggggcagcca cacctatgtg tggcaggtgc tgaaggagaa tggccccatg     900
gcctctgacc ccctgtgcct gacctacagc tacctgagcc atgtggacct ggtgaaggac     960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga gtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggat aagaacaatg aggaggctga ggactatgat    1500
gatgacctga ctgactctga gatggatgtg gtgaggtttg atgatgacaa cagccccagc    1560
ttcatccaga tcaggtctgt ggccaagaag caccccaaga cctgggtgca ctacattgct    1620
gctgaggagg aggactggga ctatgccccc ctggtgctgg cccctgatga caggagctac    1680
aagagccagt acctgaacaa tggccccag aggattggca ggaagtacaa gaaggtcagg    1740
ttcatggcct acactgatga aaccttcaag accaggagg ccatccagca tgagtctggc    1800
atcctgggcc cctgctgta tgggaggtg ggggacaccc tgctgatcat cttcaagaac    1860
caggccagca ggccctacaa catctacccc catggcatca ctgatgtgag gcccctgtac    1920
agcaggaggc tgcccaaggg ggtgaagcac ctgaaggact tccccatcct gcctggggag    1980
atcttcaagt acaagtggac tgtgactgtg gaggatggcc ccaccaagtc tgaccccagg    2040
tgcctgacca gatactacag cagctttgtg aacatggaga gggacctggc ctctggcctg    2100
```

```
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
actgagaaca tccagaggtt cctgcccaac cctgctgggg tgcagctgga ggaccctgag    2280
ttccaggcca gcaacatcat gcacagcatc aatggctatg tgtttgacag cctgcagctg    2340
tctgtgtgcc tgcatgaggt ggcctactgg tacatcctga gcattggggc ccagactgac    2400
ttcctgtctg tgttcttctc tggctacacc ttcaagcaca agatggtgta tgaggacacc    2460
ctgaccctgt tccccttctc tggggagact gtgttcatga gcatggagaa ccctggcctg    2520
tggattctgg gctgccacaa ctctgacttc aggaacaggg gcatgactgc cctgctgaaa    2580
gtctccagct gtgacaagaa cactggggac tactatgagg acagctatga ggacatctct    2640
gcctacctgc tgagcaagaa caatgccatt gagcccagga gcttcagcca gaaccccca    2700 gtgctgaaga ggcaccagag ggagatcacc aggaccaccc tgcagtctga ccaggaggag    2760
attgactatg atgacaccat ctctgtggag atgaagaagg aggactttga catctacgac    2820
gaggacgaga accagagccc caggagcttc agaagaaga ccaggcacta cttcattgct    2880
gctgtggaga ggctgtggga ctatggcatg agcagcagcc cccatgtgct gaggaacagg    2940
gcccagtctg gctctgtgcc ccagttcaag aaggtggtgt tccaggagtt cactgatggc    3000
agcttcaccc agcccctgta cagaggggag ctgaatgagc acctgggcct gctgggcccc    3060
tacatcaggg ctgaggtgga ggacaacatc atggtgacct caggaaccca ggccagcagg    3120
ccctacagct tctacagcag cctgatcagc tatgaggagg accagaggca gggggctgag    3180
cccaggaaga actttgtgaa gcccaatgaa accaagacct acttctggaa ggtgcagcac    3240
cacatggccc ccaccaagga tgagtttgac tgcaaggcct gggcctactt ctctgatgtg    3300
gacctggaga aggatgtgca ctctggcctg attggccccc tgctggtgtg ccacaccaac    3360
accctgaacc ctgcccatgg caggcaggtg actgtgcagg agtttgccct gttcttcacc    3420
atctttgatg aaaccaagag ctggtacttc actgagaaca tggagaggaa ctgcagggcc    3480
ccctgcaaca tccagatgga ggaccccacc ttcaaggaga actacaggtt ccatgccatc    3540
aatggctaca tcatggacac cctgcctggc ctggtgatgg cccaggacca ggatcagg    3600 tggtacctgc tgagcatggg cagcaatgag aacatccaca gcatccactt ctctggccat    3660
gtgttcactg tgaggaagaa ggaggagtac aagatggccc tgtacaacct gtaccctggg    3720
gtgtttgaga ctgtggagat gctgcccagc aaggctggca tctggagggt ggagtgcctg    3780
attggggagc acctgcatgc tggcatgagc accctgttcc tggtgtacag caacaagtgc    3840
cagacccccc tgggcatggc ctctggccac atcagggact tccagatcac tgcctctggc    3900
cagtatggcc agtgggcccc caagctggcc aggctgcact actctggcag catcaatgcc    3960
tggagcacca aggagccctt cagctggatc aaggtggacc tgctggcccc catgatcatc    4020
catggcatca gaccaggg ggccaggcag aagttcagca gcctgtacat cagccagttc    4080
atcatcatgt acagcctgga tggcaagaag tggcagacct cagggggcaa cagcactggc    4140
accctgatgg tgttctttgg caatgtggac agctctggca tcaagcacaa catcttcaac    4200
ccccccatca ttgccagata catcaggctg caccccaccc actacagcat caggagcacc    4260
ctgaggatgg agctgatggg ctgtgacctg aacagctgca gcatgccct gggcatggag    4320 agcaaggcca tctctgatgc ccagatcact gccagcagct acttcaccaa catgtttgcc    4380
acctggagcc ccagcaaggc caggctgcac ctgcagggca ggagcaatgc ctggaggccc    4440
```

-continued

```
caggtcaaca acccccaagga gtggctgcag gtggacttcc agaagaccat gaaggtgact     4500
ggggtgacca cccaggggt gaagagcctg ctgaccagca tgtatgtgaa ggagttcctg       4560
atcagcagca gccaggatgg ccaccagtgg accctgttct tccagaatgg caaggtgaag     4620
gtgttccagg gcaaccagga cagcttcacc cctgtggtga acagcctgga ccccccctg      4680 ctgaccagat acctgaggat tcaccccag agctgggtgc accagattgc cctgaggatg      4740
gaggtgctgg gctgtgaggc ccaggacctg tactgaaata aagatctttt atttcatta     4800 gatctgtgtg ttggttttt gtgtgaggaa cccctagtga tggagttggc cactccctct     4860
ctgcgcgctc gctcgctcac tgaggccggg cgaccaaagg tcgcccgacg cccgggcttt   4920
gcccgggcgg cctcagtgag cgagcgagcg cgcagagagg gagtggccaa                4970
```

<210> SEQ ID NO 2
<211> LENGTH: 4950
<212> TYPE: DNA
<213> ORGANISM: Adeno-Associated Virus

<400> SEQUENCE: 2

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactgtttg ctgcttgcaa tgtttgccca ttttagggtg gacacaggac    180
gctgtggttt ctgagccagg gggcgactca gatcccagcc agtggactta gcccctgttt    240
gctcctccga taactggggt gaccttggtt aatattcacc agcagcctcc cccgttgccc     300
ctctggatcc actgcttaaa tacgacgag acagggccc tgtctcctca gcttcaggca       360
ccaccactga cctgggacag tgaatcgcca ccatgcagat tgagctgagc acctgcttct    420
tcctgtgcct gctgaggttc tgcttctctg ccaccaggag atactacctg ggggctgtgg     480
agctgagctg ggactacatg cagtctgacc tgggggagct gcctgtggat gccaggttcc     540
cccccagagt gcccaagagc ttccccttca cacctctgt ggtgtacaag aagaccctgt      600
ttgtggagtt cactgaccac ctgttcaaca ttgccaagcc caggccccccc tggatgggcc    660 tgctgggccc caccatccag gctgaggtgt atgacactgt ggtgatcacc ctgaagaaca    720
tggccagcca ccctgtgagc ctgcatgctg tgggggtgag ctactggaag gcctctgagg    780
gggctgagta tgatgaccag accagccaga gggagaagga ggatgacaag gtgttccctg    840
ggggcagcca cacctatgtg tggcaggtgc tgaaggagaa tggccccatg gcctctgacc    900
ccctgtgcct gacctacagc tacctgagcc atgtggacct ggtgaaggac ctgaactctg     960
gcctgattgg ggccctgctg gtgtgcaggg agggcagcct ggccaaggag aagacccaga    1020
ccctgcacaa gttcatcctg ctgtttgctg tgtttgatga gggcaagagc tggcactctg    1080
aaaccaagaa cagcctgatg caggacaggg atgctgcctc tgccagggcc tggcccaaga   1140
tgcacactgt gaatggctat gtgaacagga gcctgcctgg cctgattggc tgccacagga    1200
agtctgtgta ctggcatgtg attggcatgg gcaccacccc tgaggtgcac agcatcttcc    1260
tggagggcca caccttcctg gtcaggaacc acaggcaggc cagcctggag atcagcccca   1320
tcaccttcct gactgcccag acccctgctga tggacctggg ccagttcctg ctgttctgcc    1380
acatcagcag ccaccagcat gatggcatgg aggcctatgt gaaggtggac agctgccctg    1440
aggagcccca gctgaggatg aagaacaat ggaggctga ggactatgat gatgacctga    1500
ctgactctga gatggatgtg gtgaggtttg atgatgacaa cagccccagc ttcatccaga    1560
tcaggtctgt ggccaagaag cacccccaaga cctgggtgca ctacattgct gctgaggagg   1620
```

```
aggactggga ctatgccccc ctggtgctgg cccctgatga caggagctac aagagccagt    1680
acctgaacaa tggcccccag aggattggca ggaagtacaa gaaggtcagg ttcatggcct    1740
acactgatga aaccttcaag accagggagg ccatccagca tgagtctggc atcctgggcc    1800
ccctgctgta tggggaggtg ggggacaccc tgctgatcat cttcaagaac caggccagca    1860
ggccctacaa catctacccc catggcatca ctgatgtgag gcccctgtac agcaggaggc    1920
tgcccaaggg ggtgaagcac ctgaaggact tccccatcct gcctggggag atcttcaagt    1980
acaagtggac tgtgactgtg gaggatggcc ccaccaagtc tgaccccagg tgcctgacca    2040
gatactacag cagctttgtg aacatggaga gggacctggc ctctggcctg attggccccc    2100
tgctgatctg ctacaaggag tctgtggacc agaggggcaa ccagatcatg tctgacaaga    2160
ggaatgtgat cctgttctct gtgtttgatg agaacaggag ctggtacctg actgagaaca    2220
tccagaggtt cctgcccaac cctgctgggg tgcagctgga ggaccctgag ttccaggcca    2280
gcaacatcat gcacagcatc aatggctatg tgtttgacag cctgcagctg tctgtgtgcc    2340
tgcatgaggt ggcctactgg tacatcctga gcattgggc ccagactgac ttcctgtctg    2400
tgttcttctc tggctacacc ttcaagcaca gatggtgta tgaggacacc ctgaccctgt    2460
tccccttctc tggggagact gtgttcatga gcatggagaa ccctggcctg tggattctgg    2520
gctgccacaa ctctgacttc aggaacaggg gcatgactgc cctgctgaaa gtctccagct    2580
gtgacaagaa cactggggac tactatgagg acagctatga ggacatctct gcctacctgc    2640
tgagcaagaa caatgccatt gagcccagga gcttcagcca gaaccccca gtgctgaaga    2700 ggcaccagag ggagatcacc aggaccaccc tgcagtctga ccaggaggag attgactatg    2760
atgacaccat ctctgtggag atgaagaagg aggactttga catctacgac gaggacgaga    2820
accagagccc caggagcttc cagaagaaga ccaggcacta cttcattgct gctgtggaga    2880
ggctgtggga ctatgcatg agcagcagcc ccatgtgct gaggaacagg gcccagtctg    2940
gctctgtgcc ccagttcaag aaggtggtgt tccaggagtt cactgatggc agcttcaccc    3000 agccctgta cagaggggag ctgaatgagc acctgggcct gctgggcccc tacatcaggg    3060
ctgaggtgga ggacaacatc atggtgacct tcaggaacca ggccagcagg ccctacagct    3120
tctacagcag cctgatcagc tatgaggagg accagaggca gggggctgag cccaggaaga    3180
actttgtgaa gcccaatgaa accaagacct acttctggaa ggtgcagcac cacatggccc    3240
ccaccaagga tgagtttgac tgcaaggcct gggcctactt ctctgatgtg acctggaga    3300 aggatgtgca ctctggcctg attggccccc tgctggtgtg ccacaccaac accctgaacc    3360
ctgcccatgg caggcaggtg actgtgcagg agtttgccct gttcttcacc atctttgatg    3420
aaaccaagag ctggtacttc actgagaaca tggagaggaa ctgcagggcc cctgcaaca    3480 tccagatgga ggaccccacc ttcaaggaga actacaggtt ccatgccatc aatggctaca    3540
tcatggacac cctgcctggc ctggtgatgg cccaggacca gaggatcagg tggtacctgc    3600
tgagcatggg cagcaatgag aacatccaca gcatccactt ctctggccat gtgttcactg    3660
tgaggaagaa ggaggagtac aagatggccc tgtacaacct gtaccctggg gtgtttgaga    3720
ctgtggagat gctgcccagc aaggctgca tctggaggt ggagtgcctg attgggagc    3780 acctgcatgc tggcatgagc accctgttcc tggtgtacag caacaagtgc cagacccccc    3840
tgggcatggc ctctggccac atcagggact tccagatcac tgcctctggc cagtatggcc    3900
agtgggcccc caagctggcc aggctgcact actctggcag catcaatgcc tggagcacca    3960
```

| | |
|---|---|
| aggagcccctt cagctggatc aaggtggacc tgctggcccc catgatcatc catggcatca | 4020 |
| agacccagggg ggccaggcag aagttcagca gcctgtacat cagccagttc atcatcatgt | 4080 |
| acagcctgga tggcaagaag tggcagacct acaggggcaa cagcactggc accctgatgg | 4140 |
| tgttctttgg caatgtggac agctctggca tcaagcacaa catcttcaac cccccccatca | 4200 |
| ttgccagata catcaggctg cacccccaccc actacagcat caggagcacc ctgaggatgg | 4260 |
| agctgatggg ctgtgacctg aacagctgca gcatgcccct gggcatggag agcaaggcca | 4320 |
| tctctgatgc ccagatcact gccagcagct acttcaccaa catgtttgcc acctggagcc | 4380 |
| ccagcaaggc caggctgcac ctgcagggca ggagcaatgc ctggaggccc caggtcaaca | 4440 |
| accccaagga gtggctgcag gtggacttcc agaagaccat gaaggtgact ggggtgacca | 4500 |
| cccaggggggt gaagagcctg ctgaccagca tgtatgtgaa ggagttcctg atcagcagca | 4560 |
| gccaggatgg ccaccagtgg accctgttct tccagaatgg caaggtgaag gtgttccagg | 4620 |
| gcaaccagga cagcttcacc cctgtggtga acagcctgga cccccccctg ctgaccagat | 4680 |
| acctgaggat tcaccccccag agctgggtgc accagattgc cctgaggatg gaggtgctgg | 4740 |
| gctgtgaggc ccaggacctg tactgaaata aagatctttt attttcatta gatctgtgtg | 4800 |
| ttggtttttt gtgtgagtga tggagttggc cactccctct ctgcgcgctc gctcgctcac | 4860 |
| tgaggccggg cgaccaaagg tcgcccgacg cccgggcttt gcccgggcgg cctcagtgag | 4920 |
| cgagcgagcg cgcagagagg gagtggccaa | 4950 |

<210> SEQ ID NO 3
<211> LENGTH: 4983
<212> TYPE: DNA
<213> ORGANISM: Adeno-Associated Virus

<400> SEQUENCE: 3

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactgggcg actcagatcc cagccagtgg acttagcccc tgtttgctcc | 180 |
| tccgataact ggggtgacct tggttaatat tcaccagcag cctcccccgt tgcccctctg | 240 |
| gatccactgc ttaaatacgg acgaggacag ggccctgtct cctcagcttc aggcaccacc | 300 |
| actgacctgg gacagtgaat cgccaccatg cagattgagc tgagcacctg cttcttcctg | 360 |
| tgcctgctga gattctgctt tagtgccacc agaagatact acctgggtgc agtggaactg | 420 |
| tcatgggact atatgcaaag tgatctcggt gagctgcctg tggacgcaag gtaaatgccc | 480 |
| taaaatgggc aaacattgca agcagcaaac aacctggctc agaaaccaca gcgtcctgtg | 540 |
| tccattctaa ttttttcctttt cttcacgcag atttcctcct agagtgccaa atctttttcc | 600 |
| attcaacacc tcagtcgtgt acaaaaagac tctgtttgta gaattcacgg atcacctttt | 660 |
| caacatcgct aagcccaggc cccctggat gggcctgctg ggccccacca tccaggctga | 720 |
| ggtgtatgac actgtggtga tcaccctgaa gaacatggcc agcccctg tgagcctgca | 780 |
| tgctgtgggg gtgagctact ggaaggcctc tgagggggct gagtatgatg accagaccag | 840 |
| ccagagggag aaggaggatg acaaggtgtt ccctgggggc agccacacct atgtgtggca | 900 |
| ggtgctgaag gagaatggcc ccatggcctc tgaccccctg tgcctgacct acagctacct | 960 |
| gagccatgtg gacctggtga aggacctgaa ctctggcctg attggggccc tgctggtgtg | 1020 |
| cagggagggc agcctggcca aggagaagac ccagaccctg cacaagttca tcctgctgtt | 1080 |
| tgctgtgttt gatgagggca agagctggca ctctgaaacc aagaacagcc tgatgcagga | 1140 |

```
cagggatgct gcctctgcca gggcctggcc caagatgcac actgtgaatg gctatgtgaa    1200
caggagcctg cctggcctga ttggctgcca caggaagtct gtgtactggc atgtgattgg    1260
catgggcacc acccctgagg tgcacagcat cttcctggag ggccacacct tcctggtcag    1320
gaaccacagg caggccagcc tggagatcag ccccatcacc ttcctgactg cccagaccct    1380
gctgatggac ctgggccagt tcctgctgtt ctgccacatc agcagccacc agcatgatgg    1440
catggaggcc tatgtgaagg tggacagctg ccctgaggag ccccagctga ggatgaagaa    1500
caatgaggag gctgaggact atgatgatga cctgactgac tctgagatgg atgtggtgag    1560
gtttgatgat gacaacagcc ccagcttcat ccagatcagg tctgtggcca agaagcaccc    1620
caagacctgg gtgcactaca ttgctgctga ggaggaggac tgggactatg ccccctggt    1680 gctgccccct gatgacagga gctacaagag ccagtacctg aacaatggcc cccagaggat    1740
tggcaggaag tacaagaagg tcaggttcat ggcctacact gatgaaacct tcaagaccag    1800
ggaggccatc cagcatgagt ctggcatcct gggccccctg ctgtatgggg aggtggggga    1860
caccctgctg atcatcttca agaaccaggc cagcaggccc tacaacatct accccccatgg    1920 catcactgat gtgaggcccc tgtacagcag gaggctgccc aaggggggtga agcacctgaa    1980 ggacttcccc atcctgcctg gggagatctt caagtacaag tggactgtga ctgtggagga    2040
tggccccacc aagtctgacc ccaggtgcct gaccagatac tacagcagct tgtgaacat    2100 ggagagggac ctggcctctg gcctgattgg ccccctgctg atctgctaca aggagtctgt    2160
ggaccagagg ggcaaccaga tcatgtctga caagaggaat gtgatcctgt tctctgtgtt    2220
tgatgagaac aggagctggt acctgactga gaacatccag aggttcctgc ccaaccctgc    2280
tggggtgcag ctggaggacc ctgagttcca ggccagcaac atcatgcaca gcatcaatgg    2340
ctatgtgttt gacagcctgc agctgtctgt gtgcctgcat gaggtggcct actggtacat    2400
cctgagcatt ggggcccaga ctgacttcct gtctgtgttc ttctctggct acaccttcaa    2460
gcacaagatg gtgtatgagg acaccctgac cctgttcccc ttctctgggg agactgtgtt    2520
catgagcatg gagaaccctg gcctgtggat tctgggctgc cacaactctg acttcaggaa    2580
caggggcatg actgccctgc tgaaagtctc cagctgtgac aagaacactg ggactacta    2640 tgaggacagc tatgaggaca tctctgcct cctgctgagc aagaacaatg ccattgagcc    2700
caggagcttc agccagaacc ccccagtgct gaagaggcac cagagggaga tcaccaggac    2760
caccctgcag tctgaccagg aggagattga ctatgatgac accatctctg tggagatgaa    2820
gaaggaggac tttgacatct acgacgagga cgagaaccag agcccagga gcttccagaa    2880 gaagaccagg cactacttca ttgctgctgt ggagaggctg tgggactatg catgagcag    2940 cagcccccat gtgctgagga cagggcccag tctggctct gtgccccagt tcaagaaggt    3000
ggtgttccag gagttcactg atggcagctt cacccagccc ctgtacagag gggagctgaa    3060
tgagcacctg gcctgctgg gccctacat cagggctgag gtgaggaca acatcatggt    3120 gaccttcagg aaccaggcca gcaggcccta cagcttctac agcagcctga tcagctatga    3180
ggaggaccag aggcaggggg ctgagcccag gaagaacttt gtgaagccca atgaaaccaa    3240
gacctacttc tggaaggtgc agcaccacat ggccccacc aaggatgagt ttgactgcaa    3300
ggcctgggcc tacttctctg atgtggacct ggagaaggat gtgcactctg cctgattgg    3360 ccccctgctg gtgtgccaca ccaacaccct gaaccctgcc catggcaggc aggtgactgt    3420
gcaggagttt gccctgttct tcaccatctt tgatgaaacc aagagctggt acttcactga    3480
```

```
gaacatggag aggaactgca gggcccctg caacatccag atggaggacc ccaccttcaa      3540
ggagaactac aggttccatg ccatcaatgg ctacatcatg acaccctgc ctggcctggt      3600 gatggcccag accagagga tcaggtggta cctgctgagc atgggcagca atgagaacat      3660
ccacagcatc cacttctctg ccatgtgtt cactgtgagg aagaaggagg agtacaagat      3720
ggccctgtac aacctgtacc ctggggtgtt tgagactgtg agatgctgc ccagcaaggc      3780 tggcatctgg agggtggagt gcctgattgg ggagcacctg catgctggca tgagcaccct      3840
gttcctggtg tacagcaaca agtgccagac cccctgggc atggcctctg ccacatcag      3900 ggacttccag atcactgcct ctggccagta tggccagtgg gccccaagc tggccaggct      3960 gcactactct ggcagcatca atgcctggag caccaaggag cccttcagct ggatcaaggt      4020
ggacctgctg gcccccatga tcatccatgg catcaagacc caggggggcca ggcagaagtt      4080 cagcagcctg tacatcagcc agttcatcat catgtacagc ctggatggca agaagtggca      4140
gacctacagg ggcaacagca ctggcaccct gatggtgttc tttggcaatg tggacagctc      4200
tggcatcaag cacaacatct tcaaccccccc catcattgcc agatacatca ggctgcaccc      4260
cacccactac agcatcagga gcaccctgag gatggagctg atgggctgtg acctgaacag      4320
ctgcagcatg cccctgggca tggagagcaa ggccatctct gatgcccaga tcactgccag      4380
cagctacttc accaacatgt tgccacctg gagccccagc aaggccaggc tgcacctgca      4440
gggcaggagc aatgcctgga ggccccaggt caacaacccc aaggagtggc tgcaggtgga      4500
cttccagaag accatgaagg tgactggggt gaccacccag ggggtgaaga gcctgctgac      4560
cagcatgtat gtgaaggagt tcctgatcag cagcagccag gatggccacc agtggaccct      4620
gttcttccag aatggcaagg tgaaggtgtt ccagggcaac caggacagct tcacccctgt      4680
ggtgaacagc ctggacccccc ccctgctgac cagatacctg aggattcacc cccagagctg      4740
ggtgcaccag attgccctga ggatggaggt gctgggctgt gaggcccagg acctgtacta      4800
ataaaagatc tttattttca ttagatctgt gtgttggttt tttgtgtgag tgatggagtt      4860
ggccactccc tctctgcgcg ctcgctcgct cactgaggcc gggcgaccaa aggtcgcccg      4920
acgcccgggc tttgcccggg cggcctcagt gagcgagcga gcgcgcagag agggagtggc      4980
caa                                                                  4983
```

<210> SEQ ID NO 4
<211> LENGTH: 4984
<212> TYPE: DNA
<213> ORGANISM: Adeno-Associated Virus

<400> SEQUENCE: 4

```
ttggccactc cctctctgcg cgctcgctcg ctcactgagg ccgccgggc aaagcccggg        60 cgtcgggcga cctttggtcg cccggcctca gtgagcgagc gagcgcgcag agagggagtg      120
gccaactcca tcactgggcg actcagatcc cagccagtgg acttagcccc tgtttgctcc      180
tccgataact ggggtgacct tggttaatat tcaccagcag cctcccccgt tgcccctctg      240
gatccactgc ttaaatacgg acgaggacag ggccctgtct cctcagcttc aggcaccacc      300
actgacctgg gacagtgaat cgccaccatg cagattgagc tgagcacctg cttcttcctg      360
tgcctgctga gattctgctt tagtgccacc agaagatact acctgggtgc agtggaactg      420
tcatgggact atatgcaaag tgatctcggt gagctgcctg tggacgcaag gtaaatgccc      480
taaaatgggc aaacattgca agcagcaaac accctaaaat gggcaaacat tgcaagcagc      540
aaacattcta atttttcctt tcttcacgca gatttcctcc tagagtgcca aaatctttc       600
```

```
cattcaacac ctcagtcgtg tacaaaaaga ctctgtttgt agaattcacg gatcacctttt      660 tcaacatcgc taagcccagg ccccctgga tgggcctgct gggccccacc atccaggctg         720
aggtgtatga cactgtggtg atcaccctga agaacatggc cagccaccct gtgagcctgc         780
atgctgtggg ggtgagctac tggaaggcct ctgaggggc tgagtatgat gaccagacca         840
gccagaggga aaggaggat gacaaggtgt tccctggggg cagccacacc tatgtgtggc          900
aggtgctgaa ggagaatggc cccatggcct ctgaccccct gtgcctgacc tacagctacc         960
tgagccatgt ggacctggtg aaggacctga actctggcct gattggggcc ctgctggtgt        1020
gcagggaggg cagcctggcc aaggagaaga cccagaccct gcacaagttc atcctgctgt        1080
ttgctgtgtt tgatgagggc aagagctggc actctgaaac caagaacagc ctgatgcagg        1140
acagggatgc tgcctctgcc agggcctggc ccaagatgca cactgtgaat ggctatgtga        1200
acaggagcct gcctggcctg attggctgcc acaggaagtc tgtgtactgg catgtgattg        1260
gcatgggcac caccctgag gtgcacagca tcttcctgga gggccacacc ttcctggtca        1320
ggaaccacag gcaggccagc ctggagatca gccccatcac cttcctgact gcccagaccc        1380
tgctgatgga cctgggccag ttcctgctgt tctgccacat cagcagccac cagcatgatg        1440
gcatggaggc ctatgtgaag gtggacagct gccctgagga gccccagctg aggatgaaga        1500
acaatgagga ggctgaggac tatgatgatg acctgactga ctctgagatg gatgtggtga        1560
ggtttgatga tgacaacagc cccagcttca tccagatcag gtctgtggcc aagaagcacc        1620
ccaagacctg ggtgcactac attgctgctg aggaggagga ctgggactat gcccccctgg        1680
tgctggcccc tgatgacagg agctacaaga gccagtacct gaacaatggc cccagaggaa        1740
ttggcaggaa gtacaagaag gtcaggttca tggcctacac tgatgaaacc ttcaagacca        1800
gggaggccat ccagcatgag tctggcatcc tgggcccct gctgtatggg gaggtggggg        1860
acaccctgct gatcatcttc aagaaccagg ccagcaggcc ctacaacatc tacccccatg        1920
gcatcactga tgtgaggccc ctgtacagca ggaggctgcc caagggggtg aagcacctga        1980
aggacttccc catcctgcct ggggagatct tcaagtacaa gtggactgtg actgtggagg        2040
atggccccac caagtctgac cccaggtgcc tgaccagata ctacagcagc tttgtgaaca        2100
tggagaggga cctggcctct ggcctgattg gccccctgct gatctgctac aaggagtctg        2160
tggaccagag gggcaaccag atcatgtctg acaagaggaa tgtgatcctg ttctctgtgt        2220
ttgatgagaa caggagctgg tacctgactg agaacatcca gaggttcctg cccaaccctg        2280
ctggggtgca gctggaggac cctgagttcc aggccagcaa catcatgcac agcatcaatg        2340
gctatgtgtt tgacagcctg cagctgtctg tgtgcctgca tgaggtggcc tactggtaca        2400
tcctgagcat ggggcccag actgacttcc tgtctgtgtt cttctctggc tacacctttca        2460 agcacaagat ggtgtatgag gacacccctga ccctgttccc cttctctggg gagactgtgt        2520
tcatgagcat ggagaaccct ggcctgtgga ttctgggctg ccacaactct gacttcagga        2580
acaggggcat gactgccctg ctgaaagtct ccagctgtga caagaacact ggggactact        2640
atgaggacag ctatgaggac atctctgcct acctgctgag caagaacaat gccattgagc        2700
ccaggagctt cagccagaac ccccagtgc tgaagaggca ccagagggag atcaccagga        2760
ccaccctgca gtctgaccag gaggagattg actatgatga caccatctct gtggagatga        2820
agaaggagga ctttgacatc tacgacgagg acgagaacca gagccccagg gcttccagaa        2880 gaagaccag gcactacttc attgctgctg tggagaggct gtgggactat ggcatgagca        2940
```

```
gcagccccca tgtgctgagg aacagggccc agtctggctc tgtgcccccag ttcaagaagg    3000
tggtgttcca ggagttcact gatggcagct cacccagcc cctgtacaga ggggagctga     3060
atgagcacct gggcctgctg gcccctaca tcagggctga ggtggaggac aacatcatgg     3120
tgaccttcag gaaccaggcc agcaggccct acagcttcta cagcagcctg atcagctatg    3180
aggaggacca gaggcagggg gctgagccca ggaagaactt tgtgaagccc aatgaaacca    3240
agacctactt ctggaaggtg cagcaccaca tggcccccac caaggatgag tttgactgca    3300
aggcctgggc ctacttctct gatgtggacc tggagaagga tgtgcactct ggcctgattg    3360
gcccctgct ggtgtgccac accaacaccc tgaaccctgc ccatggcagg caggtgactg     3420
tgcaggagtt tgccctgttc ttcaccatct ttgatgaaac caagagctgg tacttcactg    3480
agaacatgga gaggaactgc agggcccct gcaacatcca gatggaggac cccaccttca     3540
aggagaacta caggttccat gccatcaatg ctacatcat ggacaccctg cctggcctgg    3600
tgatggccca ggaccagagg atcaggtggt acctgctgag catgggcagc aatgagaaca    3660
tccacagcat ccacttctct ggccatgtgt tcactgtgag gaagaaggag gagtacaaga    3720
tggcctgta caacctgtac cctgggggtg ttgagactgt ggagatgctg cccagcaagg    3780
ctggcatctg gagggtggag tgcctgattg gggagcacct gcatgctggc atgagcaccc    3840
tgttcctggt gtacagcaac aagtgccaga ccccctgggg catggcctct ggccacatca    3900
gggacttcca gatcactgcc tctggccagt atggccagtg gccccccaag ctggccaggc    3960
tgcactactc tggcagcatc aatgcctgga gcaccaagga gcccttcagc tggatcaagg    4020
tggacctgct ggccccatg atcatccatg gcatcaagac ccaggggccc aggcagaagt     4080
tcagcagcct gtacatcagc cagttcatca tcatgtacag cctggatggc aagaagtggc    4140
agacctacag gggcaacagc actggcaccc tgatggtgtt cttttggcaat gtggacagct    4200
ctggcatcaa gcacaacatc ttcaaccccc ccatcattgc cagatacatc aggctgcacc    4260
ccacccacta cagcatcagg agcacccttga ggatggagct gatgggctgt gacctgaaca    4320
gctgcagcat gccccctggg catggagagca aggccatctc tgatgcccag atcactgcca    4380
gcagctactt caccaacatg tttgccacct ggagccccag caaggccagg ctgcacctgc    4440
agggcaggag caatgcctgg aggccccagg tcaacaaccc caaggagtgg ctgcaggtgg    4500
acttccagaa gaccatgaag gtgactgggg tgaccaccca gggggtgaag agcctgctga    4560
ccagcatgta tgtgaaggag ttcctgatca gcagcagcca ggatggccac cagtggaccc    4620
tgttcttcca gaatggcaag gtgaaggtgt tccaggcaa ccaggacagc ttcaccccctg    4680
tggtgaacag cctggacccc ccctgctga ccagatacct gaggattcac ccccagagct    4740
gggtgcacca gattgccctg aggatggagg tgctgggctg tgaggcccag gacctgtact    4800
aataaaagat cttatttc attagatctg tgtgttggt tttttgtga gtgatggagt        4860
tggccactcc ctctctgcgc gctcgctcg tcactgaggc cgggcgacca aagtgtgcccc    4920
gacgcccggg ctttgcccgg gcggcctcag tgagcgagcg agcgcgcaga gagggagtgg    4980
ccaa                                                                  4984

<210> SEQ ID NO 5
<211> LENGTH: 4805
<212> TYPE: DNA
<213> ORGANISM: Adeno-Associated Virus

<400> SEQUENCE: 5
ttggccactc cctctctgcg cgctcgctcg ctcactgagg ccgcccgggc aaagcccggg     60
```

-continued

```
cgtcgggcga cctttggtcg cccggcctca gtgagcgagc gagcgcgcag agagggagtg    120
gccaactcca tcactagggg ttcctgtttg ctgcttgcaa tgtttgccca ttttagggtg    180
gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacggacgag gacagggccc tgtctcctca    360
gcttcaggca ccaccactga cctgggacag tgaatcgcca ccatgcagat tgagctgagc    420
acctgcttct tcctgtgcct gctgaggttc tgcttctctg ccaccaggag atactacctg    480
ggggctgtgg agctgagctg ggactacatg cagtctgacc tgggggagct gcctgtggat    540
gccaggttcc cccccagagt gcccaagagc ttccccttca cacctctgt ggtgtacaag    600 aagaccctgt tgtggagtt cactgaccac ctgttcaaca ttgccaagcc caggcccccc    660
tggatgggcc tgctgggccc caccatccag gctgaggtgt atgacactgt ggtgatcacc    720
ctgaagaaca tggccagcca ccctgtgagc ctgcatgctg tgggggtgag ctactggaag    780
gcctctgagg gggctgagta tgatgaccag accagccaga gggagaagga ggatgacaag    840
gtgttccctg gggcagcca cacctatgtg tggcaggtgc tgaaggagaa tggccccatg    900
gcctctgacc ccctgtgcct gacctacagc tacctgagcc atgtggacct ggtgaaggac    960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga agtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag accctgctga tggacctggg ccagttcctg    1380
ctgttctgcc acatcagcag ccaccagcat gatggcatgg aggcctatgt gaaggtggac    1440
agctgccctg aggagcccca gctgaggatg aagaacaatg aggaggctga ggactatgat    1500
gatgacctga ctgactctga gatggatgtg gtgaggtttg atgatgacaa cagccccagc    1560
ttcatccaga tcaggtctgt ggccaagaag cacccaagga cctgggtgca ctacattgct    1620
gctgaggagg aggactggga ctatgccccc ctggtgctgg cccctgatga caggagctac    1680
aagagccagt acctgaacaa tggcccccag aggattggca ggaagtacaa gaaggtcagg    1740
ttcatggcct acactgatga aaccttcaag accaggagg ccatccagca tgagtctggc    1800
atcctgggcc ccctgctgta tggggaggtg ggggacaccc tgctgatcat cttcaagaac    1860
caggccagca ggcctacaa catctacccc catggcatca ctgatgtgag gcccctgtac    1920
agcaggaggc tgcccaaggg ggtgaagcac ctgaaggact cccccatcct gcctggggag    1980
atcttcaagt acaagtggac tgtgactgtg gaggatggcc ccaccaagtc tgaccccagg    2040
tgcctgacca gatactacag cagctttgtg aacatggaga gggacctggc ctctggcctg    2100
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
actgagaaca tccagaggtt cctgcccaac cctgctgggg tgcagctgga ggaccctgag    2280
ttccaggcca gcaacatcat gcacagcatc aatggctatg tgtttgacag cctgcagctg    2340
tctgtgtgcc tgcatgaggt ggcctactgg tacatcctga gcattggggc ccagactgac    2400
```

```
ttcctgtctg tgttcttctc tggctacacc ttcaagcaca agatggtgta tgaggacacc    2460
ctgaccctgt tccccttctc tggggagact gtgttcatga gcatggagaa ccctggcctg    2520
tggattctgg gctgccacaa ctctgacttc aggaacaggg gcatgactgc cctgctgaaa    2580
gtctccagct gtgacaagaa cactggggac tactatgagg acagctatga ggacatctct    2640
gcctacctgc tgagcaagaa caatgccatt gagcccagga gcttccagaa gaagaccagg    2700
cactacttca ttgctgctgt ggagaggctg tgggactatg gcatgagcag cagcccccat    2760
gtgctgagga cagggccca gtctggctct gtgccccagt tcaagaaggt ggtgttccag    2820
gagttcactg atggcagctt cacccagccc ctgtacagag gggagctgaa tgagcacctg    2880
ggcctgctgg gcccctacat cagggctgag gtggaggaca acatcatggt gaccttcagg    2940
aaccaggcca gcaggcccta cagcttctac agcagcctga tcagctatga ggaggaccag    3000 aggcagggg ctgagcccag gaagaacttt gtgaagccca tgaaaccaa gacctacttc    3060 tggaaggtgc agcaccacat ggcccccacc aaggatgagt ttgactgcaa ggcctgggcc    3120
tacttctctg atgtggacct ggagaaggat gtgcactctg gcctgattgg ccccctgctg    3180
gtgtgccaca ccaacaccct gaaccctgcc catggcaggc aggtgactgt gcaggagttt    3240
gccctgttct tcaccatctt tgatgaaacc aagagctggt acttcactga gaacatggag    3300
aggaactgca gggccccctg caacatccag atggaggacc ccaccttcaa ggagaactac    3360
aggttccatg ccatcaatgg ctacatcatg gacaccctgc ctggcctggt gatggcccag    3420
gaccagagga tcaggtggta cctgctgagc atgggcagca atgagaacat ccacagcatc    3480
cacttctctg gccatgtgtt cactgtgagg aagaaggagg agtacaagat ggccctgtac    3540
aacctgtacc ctgggggtgtt tgagactgtg agatgctgc ccagcaaggc tggcatctgg    3600
agggtggagt gcctgattgg ggagcacctg catgctggca tgagcaccct gttcctggtg    3660
tacagcaaca agtgccagac ccccctgggc atggcctctg ccacatcag ggacttccag    3720 atcactgcct ctggccagta tggccagtgg gcccccaagc tggccaggct gcactactct    3780
ggcagcatca atgcctggag caccaaggag cccttcagct ggatcaaggt ggacctgctg    3840
gcccccatga tcatccatgg catcaagacc cagggggcca ggcagaagtt cagcagcctg    3900
tacatcagcc agttcatcat catgtacagc ctggatggca gaagtggca gacctacagg    3960 ggcaacagca ctggcaccct gatggtgttc tttggcaatg tggacagctc tggcatcaag    4020
cacaacatct tcaaccccc catcattgcc agatacatca ggctgcaccc cacccactac    4080
agcatcagga gcaccctgag gatggagctg atgggctgtg acctgaacag ctgcagcatg    4140
cccctgggca tggagagcaa ggccatctct gatgcccaga tcactgccag cagctacttc    4200
accaacatgt ttgccacctg gagccccagc aaggccaggc tgcacctgca gggcaggagc    4260
aatgcctgga ggccccaggt caacaacccc aaggagtggc tgcaggtgga cttccagaag    4320
accatgaagg tgactggggt gaccacccag ggggtgaaga gcctgctgac cagcatgtat    4380
gtgaaggagt tcctgatcag cagcagccag gatggccacc agtggaccct gttcttccag    4440
aatggcaagg tgaaggtgtt ccagggcaac caggacagct tcaccccctgt ggtgaacagc    4500 ctggacccc ccctgctgac cagataccctg aggattcacc cccagagctg ggtgcaccag    4560
attgccctga ggatggaggt gctgggctgt gaggcccagg acctgtactg aaataaaaga    4620
tctttatttt cattagatct gtgtgttggt tttttgtgtg aggaacccct agtgatggag    4680
ttggccactc cctctctgcg cgctcgctcg ctcactgagg ccgggcgacc aaaggtcgcc    4740
cgacgcccgg gctttgcccg ggcggcctca gtgagcgagc gagcgcgcag agaggagtg    4800
``` gccaa                                                                      4805

<210> SEQ ID NO 6
<211> LENGTH: 4934
<212> TYPE: DNA
<213> ORGANISM: Adeno-Associated Virus

<400> SEQUENCE: 6

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240 gccctgttt gctcctccga taactgggt gaccttggtt aatattcacc agcagcctcc       300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgagattc tgctttagtg ccaccagaag atactacctg     480
ggtgcagtgg aactgtcatg ggactatatg caaagtgatc tcggtgagct gcctgtggac     540
gcaaggtaaa ggcatgtcct gtagggtctg atcggggcca ggattgtggg gatgtaagtc     600
tgcttggagg aaggtgcaga catcgggtta ggatggttgt gatgctattc tgactttttc     660
ctttcttcac gcagatttcc tcctagagtg ccaaaatctt ttccattcaa cacctcagtc     720
gtgtacaaaa agactctgtt tgtagaattc acggatcacc ttttcaacat cgctaagccc     780 aggccccct ggatgggcct gctgggcccc accatccagg ctgaggtgta tgacactgtg     840
gtgatcaccc tgaagaacat ggccagccac cctgtgagcc tgcatgctgt ggggtgagc     900 tactggaagg cctctgaggg ggctgagtat gatgaccaga ccagccagag ggagaaggag     960
gatgacaagg tgttccctgg gggcagccac acctatgtgt ggcaggtgct gaaggagaat    1020
ggccccatgg cctctgaccc cctgtgcctg acctacagct acctgagcca tgtggacctg    1080
gtgaaggacc tgaactctgg cctgattggg gccctgctgg tgtgcaggga gggcagcctg    1140
gccaaggaga gacccagac cctgcacaag ttcatcctgc tgtttgctgt gtttgatgag    1200
ggcaagagct ggcactctga aaccaagaac agcctgatgc aggacaggga tgctgcctct    1260
gccagggcct ggcccaagat gcacactgtg aatggctatg tgaacaggag cctgcctggc    1320
ctgattggct gccacaggaa gtctgtgtac tggcatgtga ttggcatggg caccaccct    1380 gaggtgcaca gcatcttcct ggagggccac accttcctgg tcaggaacca caggcaggcc    1440
agcctggaga tcagccccat caccttcctg actgcccaga ccctgctgat ggacctgggc    1500
cagttcctgc tgttctgcca catcagcagc caccagcatg atggcatgga ggcctatgtg    1560
aaggtggaca gctgccctga ggagcccag ctgaggatga gaacaatga ggaggctgag    1620 gactatgatg atgacctgac tgactctgag atggatgtgg tgaggtttga tgatgacaac    1680
agccccagct catccagat caggtctgtg gccaagaagc accccaagac ctgggtgcac    1740
tacattgctg ctgaggagga ggactgggac tatgccccc tggtgctggc ccctgatgac    1800
aggagctaca agagccagta cctgaacaat ggccccccag a ggattggcag gaagtacaag    1860
aaggtcaggt tcatggccta cactgatgaa accttcaaga ccagggaggc catccagcat    1920
gagtctggca tcctgggccc cctgctgtat ggggaggtgg gggacacct gctgatcatc    1980 ttcaagaacc aggccagcag gccctacaac atctaccccc atggcatcac tgatgtgagg    2040
```

```
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga aacaggagc     2340
tggtacctga ctgagaacat ccagaggttc ctgcccaacc ctgctggggt gcagctggag    2400
gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg gagaggctgt gggactatgg catgagcagc    2880
agccccatg tgctgaggaa cagggcccag tctggctctg tgcccagtt caagaaggtg     2940
gtgttccagg agttcactga tggcagcttc acccagcccc tgtacagagg ggagctgaat    3000
gagcacctgg gcctgctggg ccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg agaaggatg tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta cttcactgag    3420
aacatggaga ggaactgcag ggccccctgc aacatccaga tggaggaccc caccttcaag    3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga gaaggaggga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc cccctgggca tggcctctgg ccacatcagg    3840
gacttccaga tcactgcctc tggccagtat ggccagtggg cccccaagct ggccaggctg    3900
cactactctg gcagcatcaa tgcctggagc accaaggagc ccttcagctg gatcaaggtg    3960
gacctgctgg cccccatgat catccatggc atcaagaccc aggggccag gcagaagttc     4020
agcagcctgt acatcagcca gttcatcatc atgtacagcc tggatggcaa gaagtggcag    4080
acctacaggg gcaacagcac tggcacccctg atggtgttct ttggcaatgt ggacagctct    4140
ggcatcaagc acaacatctt caaccccccc atcattgcca gatacatcag gctgcacccc    4200
acccactaca gcatcaggag cacccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca ggccaggct gcacctgcag    4380
ggcaggagca atgcctggag gcccaggtc aacaaccca aggagtggct gcaggtggac    4440
```

```
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccctgtgt    4620
gtgaacagcc tggacccccc cctgctgacc agatacctga ggattcaccc ccagagctgg    4680
gtgcaccaga ttgccctgag gatggaggtg ctgggctgtg aggcccagga cctgtactga    4740
aataaaagat ctttattttc attagatctg tgtgttggtt ttttgtgtga ggaacccta     4800 gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934

<210> SEQ ID NO 7
<211> LENGTH: 4934
<212> TYPE: DNA
<213> ORGANISM: Adeno-Associated Virus

<400> SEQUENCE: 7
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttaggggtg    180 gacacaggac gctgtggttt ctgagccagg gggcgactca gatcccagcc agtggactta    240
gcccctgttt gctcctccga taactggggt gaccttggtt aatattcacc agcagcctcc    300
cccgttgccc ctctggatcc actgcttaaa tacgacgag  acagggccc  tgtctcctca    360 gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggctgtttgc tgcttgcaat gtttgcccat tttagggggg atgtaagtc     600 tgcttggagg aaggtgcaga catcgggtta ggatggttgt gatgctattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780 aggccccct ggatgggcct gctgggcccc accatccagg ctgaggtgta tgacactgtg     840
gtgatcaccc tgaagaacat ggccagccac cctgtgagcc tgcatgctgt ggggtgagc     900 tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg   1080
gtgaaggacc tgaactctgg cctgattggg gccctgctgg tgtgcaggga gggcagcctg   1140
gccaaggaga gacccagac  cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg taacaggag  cctgcctggc   1320 ctgattggct gccacaggaa gtctgtgtac tggcatgtga ttggcatggg caccaccctc   1380
gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
```

```
aaggtggaca gctgccctga ggagcccagc tgaggatgag aacaatgagg aggctgagg      1620 gactatgatg atgacctgac tgactctgag atggatgtgg tgaggtttga tgatgacaac      1680
agccccagct tcatccagat caggtctgtg gccaagaagc accccaagac ctgggtgcac      1740
tacattgctg ctgaggagga ggactgggac tatgcccccc tggtgctggc ccctgatgac      1800
aggagctaca agagccagta cctgaacaat ggccccagag ggattggcag gaagtacaag      1860
aaggtcaggt tcatggccta cactgatgaa accttcaaga ccaggaggc catccagcat       1920 gagtctggca tcctgggccc cctgctgtat ggggaggtgg gggacaccct gctgatcatc      1980
ttcaagaacc aggccagcag gccctacaac atctaccccc atggcatcac tgatgtgagg      2040
cccctgtaca gcaggaggct gcccaagggg gtgaagcacc tgaaggactt ccccatcctg      2100
cctggggaga tcttcaagta caagtggact gtgactgtgg aggatggccc caccaagtct      2160
gaccccaggt gcctgaccag atactacagc agctttgtga acatggagag ggacctggcc      2220
tctggcctga ttggccccct gctgatctgc tacaaggagt ctgtggacca gaggggcaac      2280
cagatcatgt ctgacaagag gaatgtgatc ctgttctctg tgtttgatga aacaggagc       2340 tggtacctga ctgagaacat ccagaggttc ctgcccaacc ctgctggggt gcagctggag      2400
gaccctgagt tccaggccag caacatcatg cacagcatca atggctatgt gtttgacagc      2460
ctgcagctgt ctgtgtgcct gcatgaggtg gcctactggt acatcctgag cattggggcc      2520
cagactgact tcctgtctgt gttcttctct ggctacacct tcaagcacaa gatggtgtat      2580
gaggacaccc tgaccctgtt cccttctct ggggagactg tgttcatgag catggagaac       2640
cctggcctgt ggattctggg ctgccacaac tctgacttca ggaacagggg catgactgcc      2700
ctgctgaaag tctccagctg tgacaagaac actggggact actatgagga cagctatgag      2760
gacatctctg cctacctgct gagcaagaac aatgccattg agcccaggag cttccagaag      2820
aagaccaggc actacttcat tgctgctgtg agaggctgt gggactatgg catgagcagc       2880
agcccccatg tgctgaggaa cagggcccag tctggctctg tgcccccagtt caagaaggtg     2940 gtgttccagg agttcactga tggcagcttc acccagcccc tgtacagagg ggagctgaat      3000
gagcacctgg gcctgctggg ccctacatc agggctgagg tggaggacaa catcatggtg        3060
accttcagga accaggccag caggccctac agcttctaca gcagcctgat cagctatgag      3120
gaggaccaga ggcaggggc tgagcccagg aagaactttg tgaagcccaa tgaaaccaag       3180
acctacttct ggaaggtgca gcaccacatg gcccccacca aggatgagtt tgactgcaag      3240
gcctgggcct acttctctga tgtggacctg gagaaggatg tgcactctgg cctgattggc      3300
cccctgctgg tgtgccacac caacacctg aaccctgccc atggcaggca ggtgactgtg       3360
caggagtttg ccctgttctt caccatcttt gatgaaacca gagctggta cttcactgag       3420 aacatggaga ggaactgcag ggcccctgc aacatccaga tggaggaccc caccttcaag       3480
gagaactaca ggttccatgc catcaatggc tacatcatgg acaccctgcc tggcctggtg      3540
atggcccagg accagaggat caggtggtac ctgctgagca tgggcagcaa tgagaacatc      3600
cacagcatcc acttctctgg ccatgtgttc actgtgagga agaaggagga gtacaagatg      3660
gccctgtaca acctgtaccc tggggtgttt gagactgtgg agatgctgcc cagcaaggct      3720
ggcatctgga gggtggagtg cctgattggg gagcacctgc atgctggcat gagcacccctg    3780 ttcctggtgt acagcaacaa gtgccagacc cccctgggca tggcctctgg ccacatcagg      3840
gacttccaga tcactgcctc tggccagtat ggccagtggg cccccaagct ggccaggctg      3900
cactactctg gcagcatcaa tgcctggagc accaaggagc ccttcagctg gatcaaggtg      3960
```

```
gacctgctgg cccccatgat catccatggc atcaagaccc aggggggccag gcagaagttc    4020 agcagcctgt acatcagcca gttcatcatc atgtacagcc tggatggcaa gaagtggcag    4080
acctacaggg gcaacagcac tggcaccctg atggtgttct ttggcaatgt ggacagctct    4140
ggcatcaagc acaacatctt caacccccccc atcattgcca gatacatcag gctgcacccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca aggccaggct gcacctgcag    4380
ggcaggagca atgcctggag gccccaggtc aacaacccca aggagtggct gcaggtggac    4440
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccccctgtg   4620 gtgaacagcc tggacccccc cctgctgacc agatacctga ggattcaccc ccagagctgg    4680
gtgcaccaga ttgccctgag gatggaggtg ctgggctgtg aggcccagga cctgtactga    4740
aataaaagat cttattttc attagatctg tgtgttggtt ttttgtgtga ggaaccccta     4800
gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934

<210> SEQ ID NO 8
<211> LENGTH: 4934
<212> TYPE: DNA
<213> ORGANISM: Adeno-Associated Virus

<400> SEQUENCE: 8
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttaggggtg    180 gacacaggac gctgtggttt ctgagccagg gggcgactca gatcccagcc agtggactta    240
gccctgtttt gctcctccga taactggggt gaccttggtt aatattcacc agcagcctcc    300
cccgttgccc ctctggatcc actgcttaaa tacgacgag gacagggccc tgtctcctca    360
gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa gcatgtcct gtaggtctg atcggggcca ggattgtggg gatgtaagtc     600
tgcttggagg aagccctaaa atgggcaaac attgcaagca gcaaacattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780 aggccccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagt gttccctgg gggcagccac acctatgtgt ggcaggtgct gaaggagaat   1020 ggcccccatgg cctctgaccc cctgtgcctg acctacagct acctgagcca tgtggacctg    1080
```

-continued

```
gtgaaggacc tgaactctgg cctgattggg gccctgctgg tgtgcaggga gggcagcctg   1140
gccaaggaga agacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccacccct   1380
gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagccccag ctgaggatga agaacaatga ggaggctgag   1620
gactatgatg atgacctgac tgactctgag atggatgtgg tgaggtttga tgatgacaac   1680
agccccagct tcatccagat caggtctgtg gccaagaagc accccaagac ctgggtgcac   1740
tacattgctg ctgaggagga ggactgggac tatgcccccc tggtgctggc ccctgatgac   1800
aggagctaca gagccagta cctgaacaat ggccccagga ggattggcag gaagtacaag   1860
aaggtcaggt tcatgcccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctacccc atggcatcac tgatgtgagg   2040
cccctgtaca gcaggaggct gcccaagggg gtgaagcacc tgaaggactt ccccatcctg   2100
cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggcccccT gctgatctgc tacaaggagt ctgtggacca gaggggcaac   2280
cagatcatgt ctgacaagag gaatgtgatc ctgttctctg tgtttgatga aacaggagc   2340 tggtacctga ctgagaacat ccagaggttc ctgcccaacc tgctggggt gcagctggag   2400 gaccctgagt ccaggccag caacatcatg cacagcatca atggctatgt gtttgacagc   2460
ctgcagctgt ctgtgtgcct gcatgaggtg gcctactggt acatcctgag cattgggcc   2520 cagactgact tcctgtctgt gttcttctct ggctacacct tcaagcacaa gatggtgtat   2580
gaggacaccc tgaccctgtt cccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg agagggctgt gggactatgg catgagcagc   2880
agcccccatg tgctgaggaa cagggcccag tctggctctg tgcccagtt caagaaggtg   2940 gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggcctac agcttctaca gcagcctgat cagctatgag   3120
gaggaccaga ggcagggggc tgagcccagg aagaactttg tgaagcccaa tgaaaccaag   3180
acctacttct ggaaggtgca gcaccacatg gcccccacca aggatgagtt tgactgcaag   3240
gcctgggcct acttctctga tgtggacctg agaaggatg tgcactctgg cctgattggc   3300
cccctgctgg tgtgccacac caacaccctg aaccctgccc atggcaggca ggtgactgtg   3360
caggagtttg ccctgttctt caccatctttt gatgaaacca gagctggta cttcactgag   3420 aacatggaga ggaactgcag ggccccctgc aacatccaga tggaggaccc cacccttcaag   3480
```

```
gagaactaca ggttccatgc catcaatggc tacatcatgg acaccctgcc tggcctggtg      3540
atggcccagg accagaggat caggtggtac ctgctgagca tgggcagcaa tgagaacatc      3600
cacagcatcc acttctctgg ccatgtgttc actgtgagga agaaggagga gtacaagatg      3660
gccctgtaca acctgtaccc tggggtgttt gagactgtgg agatgctgcc cagcaaggct      3720
ggcatctgga gggtggagtg cctgattggg agcacctgc atgctggcat gagcaccctg       3780
ttcctggtgt acagcaacaa gtgccagacc cccctgggca tggcctctgg ccacatcagg      3840
gacttccaga tcactgcctc tggccagtat ggccagtggg cccccaagct ggccaggctg      3900
cactactctg gcagcatcaa tgcctggagc accaaggagc ccttcagctg gatcaaggtg      3960
gacctgctgg cccccatgat catccatggc atcaagaccc agggggccag gcagaagttc      4020
agcagcctgt acatcagcca gttcatcatc atgtacagcc tggatggcaa gaagtggcag      4080
acctacaggg gcaacagcac tggcacccctg atggtgttct ttggcaatgt ggacagctct     4140
ggcatcaagc acaacatctt caacccccccc atcattgcca gatacatcag gctgcacccc    4200
acccactaca gcatcaggag cacccctgagg atggagctga tgggctgtga cctgaacagc     4260
tgcagcatgc ccctgggcat ggagagcaag gccatctctg atgcccagat cactgccagc     4320
agctacttca ccaacatgtt tgccacctgg agccccagca aggccaggct gcacctgcag     4380
ggcaggagca atgcctggag gcccaggtc aacaaccca aggagtggct gcaggtggac        4440
ttccagaaga ccatgaaggt gactggggtg accacccagg gggtgaagag cctgctgacc      4500
agcatgtatg tgaaggagtt cctgatcagc agcagccagg atggccacca gtggaccctg      4560
ttcttccaga atggcaaggt gaaggtgttc cagggcaacc aggacagctt caccccctgtg    4620
gtgaacagcc tggacccccc cctgctgacc agatacctga ggattcaccc ccagagctgg     4680
gtgcaccaga ttgccctgag gatggaggtg ctgggctgtg aggcccagga cctgtactga     4740
aataaaagat ctttattttc attagatctg tgtgttggtt ttttgtgtga ggaaccccta     4800
gtgatggagt tggccactcc ctctctgcgc gctcgctcgc tcactgaggc cgggcgacca     4860
aaggtcgccc gacgcccggg ctttgcccgg gcggcctcag tgagcgagcg agcgcgcaga     4920
gagggagtgg ccaa                                                       4934

<210> SEQ ID NO 9
<211> LENGTH: 5511
<212> TYPE: DNA
<213> ORGANISM: Adeno-Associated Virus 2

<400> SEQUENCE: 9
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgaccc ctctcacact       180
acctaaacca cgccaggaca acctctgctc ctctccaccg aaattccaag ggtcgagtg        240
gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg gcagggtgag cccagaaact cctgtgtgcc      480
tctgagcctg cagacgcgaa acgtcgactg gacacaggac gctgtggttt ctgagccagg      540
gggcgactca gatcccagcc agtggactta gcccctgttt gctcctccga taactgggt      600
```

```
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggcccttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt    1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tggggtgag ctactggaag gcctctgagg ggctgagta    1320
tgatgaccag accagccaga gggagaagga ggatgacaag gtgttccctg ggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt   1680
gaatggctat gtgaacagga gcctgcctgg cctgattggc tgccacagga gtctgtgta    1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc cctgctgta    2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgacccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tcccttctc    3000
```

```
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaacccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020 ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc    4380 ctctggccac atcagggact tccagatcac tgcctctggc cagtatggcc agtgggcccc    4440
caagctggcc aggctgcact actctggcag catcaatgcc tggagcacca aggagcccctt    4500 cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acagggggcaa cagcactggc accctgatgg tgttctttgg    4680
caatgtggac agctctggca tcaagcacaa catcttcaac cccccccatca ttgccagata    4740 catcaggctg caccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttccaccaa catgtttgcc acctggagcc ccagcaaggc    4920
caggctgcac ctgcagggca ggagcaatgc ctggaggccc caggtcaaca ccccaagga    4980 gtggctgcag gtggacttcc agaagaccat gaaggtgact ggggtgacca cccaggggggt    5040 gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160 cagcttcacc cctgtggtga acagcctgga cccccccctg ctgaccagat acctgaggat    5220
tcacccccag agctgggtgc accagattgc cctgaggatg gaggtgctgg gctgtgaggc    5280
ccaggacctg tactgacctc gaggaataaa ggaaatttat tttcattgca atagtgtgtt    5340
```

```
ggttttttgt gtcacgtggc ggccgcagga acccctagtg atggagttgg ccactccctc      5400
tctgcgcgct cgctcgctca ctgaggccgg gcgaccaaag gtcgcccgac gcccgggctt      5460
tgcccgggcg gcctcagtga gcgagcgagc gcgcagagag ggagtggcca a               5511

<210> SEQ ID NO 10
<211> LENGTH: 5688
<212> TYPE: DNA
<213> ORGANISM: Adeno-Associated Virus 2

<400> SEQUENCE: 10
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgaccc ctctcacact       180
acctaaacca cgccaggaca acctctgctc ctctccaccg aaattccaag gggtcgagtg       240
gatgttggag gtggcatggg cccagagagg tctctgacct ctgccccagc tccaaggtca       300
gcaggcaggg agggctgtgt gtttgctgtt tgctgcttgc aatgtttgcc cattttaggg       360
acatgagtag gctgaagttt gttcagtgtg gacttcagag gcagcacaca aacagctgct       420
ggaggatggg aactgagggg ttggaagggg gcagggtgag cccagaaact cctgtgtgcc       480
tctgagcctg cagacgcgaa acgtcgactg gacacaggac gctgtggttt ctgagccagg       540
gggcgactca gatcccagcc agtggactta gcccctgttt gctcctccga taactggggt       600
gaccttggtt aatattcacc agcagcctcc cccgttgccc ctctggatcc actgcttaaa       660 tacgacgag gacagggccc tgtctcctca gcttcaggca ccaccactga cctgggacag       720
tgaatcgtaa gtactagcag ctacaatcca gctaccattc tgctttattt ttatggttgg       780
gataaggctg gattattctg agtccaagct aggcccttt gctaatcatg ttcataccctc      840 ttatcttcct cccacagctc ctgggcaacg tgctggtctg tgtgctggcc catcactttg       900
gcaaagaatt gcgatcgcca ccatgcagat tgagctgagc acctgcttct tcctgtgcct       960
gctgaggttc tgcttctctg ccaccaggag atactacctg ggggctgtgg agctgagctg      1020
ggactacatg cagtctgacc tgggggagct gcctgtggat gccaggttcc cccccagagt      1080
gcccaagagc ttcccccttca cacctctgt ggtgtacaag aagaccctgt tgtggagtt      1140 cactgaccac ctgttcaaca ttgccaagcc caggcccccc tggatgggcc tgctgggccc      1200
caccatccag gctgaggtgt atgacactgt ggtgatcacc ctgaagaaca tggccagcca      1260
ccctgtgagc ctgcatgctg tgggggtgag ctactggaag gcctctgagg gggctgagta      1320
tgatgaccag accagccaga gggagaagga ggatgacaag gtgttccctg ggggcagcca      1380
cacctatgtg tggcaggtgc tgaaggagaa tgggcccatg gcctctgacc cctgtgcct      1440 gacctacagc tacctgagcc atgtggacct ggtgaaggac ctgaactctg gcctgattgg      1500
ggccctgctg gtgtgcaggg agggcagcct ggccaaggag aagacccaga ccctgcacaa      1560
gttcatcctg ctgtttgctg tgtttgatga gggcaagagc tggcactctg aaaccaagaa      1620
cagcctgatg caggacaggg atgctgcctc tgccagggcc tggccaaga tgcacactgt      1680 gaatggctat gtgaacagga gcctgcctgg cctgattggc tgccacagga agtctgtgta      1740
ctggcatgtg attggcatgg gcaccacccc tgaggtgcac agcatcttcc tggagggcca      1800
caccttcctg gtcaggaacc acaggcaggc cagcctggag atcagcccca tcaccttcct      1860
gactgcccag accctgctga tggacctggg ccagttcctg ctgttctgcc acatcagcag      1920
ccaccagcat gatggcatgg aggcctatgt gaaggtggac agctgccctg aggagcccca      1980
```

```
gctgaggatg aagaacaatg aggaggctga ggactatgat gatgacctga ctgactctga    2040
gatggatgtg gtgaggtttg atgatgacaa cagccccagc ttcatccaga tcaggtctgt    2100
ggccaagaag caccccaaga cctgggtgca ctacattgct gctgaggagg aggactggga    2160
ctatgccccc ctggtgctgg ccctgatga caggagctac aagagccagt acctgaacaa    2220
tggcccccag aggattggca ggaagtacaa gaaggtcagg ttcatggcct acactgatga    2280
aaccttcaag accagggagg ccatccagca tgagtctggc atcctgggcc ccctgctgta    2340
tggggaggtg ggggacaccc tgctgatcat cttcaagaac caggccagca ggccctacaa    2400
catctacccc catggcatca ctgatgtgag gcccctgtac agcaggaggc tgcccaaggg    2460
ggtgaagcac ctgaaggact tccccatcct gcctgggag atcttcaagt acaagtggac    2520
tgtgactgtg gaggatggcc ccaccaagtc tgacccagg tgcctgacca gatactacag    2580
cagctttgtg aacatggaga gggacctggc ctctggcctg attggccccc tgctgatctg    2640
ctacaaggag tctgtggacc agaggggcaa ccagatcatg tctgacaaga ggaatgtgat    2700
cctgttctct gtgtttgatg agaacaggag ctggtacctg actgagaaca tccagaggtt    2760
cctgcccaac cctgctgggg tgcagctgga ggaccctgag ttccaggcca gcaacatcat    2820
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca agatggtgta tgaggacacc ctgaccctgt tccccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020 ggacccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgcccagc aaggctggca tctggagggt ggagtgcctg attggggagc acctgcatgc    4320
```

```
tggcatgagc accctgttcc tggtgtacag caacaagtgc cagacccccc tgggcatggc      4380
ctctggccac atcagggact tccagatcac tgcctctggc cagtatggcc agtgggcccc      4440
caagctggcc aggctgcact actctggcag catcaatgcc tggagcacca aggagccctt      4500
cagctggatc aaggtggacc tgctggcccc catgatcatc catggcatca agacccaggg      4560
ggccaggcag aagttcagca gcctgtacat cagccagttc atcatcatgt acagcctgga      4620
tggcaagaag tggcagacct acaggggcaa cagcactggc accctgatgg tgttcttggg      4680
caatgtggac agctctggca tcaagcacaa catcttcaac ccccccatca ttgccagata      4740
catcaggctg cacccccaccc actacagcat caggagcacc ctgaggatgg agctgatggg      4800
ctgtgacctg aacagctgca gcatgcccct gggcatggag agcaaggcca tctctgatgc      4860
ccagatcact gccagcagct acttcaccaa catgtttgcc acctggagcc ccagcaaggc      4920
caggctgcac ctgcagggca ggagcaatgc ctggaggccc caggtcaaca accccaagga      4980
gtggctgcag gtggacttcc agaagaccat gaaggtgact ggggtgacca cccagggggt      5040
gaagagcctg ctgaccagca tgtatgtgaa ggagttcctg atcagcagca gccaggatgg      5100
ccaccagtgg accctgttct tccagaatgg caaggtgaag gtgttccagg caaccagga      5160 cagcttcacc cctgtggtga acagcctgga ccccccctg ctgaccagat acctgaggat      5220
tcacccccag agctgggtgc accagattgc cctgaggatg aggtgctgg gctgtgaggc      5280 ccaggacctg tactgacctc gaggtgtgcc ttctagttgc cagccatctg ttgtttgccc      5340
ctcccccgtg ccttccttga ccctggaagg tgccactccc actgtccttt cctaataaaa      5400
tgaggaaatt gcatcgcatt gtctgagtag gtgtcattct attctggggg gtggggtggg      5460
gcaggacagc aagggggagg attgggaaga caatagcagg catgctgggg atgcggtggg      5520
ctctatgggc acgtggcggc cgcaggaacc cctagtgatg gagttggcca ctccctctct      5580
gcgcgctcgc tcgctcactg aggccgggcg accaaaggtc gcccgacgcc cgggctttgc      5640
ccgggcggcc tcagtgagcg agcgagcgcg cagagaggga gtggccaa                   5688

<210> SEQ ID NO 11
<211> LENGTH: 5613
<212> TYPE: DNA
<213> ORGANISM: Adeno-Associated Virus 2

<400> SEQUENCE: 11
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg      120
gccaactcca tcactagggg ttcctgcggc cgcacgcgtg ttttcgaccc ctctcacact      180
acctaaacca cgccaggaca acctctgctc ctctccaccg aaattccaag ggtcgagtg      240 gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg gcagggtgag cccagaaact cctgtgtgcc      480
tctgagcctg cagacgcgaa acgtcgactg gacacaggac gctgtggttt ctgagccagg      540
gggcgactca gatcccagcc agtggactta gcccctgttt gctcctccga taactggggt      600
gaccttggtt aatattcacc agcagcctcc ccgttgccc ctctggatcc actgcttaaa      660 tacgacgag acagggccc tgtctcctca gcttcaggca ccaccactga cctgggacag      720
tgaatcgtaa gtactagcag ctacaatcca gctaccattc tgctttatt ttatggttgg      780
```

```
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca acacctctgt ggtgtacaag aagaccctgt tgtggagtt    1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggccccatg gcctctgacc cctgtgcct    1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga gtctgtgta    1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tgggaggtg ggggacaccc tgctgatcat cttcaagaac caggccagca ggccctacaa   2400
catctaccc catggcatca ctgatgtgag gcccctgtac agcaggaggc tgcccaaggg   2460
ggtgaagcac ctgaaggact tccccatcct gcctggggga tcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattgggc ccagactgac ttcctgtctg tgttcttctc   2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
```

```
cactggggac tactatgagg acagctatga ggacatctct gcctacctgc tgagcaagaa    3180
caatgccatt gagcccagga gcttcagcca gaacccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc ccctgcaaca tccagatgga    4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtacccgggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagacccccc tgggcatggc    4380
ctctggccac atcagggact tccagatcac tgcctctggc cagtatggcc agtgggcccc    4440
caagctggcc aggctgcact actctggcag catcaatgcc tggagcacca aggagcctt    4500 cagctggatc aaggtggacc tgctggcccc catgatcatc catggcatca gacccaggg    4560 ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac ccccccatca ttgccagata    4740
catcaggctg caccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttcaccaa catgtttgcc acctggagcc ccagcaaggc    4920
caggctgcac ctgcagggca ggagcaatgc ctggaggccc caggtcaaca cccccaagga    4980
gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160 cagcttcacc cctgtggtga acagcctgga ccccccctg ctgaccagat acctgaggat    5220
tcacccccag agctgggtgc accagattgc cctgaggatg gaggtgctgg gctgtgaggc    5280
ccaggacctg tactgacctc gaggcactgt cctttcctaa taaaatgagg aaattgcatc    5340
gcattgtctg agtaggtgtc attctattct gggggtggg gtgggcagg acagcaaggg    5400 ggaggattgg gaagacaata gcaggcatgc tggggatgcg gtgggctcta tgggcacgtg    5460
gcggccgcag gaaccctag tgatggagtt ggccactccc tctctgcgcg ctcgctcgct    5520
```

-continued

```
cactgaggcc gggcgaccaa aggtcgcccg acgcccgggc tttgcccggg cggcctcagt      5580
gagcgagcga gcgcgcagag agggagtggc caa                                  5613

<210> SEQ ID NO 12
<211> LENGTH: 5362
<212> TYPE: DNA
<213> ORGANISM: Adeno-Associated Virus 2

<400> SEQUENCE: 12
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgactg tttgctgttt       180
gctgcttgca atgtttgccc attttaggga catgtttgct gtttgctgct tgcaatgttt       240
gcccatttta gggacatgtt tgctgtttgc tgcttgcaat gtttgcccat tttagggaca       300
tgtttgctgt ttgctgcttg caatgtttgc ccattttagg acaacgcga aacgtcgact        360 ggacacagga cgctgtggtt tctgagccag ggggcgactc agatcccagc cagtggactt       420
agcccctgtt tgctcctccg ataactgggg tgaccttggt taatattcac cagcagcctc       480
ccccgttgcc cctctggatc cactgcttaa atacggacga ggacagggcc ctgtctcctc       540
agcttcaggc accaccactg acctgggaca gtgaatcgta agtactagca gctacaatcc       600
agctaccatt ctgcttttat tttatggttg ggataaggct ggattattct gagtccaagc       660
taggcccttt tgctaatcat gttcatacct cttatcttcc tcccacagct cctgggcaac       720
gtgctggtct gtgtgctggc ccatcacttt ggcaaagaat tgcgatcgcc accatgcaga       780
ttgagctgag cacctgcttc ttcctgtgcc tgctgaggtt ctgcttctct gccaccagga       840
gatactacct gggggctgtg agctgagct gggactacat gcagtctgac ctggggagc        900 tgcctgtgga tgccaggttc cccccagag tgcccaagag cttccccttc aacacctctg       960
tggtgtacaa gaagaccctg tttgtggagt tcactgacca cctgttcaac attgccaagc      1020
ccaggccccc ctggatgggc ctgctgggcc ccaccatcca ggctgaggtg tatgacactg      1080
tggtgatcac cctgaagaac atggccagcc acccctgtgag cctgcatgct gtgggggtga      1140
gctactggaa ggcctctgag ggggctgagt atgatgacca gaccagccag agggagaagg      1200
aggatgacaa ggtgttccct gggggcagcc acacctatgt gtggcaggtg ctgaaggaga      1260
atggccccat ggcctctgac cccctgtgcc tgacctacag ctacctgagc catgtggacc      1320
tggtgaagga cctgaactct ggcctgattg ggccctgct ggtgtgcagg agggcagcc       1380 tggccaagga agacccag accctgcaca agttcatcct gctgtttgct gtgtttgatg      1440
agggcaagag ctggcactct gaaaccaaga cagcctgat gcaggacagg atgctgcct        1500 ctgccagggc ctggcccaag atgcacactg tgaatggcta tgtgaacagg agcctgcctg     1560
gcctgattgg ctgccacagg aagtctgtgt actggcatgt gattggcatg ggcaccaccc      1620
ctgaggtgca cagcatcttc ctggagggcc acaccttcct ggtcaggaac acaggcagg      1680 ccagcctgga gatcagcccc atcaccttcc tgactgccca gaccctgctg atggaccctgg     1740 gccagttcct gctgttctgc cacatcagca gccaccagca tgatggcatg gaggcctatg      1800
tgaaggtgga cagctgccct gaggagcccc agctgaggat gaagaacaat gaggaggctg      1860
aggactatga tgatgacctg actgactctg agatggatgt ggtgaggttt gatgatgaca      1920 acagcccag cttcatccag atcaggtctg tggccaagaa gcaccccaag acctgggtgc      1980
```

```
actacattgc tgctgaggag gaggactggg actatgcccc cctggtgctg gcccctgatg    2040
acaggagcta caagagccag tacctgaaca atggccccca gaggattggc aggaagtaca    2100
agaaggtcag gttcatggcc tacactgatg aaaccttcaa gaccagggag gccatccagc    2160
atgagtctgg catcctgggc cccctgctgt atggggaggt gggggacacc ctgctgatca    2220
tcttcaagaa ccaggccagc aggccctaca acatctaccc ccatggcatc actgatgtga    2280
ggcccctgta cagcaggagg ctgcccaagg gggtgaagca cctgaaggac ttccccatcc    2340
tgcctgggga gatcttcaag tacaagtgga ctgtgactgt ggaggatggc cccaccaagt    2400
ctgaccccag gtgcctgacc agatactaca gcagctttgt gaacatggag agggacctgg    2460
cctctggcct gattggcccc ctgctgatct gctacaagga gtctgtggac cagaggggca    2520
accagatcat gtctgacaag aggaatgtga tcctgttctc tgtgtttgat gagaacagga    2580
gctggtacct gactgagaac atccagaggt tcctgcccaa ccctgctggg gtgcagctgg    2640
aggaccctga gttccaggcc agcaacatca tgcacagcat caatggctat gtgtttgaca    2700
gcctgcagct gtctgtgtgc ctgcatgagg tggcctactg gtacatcctg agcattgggg    2760
cccagactga cttcctgtct gtgttcttct ctggctacac cttcaagcac aagatggtgt    2820
atgaggacac cctgacCCtg ttccccttct ctggggagac tgtgttcatg agcatggaga    2880
accctggcct gtggattctg ggctgccaca ctctgactt caggaacagg ggcatgactg    2940
ccctgctgaa agtctccagc tgtgacaaga acactgggga ctactatgag acagctatg    3000 aggacatctc tgcctacctg ctgagcaaga acaatgccat tgagcccagg agcttcagcc    3060
agaaccccCC agtgctgaag aggcaccaga gggagatcac caggaccacc ctgcagtctg    3120
accaggagga gattgactat gatgacacca tctctgtgga gatgaagaag gaggactttg    3180
acatctacga cgaggacgag aaccagagcc ccaggagctt ccagaagaag accaggcact    3240
acttcattgc tgctgtggag aggctgtggg actatggcat gagcagcagc ccccatgtgc    3300
tgaggaacag ggcccagtct ggctctgtgc cccagttcaa gaaggtggtg ttccaggagt    3360
tcactgatgg cagcttcacc cagcccctgt acagagggga gctgaatgag cacctgggcc    3420
tgctgggccc ctacatcagg gctgaggtgg aggacaacat catggtgacc ttcaggaacc    3480
aggccagcag gccctacagc ttctacagca gcctgatcag ctatgaggag gaccagaggc    3540 aggggctga gccaggaag aactttgtga gcccaatga aaccaagacc tacttctgga    3600
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg gcaggcaggt gactgtgcag gagtttgccc    3780
tgttcttcac catctttgat gaaaccaaga gctggtactt cactgagaac atggagagga    3840
actgcagggc ccctgcaac atccagatgg aggaccccac cttcaaggag aactacaggt    3900
tccatgccat caatggctac atcatggaca ccctgcctgg cctggtgatg gcccaggacc    3960
agaggatcag gtggtacctg ctgagcatgg gcagcaatga gaacatccac agcatccact    4020
tctctggcca tgtgttcact gtgaggaaga aggaggagta caagatggcc ctgtacaacc    4080
tgtaccctgg ggtgtttgag actgtggaga tgctgcccag caaggctggc atctggaggg    4140
tggagtgcct gattggggag cacctgcatg ctggcatgag caccctgttc ctggtgtaca    4200
gcaacaagtg ccagacCCCC ctgggcatgg cctctggcca catcagggac ttccagatca    4260
ctgcctctgg ccagtatggc cagtgggccc ccaagctggc caggctgcac tactctggca    4320
gcatcaatgc ctggagcacc aaggagcCCt tcagctggat caaggtggac ctgctggccc    4380
```

-continued

```
ccatgatcat ccatggcatc aagacccagg gggccaggca gaagttcagc agcctgtaca      4440
tcagccagtt catcatcatg tacagcctgg atggcaagaa gtggcagacc tacaggggca      4500
acagcactgg caccctgatg gtgttctttg gcaatgtgga cagctctggc atcaagcaca      4560
acatcttcaa ccccccatc attgccagat acatcaggct gcaccccacc cactacagca       4620
tcaggagcac cctgaggatg gagctgatgg gctgtgacct gaacagctgc agcatgcccc      4680
tgggcatgga gagcaaggcc atctctgatg cccagatcac tgccagcagc tacttccacca    4740 acatgtttgc cacctggagc ccagcaagg ccaggctgca cctgcagggc aggagcaatg       4800
cctggaggcc ccaggtcaac aaccccaagg agtggctgca ggtggacttc agaagaccca     4860
tgaaggtgac tggggtgacc acccagggggg tgaagagcct gctgaccagc atgtatgtga    4920
aggagttcct gatcagcagc agccaggatg ccaccagtg gaccctgttc ttccagaatg      4980
gcaaggtgaa ggtgttccag ggcaaccagg acagcttcac ccctgtggtg aacagcctgg    5040
acccccccct gctgaccaga tacctgagga ttcaccccca gagctgggtg caccagattg    5100
ccctgaggat ggaggtgctg ggctgtgagg cccaggacct gtactgacct cgaggaataa     5160
aggaaattta ttttcattgc aatagtgtgt tggttttttg tgtcacgtgg cggccgcagg     5220
aacccctagt gatggagttg gccactccct ctctgcgcgc tcgctcgctc actgaggccg    5280
ggcgaccaaa ggtcgcccga cgcccgggct tgcccgggc ggcctcagtg agcgagcgag      5340
cgcgcagaga gggagtggcc aa                                                5362
```

<210> SEQ ID NO 13
<211> LENGTH: 5464
<212> TYPE: DNA
<213> ORGANISM: Adeno-Associated Virus 2

<400> SEQUENCE: 13

```
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgactg tttgctgttt     180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg acaacgcgca aacgtcgact    360
ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtactagca gctacaatcc    600
agctaccatt ctgcttttat tttatggttg ggataaggct ggattattct gagtccaagc    660
taggcccttt tgctaatcat gttcataccct cttatcttcc tcccacagct cctgggcaac   720
gtgctggtct gtgtgctggc ccatcacttt ggcaaagaat tgcgatcgcc accatgcaga    780
ttgagctgag cacctgcttc ttcctgtgcc tgctgaggtt ctgcttctct gccaccagga    840
gatactacct gggggctgtg agctgagct gggactacat gcagtctgac ctggggagc      900 tgcctgtgga tgccaggttc ccccccagag tgcccaagag cttccccttc aacacctctg    960
tggtgtacaa gaagaccctg tttgtggagt tcactgacca cctgttcaac attgccaagc   1020
ccaggccccc ctggatgggc ctgctgggcc ccaccatcca ggctgaggtg tatgacactg    1080
```

```
tggtgatcac cctgaagaac atggccagcc accctgtgag cctgcatgct gtggggtga      1140 gctactggaa ggcctctgag ggggctgagt atgatgacca gaccagccag agggagaagg    1200
aggatgacaa ggtgttccct gggggcagcc acacctatgt gtggcaggtg ctgaaggaga    1260
atggccccat ggcctctgac cccctgtgcc tgacctacag ctacctgagc catgtggacc    1320
tggtgaagga cctgaactct ggcctgattg gggccctgct ggtgtgcagg gagggcagcc    1380
tggccaagga gaagacccag accctgcaca agttcatcct gctgtttgct gtgtttgatg    1440
agggcaagag ctggcactct gaaaccaaga acagcctgat gcaggacagg gatgctgcct    1500
ctgccagggc ctggcccaag atgcacactg tgaatggcta tgtgaacagg agcctgcctg    1560
gcctgattgg ctgccacagg aagtctgtgt actggcatgt gattggcatg ggcaccaccc    1620
ctgaggtgca cagcatcttc ctggagggcc acaccttcct ggtcaggaac acacaggcagg   1680 ccagcctgga gatcagcccc atcaccttcc tgactgccca gaccctgctg atggacctgg    1740
gccagttcct gctgttctgc cacatcagca gccaccagca tgatggcatg gaggcctatg    1800
tgaaggtgga cagctgccct gaggagcccc agctgaggat gaagaacaat gaggaggctg    1860
aggactatga tgatgacctg actgactctg agatggatgt ggtgaggttt gatgatgaca    1920
acagccccag cttcatccag atcaggtctg tggccaagaa gcaccccaag acctgggtgc    1980
actacattgc tgctgaggag gaggactggg actatgcccc cctggtgctg gcccctgatg    2040
acaggagcta caagagccag tacctgaaca atggccccca gaggattggc aggaagtaca    2100
agaaggtcag gttcatggcc tacactgatg aaaccttcaa gaccagggag gccatccagc    2160
atgagtctgg catcctgggc cccctgctgt atggggaggt ggggacacc ctgctgatca     2220 tcttcaagaa ccaggccagc aggccctaca acatctaccc ccatggcatc actgatgtga    2280
ggcccctgta cagcaggagg ctgcccaagg gggtgaagca cctgaaggac ttccccatcc    2340
tgcctgggga gatcttcaag tacaagtgga ctgtgactgt ggaggatggc cccaccaagt    2400
ctgaccccag gtgcctgacc agatactaca gcagctttgt gaacatggag agggacctgg    2460
cctctggcct gattggcccc ctgctgatct gctacaagga gtctgtggac cagaggggca    2520
accagatcat gtctgacaag aggaatgtga tcctgttctc tgtgtttgat gagaacagga    2580
gctggtacct gactgagaac atccagaggt tcctgcccaa ccctgctggg gtgcagctgg    2640
aggaccctga gttccaggcc agcaacatca tgcacagcat caatggctat gtgtttgaca    2700
gcctgcagct gtctgtgtgc ctgcatgagg tggcctactg gtacatcctg agcattgggg    2760
cccagactga cttcctgtct gtgttcttct ctggctacac cttcaagcac aagatggtgt    2820
atgaggacac cctgacctg ttccccttct ctggggagac tgtgttcatg agcatggaga     2880
accctggcct gtggattctg gctgccaca actctgactt caggaacagg gcatgactg      2940 ccctgctgaa agtctccagc tgtgacaaga acactgggga ctactatgag acagctatg    3000 aggacatctc tgcctacctg ctgagcaaga acaatgccat tgagcccagg agcttcagcc    3060 agaaccccc agtgctgaag aggcaccaga gggagatcac caggaccacc ctgcagtctg    3120
accaggagga gattgactat gatgacacca tctctgtgga gatgaagaag gaggactttg   3180
acatctacga cgaggacgag aaccagagcc caggagctt ccagaagaag accaggcact    3240
acttcattgc tgctgtggag aggctgtggg actatggcat gagcagcagc cccatgtgc    3300 tgaggaacag ggcccagtct ggctctgtgc cccagttcaa gaaggtggtg ttccaggagt   3360
tcactgatga cagcttcacc cagcccctgt acagagggga gctgaatgag cacctgggcc    3420
tgctgggccc ctacatcagg gctgaggtgg aggacaacat catggtgacc ttcaggaacc    3480
```

```
aggccagcag gccctacagc ttctacagca gcctgatcag ctatgaggag gaccagaggc    3540 aggggggctga gcccaggaag aactttgtga agcccaatga aaccaagacc tacttctgga    3600
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg caggcaggt gactgtgcag gagtttgccc    3780
tgttcttcac catctttgat gaaaccaaga gctggtactt cactgagaac atggagagga    3840
actgcagggc ccctgcaac atccagatgg aggaccccac cttcaaggag aactacaggt    3900
tccatgccat caatggctac atcatggaca ccctgcctgg cctggtgatg cccaggacc    3960 agaggatcag gtggtacctg ctgagcatgg gcagcaatga aacatccac agcatccact    4020 tctctggcca tgtgttcact gtgaggaaga aggaggagta caagatgccc ctgtacaacc    4080
tgtaccctgg ggtgtttgag actgtggaga tgctgcccag caaggctggc atctggaggg    4140
tggagtgcct gattggggag cacctgcatg ctggcatgag cacctgtttc ctggtgtaca    4200
gcaacaagtg ccagaccccc ctgggcatgg cctctggcca catcagggac ttccagatca    4260
ctgcctctgg ccagtatggc cagtgggccc ccaagctggc caggctgcac tactctggca    4320
gcatcaatgc ctggagcacc aaggagccct tcagctggat caaggtggac ctgctggccc    4380
ccatgatcat ccatggcatc aagacccagg gggccaggca gaagttcagc agcctgtaca    4440
tcagccagtt catcatcatg tacagcctgg atggcaagaa gtggcagacc tacaggggca    4500
acagcactgg caccctgatg gtgttctttg gcaatgtgga cagctctggc atcaagcaca    4560
acatcttcaa ccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttcacca    4740
acatgtttgc cacctggagc cccagcaagg ccaggctgca cctgcagggc aggagcaatg    4800
cctggaggcc ccaggtcaac aaccccaagg agtggctgca ggtggacttc cagaagacca    4860
tgaaggtgac tgggggtgacc acccagggg tgaagagcct gctgaccagc atgtatgtga    4920
aggagttcct gatcagcagc agccaggatg gccaccagtg gacccctgttc ttccagaatg    4980 gcaaggtgaa ggtgttccag ggcaaccagg acagcttcac ccctgtggtg aacagcctgg    5040
acccccccct gctgaccaga tacctgagga ttcacccca gagctgggtg caccagattg    5100
ccctgaggat ggaggtgctg ggctgtgagg cccaggacct gtactgacct cgaggcactg    5160
tcctttccta ataaaatgag gaaattgcat cgcattgtct gagtaggtgt cattctattc    5220
tggggggtgg ggtggggcag gacagcaagg gggaggattg ggaagacaat agcaggcatg    5280
ctggggatgc ggtgggctct atgggcacgt ggcggccgca ggaaccccta gtgatgagt    5340 tggccactcc ctctctgcgc gctcgctcg tcactgaggc cgggcgacca aggtcgccc    5400 gacgcccggg ctttgcccgg gcggcctcag tgagcgagcg agcgcgcaga gagggagtgg    5460
ccaa                                                                 5464
```

<210> SEQ ID NO 14
<211> LENGTH: 6354
<212> TYPE: DNA
<213> ORGANISM: Adeno-Associated Virus 2

<400> SEQUENCE: 14

```
ttggccactc cctctctgcg cgctcgctcg ctcactgagg ccgcccgggc aaagcccggg    60
```

-continued

| | |
|---|---|
| cgtcgggcga cctttggtcg cccggcctca gtgagcgagc gagcgcgcag agagggagtg | 120 |
| gccaactcca tcactagggg ttcctgcggc cgcacgcgtg tttaaacgtc gacaggttaa | 180 |
| tttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa tttttaaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg gacacaggac gctgtggttt | 540 |
| ctgagccagg gggcgactca gatcccagcc agtggactta gcccctgttt gctcctccga | 600 |
| taactgggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgtaa gtactagcag ctacaatcca gctaccattc tgcttttatt | 780 |
| ttatggttgg gataaggctg gattattctg agtccaagct aggccctttt gctaatcatg | 840 |
| ttcatacctc ttatcttcct cccacagctc ctgggcaacg tgctggtctg tgtgctggcc | 900 |
| catcactttg gcaaagaatt gcgatcgcca ccatgcagat tgagctgagc acctgcttct | 960 |
| tcctgtgcct gctgaggttc tgcttctctg ccaccaggag atactacctg ggggctgtgg | 1020 |
| agctgagctg ggactacatg cagtctgacc tgggggagct gcctgtggat gccaggttcc | 1080 |
| cccccagagt gcccaagagc ttccccttca cacctctgt ggtgtacaag aagaccctgt | 1140 |
| ttgtggagtt cactgaccac ctgttcaaca ttgccaagcc caggccccc tggatgggcc | 1200 |
| tgctgggccc caccatccag gctgaggtgt atgacactgt ggtgatcacc ctgaagaaca | 1260 |
| tggccagcca ccctgtgagc ctgcatgctg tggggtgag ctactggaag gcctctgagg | 1320 |
| gggctgagta tgatgaccag accagccaga gggagaagga ggatgacaag gtgttccctg | 1380 |
| ggggcagcca cacctatgtg tggcaggtgc tgaaggagaa tggcccccatg gcctctgacc | 1440 |
| ccctgtgcct gacctacagc tacctgagcc atgtggacct ggtgaaggac ctgaactctg | 1500 |
| gcctgattgg ggccctgctg gtgtgcaggg agggcagcct ggccaaggag aagacccaga | 1560 |
| ccctgcacaa gttcatcctg ctgtttgctg tgtttgatga gggcaagagc tggcactctg | 1620 |
| aaaccaagaa cagcctgatg caggacaggg atgctgcctc tgccagggcc tggcccaaga | 1680 |
| tgcacactgt gaatggctat gtgaacagga gcctgcctgg cctgattggc tgccacagga | 1740 |
| agtctgtgta ctggcatgtg attggcatgg gcaccacccc tgaggtgcac agcatcttcc | 1800 |
| tggagggcca caccttcctg gtcaggaacc acaggcaggc cagcctggag atcagcccca | 1860 |
| tcaccttcct gactgcccag accctgctga tggacctggg ccagttcctg ctgttctgcc | 1920 |
| acatcagcag ccaccagcat gatggcatgg aggcctatgt gaaggtggac agctgccctg | 1980 |
| aggagcccca gctgaggatg aagaacaatg aggaggctga ggactatgat gatgacctga | 2040 |
| ctgactctga gatggatgtg gtgaggtttg atgatgacaa cagccccagc ttcatccaga | 2100 |
| tcaggtctgt ggccaagaag caccccaaga cctgggtgca ctacattgct gctgaggagg | 2160 |
| aggactggga ctatgccccc ctggtgctgg cccctgatga caggagctac aagagccagt | 2220 |
| acctgaacaa tggcccccag aggattggca ggaagtacaa gaaggtcagg ttcatggcct | 2280 |
| acactgatga aaccttcaag accagggagg ccatccagca tgagtctggc atcctgggcc | 2340 |
| ccctgctgta tggggaggtg ggggacaccc tgctgatcat cttcaagaac caggccagca | 2400 |
| ggccctacaa catctacccc catggcatca ctgatgtgag gccccctgta cagcaggagg c | 2460 |

```
tgcccaaggg ggtgaagcac ctgaaggact tccccatcct gcctggggag atcttcaagt    2520
acaagtggac tgtgactgtg gaggatggcc ccaccaagtc tgaccccagg tgcctgacca    2580
gatactacag cagctttgtg aacatggaga gggacctggc ctctggcctg attggccccc    2640
tgctgatctg ctacaaggag tctgtggacc agaggggcaa ccagatcatg tctgacaaga    2700
ggaatgtgat cctgttctct gtgtttgatg agaacaggag ctggtacctg actgagaaca    2760
tccagaggtt cctgcccaac cctgctgggg tgcagctgga ggaccctgag ttccaggcca    2820
gcaacatcat gcacagcatc aatggctatg tgtttgacag cctgcagctg tctgtgtgcc    2880
tgcatgaggt ggcctactgg tacatcctga gcattgggc ccagactgac ttcctgtctg    2940
tgttcttctc tggctacacc ttcaagcaca agatggtgta tgaggacacc ctgaccctgt    3000
tccccttctc tggggagact gtgttcatga gcatggagaa ccctggcctg tggattctgg    3060
gctgccacaa ctctgacttc aggaacaggg gcatgactgc cctgctgaaa gtctccagct    3120
gtgacaagaa cactggggac tactatgagg acagctatga ggacatctct gcctacctgc    3180
tgagcaagaa caatgccatt gagcccagga gcttcagcca gaaccccca gtgctgaaga    3240 ggcaccagag ggagatcacc aggaccaccc tgcagtctga ccaggaggag attgactatg    3300
atgacaccat ctctgtggag atgaagaagg aggactttga catctacgac gaggacgaga    3360
accagagccc caggagcttc cagaagaaga ccaggcacta cttcattgct gctgtggaga    3420
ggctgtggga ctatggcatg agcagcagcc cccatgtgct gaggaacagg gcccagtctg    3480
gctctgtgcc ccagttcaag aaggtggtgt tccaggagtt cactgatggc agcttcaccc    3540 agccctgta cagaggggag ctgaatgagc acctgggcct gctgggcccc tacatcaggg    3600
ctgaggtgga ggacaacatc atggtgacct tcaggaacca ggccagcagg ccctacagct    3660
tctacagcag cctgatcagc tatgaggagg accagaggca gggggctgag cccaggaaga    3720
actttgtgaa gcccaatgaa accaagacct acttctggaa ggtgcagcac acatggccc    3780 ccaccaagga tgagttttgac tgcaaggcct gggcctactt ctctgatgtg gacctggaga    3840
aggatgtgca ctctggcctg attggccccc tgctggtgtg ccacaccaac ccctgaacc    3900 ctgcccatgg caggcaggtg actgtgcagg agttttgccct gttcttcacc atctttgatg    3960
aaaccaagag ctggtacttc actgagaaca tggagaggaa ctgcagggcc ccctgcaaca    4020
tccagatgga ggaccccacc ttcaaggaga actacaggtt ccatgccatc aatggctaca    4080
tcatggacac cctgcctggc ctggtgatgg cccaggacca gaggatcagg tggtacctgc    4140
tgagcatggg cagcaatgag aacatccaca gcatccactt ctctggccat gtgttcactg    4200
tgaggaagaa ggaggagtac aagatggccc tgtacaacct gtaccctggg gtgtttgaga    4260
ctgtggagat gctgcccagc aaggctgca tctggagggt ggagtgcctg attggggagc    4320
acctgcatgc tggcatgagc accctgttcc tggtgtacag caacaagtgc cagaccccc    4380 tgggcatggc ctctggccac atcagggact tccagatcac tgcctctggc cagtatggcc    4440
agtgggcccc caagctggcc aggctgcact actctggcag catcaatgcc tggagcacca    4500
aggagccctt cagctggatc aaggtggacc tgctggcccc catgatcatc catggcatca    4560
agacccaggg ggccaggcag aagttcagca gcctgtacat cagccagttc atcatcatgt    4620
acagcctgga tggcaagaag tggcagacct acaggggcaa cagcactggc accctgatgg    4680
tgttctttgg caatgtggac agctctggca tcaagcacaa catcttcaac cccccatca    4740 ttgccagata catcaggctg cacccccacc actacagcat caggagcacc ctgaggatgg    4800
```

```
agctgatggg ctgtgacctg aacagctgca gcatgcccct gggcatggag agcaaggcca    4860
tctctgatgc ccagatcact gccagcagct acttccaccaa catgtttgcc acctggagcc    4920
ccagcaaggc caggctgcac ctgcagggca ggagcaatgc ctggaggccc aggtcaaca     4980 accccaagga gtggctgcag gtggacttcc agaagaccat gaaggtgact ggggtgacca    5040
cccagggggt gaagagcctg ctgaccagca tgtatgtgaa ggagttcctg atcagcagca    5100
gccaggatgg ccaccagtgg accctgttct tccagaatgg caaggtgaag gtgttccagg    5160
gcaaccagga cagcttcacc cctgtggtga acagcctgga cccccccctg ctgaccagat    5220
acctgaggat tcaccccag agctgggtgc accagattgc cctgaggatg gaggtgctgg     5280
gctgtgaggc ccaggacctg tactgacctc gaggtgtgcc ttctagttgc cagccatctg    5340
ttgtttgccc ctccccgtg ccttccttga ccctggaagg tgccactccc actgtcccttt     5400 cctaataaaa tgaggaaatt gcatcgcatt gtctgagtag gtgtcattct attctggggg    5460
gtggggtggg gcaggacagc aaggggggag attgggaaga caatagcagg catgctgggg    5520
atgcggtggg ctctatgggc acgtgccctc tcacactacc taaaccacgc caggacaacc    5580
tctgctcctc tccaccgaaa ttccaagggg tcgagtggat gttggaggtg catgggccc    5640 agagaggtct ctgacctctg ccccagctcc aaggtcagca ggcagggagg gctgtgtgtt    5700
tgctgtttgc tgcttgcaat gtttgcccat tttagggaca tgagtaggct gaagtttgtt    5760
cagtgtggac ttcagaggca gcacacaaac agctgctgga ggatgggaac tgaggggttg    5820
gaagggggca gggtgagccc agaaactcct gtgtgcctct gagcctgcag ccctctcaca    5880
ctacctaaac cacgccagga caacctctgc tcctctccac cgaaattcca aggggtcgag    5940
tggatgttgg agtggcatg ggcccagaga ggtctctgac ctctgcccca gctccaaggt    6000
cagcaggcag ggagggctgt gtgtttgctg tttgctgctt gcaatgtttg cccattttag    6060
ggacatgagt aggctgaagt tgttcagtg tggacttcag aggcagcaca caaacagctg    6120
ctggaggatg ggaactgagg ggttggaagg gggcagggtg agcccagaaa ctcctgtgtg    6180
cctctgagcc tgcagcacgt ggcggccgca ggaacccta gtgatggagt tggccactcc    6240
ctctctgcgc gctcgctcgc tcactgaggc cgggcgacca aggtcgccc gacgcccggg    6300 cttttgcccgg gcggcctcag tgagcgagcg agcgcgcaga gagggagtgg ccaa        6354
```

<210> SEQ ID NO 15
<211> LENGTH: 6308
<212> TYPE: DNA
<213> ORGANISM: Adeno-Associated Virus 2

<400> SEQUENCE: 15

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttaatttta aaaagcagtc    180 aaaagtccaa gtggcccttg gcagcattta ctctctctgt ttgctctggt taataatctc    240
aggagcacaa acattcctgg aggcaggaga agaaatcaac atcctggact tatcctctgg    300
gcctgttaat ttttaaaaag cagtcaaaag tccaagtggc ccttggcagc atttactctc    360
tctgtttgct ctggttaata atctcaggag cacaaacatt cctggaggca ggagaagaaa    420
tcaacatcct ggacttatcc tctgggccta ggcctgaggc tggtcaaaat tgaacctcct    480
cctgctctga gcagctgggg gggcagacta agcagagggc tgtgcagacc cacataaaga    540
gcctactgtg tgccaggcac ttcacccgag gcacttcaca agcatgcttg ggaatgaaac    600
```

```
ttccaactct ttgggatgca ggtgaaacag ttcctggttc agagaggtga agcggcctgc    660
ctgaggcagc acagctcttc tttacagatg tgcttcccca cctctaccct gtctcacggc    720
cccccatgcc agcctgacgg ttgtgtctgc ctcagtcatg ctccattttt ccatcgggac    780
catcaagagg gtgtttgtgt ctaaggctga ctgggtaact ttggatgagc ggtctctccg    840
ctctgagcct gtttcctcat ctgtcaaatg ggctctaacc cactctgatc tcccagggcg    900
gcagtaagtc ttcagcatca ggcattttgg ggtgactcag taaatggtag atcttgctac    960
cagtggaaca gccactaagg attctgcagt gagagcagag ggccagctaa gtggtactct   1020
cccagagact gtctgactca cgccacccccc tccaccttgg acacaggacg ctgtggtttc   1080
tgagccaggt acaatgactc ctttcggtaa gtgcagtgga agctgtacac tgcccaggca   1140
aagcgtccgg gcagcgtagg cgggcgactc agatcccagc cagtggactt agcccctgtt   1200
tgctcctccg ataactgggg tgaccttggt taatattcac cagcagcctc ccccgttgcc   1260
cctctggatc cactgcttaa atacggacga ggacagggcc ctgtctcctc agcttcaggc   1320
accaccactg acctgggaca gtgaatcgta agtactagca gctacaatcc agctaccatt   1380
ctgcttttat tttatggttg ggataaggct ggattattct gagtccaagc taggccccttt   1440
tgctaatcat gttcatacct cttatcttcc tcccacagct cctgggcaac gtgctggtct   1500
gtgtgctggc ccatcacttt ggcaaagaat tgcgatcgcc accatgcaga ttgagctgag   1560
cacctgcttc ttcctgtgcc tgctgaggtt ctgcttctct gccaccagga gatactacct   1620
gggggctgtg gagctgagct gggactacat gcagtctgac ctgggggagc tgcctgtgga   1680
tgccaggttc cccccccagag tgcccaagag cttccccttc aacacctctg tggtgtacaa   1740
gaagaccctg tttgtggagt tcactgacca cctgttcaac attgccaagc ccaggccccc   1800
ctggatgggc ctgctgggcc ccaccatcca ggctgaggtg tatgacactg tggtgatcac   1860
cctgaagaac atggccagcc accctgtgag cctgcatgct gtgggggtga gctactggaa   1920
ggcctctgag ggggctgagt atgatgacca gaccagccag agggagaagg aggatgacaa   1980
ggtgttccct gggggcagcc acacctatgt gtggcaggtg ctgaaggaga atggcccccat   2040
ggcctctgac cccctgtgcc tgacctacag ctacctgagc catgtggacc tggtgaagga   2100
cctgaactct ggcctgattg gggcctgct ggtgtgcagg gagggcagcc tggccaagga   2160
gaagacccag accctgcaca gttcatcct gctgtttgct gtgtttgatg agggcaagag   2220
ctggcactct gaaaccaaga cagcctgat gcaggacagg gatgctgcct ctgccagggc   2280
ctggcccaag atgcacactg tgaatggcta tgtgaacagg agcctgcctg gcctgattgg   2340
ctgccacagg aagtctgtgt actggcatgt gattggcatg ggcaccaccc tgaggtgca   2400
cagcatcttc ctggagggcc acaccttcct ggtcaggaac acaggcagg ccagcctgga   2460
gatcagcccc atcaccttcc tgactgccca gaccctgctg atggacctgg ccagttcct   2520
gctgttctgc cacatcagca gccaccagca tgatggcatg gaggcctatg tgaaggtgga   2580
cagctgccct gaggagcccc agctgaggat gaagaacaat gaggaggctg aggactatga   2640
tgatgacctg actgactctg agatggatgt ggtgaggttt gatgatgaca acagccccag   2700
cttcatccag atcaggtctg tggccaagaa gcaccccaag acctgggtgc actacattgc   2760
tgctgaggag gaggactggg actatgcccc cctggtgctg gccctgatg acaggagcta   2820
caagagccag tacctgaaca atggccccca ggagattggc aggaagtaca agaaggtcag   2880
gttcatggcc tacactgatg aaaccttcaa gaccagggag gccatccagc atgagtctgg   2940
```

```
catcctgggc ccctgctgt atggggaggt ggggacacc ctgctgatca tcttcaagaa    3000
ccaggccagc aggccctaca acatctaccc ccatggcatc actgatgtga ggccctgta    3060 cagcaggagg ctgcccaagg gggtgaagca cctgaaggac ttccccatcc tgcctggga    3120 gatcttcaag tacaagtgga ctgtgactgt ggaggatggc cccaccaagt ctgaccccag    3180
gtgcctgacc agatactaca gcagctttgt gaacatggag agggacctgg cctctggcct    3240
gattggcccc ctgctgatct gctacaagga gtctgtggac cagaggggca accagatcat    3300
gtctgacaag aggaatgtga tcctgttctc tgtgtttgat gagaacagga gctggtacct    3360
gactgagaac atccagaggt tcctgcccaa ccctgctggg gtgcagctgg aggaccctga    3420
gttccaggcc agcaacatca tgcacagcat caatggctat gtgtttgaca gcctgcagct    3480
gtctgtgtgc ctgcatgagg tggcctactg gtacatcctg agcattgggg cccagactga    3540
cttcctgtct gtgttcttct ctggctacac cttcaagcac aagatggtgt atgaggacac    3600
cctgaccctg ttcccttct ctggggagac tgtgttcatg agcatggaga ccctggcct    3660 gtggattctg ggctgccaca actctgactt caggaacagg gcatgactg ccctgctgaa    3720 agtctccagc tgtgacaaga acactgggga ctactatgag gacagctatg aggacatctc    3780
tgcctacctg ctgagcaaga acaatgccat tgagcccagg agcttcagcc agaaccccc    3840 agtgctgaag aggcaccaga gggagatcac caggaccacc ctgcagtctg accaggagga    3900
gattgactat gatgacacca tctctgtgga gatgaagaag gaggactttg acatctacga    3960
cgaggacgag aaccagagcc caggagctt ccagaagaag accaggcact acttcattgc    4020
tgctgtggag aggctgtggg actatggcat gagcagcagc ccccatgtgc tgaggaacag    4080
ggcccagtct ggctctgtgc cccagttcaa gaaggtggtg ttccaggagt cactgatgg    4140 cagcttcacc cagcccctgt acagagggga gctgaatgag cacctgggcc tgctgggccc    4200
ctacatcagg gctgaggtgg aggacaacat catggtgacc ttcaggaacc aggccagcag    4260
gccctacagc ttctacagca gcctgatcag ctatgaggag gaccagaggc aggggctga    4320 gcccaggaag aactttgtga gccccaatga aaccaagacc tacttctgga aggtgcagca    4380
ccacatggcc cccaccaagg atgagtttga ctgcaaggcc tggcctact tctctgatgt    4440 ggacctggag aaggatgtgc actctggcct gattggcccc ctgctggtgt gccacaccaa    4500 cacctgaac cctgcccatg gcaggcaggt gactgtgcag gagtttgccc tgttcttcac    4560
catctttgat gaaaccaaga ctggtactt cactgagaac atggagagga actgcagggc    4620 ccctgcaac atccagatgg aggacccac cttcaaggag aactacaggt tccatgccat    4680
caatggctac atcatggaca ccctgcctgg cctggtgatg gcccaggacc agaggatcag    4740
gtggtacctg ctgagcatgg gcagcaatga gaacatccac agcatccact tctctggcca    4800
tgtgttcact gtgaggaaga aggaggagta caagatggcc ctgtacaacc tgtaccctgg    4860
ggtgtttgag actgtggaga tgctgcccag caaggctggc atctggaggg tggagtgcct    4920 gattgggag cacctgcatg ctggcatgag caccctgttc ctggtgtaca gcaacaagtg    4980
ccagaccccc ctgggcatgg cctctggcca tcagggac ttccagatca ctgcctctgg    5040
ccagtatggc cagtggggccc caagctggcc caggctgcac tactctggca gcatcaatgc    5100
ctggagcacc aaggagccct tcagctggat caaggtggac ctgctggccc ccatgatcat    5160
ccatggcatc aagacccagg ggccaggca gaagttcagc agcctgtaca tcagccagtt    5220
catcatcatg tacagcctgg atggcaagaa gtggcagacc tacaggggca acagcactgg    5280
caccctgatg gtgttctttg gcaatgtgga cagctctggc atcaagcaca acatcttcaa    5340
```

```
cccccccatc attgccagat acatcaggct gcaccccacc cactacagca tcaggagcac   5400
cctgaggatg gagctgatgg gctgtgacct gaacagctgc agcatgcccc tgggcatgga   5460
gagcaaggcc atctctgatg cccagatcac tgccagcagc tacttcacca acatgtttgc   5520
cacctggagc cccagcaagg ccaggctgca cctgcagggc aggagcaatg cctggaggcc   5580
ccaggtcaac aaccccaagg agtggctgca ggtggacttc agaagacca tgaaggtgac   5640 tggggtgacc acccaggggg tgaagagcct gctgaccagc atgtatgtga aggagttcct   5700
gatcagcagc agccaggatg gccaccagtg gaccctgttc ttccagaatg caaggtgaa   5760 ggtgttccag ggcaaccagg acagcttcac ccctgtggtg aacagcctgg acccccccct   5820
gctgaccaga tacctgagga ttcaccccca gagctgggtg caccagattg ccctgaggat   5880
ggaggtgctg ggctgtgagg cccaggacct gtactgacct cgagctgtgc cttctagttg   5940
ccagccatct gttgtttgcc cctccccgt gccttccttg accctggaag gtgccactcc   6000
cactgtcctt tcctaataaa atgaggaaat tgcatcgcat tgtctgagta ggtgtcattc   6060
tattctgggg ggtggggtgg ggcaggacag caaggggggag gattgggaag acaatagcag   6120
gcatgctggg gatgcggtgg gctctatgga ccggtgcggc cgcaggaacc cctagtgatg   6180
gagttggcca ctccctctct gcgcgctcgc tcgctcactg aggccgggcg accaaaggtc   6240
gcccgacgcc cgggctttgc ccgggcggcc tcagtgagcg agcgagcgcg cagagaggga   6300
gtggccaa                                                           6308

<210> SEQ ID NO 16
<211> LENGTH: 5635
<212> TYPE: DNA
<213> ORGANISM: Adeno-Associate Virus 2

<400> SEQUENCE: 16
ttggccactc cctctctgcg cgctcgctcg ctcactgagg ccgccgggc aaagcccggg     60 cgtcgggcga cctttggtcg cccggcctca gtgagcgagc gagcgcgcag agagggagtg    120
gccaactcca tcactagggg ttcctgcggc cgcacgcgtg ttaattttta aaaagcagtc    180
aaaagtccaa gtggcccttg gcagcattta ctctctctgt ttgctctggt taataatctc    240
aggagcacaa acattcctgg aggcaggaga agaaatcaac atcctggact tatcctctgg    300
gcctgttaat ttttaaaaag cagtcaaaag tccaagtggc ccttggcagc atttactctc    360
tctgtttgct ctggttaata atctcaggag cacaaacatt cctggaggca ggagaagaaa    420
tcaacatcct ggacttatcc tctgggccta gtcgactgga cacaggacgc tgtggtttct    480
gagccagggg gcgactcaga tcccagccag tggacttagc ccctgtttgc tcctccgata    540
actggggtga ccttggttaa tattcaccag cagcctcccc cgttgcccct ctggatccac    600
tgcttaaata cggacgagga cagggccctg tctcctcagc ttcaggcacc accactgacc    660
tgggacagtg aatcgtaagt actagcagct acaatccagc taccattctg cttttatttt    720
atggttggga taaggctgga ttattctgag tccaagctag gccctttgc taatcatgtt    780 catacctctt atcttcctcc cacagctcct gggcaacgtg ctggtctgtg tgctggccca    840
tcactttggc aaagaattgc gatcgccacc atgcagattg agctgagcac tgcttcttc    900 ctgtgcctgc tgaggttctg cttctctgcc accaggagat actacctggg ggctgtggag    960
ctgagctgga ctacatgca gtctgacctg ggggagctgc ctgtggatgc caggttcccc    1020
cccagagtgc ccaagagctt ccccttcaac acctctgtgg tgtacaagaa gacccctgttt   1080
```

```
gtggagttca ctgaccacct gttcaacatt gccaagccca ggccccctg dtgggcctg      1140
ctgggcccca ccatccaggc tgaggtgtat gacactgtgg tgatcaccct gaagaacatg    1200
gccagccacc ctgtgagcct gcatgctgtg ggggtgagct actggaaggc ctctgagggg    1260
gctgagtatg atgaccagac cagccagagg gagaaggagg atgacaaggt gttccctggg    1320
ggcagccaca cctatgtgtg gcaggtgctg aaggagaatg gccccatggc ctctgacccc    1380
ctgtgcctga cctacagcta cctgagccat gtggacctgg tgaaggacct gaactctggc    1440
ctgattgggg ccctgctggt gtgcagggag ggcagcctgg ccaaggagaa gacccagacc    1500
ctgcacaagt tcatcctgct gtttgctgtg tttgatgagg gcaagagctg gcactctgaa    1560
accaagaaca gcctgatgca ggacagggat gctgcctctg ccagggcctg gcccaagatg    1620
cacactgtga atggctatgt gaacaggagc ctgcctggcc tgattggctg ccacaggaag    1680
tctgtgtact ggcatgtgat tggcatgggc accaccctg aggtgcacag catcttcctg     1740
gagggccaca ccttcctggt caggaaccac aggcaggcca gcctggagat cagccccatc    1800
accttcctga ctgcccagac cctgctgatg gacctgggcc agttcctgct gttctgccac    1860
atcagcagcc accagcatga tggcatggag gcctatgtga aggtggacag ctgccctgag    1920
gagccccagc tgaggatgaa gaacaatgag gaggctgagg actatgatga tgacctgact    1980
gactctgaga tggatgtggt gaggtttgat gatgacaaca gccccagctt catccagatc    2040
aggtctgtgg ccaagaagca ccccaagacc tgggtgcact acattgctgc tgaggaggag    2100
gactgggact atgccccct ggtgctggcc cctgatgaca ggagctacaa gagccagtac    2160
ctgaacaatg gccccagag gattggcagg aagtacaaga aggtcaggtt catggcctac    2220
actgatgaaa ccttcaagac cagggaggcc atccagcatg agtctggcat cctgggcccc    2280
ctgctgtatg gggaggtggg ggacaccctg ctgatcatct tcaagaacca ggccagcagg    2340
ccctacaaca tctacccca tggcatcact gatgtgaggc cctgtacag caggaggctg      2400
cccaaggggg tgaagcacct gaaggacttc cccatcctgc tggggagat cttcaagtac     2460
aagtggactg tgactgtgga ggatggcccc accaagtctg accccaggtg cctgaccaga    2520
tactacagca gctttgtgaa catggagagg gacctggcct ctggcctgat ggcccccctg    2580
ctgatctgct acaaggagtc tgtggaccag aggggcaacc agatcatgtc tgacaagagg    2640
aatgtgatcc tgttctctgt gtttgatgag aacaggagcc ggtacctgac tgagaacatc    2700
cagaggttcc tgcccaaccc tgctggggtg cagctggagg accctgagtt ccaggccagc    2760
aacatcatgc acagcatcaa tggctatgtg tttgacagcc tgcagctgtc tgtgtgcctg    2820
catgaggtgg cctactggta catcctgagc attggggccc agactgactt cctgtctgtg    2880
ttcttctctg gctacacctt caagcacaag atggtgtatg aggacaccct gacccctgttc    2940
cccttctctg gggagactgt gttcatgagc atggagaacc ctggcctgtg gattctgggc    3000
tgccacaact ctgacttcag gaacaggggc atgactgccc tgctgaaagt ctccagctgt    3060
gacaagaaca ctggggacta ctatgaggac agctatgagg acatctctgc ctacctgctg    3120
agcaagaaca atgccattga gcccaggagc ttcagccaga accccccagt gctgaagagg    3180
caccagaggg agatcaccag gaccacctg cagtctgacc aggaggagat tgactatgat    3240
gacaccatct ctgtggagat gaagaaggag gactttgaca tctacgacga ggacgagaac    3300
cagagcccca ggagcttcca gaagaagacc aggcactact tcattgctgc tgtggagagg    3360
ctgtgggact atggcatgag cagcagcccc catgtgctga ggaacaggg ccagtctggc     3420
tctgtgcccc agttcaagaa ggtggtgttc caggagttca ctgatggcag cttcacccag    3480
```

```
cccctgtaca gaggggagct gaatgagcac ctgggcctgc tgggccccta catcagggct    3540
gaggtggagg acaacatcat ggtgaccttc aggaaccagg ccagcaggcc ctacagcttc    3600
tacagcagcc tgatcagcta tgaggaggac cagaggcagg gggctgagcc caggaagaac    3660
tttgtgaagc ccaatgaaac caagacctac ttctggaagg tgcagcacca catggccccc    3720
accaaggatg agtttgactg caaggcctgg gcctacttct ctgatgtgga cctggagaag    3780
gatgtgcact ctggcctgat tggcccctg ctggtgtgcc acaccaacac cctgaaccct    3840
gcccatggca ggcaggtgac tgtgcaggag tttgccctgt tcttcaccat ctttgatgaa    3900
accaagagct ggtacttcac tgagaacatg gagaggaact gcagggcccc ctgcaacatc    3960
cagatggagg accccacctt caaggagaac tacaggttcc atgccatcaa tggctacatc    4020
atggacaccc tgcctggcct ggtgatggcc caggaccaga ggatcaggtg gtacctgctg    4080
agcatgggca gcaatgagaa catccacagc atccacttct ctggccatgt gttcactgtg    4140
aggaagaagg aggagtacaa gatggccctg tacaacctgt accctggggt gtttgagact    4200
gtggagatgc tgcccagcaa ggctggcatc tggagggtgg agtgcctgat tggggagcac    4260
ctgcatgctg gcatgagcac cctgttcctg gtgtacagca acaagtgcca gacccccctg    4320
ggcatggcct ctggccacat cagggacttc cagatcactg cctctggcca gtatggccag    4380
tgggccccca gctggccag gctgcactac tctggcagca tcaatgcctg gagcaccaag    4440
gagcccttca gctggatcaa ggtggacctg ctggcccca tgatcatcca tggcatcaag    4500
acccagggggg ccaggcagaa gttcagcagc ctgtacatca gccagttcat catcatgtac    4560
agcctggatg caagaagtg gcagacctac aggggcaaca gcactggcac cctgatggtg    4620
ttctttggca atgtggacag ctctggcatc aagcacaaca tcttcaaccc ccccatcatt    4680
gccagataca tcaggctgca ccccaccac tacagcatca ggagcaccct gaggatggag    4740
ctgatgggct gtgacctgaa cagctgcagc atgcccctgg gcatggagag caaggccatc    4800
tctgatgccc agatcactgc cagcagctac ttcaccaaca tgtttgccac ctggagcccc    4860
agcaaggcca ggctgcacct gcagggcagg agcaatgcct ggaggcccca ggtcaacaac    4920
cccaaggagt ggctgcaggt ggacttccag aagaccatga aggtgactgg ggtgaccacc    4980
caggggggtga agagcctgct gaccagcatg tatgtgaagg agttcctgat cagcagcagc    5040
caggatggcc accagtggac cctgttcttc cagaatggca aggtgaaggt gttccagggc    5100
aaccaggaca gcttcacccc tgtggtgaac agcctggacc cccccctgct gaccagatac    5160
ctgaggattc accccagag ctgggtgcac cagattgccc tgaggatgga ggtgctgggc    5220
tgtgaggccc aggacctgta ctgacctcga gctgtgcctt ctagttgcca gccatctgtt    5280
gtttgcccct ccccgtgcc ttccttgacc ctggaaggtg ccactcccac tgtcctttcc    5340
taataaaatg aggaaattgc atcgcattgt ctgagtaggt gtcattctat tctggggggt    5400
ggggtggggc aggacagcaa gggggaggat tgggaagaca atagcaggca tgctgggat    5460
gcggtgggct ctatggaccg gtgcggccgc aggaacccct agtgatggag ttggccactc    5520
cctctctgcg cgctcgctcg ctcactgagg ccgggcgacc aaaggtcgcc cgacgcccgg    5580
gctttgcccg gcggcctca gtgagcgagc gagcgcgcag agagggagtg gccaa         5635
```

<210> SEQ ID NO 17
<211> LENGTH: 6962
<212> TYPE: DNA
<213> ORGANISM: Adeno-Associated Virus 2

<400> SEQUENCE: 17

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgta ggctcagagg cacacaggag     180
tttctgggct caccctgccc ccttccaacc cctcagttcc catcctccag cagctgtttg     240
tgtgctgcct ctgaagtcca cactgaacaa acttcagcct actcatgtcc ctaaaatggg     300
caaacattgc aagcagcaaa cagcaaacac acagccctcc ctgcctgctg accttggagc     360
tggggcagag gtcagagacc tctctgggcc catgccacct ccaacatcca ctcgacccct     420
tggaatttcg gtggagagga gcagaggttg tcctggcgtg gtttaggtag tgtgagaggg     480
gtcgacaggc tcagaggcac acaggagttt ctgggctcac cctgcccct tccaacccct      540
cagttcccat cctccagcag ctgtttgtgt gctgcctctg aagtccacac tgaacaaact     600
tcagcctact catgtcccta aaatgggcaa acattgcaag cagcaaacag caaacacaca     660
gccctccctg cctgctgacc ttggagctgg ggcagaggtc agagacctct ctgggcccat     720
gccacctcca acatccactc gacccctttgg aatttcggtg gagaggagca gaggttgtcc    780
tggcgtggtt taggtagtgt gagaggggtc gacgttaatt tttaaaaagc agtcaaaagt     840
ccaagtggcc cttggcagca tttactctct ctgtttgctc tggttaataa tctcaggagc     900
acaaacattc ctggaggcag gagaagaaat caacatcctg gacttatcct ctgggcctgt     960
taattttttaa aaagcagtca aaagtccaag tggcccttgg cagcatttac tctctctgtt    1020
tgctctggtt aataatctca ggagcacaaa cattcctgga ggcaggagaa gaaatcaaca    1080
tcctggactt atcctctggg cctaggcctg aggctggtca aaattgaacc tcctcctgct    1140
ctgagcagcc tggggggcag actaagcaga gggctgtgca gacccacata aagagcctac    1200
tgtgtgccag gcacttcacc cgaggcactt cacaagcatg cttgggaatg aaacttccaa    1260
ctcctttgga tgcaggtgaa acagttcctg gttcagagag gtgaagcggc ctgcctgagg    1320
cagcacagct cttctttaca gatgtgcttc cccacctcta ccctgtctca cggcccccca    1380
tgccagcctg acgttgtgt ctgcctcagt catgctccat tttccatcg ggaccatcaa      1440
gagggtgttt gtgtctaagg ctgactgggt aactttggat gagcggtctc tccgctctga    1500
gcctgtttcc tcatctgtca atgggctct aacccactct gatctcccag ggcggcagta     1560
agtcttcagc atcaggcatt tgggggtgac tcagtaaatg gtagatcttg ctaccagtgg    1620
aacagccact aaggattctg cagtgagagc agagggccag ctaagtggta ctctcccaga    1680
gactgtctga ctcacgccac cccctccacc ttggacacag gacgctgtgg tttctgagcc    1740
aggtacaatg actcctttcg gtaagtgcag tggaagctgt acactgccca ggcaaagcgt    1800
ccgggcagcg taggcgggcg actcagatcc cagccagtgg acttagcccc tgtttgctcc    1860
tccgataact ggggtgacct tggttaatat tcaccagcag cctccccgt tgcccctctg      1920
gatccactgc ttaaatacgg acgaggacag ggccctgtct cctcagcttc aggcaccacc    1980
actgacctgg gacagtgaat cgtaagtact agcagctaca atccagctac cattctgctt    2040
ttatttatg gttgggataa ggctggatta ttctgagtcc aagctaggcc cttttgctaa     2100
tcatgttcat acctcttatc ttcctcccac agctcctggg caacgtgctg gtctgtgtgc    2160
tggcccatca ctttggcaaa gaattgcgat cgccaccatg cagattgagc tgagcacctg    2220
cttcttcctg tgcctgctga ggttctgctt ctctgccacc aggagatact acctgggggc    2280
tgtggagctg agctgggact acatgcagtc tgacctgggg gagctgcctg tggatgccag    2340
```

-continued

```
gttccccccc agagtgccca agagcttccc cttcaacacc tctgtggtgt acaagaagac    2400
cctgtttgtg gagttcactg accacctgtt caacattgcc aagcccaggc cccctggat     2460 gggcctgctg ggccccacca tccaggctga ggtgtatgac actgtggtga tcaccctgaa    2520
gaacatggcc agccaccctg tgagcctgca tgctgtgggg gtgagctact ggaaggcctc    2580
tgagggggct gagtatgatg accagaccag ccagagggag aaggaggatg caaggtgtt    2640 ccctgggggc agccacacct atgtgtggca ggtgctgaag gagaatggcc ccatggcctc    2700
tgaccccctg tgcctgacct acagctacct gagccatgtg gacctggtga aggacctgaa    2760
ctctggcctg attggggccc tgctggtgtg cagggagggc agcctggcca aggagaagac    2820
ccagaccctg cacaagttca tcctgctgtt tgctgtgttt gatgagggca gagctggca    2880 ctctgaaacc aagaacagcc tgatgcagga cagggatgct gcctctgcca gggcctggcc    2940
caagatgcac actgtgaatg ctatgtgaa caggagcctg cctggcctga ttggctgcca    3000
caggaagtct gtgtactggc atgtgattgg catgggcacc accctgagg tgcacagcat     3060 cttcctggag ggccacacct tcctggtcag gaaccacagg caggccagcc tggagatcag    3120
ccccatcacc ttcctgactg cccagaccct gctgatggac ctgggccagt tcctgctgtt    3180
ctgccacatc agcagccacc agcatgatgg catggaggcc tatgtgaagg tggacagctg    3240
ccctgaggag ccccagctga ggatgaagaa caatgaggag gctgaggact atgatgatga    3300
cctgactgac tctgagatgg atgtggtgag gtttgatgat gacaacagcc cagcttcat    3360 ccagatcagg tctgtggcca agaagcaccc caagacctgg gtgcactaca ttgctgctga    3420
ggaggaggac tgggactatg ccccctggt gctggcccct gatgacagga gctacaagag    3480
ccagtacctg aacaatggcc cccagaggat tggcaggaag tacaagaagg tcaggttcat    3540
ggcctacact gatgaaacct tcaagaccag ggaggccatc cagcatgagt ctggcatcct    3600
gggccccctg ctgtatgggg aagtgggggga caccctgctg atcatcttca agaaccaggc    3660
cagcaggccc tacaacatct accccatgg catcactgat gtgaggcccc tgtacagcag    3720
gaggctgccc aaggggggtga agcacctgaa ggacttcccc atcctgcctg gggagatctt    3780
caagtacaag tggactgtga ctgtggagga tggccccacc aagtctgacc ccaggtgcct    3840
gaccagatac tacagcagct ttgtgaacat ggagagggac ctggcctctg gcctgattgg    3900
ccccctgctg atctgctaca aggagtctgt ggaccagagg ggcaaccaga tcatgtctga    3960
caagaggaat gtgatcctgt tctctgtgtt tgatgagaac aggagctggt acctgactga    4020
gaacatccag aggttcctgc caacctgc tggggtgcag ctggaggacc ctgagttcca    4080
ggccagcaac atcatgcaca gcatcaatgg ctatgtgttt gacagcctgc agctgtctgt    4140
gtgcctgcat gaggtggcct actggtacat cctgagcatt ggggcccaga ctgacttcct    4200
gtctgtgttc ttctctggct acccttcaa gcacaagatg gtgtatgagg acaccctgac    4260
cctgttcccc ttctctgggg agactgtgtt catgagcatg gagaaccctg gcctgtggat    4320
tctgggctgc cacaactctg acttcaggaa caggggcatg actgccctgc tgaaagtctc    4380
cagctgtgac aagaacactg gggactacta tgaggacagc tatgaggaca tctctgccta    4440
cctgctgagc aagaacaatg ccattgagcc caggagcttc agccagaacc ccagtgct     4500 gaagaggcac cagagggaga tcaccaggac caccctgcag tctgaccagg aggagattga    4560
ctatgatgac accatctctg tggagatgaa gaaggaggac tttgacatct acgacgagga    4620
cgagaaccag agcccccagga gcttccagaa gaagaccagg cactacttca ttgctgctgt    4680
```

```
ggagaggctg tgggactatg gcatgagcag cagcccccat gtgctgagga acagggccca    4740
gtctggctct gtgccccagt tcaagaaggt ggtgttccag gagttcactg atggcagctt    4800
cacccagccc ctgtacagag gggagctgaa tgagcacctg gcctgctgg ccccctacat     4860
cagggctgag gtgaggaca acatcatggt gaccttcagg aaccaggcca gcaggcccta    4920
cagcttctac agcagcctga tcagctatga ggaggaccag aggcaggggg ctgagcccag    4980
gaagaacttt gtgaagccca atgaaaccaa gacctacttc tggaaggtgc agcaccacat    5040
ggcccccacc aaggatgagt ttgactgcaa ggcctgggcc tacttctctg atgtggacct    5100
ggagaaggat gtgcactctg gcctgattgg ccccctgctg gtgtgccaca ccaacaccct    5160
gaaccctgcc catggcaggc aggtgactgt gcaggagttt gccctgttct tcaccatctt    5220
tgatgaaacc aagagctggt acttcactga aacatggag aggaactgca gggcccctg     5280
caacatccag atggaggacc ccaccttcaa ggagaactac aggttccatg ccatcaatgg    5340
ctacatcatg gacaccctgc ctggcctggt gatggcccag gaccagagga tcaggtggta    5400
cctgctgagc atgggcagca atgagaacat ccacagcatc cacttctctg gccatgtgtt    5460
cactgtgagg aagaaggagg agtacaagat ggccctgtac aacctgtacc tggggtgtt    5520
tgagactgtg gagatgctgc ccagcaaggc tggcatctgg agggtggagt gcctgattgg    5580
ggagcacctg catgctggca tgagcaccct gttcctggtg tacagcaaca agtgccagac    5640
cccccctgggc atggcctctg gccacatcag ggacttccag atcactgcct ctggccagta    5700
tggccagtgg gcccccaagc tggccaggct gcactactct ggcagcatca atgcctggag    5760
caccaaggag cccttcagct ggatcaaggt ggacctgctg gcccccatga tcatccatgg    5820
catcaagacc caggggggcca ggcagaagtt cagcagcctg tacatcagcc agttcatcat    5880
catgtacagc ctgatggca agaagtggca gacctacagg ggcaacagca ctggcaccct    5940
gatggtgttc tttggcaatg tggacagctc tggcatcaag cacaacatct tcaaccccc    6000
catcattgcc agatacatca ggctgcaccc cacccactac agcatcagga gcaccctgag    6060
gatggagctg atgggctgtg acctgaacag ctgcagcatg cccctgggca tggagagcaa    6120
ggccatctct gatgcccaga tcactgccag cagctacttc accaacatgt tgccacctg    6180
gagccccagc aaggccaggc tgcacctgca gggcaggagc aatgcctgga ggccccaggt    6240
caacaacccc aaggagtggc tgcaggtgga cttccagaag accatgaagg tgactggggt    6300
gaccacccag ggggtgaaga gcctgctgac cagcatgtat gtgaaggagt tcctgatcag    6360
cagcagccag gatggccacc agtggaccct gttcttccag aatggcaagg tgaaggtgtt    6420
ccagggcaac caggacagct tcacccctgt ggtgaacagc ctggaccccc cctgctgac    6480
cagatacctg aggattcacc cccagagctg ggtgcaccag attgccctga ggatggaggt    6540
gctgggctgt gaggcccagg acctgtactg acctcgagct gtgccttcta gttgccagcc    6600
atctgttgtt tgcccctccc ccgtgccttc cttgaccctg gaaggtgcca ctcccactgt    6660
cctttcctaa taaaatgagg aaattgcatc gcattgtctg agtaggtgtc attctattct    6720
ggggggtggg gtgggcagg acagcaaggg ggaggattgg gaagacaata gcaggcatgc    6780
tggggatgcg gtgggctcta tggaccggt cggccgcagg aaccctagt gatggagttg     6840
gccactccct ctctgcgcgc tcgctcgctc actgaggccg gcgaccaaa ggtcgcccga    6900
cgcccgggct ttgcccgggc ggcctcagtg agcgagcgag cgcgcagaga gggagtggcc    6960
aa                                                                   6962
```

```
<210> SEQ ID NO 18
<211> LENGTH: 6289
<212> TYPE: DNA
<213> ORGANISM: Adeno-Associated Virus 2

<400> SEQUENCE: 18
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgta ggctcagagg cacacaggag     180
tttctgggct caccctgccc ccttccaacc cctcagttcc catcctccag cagctgtttg     240
tgtgctgcct ctgaagtcca cactgaacaa acttcagcct actcatgtcc ctaaaatggg     300
caaacattgc aagcagcaaa cagcaaacac acagccctcc ctgcctgctg accttggagc     360
tggggcagag gtcagagacc tctctgggcc catgccacct ccaacatcca ctcgaccct      420 tggaatttcg gtggagagga gcagaggttg tcctggcgtg gtttaggtag tgtgagaggg     480
gtcgacaggt cagaggcac acaggagttt ctgggctcac cctgcccct tccaacccct      540 cagttcccat cctccagcag ctgtttgtgt gctgcctctg aagtccacac tgaacaaact     600
tcagcctact catgtcccta aaatgggcaa acattgcaag cagcaaacag caaacacaca     660
gccctccctg cctgctgacc ttggagctgg gcagaggtc agagacctct ctgggcccat     720
gccacctcca acatccactc gacccctggt aatttcggtg gagaggagca gaggttgtcc     780
tggcgtggtt taggtagtgt gagaggggtc gacgttaatt tttaaaagc agtcaaagt      840 ccaagtggcc cttggcagca tttactctct ctgtttgctc tggttaataa tctcaggagc     900
acaaacattc ctggaggcag gagaagaaat caacatcctg gacttatcct ctgggcctgt     960
taatttttaa aaagcagtca aaagtccaag tggcccttgg cagcatttac tctctctgtt    1020
tgctctggtt aataatctca ggagcacaaa cattcctgga ggcaggagaa gaaatcaaca    1080
tcctggactt atcctctggg cctagtcgac tggacacagg acgctgtggt ttctgagcca    1140
gggggcgact cagatcccag ccagtggact tagcccctgt ttgctcctcc gataactggg    1200
gtgaccttgg ttaatattca ccagcagcct ccccgttgc ccctctggat ccactgctta    1260
aatacggacg aggacagggc cctgtctcct cagcttcagg caccaccact gacctgggac    1320
agtgaatcgt aagtactagc agctacaatc cagctaccat tctgctttta ttttatggtt    1380
gggataaggc tggattattc tgagtccaag ctaggccctt ttgctaatca tgttcatacc    1440
tcttatcttc ctcccacagc tcctgggcaa cgtgctggtc tgtgtgctgg cccatcactt    1500
tggcaaagaa ttgcgatcgc caccatgcag attgagctga gcacctgctt cttcctgtgc    1560
ctgctgaggt tctgcttctc tgccaccagg agatactacc tggggctgt ggagctgagc    1620 tgggactaca tgcagtctga cctggggag ctgcctgtgg atgccaggtt ccccccaga    1680 gtgcccaaga gcttccccctt caacacctct gtggtgtaca agaagaccct gtttgtggag    1740
ttcactgacc acctgttcaa cattgccaag cccaggcccc ctggatggg cctgctgggc    1800 cccaccatcc aggctgaggt gtatgacact gtggtgatca ccctgaagaa catggccagc    1860
caccctgtga gcctgcatgc tgtggggtg agctactgga aggcctctga ggggctgag    1920 tatgatgacc agaccagcca gaggagaag gaggatgaca aggtgttccc tgggggcagc    1980
cacacctatg tgtggcaggt gctgaaggag aatggcccca tggcctctga cccctgtgc    2040 ctgacctaca gctacctgag ccatgtggac ctggtgaagg acctgaactc tggcctgatt    2100
ggggccctgc tggtgtgcag ggagggcagc ctggccaagg agaagaccca gacctgcac    2160
```

```
aagttcatcc tgctgtttgc tgtgtttgat gagggcaaga gctggcactc tgaaaccaag    2220
aacagcctga tgcaggacag ggatgctgcc tctgccaggg cctggcccaa gatgcacact    2280
gtgaatggct atgtgaacag gagcctgcct ggcctgattg gctgccacag gaagtctgtg    2340
tactggcatg tgattggcat gggcaccacc cctgaggtgc acagcatctt cctggagggc    2400
cacaccttcc tggtcaggaa ccacaggcag gccagcctgg agatcagccc catccccttc    2460
ctgactgccc agaccctgct gatggacctg ggccagttcc tgctgttctg ccacatcagc    2520
agccaccagc atgatggcat ggaggcctat gtgaaggtgg acagctgccc tgaggagccc    2580
cagctgagga tgaagaacaa tgaggaggct gaggactatg atgatgacct gactgactct    2640
gagatggatg tggtgaggtt tgatgatgac aacagcccca gcttcatcca gatcaggtct    2700
gtggccaaga agcaccccaa gacctgggtg cactacattg ctgctgagga ggaggactgg    2760
gactatgccc ccctggtgct ggcccctgat gacaggagct acaagagcca gtacctgaac    2820
aatggccccc agaggattgg caggaagtac aagaaggtca ggttcatggc ctacactgat    2880
gaaaccttca gaccaggga ggccatccag catgagtctg gcatcctggg ccccctgctg    2940
tatggggagg tgggggacac cctgctgatc atcttcaaga accaggccag caggccctac    3000
aacatctacc cccatggcat cactgatgtg aggcccctgt acagcaggag gctgcccaag    3060
ggggtgaagc acctgaagga cttccccatc ctgcctgggg agatcttcaa gtacaagtgg    3120
actgtgactg tggaggatgg ccccaccaag tctgaccccca ggtgcctgac agatactac    3180 agcagctttg tgaacatgga gagggacctg gcctctggcc tgattggccc cctgctgatc    3240
tgctacaagg agtctgtgga ccagagggc aaccagatca tgtctgacaa gaggaatgtg    3300
atcctgttct ctgtgtttga tgagaacagg agctggtacc tgactgagaa catccagagg    3360
ttcctgccca ccctgctggg ggtgcagctg gaggaccctg agttccaggc cagcaacatc    3420
atgcacagca tcaatggcta tgtgtttgac agcctgcagc tgtctgtgtg cctgcatgag    3480
gtggcctact ggtacatcct gagcattggg gcccagactg acttcctgtc tgtgttcttc    3540
tctggctaca ccttcaagca caagatggtg tatgaggaca ccctgaccct gttccccttc    3600
tctggggaga ctgtgttcat gagcatggag aaccctggcc tgtggattct gggctgccac    3660
aactctgact tcaggaacag gggcatgact gccctgctga aagtctccag ctgtgacaag    3720
aacactgggg actactatga ggacagctat gaggacatct ctgcctacct gctgagcaag    3780
aacaatgcca ttgagcccag gagcttcagc cagaaccccc cagtgctgaa gaggcaccag    3840
agggagatca ccaggaccac cctgcagtct gaccaggagg agattgacta tgatgacacc    3900
atctctgtgg agatgaagaa ggaggacttt gacatctacg acgaggacga gaaccagagc    3960
cccaggagct tccagaagaa gaccaggcac tacttcattg ctgctgtgga gaggctgtgg    4020
gactatggca tgagcagcag ccccccatgtg ctgaggaaca gggcccagtc tggctctgtg    4080
ccccagttca gaaggtggt gttccaggag ttcactgatg gcagcttcac ccagcccctg    4140
tacagagggg agctgaatga gcacctgggc ctgctgggcc cctacatcag ggctgaggtg    4200
gaggacaaca tcatggtgac cttcaggaac caggccagca ggccctacag cttctacagc    4260
agcctgatca gctatgagga ggaccagagg cagggggctg agcccaggaa gaactttgtg    4320
aagcccaatg aaaccaagac ctacttctgg aaggtgcagc accacatggc ccccaccaag    4380
gatgagtttg actgcaaggc ctgggcctac ttctctgatg tggacctgga gaaggatgtg    4440
cactctggcc tgattggccc cctgctggtg tgccacacca cacccctgaa ccctgcccat    4500
ggcaggcagg tgactgtgca ggagtttgcc ctgttcttca ccatctttga tgaaaccaag    4560
```

```
agctggtact tcactgagaa catggagagg aactgcaggg cccctgcaa catccagatg    4620 gaggacccca ccttcaagga gaactacagg ttccatgcca tcaatggcta catcatggac    4680
accctgcctg gcctggtgat ggcccaggac cagaggatca ggtggtacct gctgagcatg    4740
ggcagcaatg agaacatcca cagcatccac ttctctggcc atgtgttcac tgtgaggaag    4800
aaggaggagt acaagatggc cctgtacaac ctgtaccctg gggtgtttga ctgtggag     4860 atgctgccca gcaaggctgg catctggagg gtggagtgcc tgattgggga gcacctgcat    4920
gctggcatga gcaccctgtt cctggtgtac agcaacaagt gccagacccc cctgggcatg    4980
gcctctggcc acatcaggga cttccagatc actgcctctg ccagtatgg ccagtgggcc      5040 cccaagctgg ccaggctgca ctactctggc agcatcaatg cctggagcac aaggagccc     5100 ttcagctgga tcaaggtgga cctgctggcc ccatgatca tccatggcat caagacccag      5160
ggggccaggc agaagttcag cagcctgtac atcagccagt tcatcatcat gtacagcctg    5220
gatggcaaga gtggcagac ctacagggc aacagcactg gcaccctgat ggtgttcttt     5280
ggcaatgtgg acagctctgg catcaagcac aacatcttca accccccat cattgccaga    5340 tacatcaggc tgcaccccac ccactacagc atcaggagca ccctgaggat ggagctgatg   5400
ggctgtgacc tgaacagctg cagcatgccc ctgggcatgg agagcaaggc catctctgat     5460
gcccagatca ctgccagcag ctacttcacc aacatgtttg ccacctggag ccccagcaag    5520
gccaggctgc acctgcaggg caggagcaat gcctggagc cccaggtcaa caaccccaag     5580
gagtggctgc aggtggactt ccagaagacc atgaaggtga ctggggtgac cacccaggg    5640 gtgaagagcc tgctgaccag catgtatgtg aaggagttcc tgatcagcag cagccaggat    5700
ggccaccagt ggacctgtt cttccagaat ggcaaggtga aggtgttcca gggcaaccag    5760
gacagcttca ccctgtggt gaacagctg gaccccccc tgctgaccag atacctgagg      5820
attcaccccc agagctgggt gcaccagatt gccctgagga tggaggtgct gggctgtgag   5880
gcccaggacc tgtactgacc tcgagctgtg ccttctagtt gccagccatc tgttgtttgc    5940
ccctcccccg tgccttcctt gaccctggaa ggtgccactc ccactgtcct ttcctaataa    6000
aatgaggaaa ttgcatcgca ttgtctgagt aggtgtcatt ctattctggg gggtggggtg    6060
gggcaggaca gcaaggggga ggattgggaa gacaatagca ggcatgctgg ggatgcggtg    6120
ggctctatgg accggtgcgg ccgcaggaac ccctagtgat ggagttggcc actccctctc    6180
tgcgcgctcg ctcgctcact gaggccgggc gaccaaaggt cgcccgacgc ccgggctttg    6240
cccgggcggc ctcagtgagc gagcgagcgc gcagagaggg agtggccaa                6289
```

<210> SEQ ID NO 19
<211> LENGTH: 5430
<212> TYPE: DNA
<213> ORGANISM: Adeno-Associated Virus 2

<400> SEQUENCE: 19

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgacgt ggacttagcc    180
cctgtttgct cctccgataa ctggggtgac cttggttaat attcaccagc agcctcccg     240 tggacttagc cctgtttgc tcctccgata actgggtga ccttggttaa tattcaccag     300
cagcctcccc acgcgaaacg tcgactggac acaggacgct gtggtttctg agccagggg    360
```

```
cgactcagat cccagccagt ggacttagcc cctgtttgct cctccgataa ctggggtgac    420
cttggttaat attcaccagc agcctccccc gttgcccctc tggatccact gcttaaatac    480
ggacgaggac agggccctgt ctcctcagct tcaggcacca ccactgacct gggacagtga    540
atcgtaagta ctagcagcta caatccagct accattctgc ttttatttta tggttgggat    600
aaggctggat tattctgagt ccaagctagg ccctttgct aatcatgttc atacctctta    660
tcttcctccc acagctcctg gcaacgtgc tggtctgtgt gctggcccat cactttggca    720
aagaattgcg atcgccacca tgcagattga gctgagcacc tgcttcttcc tgtgcctgct    780
gaggttctgc ttctctgcca ccaggagata ctacctgggg gctgtggagc tgagctggga    840
ctacatgcag tctgacctgg gggagctgcc tgtggatgcc aggttccccc ccagagtgcc    900
caagagcttc cccttcaaca cctctgtggt gtacaagaag accctgtttg tggagttcac    960
tgaccacctg ttcaacattg ccaagcccag gccccctgg atgggcctgc tgggccccac   1020
catccaggct gaggtgtatg acactgtggt gatcaccctg aagaacatgg ccagccaccc   1080
tgtgagcctg catgctgtgg gggtgagcta ctggaaggcc tctgaggggg ctgagtatga   1140
tgaccagacc agccagaggg agaaggagga tgacaaggtg ttccctgggg gcagccacac   1200
ctatgtgtgg caggtgctga aggagaatgg ccccatggcc tctgaccccc tgtgcctgac   1260
ctacagctac ctgagccatg tggacctggt gaaggacctg aactctggcc tgattggggc   1320
cctgctggtg tgcagggagg gcagcctggc caaggagaag acccagaccc tgcacaagtt   1380
catcctgctg tttgctgtgt tgatgaggg caagagctgg cactctgaaa ccaagaacag   1440
cctgatgcag gacagggatg ctgcctctgc cagggcctgg cccaagatgc acactgtgaa   1500
tggctatgtg aacaggagcc tgcctggcct gattggctgc acaggaagt ctgtgtactg   1560 gcatgtgatt ggcatgggca ccacccctga ggtgcacagc atcttcctgg agggccacac   1620
cttcctggtc aggaaccaca ggcaggccag cctggagatc agccccatca ccttcctgac   1680
tgcccagacc ctgctgatgg acctgggcca gttcctgctg ttctgccaca tcagcagcca   1740
ccagcatgat ggcatggagg cctatgtgaa ggtggacagc tgccctgagg agcccagct   1800 gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980 tgccccctg gtgctggccc ctgatgacag gagctacaag agccagtacc tgaacaatgg   2040
cccccagagg attggcagga gtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220
ctacccccat ggcatcactg atgtgaggcc cctgtacagc aggaggctgc caagggggt   2280 gaagcacctg aaggacttcc ccatcctgcc tggggagatc ttcaagtaca gtggactgt   2340 gactgtggag gatggcccca ccaagtctga ccccaggtgc ctgaccagat actacagcag   2400
ctttgtgaac atggagaggg acctggcctc tggcctgatt ggccccctgc tgatctgcta   2460
caaggagtct gtgaccagag gggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt ttgacagcct gcagctgtct gtgtgcctgc atgaggtggc   2700
ctactggtac atcctgagca ttggggccca gactgacttc ctgtctgtgt tcttctctgg   2760
```

```
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
tgacttcagg aacaggggca tgactgccct gctgaaagtc tccagctgtg acaagaacac    2940
tggggactac tatgaggaca gctatgagga catctctgcc tacctgctga gcaagaacaa    3000
tgccattgag cccaggagct tcagccagaa ccccccagtg ctgaagaggc accagaggga    3060
gatcaccagg accaccctgc agtctgacca ggaggagatt gactatgatg acaccatctc    3120
tgtggagatg aagaaggagg actttgacat ctacgacgag gacgagaacc agagccccag    3180
gagcttccag aagaagacca ggcactactt cattgctgct gtggagaggc tgtgggacta    3240
tggcatgagc agcagccccc atgtgctgag gaacagggcc cagtctggct ctgtgcccca    3300
gttcaagaag gtggtgttcc aggagttcac tgatggcagc ttcacccagc ccctgtacag    3360
aggggagctg aatgagcacc tgggcctgct gggcccctac atcagggctg aggtggagga    3420
caacatcatg gtgaccttca ggaaccaggc cagcaggccc tacagcttct acagcagcct    3480
gatcagctat gaggaggacc agaggcaggg ggctgagccc aggaagaact tgtgaagcc     3540 caatgaaacc aagacctact tctggaaggt gcagcaccac atggccccca ccaaggatga    3600
gtttgactgc aaggcctggg cctacttctc tgatgtggac ctggagaagg atgtgcactc    3660
tggcctgatt ggccccctgc tggtgtgcca caccaacacc ctgaaccctg ccatgcag     3720 gcaggtgact gtgcaggagt ttgccctgtt cttcaccatc tttgatgaaa ccaagagctg    3780
gtacttcact gagaacatgg agaggaactg caggcccccc tgcaacatcc agatggagga    3840
ccccaccttc aaggagaact acaggttcca tgccatcaat ggctacatca tggacaccct    3900
gcctggcctg gtgatggccc aggaccgag gatcaggtgg tacctgctga gcatgggcag    3960
caatgagaac atccacagca tccacttctc tggccatgtg ttcactgtga ggaagaagga    4020
ggagtacaag atggccctgt acaacctgta ccctggggtg tttgagactg tggagatgct    4080
gcccagcaag gctggcatct ggagggtgga gtgcctgatt ggggagcacc tgcatgctgg    4140
catgagcacc ctgttcctgg tgtacagcaa caagtgccag accccctgg gcatggcctc    4200 tggccacatc agggacttcc agatcactgc ctctggccag tatggccagt gggcccccaa    4260
gctggccagg ctgcactact ctggcagcat caatgcctgg agcaccaagg agcccttcag    4320
ctggatcaag gtgaccctgc tgcccccat gatcatccat ggcatcaaga cccaggggc     4380 caggcagaag ttcagcagcc tgtacatcag ccagttcatc atcatgtaca gcctggatgg    4440
caagaagtgg cagacctaca ggggcaacag cactggcacc ctgatggtgt tctttggcaa    4500
tgtggacagc tctggcatca agcacaacat cttcaacccc ccatcattg ccagatacat     4560 caggctgcac cccaccccact acagcatcag gagcaccctg aggatggagc tgatgggctg    4620
tgacctgaac agctgcagca tgccctgggg catggagagc aaggccatct ctgatgccca    4680
gatcactgcc agcagctact tcaccaacat gtttgccacc tggagcccca gcaaggccag    4740
gctgcacctg cagggcagga gcaatgcctg gaggcccag gtcaacaacc caaggagtg     4800 gctgcaggtg gacttccaga agaccatgaa ggtgactggg gtgaccaccc agggggtgaa    4860
gagcctgctg accagcatgt atgtgaagga gttcctgatc agcagcagcc aggatggcca    4920
ccagtggacc ctgttcttcc agaatggcaa ggtgaaggtg ttccagggca accaggacag    4980
cttcaccccc tgtggtgaaca gcctggaccc cccctgctg accagatacc tgaggattca    5040
cccccagagc tgggtgcacc agattgccct gaggatggag gtgctgggct gtgaggccca    5100
```

-continued

| | |
|---|---|
| ggacctgtac tgacctcgag gcactgtcct ttcctaataa aatgaggaaa ttgcatcgca | 5160 |
| ttgtctgagt aggtgtcatt ctattctggg gggtggggtg gggcaggaca gcaaggggga | 5220 |
| ggattgggaa gacaatagca ggcatgctgg ggatgcggtg ggctctatgg gcacgtggcg | 5280 |
| gccgcaggaa ccccctagtga tggagttggc cactccctct ctgcgcgctc gctcgctcac | 5340 |
| tgaggccggg cgaccaaagg tcgcccgacg cccgggcttt gcccgggcgg cctcagtgag | 5400 |
| cgagcgagcg cgcagagagg gagtggccaa | 5430 |

<210> SEQ ID NO 20
<211> LENGTH: 5779
<212> TYPE: DNA
<213> ORGANISM: Adeno-Associated Virus 2

<400> SEQUENCE: 20

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgacgt ggacttagcc | 180 |
| cctgtttgct cctccgataa ctggggtgac cttggttaat attcaccagc agcctccccg | 240 |
| tggacttagc ccctgtttgc tcctccgata actggggtga ccttggttaa tattcaccag | 300 |
| cagcctcccc acgcgaaacg tcgactggac acaggacgct gtggtttctg agccaggggg | 360 |
| cgactcagat cccagccagt ggacttagcc cctgtttgct cctccgataa ctggggtgac | 420 |
| cttggttaat attcaccagc agcctccccc gttgcccctc tggatccact gcttaaatac | 480 |
| ggacgaggac agggccctgt ctcctcagct tcaggcacca ccactgacct gggacagtga | 540 |
| atcgtaagta ctagcagcta caatccagct accattctgc ttttatttta tggttgggat | 600 |
| aaggctggat tattctgagt ccaagctagg ccctttttgct aatcatgttc atacctctta | 660 |
| tcttcctccc acagctcctg gcaacgtgc tggtctgtgt gctggcccat cactttggca | 720 |
| aagaattgcg atcgccacca tgcagattga gctgagcacc tgcttcttcc tgtgcctgct | 780 |
| gaggttctgc ttctctgcca ccaggagata ctacctgggg gctgtggagc tgagctggga | 840 |
| ctacatgcag tctgacctgg gggagctgcc tgtggatgcc aggttccccc ccagagtgcc | 900 |
| caagagcttc ccccttcaaca cctctgtggt gtacaagaag accctgtttg tggagttcac | 960 |
| tgaccacctg ttcaacattg ccaagcccag gcccccctgg atgggcctgc tgggccccac | 1020 |
| catccaggct gaggtgtatg acactgtggt gatcaccctg aagaacatgg ccagccaccc | 1080 |
| tgtgagcctg catgctgtgg gggtgagcta ctggaaggcc tctgaggggg ctgagtatga | 1140 |
| tgaccagacc agccagaggg agaaggagga tgacaaggtg ttccctgggg gcagccacac | 1200 |
| ctatgtgtgg caggtgctga aggagaatgg ccccatggcc tctgaccccc tgtgcctgac | 1260 |
| ctacagctac ctgagccatg tggacctggt gaaggacctg aactctggcc tgattggggc | 1320 |
| cctgctggtg tgcagggagg gcagcctggc caaggagaag acccagaccc tgcacaagtt | 1380 |
| catcctgctg tttgctgtgt tgatgagggg caagagctgg cactctgaaa ccaagaacag | 1440 |
| cctgatgcag gacagggatg ctgcctctgc cagggcctgg cccaagatgc acactgtgaa | 1500 |
| tggctatgtg aacaggagcc tgcctggcct gattggctgc cacaggaagt ctgtgtactg | 1560 |
| gcatgtgatt ggcatgggca cccccctga ggtgcacagc atcttcctgg agggccacac | 1620 |
| cttcctggtc aggaaccaca ggcaggccag cctggagatc agccccatca ccttcctgac | 1680 |
| tgcccagacc ctgctgatgg acctgggcca gttcctgctg ttctgccaca tcagcagcca | 1740 |
| ccagcatgat ggcatggagg cctatgtgaa ggtggacagc tgccctgagg agccccagct | 1800 |

```
gaggatgaag aacaatgagg aggctgagga ctatgatgat gacctgactg actctgagat   1860
ggatgtggtg aggtttgatg atgacaacag ccccagcttc atccagatca ggtctgtggc   1920
caagaagcac cccaagacct gggtgcacta cattgctgct gaggaggagg actgggacta   1980
tgcccccctg gtgctggccc ctgatgcacag gagctacaag agccagtacc tgaacaatgg   2040
cccccagagg attggcagga agtacaagaa ggtcaggttc atggcctaca ctgatgaaac   2100
cttcaagacc agggaggcca tccagcatga gtctggcatc ctgggccccc tgctgtatgg   2160
ggaggtgggg gacaccctgc tgatcatctt caagaaccag gccagcaggc cctacaacat   2220 ctaccccat ggcatcactg atgtgaggcc cctgtacagc aggaggctgc caagggggt    2280 gaagcacctg aaggacttcc ccatcctgcc tggggagatc ttcaagtaca gtggactgt    2340 gactgtggag gatggccccca ccaagtctga ccccaggtgc ctgaccagat actacagcag   2400
ctttgtgaac atggagaggg acctggcctc tggcctgatt ggccccctgc tgatctgcta   2460
caaggagtct gtggaccaga ggggcaacca gatcatgtct gacaagagga atgtgatcct   2520
gttctctgtg tttgatgaga acaggagctg gtacctgact gagaacatcc agaggttcct   2580
gcccaaccct gctggggtgc agctggagga ccctgagttc caggccagca acatcatgca   2640
cagcatcaat ggctatgtgt tgacagcct gcagctgtct gtgtgcctgc atgaggtggc    2700
ctactggtac atcctgagca ttggggccca gactgacttc ctgtctgtgt tcttctctgg   2760
ctacaccttc aagcacaaga tggtgtatga ggacaccctg accctgttcc ccttctctgg   2820
ggagactgtg ttcatgagca tggagaaccc tggcctgtgg attctgggct gccacaactc   2880
tgacttcagg aacagggggca tgactgccct gctgaaagtc tccagctgtg acaagaacac   2940
tggggactac tatgaggaca gctatgagga catctctgcc tacctgctga gcaagaacaa   3000
tgccattgag cccaggagct tcagccagaa ccccccagtg ctgaagaggc accagaggga   3060
gatcaccagg accaccctgc agtctgacca ggaggagatt gactatgatg acaccatctc   3120
tgtggagatg aagaaggagg actttgacat ctacgacgag gacgagaacc agagccccag   3180
gagcttccag aagaagacca ggcactactt cattgctgct gtggagaggc tgtgggacta   3240
tggcatgagc agcagccccc atgtgctgag gaacagggcc cagtctggct ctgtgcccca   3300
gttcaagaag gtggtgttcc aggagttcac tgatggcagc ttcacccagc ccctgtacag   3360
aggggagctg aatgagcacc tgggcctgct gggcccctac atcagggctg aggtggagga   3420
caacatcatg gtgaccttca ggaaccaggc cagcaggccc tacagcttct acagcagcct   3480
gatcagctat gaggaggacc agaggcaggg ggctgagccc aggaagaact tgtgaagcc    3540 caatgaaacc aagacctact tctggaaggt gcagcaccac atggccccca ccaaggatga   3600
gtttgactgc aaggcctggg cctacttctc tgatgtggac ctggagaagg atgtgcactc   3660
tggcctgatt ggccccctgc tggtgtgcca caccaacacc ctgaaccctg cccatggcag   3720
gcaggtgact gtgcaggagt ttgccctgtt cttcaccatc tttgatgaaa ccaagagctg   3780
gtacttcact gagaacatgg agaggaactg cagggccccc tgcaacatcc agatggagga   3840 ccccacctc aaggagaact acaggttcca tgccatcaat ggctacatca tggacaccct    3900
gcctggcctg tgatggccc aggaccagag atcaggtgg tacctgctga gcatgggcag     3960
caatgagaac atccacagca tccacttctc tggccatgtg ttcactgtga ggaagaagga   4020
ggagtacaag atgccctgt acaacctgta ccctgggggtg tttgagactg tggagatgct   4080
gcccagcaag gctggcatct ggaggggtgga gtgcctgatt ggggagcacc tgcatgctgg   4140
```

-continued

```
catgagcacc ctgttcctgg tgtacagcaa caagtgccag accccctgg gcatggcctc      4200 tggccacatc agggacttcc agatcactgc ctctggccag tatggccagt gggcccccaa      4260
gctggccagg ctgcactact ctggcagcat caatgcctgg agcaccaagg agcccttcag      4320
ctggatcaag gtggacctgc tggcccccat gatcatccat ggcatcaaga cccaggggggc     4380 caggcagaag ttcagcagcc tgtacatcag ccagttcatc atcatgtaca gcctggatgg      4440
caagaagtgg cagacctaca ggggcaacag cactggcacc ctgatggtgt tctttggcaa      4500
tgtggacagc tctggcatca agcacaacat cttcaacccc cccatcattg ccagatacat      4560
caggctgcac cccacccact acagcatcag gagcaccctg aggatggagc tgatgggctg      4620
tgacctgaac agctgcagca tgcccctggg catggagagc aaggccatct ctgatgccca      4680
gatcactgcc agcagctact tcaccaacat gtttgccacc tggagcccca gcaaggccag      4740
gctgcacctg cagggcagga gcaatgcctg gaggccccag gtcaacaacc ccaaggagtg      4800
gctgcaggtg gacttccaga agaccatgaa ggtgactggg gtgaccaccc aggggggtgaa     4860 gagcctgctg accagcatgt atgtgaagga gttcctgatc agcagcagcc aggatggcca      4920
ccagtggacc ctgttcttcc agaatggcaa ggtgaaggtg ttccagggca accaggacag      4980
cttcacccct gtggtgaaca gcctggaccc cccctgctg accagatacc tgaggattca      5040
cccccagagc tgggtgcacc agattgccct gaggatggag gtgctgggct gtgaggccca      5100
ggacctgtac tgacctcgag gcactgtcct ttcctaataa aatgaggaaa ttgcatcgca      5160
ttgtctgagt aggtgtcatt ctattctggg gggtggggtg gggcaggaca gcaaggggga      5220
ggattgggaa gacaatagca ggcatgctgg ggatgcggtg ggctctatgg gcactcgaca      5280
ggttaatttt taaaaagcag tcaaaagtcc aagtggccct tggcagcatt tactctctct      5340
gtttgctctg gttaataatc tcaggagcac aaacattcct ggaggcagga gaagaaatca      5400
acatcctgga cttatcctct gggcctctcc ccaccccag gagaggctca ggttaatttt      5460
taaaaagcag tcaaaagtcc aagtggccct tggcagcatt tactctctct gtttgctctg      5520
gttaataatc tcaggagcac aaacattcct ggaggcagga gaagaaatca acatcctgga      5580
cttatcctct gggcctctcc ccaccccag gagaggctgt cgagtggcgg ccgcaggaac      5640
ccctagtgat ggagttggcc actccctctc tgcgcgctcg ctcgctcact gaggccgggc      5700
gaccaaaggt cgcccgacgc ccgggctttg cccgggcggc ctcagtgagc gagcgagcgc      5760
gcagagaggg agtggccaa                                                  5779
```

<210> SEQ ID NO 21
<211> LENGTH: 5962
<212> TYPE: DNA
<213> ORGANISM: Adeno-Associated Virus 2

<400> SEQUENCE: 21

```
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgaccc ctctcacact       180
acctaaacca cgccaggaca acctctgctc ctctccaccg aaattccaag gggtcgagtg       240
gatgttggag gtggcatggg cccagagagg tctctgacct ctgccccagc tccaaggtca       300
gcaggcaggg agggctgtgt gtttgctgtt tgctgcttgc aatgtttgcc cattttaggg       360
acatgagtag gctgaagttt gttcagtgtg gacttcagag gcagcacaca aacagctgct       420
ggaggatggg aactgagggg ttggaagggg gcagggtgag cccagaaact cctgtgtgcc       480
```

```
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag gacagggccc tgtctcctca gcttcaggca ccaccactga cctgggacag    720
tgaatcgtaa gtactagcag ctacaatcca gctaccattc tgctttttatt ttatggttgg    780 gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt    1140 cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tggggtgag ctactggaag gcctctgagg gggctgagta   1320
tgatgaccag accagccaga gggagaagga ggatgacaag gtgttccctg ggggcagcca   1380
cacctatgtg tggcaggtgc tgaaggagaa tggccccatg gcctctgacc cctgtgcct    1440 gacctacagc tacctgagcc atgtggacct ggtgaaggac ctgaactctg gcctgattgg   1500
ggccctgctg gtgtgcaggg agggcagcct ggccaaggaa aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt   1680 gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag cacccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accaggagg ccatccagca tgagtctggc atcctgggcc cctgctgta    2340 tgggaggtg ggacaccc tgctgatcat cttcaagaac caggccagca ggccctacaa    2400
catctacccc catggcatca ctgatgtgag gccctgtac agcaggaggc tgcccaaggg   2460
ggtgaagcac ctgaaggact cccccatcct gcctggggag atcttcaagt acaagtggac   2520
tgtgactgtg gaggatggcc ccaccaagtc tgacccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
```

```
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca agatggtgta tgaggacacc ctgaccctgt tcccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg ctctgtgcc    3480
ccagttcaag aaggtggtgt tccaggagtt cactgatggc agcttcaccc agcccctgta    3540
cagagggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca gggggctgag cccaggaaga actttgtgaa    3720
gcccaatgaa accaagacct acttctggaa ggtgcagcac cacatggccc ccaccaagga    3780
tgagtttgac tgcaaggcct gggcctactt ctctgatgtg acctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020
ggacccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260
gctgccagc aaggctggca tctggagggt ggagtgcctg attggggagc acctgcatgc    4320
tggcatgagc accctgttcc tggtgtacag caacaagtgc cagaccccc tgggcatggc    4380
ctctggccac atcagggact ccagatcac tgcctctggc cagtatgcc agtgggcccc    4440
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac cccccatca ttgccagata    4740
catcaggctg caccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttcaccaa catgtttgcc acctggagcc ccagcaaggc    4920
caggctgcac ctgcagggca ggagcaatgc ctggaggccc caggtcaaca ccccaagga    4980
gtggctgcag gtggacttcc agaagaccat gaaggtgact ggggtgacca cccaggggt    5040
gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160
cagcttcacc cctgtggtga acagcctgga ccccccctg ctgaccagat acctgaggat    5220
```

-continued

```
tcaccccag agctgggtgc accagattgc cctgaggatg gaggtgctgg gctgtgaggc      5280
ccaggacctg tactgacctc gaggcactgt ccttccctaa taaaatgagg aaattgcatc      5340
gcattgtctg agtaggtgtc attctattct gggggtggg gtgggcagg acagcaaggg       5400 ggaggattgg gaagacaata gcaggcatgc tggggatgcg gtgggctcta tgggcactcg      5460
acaggttaat ttttaaaaag cagtcaaaag tccaagtggc ccttggcagc atttactctc      5520
tctgtttgct ctggttaata atctcaggag cacaaacatt cctggaggca ggagaagaaa      5580
tcaacatcct ggacttatcc tctgggcctc tccccacccc caggagaggc tcaggttaat      5640
ttttaaaaag cagtcaaaag tccaagtggc ccttggcagc atttactctc tctgtttgct      5700
ctggttaata atctcaggag cacaaacatt cctggaggca ggagaagaaa tcaacatcct      5760
ggacttatcc tctgggcctc tccccacccc caggagaggc tgtcgagtgg cggccgcagg      5820 aaccccctagt gatggagttg ccactccct ctctgcgcgc tcgctcgctc actgaggccg      5880
ggcgaccaaa ggtcgcccga cgccggggct tgcccgggc ggcctcagtg agcgagcgag      5940
cgcgcagaga gggagtggcc aa                                              5962

<210> SEQ ID NO 22
<211> LENGTH: 5919
<212> TYPE: DNA
<213> ORGANISM: Adeno-Associated Virus 2

<400> SEQUENCE: 22
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgta ggctcagagg cacacaggag       180
tttctgggct caccctgccc ccttccaacc cctcagttcc catcctccag cagctgtttg       240
tgtgctgcct ctgaagtcca cactgaacaa acttcagcct actcatgtcc ctaaaatggg       300
caaacattgc aagcagcaaa cagcaaacac acagccctcc ctgcctgctg accttggagc       360
tggggcagag gtcagagacc tctctggcc catgccacct ccaacatcca ctcgacccct       420
tggaatttcg gtggagagga gcagaggttg tcctggcgtg gtttaggtag tgtgagaggg       480
gtcgacgatc ttgctaccag tggaacagcc actaaggatt ctgcagtgag agcagagggc       540
cagctaagtg gtactctccc agagactgtc tgactcacgc cacccctcc accttggaca       600 caggacgctg tggtttctga gccaggtaca atgactcctt tcggtaagtg cagtggaagc       660
tgtacactgc ccaggcaaag cgtccgggca gcgtaggcgg gcgactcaga tcccagccag       720
tggacttagc ccctgtttgc tcctccgata actgggtga ccttggttaa tattccaccag      780 cagcctcccc cgttgcccct ctggatccac tgcttaaata cggacgagga cagggccctg      840
tctcctcagc ttcaggcacc accactgacc tgggacagtg aatcgtaagt atgcctttca      900
ctgcgagagt ttctggagag gcttctgagc tccccatggc ccaggcaggc agcaggtctg      960
gggcaggagg gggttgtgg agtgggtatc cgcctgctga ggtgcagggc agatcatcat     1020
gtgccttgac tcggggcctg ccccccccat ctctgtcttg caggacaatt gccgtcttct     1080
gtctcgtggg gcatcctcct gctggcaggc ctgtgctgcc tggtccctgt ctccctggct     1140
gaggaccggc caccatgcag attgagctga gcacctgctt cttcctgtgc ctgctgaggt     1200
tctgcttctc tgccaccagg agatactacc tgggggctgt ggagctgagc tgggactaca     1260
tgcagtctga cctggggag ctgcctgtgg atgccaggtt cccccccaga gtgcccaaga     1320
```

```
gcttcccctt caacacctct gtggtgtaca agaagaccct gtttgtggag ttcactgacc   1380
acctgttcaa cattgccaag cccaggcccc cctggatggg cctgctgggc ccaccatcc   1440
aggctgaggt gtatgacact gtggtgatca ccctgaagaa catggccagc cacctgtga   1500
gcctgcatgc tgtgggggtg agctactgga aggcctctga gggggctgag tatgatgacc   1560
agaccagcca gagggagaag gaggatgaca aggtgttccc tgggggcagc cacacctatg   1620
tgtggcaggt gctgaaggag aatggcccca tggcctctga cccctgtgc ctgacctaca   1680
gctacctgag ccatgtggac ctggtgaagg acctgaactc tggcctgatt ggggccctgc   1740
tggtgtgcag ggagggcagc ctggccaagg agaagaccca gacctgcac aagttcatcc   1800
tgctgtttgc tgtgtttgat gagggcaaga gctggcactc tgaaaccaag aacagcctga   1860
tgcaggacag ggatgctgcc tctgccaggg cctggcccaa gatgcacact gtgaatggct   1920
atgtgaacag gagcctgcct ggcctgattg ctgccacag gaagtctgtg tactggcatg   1980
tgattggcat gggcaccacc cctgaggtgc acagcatctt cctggagggc acaccttcc   2040
tggtcaggaa ccacaggcag gccagcctgg agatcagccc catcaccttc ctgactgccc   2100
agaccctgct gatggacctg ggccagttcc tgctgttctg ccacatcagc agccaccagc   2160
atgatggcat ggaggcctat gtgaaggtgg acagctgccc tgaggagccc agctgagga   2220
tgaagaacaa tgaggaggct gaggactatg atgatgacct gactgactct gagatggatg   2280
tggtgaggtt tgatgatgac aacagcccca gcttcatcca gatcaggtct gtggccaaga   2340
agcaccccaa gacctgggtg cactacattg ctgctgagga ggaggactgg gactatgccc   2400
ccctggtgct ggcccctgat gacaggagct acaagagcca gtacctgaac aatggccccc   2460
agaggattgg caggaagtac aagaaggtca ggttcatggc ctacactgat gaaaccttca   2520
agaccaggga ggccatccag catgagtctg gcatcctggg cccctgctg tatggggagg   2580
tggggacac cctgctgatc atcttcaaga accaggccag caggccctac aacatctacc   2640
cccatggcat cactgatgtg aggccctgt acagcaggag gctgcccaag ggggtgaagc   2700
acctgaagga cttcccatc ctgcctgggg agatcttcaa gtacaagtgg actgtgactg   2760
tggaggatgg ccccaccaag tctgaccca ggtgcctgac cagatactac agcagctttg   2820
tgaacatgga gagggacctg gcctctggcc tgattggccc cctgctgatc tgctacaagg   2880
agtctgtgga ccagaggggc aaccagatca tgtctgacaa gaggaatgtg atcctgttct   2940
ctgtgtttga tgagaacagg agctggtacc tgactgagaa catccagagg ttcctgccca   3000
accctgctgg ggtgcagctg gaggaccctg agttccaggc cagcaacatc atgcacagca   3060
tcaatggcta tgtgtttgac agcctgcagc tgtctgtgtg cctgcatgag gtggcctact   3120
ggtacatcct gagcattggg gcccagactg acttcctgtc tgtgttcttc tctggctaca   3180
ccttcaagca caagatggtg tatgaggaca ccctgaccct gttccccttc tctggggaga   3240
ctgtgttcat gagcatggag aaccctggcc tgtggattct gggctgccac aactctgact   3300
tcaggaacag gggcatgact gccctgctga aagtctccag ctgtgacaag aacactgggg   3360
actactatga ggacagctat gaggacatct ctgcctacct gctgagcaag aacaatgcca   3420
ttgagcccag gagcttcagc cagaaccccc cagtgctgaa aggcaccag agggagatca   3480
ccaggaccac cctgcagtct gaccaggagg agattgacta tgatgacacc atctctgtgg   3540
agatgaagaa ggaggacttt gacatctacg acgaggacga gaaccagagc ccaggagct   3600
tccagaagaa gaccaggcac tacttcattg ctgctgtgga ggctgtgg gactatggca   3660
tgagcagcag ccccatgtg ctgaggaaca gggcccagtc tggctctgtg cccagttca   3720
```

```
agaaggtggt gttccaggag ttcactgatg gcagcttcac ccagcccctg tacagagggg   3780
agctgaatga gcacctgggc ctgctgggcc cctacatcag ggctgaggtg gaggacaaca   3840
tcatggtgac cttcaggaac caggccagca ggccctacag cttctacagc agcctgatca   3900
gctatgagga ggaccagagg caggggctg agcccaggaa gaactttgtg aagcccaatg    3960
aaaccaagac ctacttctgg aaggtgcagc accacatggc ccccaccaag gatgagtttg   4020
actgcaaggc ctgggcctac ttctctgatg tggacctgga gaaggatgtg cactctggcc   4080
tgattggccc cctgctggtg tgccacacca cacccctgaa ccctgcccat ggcaggcagg   4140
tgactgtgca ggagttttgcc ctgttcttca ccatctttga tgaaaccaag agctggtact   4200
tcactgagaa catggagagg aactgcaggg cccctgcaa catccagatg gaggaccccca   4260 ccttcaagga gaactacagg ttccatgcca tcaatggcta catcatggac accctgcctg   4320
gcctggtgat ggcccaggac cagaggatca ggtggtacct gctgagcatg ggcagcaatg   4380
agaacatcca cagcatccac ttctctggcc atgtgttcac tgtgaggaag aaggaggagt   4440
acaagatggc cctgtacaac ctgtaccctg gggtgtttga gactgtggag atgctgccca   4500
gcaaggctgg catctggagg gtggagtgcc tgattgggga gcacctgcat gctggcatga   4560
gcaccctgtt cctggtgtac agcaacaagt gccagacccc cctgggcatg gcctctggcc   4620
acatcaggga cttccagatc actgcctctg gccagtatgg ccagtgggcc ccaagctgg    4680 ccaggctgca ctactctggc agcatcaatg cctggagcac caaggagccc ttcagctgga   4740
tcaaggtgga cctgctggcc ccatgatca tccatggcat caagacccag ggggccaggc   4800
agaagttcag cagcctgtac atcagccagt tcatcatcat gtacagcctg gatggcaaga   4860
agtggcagac ctacaggggc aacagcactg gcaccctgat ggtgttcttt ggcaatgtgg   4920
acagctctgg catcaagcac aacatcttca acccccccat cattgccaga tacatcaggc   4980
tgcaccccac ccactacagc atcaggagca ccctgaggat ggagctgatg ggctgtgacc   5040
tgaacagctg cagcatgccc ctgggcatgg agagcaaggc catctctgat gcccagatca   5100
ctgccagcag ctacttcacc aacatgtttg ccacctggag ccccagcaag gccaggctgc   5160
acctgcaggg caggagcaat gcctggaggc cccaggtcaa caaccccaag gagtggctgc   5220
aggtggactt ccagaagacc atgaaggtga ctggggtgac cacccagggg gtgaagagcc   5280
tgctgaccag catgtatgtg aaggagttcc tgatcagcag cagccaggat ggccaccagt   5340
ggaccctgtt cttccagaat ggcaaggtga aggtgttcca gggcaaccag gacagcttca   5400
cccctgtggt gaacagcctg gaccccccccc tgctgaccag atacctgagg attcacccccc   5460 agagctgggt gcaccagatt gccctgagga tggaggtgct gggctgtgag gcccaggacc   5520
tgtactgagc tcgagctgtg ccttctagtt gccagccatc tgttgtttgc cctcccccg    5580 tgccttcctt gaccctggaa ggtgccactc ccactgtcct ttcctaataa aatgaggaaa   5640
ttgcatcgca ttgtctgagt aggtgtcatt ctattctggg gggtggggtg gggcaggaca   5700
gcaaggggga ggattgggaa gacaatagca ggcatgctgg ggatgcggtg ggctctatgg   5760
accggtgcgg ccgcaggaac ccctagtgat ggagttggcc actccctctc tgcgcgctcg   5820
ctcgctcact gaggccgggc gaccaaaggt cgcccgacgc ccgggctttg cccgggcggc   5880
ctcagtgagc gagcgagcgc gcagagaggg agtggccaa                          5919

<210> SEQ ID NO 23
<211> LENGTH: 5306
<212> TYPE: DNA
```

<213> ORGANISM: Adeno-Associated Virus 2

<400> SEQUENCE: 23

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttaaacgt cgaccctaaa     180
atgggcaaac attgcaagca gcaaacagca aactgacctt ggagctgggg cagaggtcag     240
agacctctct gggcactcga ccccttggaa tttcggtgga gaggagcaga ggtacacagc     300
cctccctgcc tgcccatgc cacctccaac atctgtcctg cgtggttta ggtagtgtga      360
gaggggaatg actcctttcg gtaagtgcag tggaagctgt acactgccca ggcaaagcgt     420
ccgggcagcg taggcgggcg actcagatcc cagccagtgg acttagcccc tgtttgctcc     480
tccgataact ggggtgacct tggttaatat tcaccagcag cctcccccgt tgcccctctg     540
gatccactgc ttaaatacgg acgaggacag ggcctgtct cctcagcttc aggcaccacc      600
actgacctgg gacagtgaat cgcgatcgca ctgcttaaat acggacgagg acagggccct     660
gtctcctcag cttcaggcac caccactgac ctgggacagt gaatcgcgat cgccaccatg     720
cagattgagc tgagcacctg cttcttcctg tgcctgctga ggttctgctt ctctgccacc     780
aggagatact acctgggggc tgtggagctg agctgggact acatgcagtc tgacctgggg     840
gagctgcctg tggatgccag gttccccccc agagtgccca gagcttccc cttcaacacc      900
tctgtggtgt acaagaagac cctgtttgtg gagttcactg accacctgtt caacattgcc     960
aagcccaggc ccccctggat gggcctgctg gccccacca tccaggctga ggtgtatgac      1020
actgtggtga tcaccctgaa gaacatggcc agccaccctg tgagcctgca tgctgtgggg    1080
gtgagctact ggaaggcctc tgaggggggct gagtatgatg accagaccag ccagaggag    1140
aaggaggatg acaaggtgtt ccctgggggc agccacacct atgtgtggca ggtgctgaag    1200
gagaatggcc ccatggcctc tgaccccctg tgcctgacct acagctacct gagccatgtg    1260
gacctggtga aggacctgaa ctctggcctg attggggccc tgctggtgtg cagggagggc    1320
agcctggcca aggagaagac ccagaccctg cacaagttca tcctgctgtt tgctgtgttt    1380
gatgagggca gagctggca ctctgaaacc aagaacagcc tgatgcagga cagggatgct    1440
gcctctgcca gggcctggcc caagatgcac actgtgaatg ctatgtgaa caggagcctg     1500
cctggcctga ttggctgcca caggaagtct gtgtactggc atgtgattgg catgggcacc    1560
accccctgagg tgcacagcat cttcctggag ggccacacct tcctggtcag gaaccacagg    1620
caggccagcc tggagatcag ccccatcacc ttcctgactg cccagaccct gctgatggac    1680
ctgggccagt cctgctgtt ctgccacatc agcagccacc agcatgatgg catggaggcc     1740
tatgtgaagg tggacagctg ccctgaggag cccagctga ggatgaagaa caatgaggag    1800
gctgaggact atgatgatga cctgactgac tctgagatgg atgtggtgag gtttgatgat    1860
gacaacagcc ccagcttcat ccagatcagg tctgtggcca gaagcacccc caagacctgg    1920
gtgcactaca ttgctgctga ggaggaggac tgggactatg cccccctggt gctggcccct    1980
gatgacagga gctacaagag ccagtacctg aacaatggcc cccagaggat tggcaggaag    2040
tacaagaagg tcaggttcat ggcctacact gatgaaacct caagaccag ggaggccatc     2100
cagcatgagt ctggcatcct gggcccctg ctgtatgggg aggtggggga cacctgctg    2160
atcatcttca agaaccaggc cagcaggccc tacaacatct accccatgg catcactgat    2220
gtgaggcccc tgtacagcag gaggctgccc aaggggtga agcacctgaa ggacttcccc   2280
```

```
atcctgcctg gggagatctt caagtacaag tggactgtga ctgtggagga tggccccacc   2340
aagtctgacc ccaggtgcct gaccagatac tacagcagct ttgtgaacat ggagagggac   2400
ctggcctctg gcctgattgg ccccctgctg atctgctaca aggagtctgt ggaccagagg   2460
ggcaaccaga tcatgtctga caagaggaat gtgatcctgt tctctgtgtt tgatgagaac   2520
aggagctggt acctgactga aacatccag aggttcctgc ccaaccctgc tggggtgcag   2580
ctggaggacc ctgagttcca ggccagcaac atcatgcaca gcatcaatgg ctatgtgttt   2640
gacagcctgc agctgtctgt gtgcctgcat gaggtggcct actggtacat cctgagcatt   2700
ggggcccaga ctgacttcct gtctgtgttc ttctctggct acaccttcaa gcacaagatg   2760
gtgtatgagg acaccctgac cctgttcccc ttctctgggg agactgtgtt catgagcatg   2820
gagaaccctg gctgtggat tctgggctgc acaactctg acttcaggaa caggggcatg   2880
actgccctgc tgaaagtctc cagctgtgac aagaacactg gggactacta tgaggacagc   2940
tatgaggaca tctctgccta cctgctgagc aagaacaatg ccattgagcc caggagcttc   3000
agccagaacc ccccagtgct gaagaggcac cagagggaga tcaccaggac caccctgcag   3060
tctgaccagg aggagattga ctatgatgac accatctctg tggagatgaa gaaggaggac   3120
tttgacatct acgacgagga cgagaaccag agccccagga gcttccagaa gaagaccagg   3180
cactacttca ttgctgctgt ggagaggctg tgggactatg gcatgagcag cagcccccat   3240
gtgctgagga acagggccca gtctggctct gtgccccagt tcaagaaggt ggtgttccag   3300
gagttcactg atggcagctt cacccagccc ctgtacagag gggagctgaa tgagcacctg   3360
ggcctgctgg gcccctacat cagggctgag gtggaggaca acatcatggt gaccttcagg   3420
aaccaggcca gcaggcccta cagcttctac agcagcctga tcagctatga ggaggaccag   3480
aggcagggg ctgagcccag gaagaacttt gtgaagccca tgaaaccaa gacctacttc   3540
tggaaggtgc agcaccacat gggcccccacc aaggatgagt ttgactgcaa ggcctgggcc   3600
tacttctctg atgtggacct ggagaaggat gtgcactctg gcctgattgg ccccctgctg   3660
gtgtgccaca ccaacaccct gaaccctgcc catggcaggc aggtgactgt gcaggagttt   3720
gccctgttct tcaccatctt tgatgaaacc aagagctggt acttcactga aacatggag   3780
aggaactgca gggcccccctg caacatccag atggaggacc ccaccttcaa ggagaactac   3840
aggttccatg ccatcaatgg ctacatcatg gacacccctgc ctggcctggt gatggcccag   3900
gaccagagga tcaggtggta cctgctgagc atgggcagca atgagaacat ccacagcatc   3960
cacttctctg gccatgtgtt cactgtgagg aagaaggagg agtacaagat ggccctgtac   4020
aacctgtacc ctgggggtgtt tgagactgtg gagatgctgc ccagcaaggc tggcatctgg   4080
agggtggagt gcctgattgg ggagcacctg catgctggca tgagcaccct gttcctggtg   4140
tacagcaaca agtgccagac ccccctgggc atggcctctg ccacatcag ggacttccag   4200
atcactgcct ctggccagta tggccagtgg gcccccaagc tggccaggct gcactactct   4260
ggcagcatca atgcctggag caccaaggag cccttcagct ggatcaaggt ggacctgctg   4320
gcccccatga tcatccatgg catcaagacc caggggggcca ggcagaagtt cagcagcctg   4380
tacatcagcc agttcatcat catgtacagc ctggatggca gaagtggca gacctacagg   4440
ggcaacagca ctggcaccct gatggtgttc tttggcaatg tggacagctc tggcatcaag   4500
cacaacatct tcaacccccc catcattgcc agatacatca ggctgcaccc cacccactac   4560
agcatcagga gcacccctgag gatggagctg atgggctgtg acctgaacag ctgcagcatg   4620
```

| | |
|---|---|
| cccctgggca tggagagcaa ggccatctct gatgcccaga tcactgccag cagctacttc | 4680 |
| accaacatgt ttgccacctg gagccccagc aaggccaggc tgcacctgca gggcaggagc | 4740 |
| aatgcctgga ggccccaggt caacaacccc aaggagtggc tgcaggtgga cttccagaag | 4800 |
| accatgaagg tgactggggt gaccaccag ggggtgaaga gcctgctgac cagcatgtat | 4860 |
| gtgaaggagt tcctgatcag cagcagccag gatggccacc agtggaccct gttcttccag | 4920 |
| aatggcaagt gaaggtgtt ccagggcaac caggacagct tcacccctgt ggtgaacagc | 4980 |
| ctggacccc cctgctgac cagatacctg aggattcacc cccagagctg ggtgcaccag | 5040 |
| attgccctga ggatggaggt gctgggctgt gaggcccagg acctgtactg acctcgagga | 5100 |
| ataaaggaaa tttattttca ttgcaatagt gtgttggttt tttgtgtcac gtggcggccg | 5160 |
| caggaacccc tagtgatgga gttggccact ccctctctgc gcgctcgctc gctcactgag | 5220 |
| gccgggcgac caaaggtcgc ccgacgcccg ggctttgccc gggcggcctc agtgagcgag | 5280 |
| cgagcgcgca gagagggagt ggccaa | 5306 |

<210> SEQ ID NO 24
<211> LENGTH: 5461
<212> TYPE: DNA
<213> ORGANISM: Adeno-Associated Virus 2

<400> SEQUENCE: 24

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgactt tatttgccac | 180 |
| aaaaacccta tcagatgggc gtctttatca tttccattgt acagatgggg aaacaggctt | 240 |
| cggggtcggg gcatagccac ttactgacga ctccccaccc agcaagtggt tttgaacccg | 300 |
| gaccctctca cactacctaa accacgccag acaacctct gctcctctcc accgaaattc | 360 |
| caaggggtcg agtggatgtt ggaggtggca tgggcccaga gaggtctctg acctctgccc | 420 |
| cagctccaag gtcagcaggc agggagggct gtgtgtttgc tgtttgctgc ttgcaatgtt | 480 |
| tgcccatttt agggacatga gtaggctgaa gtttgttcag tgtggacttc agaggcagca | 540 |
| cacaaacagc tgctggagga tgggaactga ggggttggaa gggggcaggg tgagcccaga | 600 |
| aactcctgtg tgcctctgag cctgcagacg cgaaacgtcg actggacaca ggacgctgtg | 660 |
| gtttctgagc caggggggcga ctcagatccc agccagtgga cttagcccct gtttgctcct | 720 |
| ccgataactg gggtgacctt ggttaatatt caccagcagc ctccccgtt gcccctctgg | 780 |
| atccactgct taaatacgga cgaggacagg gccctgtctc ctcagcttca ggcaccacca | 840 |
| ctgacctggg acagtgaatc gcgatcgcca ccatgcagat tgagctgagc acctgcttct | 900 |
| tcctgtgcct gctgaggttc tgcttctctg ccaccaggag atactacctg ggggctgtgg | 960 |
| agctgagctg ggactacatg cagtctgacc tggggggagct gcctgtggat gccaggttcc | 1020 |
| ccccagagt gcccaagagc ttccccttca acacctctgt ggtgtacaag aagacccctgt | 1080 |
| ttgtggagtt cactgaccac ctgttcaaca ttgccaagcc caggccccc tggatgggcc | 1140 |
| tgctgggccc caccatccag gctgaggtgt atgacactgt ggtgatcacc ctgaagaaca | 1200 |
| tggccagcca cctgtgagc ctgcatgctg tggggtgag ctactggaag gcctctgagg | 1260 |
| gggctgagta tgatgaccag accagccaga gggagaagga ggatgacaag gtgttccctg | 1320 |
| ggggcagcca cacctatgtg tggcaggtgc tgaaggagaa tggcccatg gcctctgacc | 1380 |
| ccctgtgcct gacctacagc tacctgagcc atgtggacct ggtgaaggac ctgaactctg | 1440 |

```
gcctgattgg ggccctgctg gtgtgcaggg agggcagcct ggccaaggag aagacccaga    1500
ccctgcacaa gttcatcctg ctgtttgctg tgtttgatga gggcaagagc tggcactctg    1560
aaaccaagaa cagcctgatg caggacaggg atgctgcctc tgccaggcc tggcccaaga     1620 tgcacactgt gaatggctat gtgaacagga gcctgcctgg cctgattggc tgccacagga    1680
agtctgtgta ctggcatgtg attggcatgg gcaccacccc tgaggtgcac agcatcttcc    1740
tggagggcca caccttcctg gtcaggaacc acaggcaggc cagcctggag atcagcccca    1800
tcaccttcct gactgcccag accctgctga tggacctggg ccagttcctg ctgttctgcc    1860
acatcagcag ccaccagcat gatggcatgg aggcctatgt gaaggtggac agctgccctg    1920
aggagcccca gctgaggatg aagaacaatg aggaggctga ggactatgat gatgacctga    1980
ctgactctga gatggatgtg gtgaggtttg atgatgacaa cagccccagc ttcatccaga    2040
tcaggtctgt ggccaagaag cacccccaag acctgggtgca ctacattgct gctgaggagg    2100
aggactggga ctatgccccc ctggtgctgg cccctgatga caggagctac aagagccagt    2160
acctgaacaa tggcccccag aggattggca ggaagtacaa gaaggtcagg ttcatggcct    2220
acactgatga aaccttcaag accagggagg ccatccagca tgagtctggc atcctgggcc    2280
ccctgctgta tggggaggtg ggggacaccc tgctgatcat cttcaagaac caggccagca    2340
ggccctacaa catctacccc catggcatca ctgatgtgag gcccctgtac agcaggaggc    2400
tgcccaaggg ggtgaagcac ctgaaggact cccccatcct gcctggggag atcttcaagt    2460
acaagtggac tgtgactgtg gaggatggcc ccaccaagtc tgaccccagg tgcctgacca    2520
gatactacag cagctttgtg aacatggaga gggacctggc ctctggcctg attggccccc    2580
tgctgatctg ctacaaggag tctgtggacc agagggcaa ccagatcatg tctgacaaga    2640
ggaatgtgat cctgttctct gtgtttgatg agaacaggag ctggtacctg actgagaaca    2700
tccagaggtt cctgcccaac cctgctgggg tgcagctgga ggaccctgag ttccaggcca    2760
gcaacatcat gcacagcatc aatggctatg tgtttgacag cctgcagctg tctgtgtgcc    2820
tgcatgaggt ggcctactgg tacatcctga gcattggggc ccagactgac ttcctgtctg    2880
tgttcttctc tggctacacc ttcaagcaca agatggtgta tgaggacacc ctgacccctgt   2940
```

```
aggatgtgca ctctggcctg attggccccc tgctggtgtg ccacaccaac ccctgaacc    3840 ctgcccatgg caggcaggtg actgtgcagg agtttgccct gttcttcacc atctttgatg    3900
aaaccaagag ctggtacttc actgagaaca tggagaggaa ctgcagggcc ccctgcaaca    3960
tccagatgga ggaccccacc ttcaaggaga actacaggtt ccatgccatc aatggctaca    4020
tcatggacac cctgcctggc ctggtgatgg cccaggacca gaggatcagg tggtacctgc    4080
tgagcatggg cagcaatgag aacatccaca gcatccactt ctctggccat gtgttcactg    4140
tgaggaagaa ggaggagtac aagatggccc tgtacaacct gtaccctggg gtgtttgaga    4200
ctgtggagat gctgcccagc aaggctgcac tctggagggt ggagtgcctg attggggagc    4260
acctgcatgc tggcatgagc accctgttcc tggtgtacag caacaagtgc cagaccccc    4320 tgggcatggc ctctggccac atcagggact tccagatcac tgcctctggc cagtatggcc    4380
agtgggcccc caagctggcc aggctgcact actctggcag catcaatgcc tggagcacca    4440
aggagccctt cagctggatc aaggtggacc tgctggcccc catgatcatc catggcatca    4500
agacccaggg ggccaggcag aagttcagca gcctgtacat cagccagttc atcatcatgt    4560
acagcctgga tggcaagaag tggcagacct acaggggcaa cagcactggc accctgatgg    4620
tgttctttgg caatgtggac agctctggca tcaagcacaa catcttcaac ccccccatca    4680
ttgccagata catcaggctg caccccaccc actacagcat caggagcacc ctgaggatgg    4740
agctgatggg ctgtgacctg aacagctgca gcatgccct gggcatggag agcaaggcca    4800
tctctgatgc ccagatcact gccagcagct acttcaccaa catgtttgcc acctggagcc    4860
ccagcaaggc caggctgcac ctgcaggca ggagcaatgc ctggaggccc caggtcaaca    4920
accccaagga gtggctgcag gtggacttcc agaagaccat gaaggtgact ggggtgacca    4980
cccagggggt gaagagcctg ctgaccagca tgtatgtgaa ggagttcctg atcagcagca    5040
gccaggatgg ccaccagtgg accctgttct tccagaatgg caaggtgaag gtgttccagg    5100
gcaaccagga cagcttcacc cctgtggtga acagcctgga cccccccctg ctgaccagat    5160
acctgaggat tcaccccag agctgggtgc accagattgc cctgaggatg gaggtgctgg    5220
gctgtgaggc ccaggacctg tactgacctc gaggaataaa ggaaatttat tttcattgca    5280
atagtgtgtt ggtttttttgt gtcacgtggc ggccgcagga ccccctagtg atggagttgg    5340
ccactccctc tctgcgcgct cgctcgctca ctgaggccgg gcgaccaaag gtcgcccgac    5400
gcccgggctt tgcccgggcg gcctcagtga gcgagcgagc gcgcagagag ggagtggcca    5460
a                                                                  5461
```

<210> SEQ ID NO 25
<211> LENGTH: 5327
<212> TYPE: DNA
<213> ORGANISM: Adeno-Associated Virus 2

<400> SEQUENCE: 25

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc catttaggg    360 acatgagtag gctgaagttt gttcagtgtg gacttcagag gcagcacaca aacagctgct    420
```

```
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttccccc cagagtgccc    900
aagagcttcc ccttcaacac ctctgtggtg tacaagaaga ccctgtttgt ggagttcact    960
gaccacctgt tcaacattgc caagcccagg ccccctgga tgggcctgct gggccccacc   1020
atccaggctg aggtgtatga cactgtggtg atcaccctga agaacatggc cagccaccct   1080
gtgagcctgc atgctgtggg ggtgagctac tggaaggcct ctgaggggc tgagtatgat   1140
gaccagacca gccagaggga aaggaggat gacaaggtgt ccctgggggg cagccacacc   1200
tatgtgtggc aggtgctgaa ggagaatggc cccatggcct ctgaccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc caagatgca cactgtgaat   1500
ggctatgtga acaggagcct gcctggcctg attggctgcc acaggaagtc tgtgtactgg   1560
catgtgattg gcatgggcac caccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagc ccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggcccct gctgtatggg   2160
gaggtggggg acaccctgct gatcatcttc aagaaccagg ccagcaggcc ctacaacatc   2220
tacccccatg gcatcactga tgtgaggccc ctgtacagca ggaggctgcc caaggggtg   2280
aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gccccctgct gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggcagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
```

```
tacaccttca agcacaagat ggtgtatgag gacaccctga ccctgttccc cttctctggg    2820
gagactgtgt tcatgagcat ggagaaccct ggcctgtgga ttctgggctg ccacaactct    2880
gacttcagga acaggggcat gactgccctg ctgaaagtct ccagctgtga caagaacact    2940
ggggactact atgaggacag ctatgaggac atctctgcct acctgctgag caagaacaat    3000
gccattgagc ccaggagctt cagccagaac cccccagtgc tgaagaggca ccagagggag    3060
atcaccagga ccaccctgca gtctgaccag gaggagattg actatgatga ccatctctct    3120
gtggagatga agaaggagga ctttgacatc tacgacgagg acgagaacca gagccccagg    3180
agcttccaga agaagaccag gcactacttc attgctgctg tggagaggct gtgggactat    3240
ggcatgagca gcagccccca tgtgctgagg aacagggccc agtctggctc tgtgccccag    3300
ttcaagaagg tggtgttcca ggagttcact gatggcagct tcacccagcc cctgtacaga    3360
ggggagctga atgagcacct gggcctgctg ggcccctaca tcagggctga ggtggaggac    3420
aacatcatgg tgaccttcag gaaccaggcc agcaggccct acagcttcta cagcagcctg    3480
atcagctatg aggaggacca gaggcagggg gctgagccca ggaagaactt tgtgaagccc    3540
aatgaaacca agacctactt ctggaaggtg cagcaccaca tggcccccac caaggatgag    3600
tttgactgca aggcctgggc ctacttctct gatgtggacc tggagaagga tgtgcactct    3660
ggcctgattg gcccctgct ggtgtgccac accaacaccc tgaaccctgc ccatggcagg    3720
caggtgactg tgcaggagtt tgccctgttc ttcaccatct tgatgaaac caagagctgg    3780 tacttcactg agaacatgga gaggaactgc agggcccct gcaacatcca gatggaggac    3840
cccaccttca aggagaacta caggttccat gccatcaatg ctacatcat ggacaccctg    3900 cctggcctgg tgatggccca ggaccagagg atcaggtggt acctgctgag catgggcagc    3960
aatgagaaca tccacagcat ccacttctct ggccatgtgt tcactgtgag gaagaaggag    4020
gagtacaaga tggccctgta caacctgtac cctggggtgt ttgagactgt ggagatgctg    4080
cccagcaagg ctggcatctg gagggtggag tgcctgattg gggagcacct gcatgctggc    4140
atgagcaccc tgttcctggt gtacagcaac aagtgccaga cccccctggg catggcctct    4200
ggccacatca gggacttcca gatcactgcc tctggccagt atggccagtg ggcccccaag    4260
ctggccaggc tgcactactc tggcagcatc aatgcctgga gcaccaagga gcccttcagc    4320
tggatcaagg tggacctgct ggcccccatg atcatccatg gcatcaagac caggggggcc    4380
aggcagaagt tcagcagcct gtacatcagc cagttcatca tcatgtacag cctggatggc    4440
aagaagtggc agacctacag gggcaacagc actggcaccc tgatggtgtt ctttggcaat    4500
gtggacagct ctggcatcaa gcacaacatc ttcaaccccc ccatcattgc cagatacatc    4560
aggctgcacc ccacccacta cagcatcagg agcaccctga ggatggagct gatgggctgt    4620
gacctgaaca gctgcagcat gcccctgggc atggagagca aggccatctc tgatgcccag    4680
atcactgcca gcagctactt caccaacatg tttgccacct ggagcccag caaggccagg    4740 ctgcacctgc agggcaggag caatgcctgg aggccccagg tcaacaaccc caaggagtgg    4800
ctgcaggtgg acttccagaa gaccatgaag gtgactgggg tgaccaccca gggggtgaag    4860
agcctgctga ccagcatgta tgtgaaggag ttcctgatca gcagcagcca ggatggccac    4920
cagtggaccc tgttcttcca gaatggcaag gtgaaggtgt tccagggcaa ccaggacagc    4980
ttcacccctg tggtgaacag cctggacccc cccctgctga ccagatacct gaggattcac    5040
ccccagagct gggtgcacca gattgccctg aggatggagg tgctgggctg tgaggccag    5100 gacctgtact gacctcgagg aataaaggaa atttatttc attgcaatag tgtgttggtt    5160
```

```
ttttgtgtca cgtggcggcc gcaggaaccc ctagtgatgg agttggccac tccctctctg      5220
cgcgctcgct cgctcactga ggccgggcga ccaaaggtcg cccgacgccc gggctttgcc      5280
cgggcggcct cagtgagcga gcgagcgcgc agagagggag tggccaa                   5327
```

<210> SEQ ID NO 26
<211> LENGTH: 5309
<212> TYPE: DNA
<213> ORGANISM: Adeno-Associated Virus 2

<400> SEQUENCE: 26

```
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtc tgcaggctca gaggcacaca       180
ggagtttctg ggctcaccct gccccctccc aaccctcag ttcccatcct ccagcagctg       240
tttgtgtgct gcctctgaag tccacactga acaaacttca gcctactcat gtccctaaaa      300
tgggcaaaca ttgcaagcag caaacagcaa acacacagcc ctccctgcct gctgaccttg      360
gagctggggc agaggtcaga gacctctctg ggcccatgcc acctccaaca tccactcgac      420
cccttggaat tcggtggag aggagcagag gttgtcctgg cgtggtttag gtagtgtgag      480
aggggtcgac tggacacagg acgctgtggt ttctgagcca gggggcgact cagatcccag      540
ccagtggact tagcccctgt tgctcctcc gataactggg gtgaccttgg ttaatattca      600
ccagcagcct cccccgttgc ccctctggat ccactgctta aatacggacg aggacagggc      660
cctgtctcct cagcttcagg caccaccact gacctgggac agtgaatcgc gatcgccacc      720
atgcagattg agctgagcac ctgcttcttc ctgtgcctgc tgaggttctg cttctctgcc      780
accaggagat actacctggg ggctgtggag ctgagctgga ctacatgca gtctgacctg      840 ggggagctgc ctgtggatgc caggttcccc ccagagtgc caagagctt ccccttcaac      900 acctctgtgg tgtacaagaa gacctgtttt gtggagttca ctgaccacct gttcaacatt      960
gccaagccca ggccccctg gatgggcctg ctgggcccca ccatccaggc tgaggtgtat     1020
gacactgtgg tgatcaccct gaagaacatg gccagccacc ctgtgagcct gcatgctgtg     1080
ggggtgagct actggaaggc ctctgagggg gctgagtatg atgaccagac cagccagagg     1140
gagaaggagg atgacaaggt gttccctggg ggcagccaca cctatgtgtg gcaggtgctg     1200
aaggagaatg gccccatggc ctctgacccc ctgtgcctga cctacagcta cctgagccat     1260
gtggacctgt tgaaggacct gaactctggc ctgattgggg ccctgctggt gtgcaggag     1320 ggcagcctgg ccaaggagaa gaccagacc ctgcacaagt tcatcctgct gtttgctgtg     1380
tttgatgagg gcaagagctg gcactctgaa accaagaaca gcctgatgca ggacagggat     1440
gctgcctctg ccagggcctg gcccaagatg cacactgtga atggctatgt gaacaggagc     1500
ctgcctggcc tgattggctg ccacaggaag tctgtgtact ggcatgtgat tggcatgggc     1560
accacccctg aggtgcacag catcttcctg gagggccaca ccttcctggt caggaaccac     1620
aggcaggcca gctgagat cagccccatc accttcctga ctgccagac cctgctgatg     1680 gacctgggcc agttcctgct gttctgccac atcagcagcc accagcatga tggcatggag     1740
gcctatgtga aggtggacag ctgccctgag gagcccagc tgaggatgaa gaacaatgag     1800
gaggctgagg actatgatga tgacctgact gactctgaga tggatgtggt gaggtttgat     1860
gatgacaaca gccccagctt catccagatc aggtctgtgg ccaagaagca ccccaagacc     1920
```

```
tgggtgcact acattgctgc tgaggaggag gactgggact atgcccccct ggtgctggcc      1980
cctgatgaca ggagctacaa gagccagtac ctgaacaatg ccccccagag gattggcagg      2040
aagtacaaga aggtcaggtt catggcctac actgatgaaa ccttcaagac cagggaggcc      2100
atccagcatg agtctggcat cctgggcccc ctgctgtatg gggaggtggg ggacaccctg      2160
ctgatcatct tcaagaacca ggccagcagg ccctacaaca tctaccccca tggcatcact      2220
gatgtgaggc ccctgtacag caggaggctg cccaagggg tgaagcacct gaaggacttc       2280
cccatcctgc tggggagat cttcaagtac aagtggactg tgactgtgga ggatggcccc       2340
accaagtctg accccaggtg cctgaccaga tactacagca gctttgtgaa catggagagg      2400
gacctggcct ctggcctgat ggcccctg ctgatctgct acaaggagtc tgtggaccag        2460
aggggcaacc agatcatgtc tgacaagagg aatgtgatcc tgttctctgt gtttgatgag      2520
aacaggagct ggtacctgac tgagaacatc cagaggttcc tgcccaaccc tgctggggtg     2580
cagctggagg accctgagtt ccaggccagc aacatcatgc acagcatcaa tggctatgtg     2640
tttgacagcc tgcagctgtc tgtgtgcctg catgaggtgg cctactggta catcctgagc    2700
attggggccc agactgactt cctgtctgtg ttcttctctg gctacacctt caagcacaag     2760
atggtgtatg aggacaccct gaccctgttc cccttctctg gggagactgt gttcatgagc    2820
atggagaacc ctggcctgtg gattctgggc tgccacaact ctgacttcag gaacaggggc    2880
atgactgccc tgctgaaagt ctccagctgt gacaagaaca ctgggggacta ctatgaggac   2940
agctatgagg acatctctgc ctacctgctg agcaagaaca atgccattga gcccaggagc    3000
ttcagccaga accccccagt gctgaagagg caccagaggg agatcaccag gaccaccctg    3060
cagtctgacc aggaggagat tgactatgat gacaccatct ctgtggagat gaagaaggag   3120
gactttgaca tctacgacga ggacgagaac cagagcccca ggagcttcca ggaagaagacc  3180
aggcactact tcattgctgc tgtggagagg ctgtgggact atggcatgag cagcagcccc   3240
catgtgctga ggaacagggc ccagtctggc tctgtgcccc agttcaagaa ggtggtgttc    3300
caggagttca ctgatggcag cttcacccag cccctgtaca gggggagct gaatgagcac     3360
ctgggcctgc tgggccccta catcagggct gaggtggagg acaacatcat ggtgaccttc    3420
aggaaccagg ccagcaggcc ctacagcttc tacagcagcc tgatcagcta tgaggaggac    3480
cagaggcagg ggctgagcc caggaagaac tttgtgaagc ccaatgaaac caagacctac    3540
ttctggaagg tgcagcacca catggccccc accaaggatg agtttgactg caaggcctgg    3600
gcctacttct ctgatgtgga cctggagaag gatgtgcact ctggcctgat ggccccctg   3660
ctggtgtgcc acaccaacac cctgaaccct gcccatggca ggcaggtgac tgtgcaggag    3720
tttgccctgt tcttcaccat cttttgatgaa accaagagct ggtacttcac tgagaacatg  3780
gagaggaact gcagggcccc ctgcaacatc cagatggagg acccccctt caaggagaac    3840
tacaggttcc atgccatcaa tggctacatc atggacaccc tgcctggcct ggtgatggcc    3900
caggaccaga ggatcaggtg gtacctgctg agcatgggca gcaatgagaa catccacagc   3960
atccacttct ctggccatgt gttcactgtg aggaagaagg aggagtacaa gatggccctg   4020
tacaacctgt accctgggt gtttgagact gtggagatgc tgcccagcaa ggctggcatc    4080
tggagggtgg agtgcctgat tggggagcac ctgcatgctg gcatgagcac cctgttcctg   4140
gtgtacagca acaagtgcca gaccccctg ggcatggcct ctggccacat cagggacttc    4200
cagatcactg cctctggcca gtatggccag tgggcccca agctggccag gctgcactac    4260
tctggcagca tcaatgcctg gagcaccaag gagcccttca gctggatcaa ggtggacctg    4320
```

```
ctggccccca tgatcatcca tggcatcaag acccagyggg ccaggcagaa gttcagcagc    4380
ctgtacatca gccagttcat catcatgtac agcctggatg caagaagtg gcagacctac     4440
aggggcaaca gcactggcac cctgatggtg ttctttggca atgtggacag ctctggcatc    4500
aagcacaaca tcttcaaccc ccccatcatt gccagataca tcaggctgca ccccacccac    4560
tacagcatca ggagcaccct gaggatggag ctgatgggct gtgacctgaa cagctgcagc    4620
atgcccctgg gcatggagag caaggccatc tctgatgccc agatcactgc cagcagctac    4680
ttcaccaaca tgtttgccac ctggagcccc agcaaggcca ggctgcacct gcagggcagg    4740
agcaatgcct ggaggcccca ggtcaacaac cccaaggagt ggctgcaggt ggacttccag    4800
aagaccatga aggtgactgg ggtgaccacc aggggggtga agagcctgct gaccagcatg    4860
tatgtgaagg agttcctgat cagcagcagc caggatggcc accagtggac cctgttcttc    4920
cagaatggca aggtgaaggt gttccagggc aaccaggaca gcttcacccc tgtggtgaac    4980
agcctggacc ccccccctgct gaccagatac ctgaggattc accccagag ctgggtgcac    5040
cagattgccc tgaggatgga ggtgctgggc tgtgaggccc aggacctgta ctgacctcga    5100
ggaataaagg aaatttattt tcattgcaat agtgtgttgg ttttttgtgt cacgtggcgg    5160
ccgcaggaac ccctagtgat ggagttggcc actccctctc tgcgcgctcg ctcgctcact    5220
gaggccgggc gaccaaaggt cgcccgacgc ccgggctttg cccgggcggc ctcagtgagc    5280
gagcgagcgc gcagagaggg agtggccaa                                      5309

<210> SEQ ID NO 27
<211> LENGTH: 5532
<212> TYPE: DNA
<213> ORGANISM: Adeno-Associated Virus 2

<400> SEQUENCE: 27
ttggccactc cctctctgcg cgctcgctcg ctcactgagg ccgccgggc aaagcccggg       60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaact cctgtgtgcc      480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacgacgag acagggccc tgtctcctca gcttcaggca ccaccactga cctgggacag      720
tgaatcgtaa gtatgccttt cactgcgaga ggttctggag aggcttctga gctccccatg    780
gcccaggcag gcagcaggtc tggggcagga gggggttgt ggagtgcctt gactcggggc     840
ctggccccc catctctgtc ttgcaggaca attgccgtct tctgtctcgt ggggcatcct    900
cctgctggca ggcctgtgct gcctggtccc tgcgatcgcc accatgcaga ttgagctgag    960
cacctgcttc ttcctgtgcc tgctgaggtt ctgcttctct gccaccagga gatactacct    1020
gggggctgtg gagctgagct gggactacat gcagtctgac ctgggggagc tgcctgtgga    1080
```

```
tgccaggttc cccccagag tgcccaagag cttcccttc aacacctctg tggtgtacaa    1140
gaagaccctg tttgtggagt tcactgacca cctgttcaac attgccagcc caggccccc    1200
ctggatgggc ctgctgggcc ccaccatcca ggctgaggtg tatgacactg tggtgatcac    1260
cctgaagaac atggccagcc accctgtgag cctgcatgct gtggggtga gctactggaa    1320
ggcctctgag ggggctgagt atgatgacca gaccagccag agggagaagg aggatgacaa    1380
ggtgttccct gggggcagcc acacctatgt gtggcaggtg ctgaaggaga atggcccat    1440
ggcctctgac cccctgtgcc tgacctacag ctacctgagc catgtggacc tggtgaagga    1500
cctgaactct ggcctgattg gggccctgct ggtgtgcagg gagggcagcc tggccaagga    1560
gaagacccag accctgcaca agttcatcct gctgtttgct gtgtttgatg agggcaagag    1620
ctggcactct gaaaccaaga acagcctgat gcaggacagg gatgctgcct ctgccagggc    1680
ctggcccaag atgcacactg tgaatggcta tgtgaacagg agcctgcctg gcctgattgg    1740
ctgccacagg aagtctgtgt actggcatgt gattggcatg gcaccaccc ctgaggtgca    1800
cagcatcttc ctggagggcc acaccttcct ggtcaggaac cacaggcagg ccagcctgga    1860
gatcagcccc atcaccttcc tgactgccca gaccctgctg atggacctgg gccagttcct    1920
gctgttctgc cacatcagca gccaccagca tgatggcatg gaggcctatg tgaaggtgga    1980
cagctgccct gaggagcccc agctgaggat gaagaacaat gaggaggctg aggactatga    2040
tgatgacctg actgactctg agatggatgt ggtgaggttt gatgatgaca cagccccag    2100
cttcatccag atcaggtctg tggccaagaa gcaccccaag acctgggtgc actacattgc    2160
tgctgaggag gaggactggg actatgcccc cctggtgctg gcccctgatg acaggagcta    2220
caagagccag tacctgaaca atggccccca gaggattggc aggaagtaca agaaggtcag    2280
gttcatggcc tacactgatg aaaccttcaa gaccagggag gccatccagc atgagtctgg    2340
catcctgggc cccctgctgt atgggggggt gggggacacc ctgctgatca tcttcaagaa    2400
ccaggccagc aggccctaca acatctaccc catggcatc actgatgtga ggcccctgta    2460
cagcaggagg ctgcccaagg gggtgaagca cctgaaggac ttccccatcc tgcctgggga    2520
gatcttcaag tacaagtgga ctgtgactgt ggaggatggc cccaccaagt ctgaccccag    2580
gtgcctgacc agatactaca gcagctttgt gaacatggag agggacctgg cctctggcct    2640
gattggcccc ctgctgatct gctacaagga gtctgtggac cagagggca accagatcat    2700
gtctgacaag aggaatgtga tcctgttctc tgtgtttgat gagaacagga gctggtacct    2760
gactgagaac atccagaggt tcctgcccaa ccctgctggg gtgcagctgg aggaccctga    2820
gttccaggcc agcaacatca tgcacagcat caatggctat gtgtttgaca gcctgcagct    2880
gtctgtgtgc ctgcatgagg tggcctactg gtacatcctg agcattgggg cccagactga    2940
cttcctgtct gtgttcttct ctggctacac cttcaagcac aagatggtgt atgaggacac    3000
cctgaccctg ttccccttct ctggggagac tgtgttcatg agcatggaga ccctggcct    3060
gtggattctg ggctgccaca actctgactt caggaacagg gcatgactg ccctgctgaa    3120
agtctccagc tgtgacaaga acactgggga ctactatgag acagctatg aggacatctc    3180
tgcctacctg ctgagcaaga caatgccat tgagcccagg agcttcagcc agaaccccc    3240
agtgctgaag aggcaccaga gggagatcac caggaccacc ctgcagtctg accaggagga    3300
gattgactat gatgacacca tctctgtgga gatgaagaag gaggactttg acatctacga    3360
cgaggacgag aaccagagcc ccaggagctt ccagaagaag accaggcact acttcattgc    3420
tgctgtggag aggctgtggg actatggcat gagcagcagc ccccatgtgc tgaggaacag    3480
```

```
ggcccagtct ggctctgtgc cccagttcaa gaaggtggtg ttccaggagt tcactgatgg   3540
cagcttcacc cagcccctgt acagagggga gctgaatgag cacctgggcc tgctgggccc   3600
ctacatcagg gctgaggtgg aggacaacat catggtgacc ttcaggaacc aggccagcag   3660
gccctacagc ttctacagca gcctgatcag ctatgaggag gaccagaggc agggggctga   3720
gcccaggaag aactttgtga agcccaatga aaccaagacc tacttctgga aggtgcagca   3780
ccacatggcc cccaccaagg atgagtttga ctgcaaggcc tgggcctact tctctgatgt   3840
ggacctggag aaggatgtgc actctggcct gattggcccc ctgctggtgt gccacaccaa   3900
caccctgaac cctgcccatg gcaggcaggt gactgtgcag gagtttgccc tgttcttcac   3960
catctttgat gaaaccaaga gctggtactt cactgagaac atggagagga actgcagggc   4020
cccctgcaac atccagatgg aggaccccac cttcaaggag aactacaggt tccatgccat   4080
caatggctac atcatggaca ccctgcctgg cctggtgatg gcccaggacc agaggatcag   4140
gtggtacctg ctgagcatgg gcagcaatga aaacatccac agcatccact tctctggcca   4200
tgtgttcact gtgaggaaga aggaggagta caagatggcc ctgtacaacc tgtaccctgg   4260
ggtgtttgag actgtggaga tgctgcccag caaggctggc atctggagg tggagtgcct   4320 gattggggag cacctgcatg ctggcatgag cacccctgttc ctggtgtaca gcaacaagtg   4380
ccagaccccc ctgggcatgg cctctggcca catcagggac ttccagatca ctgcctctgg   4440
ccagtatggc cagtgggccc ccaagctggc caggctgcac tactctggca gcatcaatgc   4500
ctggagcacc aaggagccct tcagctggat caaggtggac ctgctggccc ccatgatcat   4560
ccatggcatc aagacccagg gggccaggca gaagttcagc agcctgtaca tcagccagtt   4620
catcatcatg tacagcctgg atggcaagaa gtggcagacc tacaggggca acagcactgg   4680
caccctgatg gtgttctttg gcaatgtgga cagctctggc atcaagcaca acatcttcaa   4740
cccccccatc attgccagat acatcaggct gcaccccacc cactacagca tcaggagcac   4800
cctgaggatg gagctgatgg gctgtgacct gaacagctgc agcatgcccc tgggcatgga   4860
gagcaaggcc atctctgatg cccagatcac tgccagcagc tacttcacca acatgtttgc   4920
cacctggagc cccagcaagg ccaggctgca cctgcagggc aggagcaatg cctggaggcc   4980
ccaggtcaac aaccccaagg agtggctgca ggtggacttc cagaagacca tgaaggtgac   5040
tggggtgacc acccagggg tgaagagcct gctgaccagc atgtatgtga aggagttcct   5100
gatcagcagc agccaggatg gccaccagtg gaccctgttc ttccagaatg gcaaggtgaa   5160
ggtgttccag ggcaaccagg acagcttcac ccctgtggtg aacagcctgg accccccct   5220 gctgaccaga tacctgagga ttcacccccca gagctggtg caccagattg ccctgaggat   5280
ggaggtgctg ggctgtgagg cccaggacct gtactgacct cgaggaataa ggaaatttta   5340
ttttcattgc aatagtgtgt tggttttttg tgtcacgtgg cggccgcagg aacccctagt   5400
gatggagttg gccactccct ctctgcgcgc tcgctcgctc actgaggccg ggcgaccaaa   5460
ggtcgcccga cgcccgggct ttgcccgggc ggcctcagtg agcgagcgag cgcgcagaga   5520
gggagtggcc aa                                                     5532
```

<210> SEQ ID NO 28
<211> LENGTH: 5877
<212> TYPE: DNA
<213> ORGANISM: Adeno-Associated Virus 2

<400> SEQUENCE: 28

```
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcctgcggc cgcacgcgtg ttttcgaccc ctctcacact   180
acctaaacca cgccaggaca acctctgctc ctctccaccg aaattccaag gggtcgagtg   240
gatgttggag gtggcatggg cccagagagg tctctgacct ctgccccagc tccaaggtca   300
gcaggcaggg agggctgtgt gtttgctgtt tgctgcttgc aatgtttgcc cattttaggg   360
acatgagtag gctgaagttt gttcagtgtg gacttcagag gcagcacaca aacagctgct   420
ggaggatggg aactgagggg ttggaagggg gcagggtgag cccagaaact cctgtgtgcc   480
tctgagcctg cagacgcgaa acgtcgacag gttaattttt aaaaagcagt caaaagtcca   540
agtggccctt ggcagcattt actctctctg tttgctctgg ttaataatct caggagcaca   600
aacattcctg gaggcaggag aagaaatcaa catcctggac ttatcctctg ggcctctccc   660
cacccccagg agaggctcag gttaattttt aaaaagcagt caaaagtcca agtggccctt   720
ggcagcattt actctctctg tttgctctgg ttaataatct caggagcaca aacattcctg   780
gaggcaggag aagaaatcaa catcctggac ttatcctctg ggcctctccc cacccccagg   840
agaggctgtc gactggacac aggacgctgt ggtttctgag ccaggggcg actcagatcc   900
cagccagtgg acttagcccc tgtttgctcc tccgataact ggggtgacct tggttaatat   960
tcaccagcag cctcccccgt tgcccctctg gatccactgc ttaaatacgg acgaggacag  1020
ggccctgtct cctcagcttc aggcaccacc actgacctgg gacagtgaat cgtaagtatg  1080
cctttcactg cgagaggttc tggagaggct tctgagctcc ccatggccca ggcaggcagc  1140
aggtctgggg caggaggggg gttgtggagt gccttgactc ggggcctggc cccccatct  1200
ctgtcttgca ggacaattgc cgtcttctgt ctcgtgggc atcctcctgc tggcaggcct  1260
gtgctgcctg gtccctgcga tcgccaccat gcagattgag ctgagcacct gcttcttcct  1320
gtgcctgctg aggttctgct tctctgccac caggagatac tacctggggg ctgtggagct  1380
gagctgggac tacatgcagt ctgacctggg ggagctgcct gtggatgcca ggttccccc  1440
cagagtgccc aagagcttcc ccttcaacac ctctgtggtg tacaagaaga ccctgtttgt  1500
ggagttcact gaccacctgt tcaacattgc caagcccagg cccccctgga tgggcctgct  1560
gggccccacc atccaggctg aggtgtatga cactgtggtg atcaccctga gaacatggc  1620
cagccaccct gtgagcctgc atgctgtggg ggtgagctac tggaaggcct ctgaggggc  1680
tgagtatgat gaccagacca gccagaggga aaggaggat gacaaggtgt ccctgggg   1740
cagccacacc tatgtgtggc aggtgctgaa ggagaatggc cccatggcct ctgaccccct  1800
gtgcctgacc tacagctacc tgagccatgt ggaccggtg aaggacctga actctggcct  1860
gattggggcc ctgctggtgt gcagggaggg cagcctggcc aaggagaaga cccagaccct  1920
gcacaagttc atcctgctgt ttgctgtgtt tgatgagggc aagagctggc actctgaaac  1980
caagaacagc ctgatgcagg acagggatgc tgcctctgcc agggcctggc caagatgca  2040
cactgtgaat ggctatgtga acaggagcct gcctggcctg attggctgcc acaggaagtc  2100
tgtgtactgg catgtgattg gcatgggcac caccctgag gtgcacagca tcttcctgga  2160
gggccacacc ttcctggtca ggaaccacag gcaggccagc ctggagatca gccccatcac  2220
cttcctgact gcccagaccc tgctgatgga cctgggccag ttcctgctgt tctgccacat  2280
cagcagccac cagcatgatg gcatggaggc ctatgtgaag gtggacagct gccctgagga  2340
gccccagctg aggatgaaga acaatgagga ggctgaggac tatgatgatg acctgactga  2400
```

```
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gccccctgg tgctggcccc tgatgacagg agctacaaga gccagtacct     2580
gaacaatggc ccccagagga ttggcaggaa gtacaagaag gtcaggttca tggcctacac    2640
tgatgaaacc ttcaagacca gggaggccat ccagcatgag tctggcatcc tgggccccct    2700
gctgtatggg gaggtggggg acaccctgct gatcatcttc aagaaccagg ccagcaggcc    2760
ctacaacatc taccccatg gcatcactga tgtgaggccc ctgtacagca ggaggctgcc     2820 caaggggtg aagcacctga aggacttccc catcctgcct ggggagatct tcaagtacaa     2880
gtggactgtg actgtggagg atggccccac caagtctgac cccaggtgcc tgaccagata    2940
ctacagcagc tttgtgaaca tggagaggga cctggcctct ggcctgattg ccccctgct    3000 gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctggggtgca gctggaggac cctgagttcc aggccagcaa    3180
catcatgcac agcatcaatg gctatgtgtt tgacagcctg cagctgtctg tgtgcctgca    3240
tgaggtggcc tactggtaca tcctgagcat tggggcccag actgacttcc tgtctgtgtt    3300
cttctctggc tacaccttca gcacaagat ggtgtatgag gacaccctga ccctgttccc     3360
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840 tgtgcccag ttcaagaagg tggtgttcca ggagttcact gatggcagct tcacccagcc     3900
cctgtacaga ggggagctga atgagcacct gggcctgctg ggcccctaca tcagggctga    3960
ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca gacctactt ctggaaggtg cagcaccaca tggccccac    4140 caaggatgag tttgactgca aggcctgggc ctacttctct gatgtggacc tggagaagga    4200
tgtgcactct ggcctgattg ccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga gaggaactgc agggcccct gcaacatcca    4380 gatggaggac cccaccttca aggagaacta caggttccat gccatcaatg gctacatcat    4440
ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctgggggtgt ttgagactgt    4620 ggagatgctg cccagcaagg ctggcatctg gagggtggag tgcctgattg gggagcacct    4680
gcatgctggc atgagcaccc tgttcctggt gtacagcaac aagtgccaga ccccctggg     4740
```

```
catggcctct ggccacatca gggacttcca gatcactgcc tctggccagt atggccagtg    4800 ggccccaag ctggccaggc tgcactactc tggcagcatc aatgcctgga gcaccaagga    4860
gcccttcagc tggatcaagg tggacctgct ggcccccatg atcatccatg catcaagac    4920 ccagggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaaccccc ccatcattgc    5100
cagatacatc aggctgcacc ccacccacta cagcatcagg agcaccctga ggatggagct    5160
gatgggctgt gacctgaaca gctgcagcat gccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggcccccagg tcaacaaccc    5340 caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt ccagggcaa    5520 ccaggacagc ttcacccctg tggtgaacag cctggacccc cccctgctga ccagatacct    5580
gaggattcac ccccagagct gggtgcacca gattgccctg aggatggagg tgctgggctg    5640
tgaggcccag gacctgtact gacctcgagg aataaaggaa atttatttc attgcaatag    5700 tgtgttggtt ttttgtgtca cgtggcggcc gcaggaaccc ctagtgatgg agttggccac    5760
tccctctctg cgcgctcgct cgctcactga ggccgggcga ccaaaggtcg cccgacgccc    5820
gggctttgcc cggcggcct cagtgagcga gcgagcgcgc agagagggag tggccaa    5877

<210> SEQ ID NO 29
<211> LENGTH: 6054
<212> TYPE: DNA
<213> ORGANISM: Adeno-Associated Virus 2

<400> SEQUENCE: 29
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag gggtcgagtg     240
gatgttggag gtggcatggg cccagagagg tctctgacct ctgccccagc tccaaggtca     300
gcaggcaggg agggctgtgt gtttgctgtt tgctgcttgc aatgtttgcc cattttaggg     360
acatgagtag gctgaagttt gttcagtgtg gacttcagag gcagcacaca aacagctgct     420
ggaggatggg aactgagggg ttggaagggg gcagggtgag cccagaaact cctgtgtgcc     480
tctgagcctg cagacgcgaa acgtcgacag gttaattttt aaaaagcagt caaaagtcca     540
agtggccctt ggcagcattt actctctctg tttgctctgg ttaataatct caggagcaca     600
aacattcctg gaggcaggag aagaaatcaa catcctggac ttatcctctg ggcctctccc     660
cacccccagg agaggctcag gttaattttt aaaaagcagt caaaagtcca agtggccctt     720
ggcagcattt actctctctg tttgctctgg ttaataatct caggagcaca aacattcctg     780
gaggcaggag aagaaatcaa catcctggac ttatcctctg ggcctctccc cacccccagg     840
agaggctgtc gactgacac aggacgctgt ggtttctgag ccaggggcg actcagatcc     900 cagccagtga acttagcccc tgtttgctcc tccgataact ggggtgacct tggttaatat     960
tcaccagcag cctccccccgt tgcccctctg gatccactgc ttaaatacgg acgaggacag    1020
```

```
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc cccccatct    1200 ctgtcttgca ggacaattgc cgtcttctgt ctcgtggggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccctggat gggcctgct   1560 gggccccacc atccaggctg aggtgtatga cactgtggtg atcaccctga gaacatggc   1620 cagccaccct gtgagcctgc atgctgtggg ggtgagctac tggaaggcct ctgaggggc    1680 tgagtatgat gaccagacca gccagaggga aaggaggat gacaaggtgt ccctggggg    1740 cagccacacc tatgtgtggc aggtgctgaa ggagaatggc cccatggcct ctgaccccct   1800
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac cacccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt ctgccacat    2280 cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccctgg tgctggccc tgatgacagg agctacaaga gccagtacct    2580
gaacaatggc cccagagga ttggcaggaa gtacaagaag gtcaggttca tggcctacac   2640
tgatgaaacc ttcaagacca gggaggccat ccagcatgag tctggcatcc tgggcccct    2700 gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820 caaggggtg aagcacctga aggacttccc catcctgcct ggggagatct tcaagtacaa    2880
gtggactgtg actgtggagg atggccccac caagtctgac cccaggtgcc tgaccagata   2940
ctacagcagc tttgtgaaca tggagaggga cctggcctct ggcctgattg ccccctgct    3000 gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctgggtgca gctggaggac cctgagttcc aggccagcaa    3180
catcatgcac agcatcaatg gctatgtgtt tgacagcctg cagctgtctg tgtgcctgca   3240
tgaggtggcc tactggtaca tcctgagcat tgggccccag actgacttcc tgtctgtgtt   3300
cttctctggc tacaccttca agcacaagat ggtgtatgag gacaccctga cccctgttcc   3360
```

-continued

```
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga atgagcacct gggcctgctg gcccctaca tcagggctga    3960 ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggcccccac    4140
caaggatgag tttgactgca aggcctgggc ctacttctct gatgtggacc tggagaagga    4200
tgtgcactct ggcctgattg gccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga aggaactgc agggccccct gcaacatcca    4380
gatggaggac cccaccttca aggagaacta caggttccat gccatcaatg ctacatcat    4440 ggacaccctg cctggcctgg tgatgcccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctggg atgagcaccc tgttcctggt gtacagcaac aagtgccaga cccccctggg    4740
catggcctct ggccacatca gggacttcca gatcactgcc tctggccagt atggccagtg    4800 ggccccaag ctggccaggc tgcactactc tggcagcatc aatgcctgga gcaccaagga    4860
gcccttcagc tggatcaagg tggacctgct ggcccccatg atcatccatg gcatcaagac    4920 ccaggggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaaccccc ccatcattgc    5100
cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagc tgcacctgc agggcaggag caatgcctgg aggccccagg tcaacaaccc    5340
caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcacccctg tggtgaacag cctggaccc cccctgctga ccagatacct    5580
gaggattcac ccccagagct gggtgcacca gattgccctg aggatggagg tgctgggctg    5640
tgaggcccag gacctgtact gacctcgagg tgtgccttct agttgccagc catctgttgt    5700
ttgcccctcc cccgtgcctt ccttgaccct ggaaggtgcc actcccactg tcctttccta    5760
```

-continued

| | |
|---|---|
| ataaaatgag gaaattgcat cgcattgtct gagtaggtgt cattctattc tgggggtgg | 5820 |
| ggtggggcag gacagcaagg gggaggattg ggaagacaat agcaggcatg ctggggatgc | 5880 |
| ggtgggctct atgggcacgt ggcggccgca ggaacccta gtgatggagt tggccactcc | 5940 |
| ctctctgcgc gctcgctcgc tcactgaggc cgggcgacca aggtcgccc gacgcccggg | 6000 |
| cttttgcccgg gcggcctcag tgagcgagcg agcgcgcaga gagggagtgg ccaa | 6054 |

<210> SEQ ID NO 30
<211> LENGTH: 6054
<212> TYPE: DNA
<213> ORGANISM: Adeno-Associated Virus 2

<400> SEQUENCE: 30

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaacca cgccaggaca acctctgctc ctctccaccg aaattccaag gggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |
| ggaggatggg aactgagggg ttggaagggg gcagggtgag cccagaaact cctgtgtgcc | 480 |
| tctgagcctg cagacgcgaa acgtcgaagc ctctcctggg ggtggggaga ggcccagagg | 540 |
| ataagtccag gatgttgatt tcttctcctg cctccaggaa tgtttgtgct cctgagatta | 600 |
| ttaaccagag caaacagaga gagtaaatgc tgccaagggc cacttggact tttgactgct | 660 |
| ttttaaaaat taacctgagc ctctcctggg ggtggggaga ggcccagagg ataagtccag | 720 |
| gatgttgatt tcttctcctg cctccaggaa tgtttgtgct cctgagatta ttaaccagag | 780 |
| caaacagaga gagtaaatgc tgccaagggc cacttggact tttgactgct ttttaaaaat | 840 |
| taacctggtc gactggacac aggacgctgt ggtttctgag ccaggggcg actcagatcc | 900 |
| cagccagtgg acttagcccc tgtttgctcc tccgataact ggggtgacct tggttaatat | 960 |
| tcaccagcag cctcccccgt tgcccctctg gatccactgc ttaaatacgg acgaggacag | 1020 |
| ggccctgtct cctcagcttc aggcaccacc actgacctgg gacagtgaat cgtaagtatg | 1080 |
| cctttcactg cgagaggttc tggagaggct tctgagctcc ccatggccca ggcaggcagc | 1140 |
| aggtctgggg caggaggggg gttgtggagt gccttgactc ggggcctggc cccccatct | 1200 |
| ctgtcttgca ggacaattgc cgtcttctgt ctcgtggggc atcctcctgc tggcaggcct | 1260 |
| gtgctgcctg gtccctgcga tcgccaccat gcagattgag ctgagcacct gcttcttcct | 1320 |
| gtgcctgctg aggttctgct tctctgccac caggagatac tacctggggg ctgtggagct | 1380 |
| gagctgggac tacatgcagt ctgacctggg ggagctgcct gtggatgcca ggttcccccc | 1440 |
| cagagtgccc aagagcttcc ccttcaacac ctctgtggtg tacaagaaga ccctgtttgt | 1500 |
| ggagttcact gaccacctgt tcaacattgc caagcccagg ccccctggga tgggcctgct | 1560 |
| gggccccacc atccaggctg aggtgtatga cactgtggtg atcaccctga agaacatggc | 1620 |
| cagccaccct gtgagcctgc atgctgtggg ggtgagctac tggaaggcct ctgaggggc | 1680 |
| tgagtatgat gaccagacca gcagaggga aaggaggat gacaaggtgt ccctggggg | 1740 |
| cagccacacc tatgtgtggc aggtgctgaa ggagaatggc cccatggcct ctgacccct | 1800 |

```
gtgcctgacc tacagctacc tgagccatgt ggacctggtg aaggacctga actctggcct    1860
gattggggcc ctgctggtgt gcagggaggg cagcctggcc aaggagaaga cccagaccct    1920
gcacaagttc atcctgctgt ttgctgtgtt tgatgagggc aagagctggc actctgaaac    1980
caagaacagc ctgatgcagg acagggatgc tgcctctgcc agggcctggc caagatgca    2040 cactgtgaat ggctatgtga acaggagcct gcctggcctg attggctgcc acaggaagtc    2100
tgtgtactgg catgtgattg gcatgggcac caccctgag gtgcacagca tcttcctgga    2160
gggccacacc ttcctggtca ggaaccacag gcaggccagc ctggagatca gccccatcac    2220
cttcctgact gcccagaccc tgctgatgga cctgggccag ttcctgctgt tctgccacat    2280
cagcagccac cagcatgatg gcatggaggc ctatgtgaag gtggacagct gccctgagga    2340
gccccagctg aggatgaaga caatgagga ggctgaggac tatgatgatg acctgactga    2400
ctctgagatg gatgtggtga ggtttgatga tgacaacagc cccagcttca tccagatcag    2460
gtctgtggcc aagaagcacc ccaagacctg ggtgcactac attgctgctg aggaggagga    2520
ctgggactat gcccccctgg tgctggcccc tgatgacagg agctacaaga gccagtacct    2580
gaacaatggc ccccagagga ttggcaggaa gtacaagaag gtcaggttca tggcctacac    2640
tgatgaaacc ttcaagacca gggaggcat ccagcatgag tctggcatcc tgggcccct    2700 gctgtatggg gaggtggggg acaccctgct gatcatcttc aagaaccagg ccagcaggcc    2760
ctacaacatc taccccatg gcatcactga tgtgaggccc ctgtacagca ggaggctgcc    2820
caagggggtg aagcacctga aggacttccc catcctgcct ggggagatct tcaagtacaa    2880
gtggactgtg actgtggagg atggccccac caagtctgac cccaggtgcc tgaccagata    2940
ctacagcagc tttgtgaaca tggagaggga cctggcctct ggcctgattg gccccctgct    3000
gatctgctac aaggagtctg tggaccagag gggcaaccag atcatgtctg acaagaggaa    3060
tgtgatcctg ttctctgtgt ttgatgagaa caggagctgg tacctgactg agaacatcca    3120
gaggttcctg cccaaccctg ctggggtgca gctggaggac cctgagttcc aggccagcaa    3180
catcatgcac agcatcaatg gctatgtgtt tgacagcctg cagctgtctg tgtgcctgca    3240
tgaggtggcc tactgggtaca tcctgagcat tgggggccag actgacttcc tgtctgtgtt    3300
cttctctggc tacaccttca gcacaagat ggtgtatgag gacaccctga ccctgttccc    3360
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac ccccagtgc tgaagaggca    3600 ccagagggag atcaccagga ccaccctgca gtctgaccag gaggagattg actatgatga    3660
caccatctct gtggagatga agaaggagga cttttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga tgagcacctg ggcctgctg ggcccctaca tcagggctga    3960
ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agaccctactt ctggaaggtg cagcaccaca tggcccccac    4140
caaggatgag tttgactgca aggcctgggc ctacttctct gatgtggacc tggagaagga    4200
```

```
tgtgcactct ggcctgattg gccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggcccct gcaacatcca    4380 gatggaggac cccaccttca aggagaacta caggttccat gccatcaatg ctacatcat   4440 ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggccctgta caacctgtac cctggggtgt tgagactgt    4620 ggagatgctg cccagcaagg ctggcatctg gaggtggga tgcctgattg gggagcacct    4680
gcatgctggc atgagcaccc tgttcctggt gtacagcaac aagtgccaga cccccctggg   4740
catggcctct ggccacatca gggacttcca gatcactgcc tctggccagt atggccagtg   4800 ggccccccaag ctggccaggc tgcactactc tggcagcatc aatgcctgga gcaccaagga  4860
gcccttcagc tggatcaagg tggacctgct ggccccatg atcatccatg gcatcaagac    4920 ccaggggggcc aggcagaagt tcagcagcct gtacatcagc cagttcatca tcatgtacag  4980
cctggatggc aagaagtggc agacctacag gggcaacagc actggcaccc tgatggtgtt   5040
ctttggcaat gtggacagct ctggcatcaa gcacaacatc ttcaaccccc ccatcattgc   5100
cagatacatc aggctgcacc ccacccacta cagcatcagg agcaccctga ggatggagct   5160
gatgggctgt gacctgaaca gctgcagcat gccctgggc atggagagca aggccatctc    5220
tgatgcccag atcactgcca gcagctactt caccaacatg tttgccacct ggagccccag   5280
caaggccagg ctgcacctgc agggcaggag caatgcctgg aggccccagg tcaacaaccc   5340
caaggagtgg ctgcaggtgg acttccagaa gaccatgaag gtgactgggg tgaccaccca   5400
gggggtgaag agcctgctga ccagcatgta tgtgaaggag ttcctgatca gcagcagcca   5460
ggatggccac cagtggaccc tgttcttcca gaatggcaag gtgaaggtgt tccagggcaa   5520
ccaggacagc ttcacccctg tggtgaacag cctggaccc ccctgctga ccagatacct     5580 gaggattcac ccccagagct gggtgcacca gattgccctg aggatggagg tgctgggctg   5640
tgaggcccag gacctgtact gacctcgagg tgtgccttct agttgccagc catctgttgt   5700
ttgcccctcc cccgtgcctt ccttgaccct ggaaggtgcc actcccactg tcctttccta   5760
ataaaatgag gaaattgcat cgcattgtct gagtaggtgt cattctattc tggggggtgg   5820
ggtggggcag gacagcaagg gggaggattg ggaagacaat agcaggcatg ctggggatgc   5880
ggtgggctct atgggcacgt ggcggccgca ggaaccccta gtgatggagt tggccactcc   5940
ctctctgcgc gctcgctcgc tcactgaggc cgggcgacca aggtcgcccc gacgcccggg   6000
ctttgcccgg gcggcctcag tgagcgagcg agcgcgcaga gagggagtgg ccaa         6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
```

```
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccctggaa tgggcctgct gggccccacc   1020
atccaggctg aggtgtatga cactgtggtg atcaccctga gaacatggc cagccaccct   1080 gtgagcctgc atgctgtggg ggtgagctac tggaaggcct ctgaggggc tgagtatgat   1140 gaccagacca gccagaggga aaggaggat gacaaggtgt cccctggggg cagccacacc   1200
tatgtgtggc aggtgctgaa ggagaatggc cccatgcct ctgacccct gtgcctgacc   1260 tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc caagatgca cactgtgaat   1500 ggctatgtga acaggagcct gcctggcctg attggctgcc acaggaagtc tgtgtactgg   1560
catgtgattg gcatgggcac caccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct ccctgaggg ccccagctg   1800 aggatgaaga caatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980 gccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggcccct gctgtatggg   2160 gaggtggggg acaccctgct gatcatcttc aagaaccagg ccagcaggcc ctacaacatc   2220
tacccccatg gcatcactga tgtgaggccc ctgtacagca ggaggctgcc caaggggtg   2280 aagcacctga aggacttccc catcctgcct ggggagatct tcaagtacaa gtggactgtg   2340
actgtggagg atggcccac caagtctgac cccaggtgcc tgaccagata ctacagcagc   2400
tttgtgaaca tggagaggga cctggcctct ggcctgattg gccccctgct gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
```

```
agcatcaatg gctatgtgtt tgacagcctg cagctgtctg tgtgcctgca tgaggtggcc      2700
tactggtaca tcctgagcat tggggcccag actgacttcc tgtctgtgtt cttctctggc      2760
tacaccttca agcacaagat ggtgtatgag acaccctga ccctgttccc cttctctggg       2820
gagactgtgt tcatgagcat ggagaaccct ggcctgtgga ttctgggctg ccacaactct      2880
gacttcagga acaggggcat gactgccctg ctgaaagtct ccagctgtga caagaacact      2940
ggggactact atgaggacag ctatgaggac atctctgcct acctgctgag caagaacaat      3000
gccattgagc ccaggagctt cagccagaac cccccagtgc tgaagaggca ccagagggag      3060
atcaccagga ccaccctgca gtctgaccag gaggagattg actatgatga ccatctctct      3120
gtggagatga agaaggagga ctttgacatc tacgacgagg acgagaacca gagccccagg      3180
agcttccaga agaagaccag gcactacttc attgctgctg tggagaggct gtgggactat      3240
ggcatgagca gcagccccca tgtgctgagg aacagggccc agtctggctc tgtgcccag       3300
ttcaagaagg tggtgttcca ggagttcact gatggcagct tcacccagcc cctgtacaga      3360
ggggagctga atgagcacct gggcctgctg ggcccctaca tcagggctga ggtggaggac      3420
aacatcatgg tgaccttcag gaaccaggcc agcaggccct acagcttcta cagcagcctg      3480
atcagctatg aggaggacca gaggcagggg gctgagccca ggaagaactt tgtgaagccc      3540
aatgaaacca agacctactt ctggaaggtg cagcaccaca tggcccccac caaggatgag      3600
tttgactgca aggcctgggc ctacttctct gatgtggacc tggagaagga tgtgcactct      3660
ggcctgattg ccccctgct ggtgtgccac accaacaccc tgaaccctgc ccatggcagg       3720
caggtgactg tgcaggagtt tgccctgttc ttcaccatct ttgatgaaac caagagctgg      3780
tacttcactg agaacatgga gaggaactgc agggcccccct gcaacatcca gatggaggac     3840
cccaccttca aggagaacta caggttccat gccatcaatg ctacatcat ggacaccctg       3900
cctggcctgg tgatggccca ggaccagagg atcaggtggt acctgctgag catgggcagc      3960
aatgagaaca tccacagcat ccacttctct ggccatgtgt tcactgtgag gaagaaggag      4020
gagtacaaga tggcccctgta caacctgtac cctggggtgt ttgagactgt ggagatgctg     4080
cccagcaagg ctggcatctg gagggtggag tgcctgattg gggagcacct gcatgctggc     4140
atgagcaccc tgttcctggt gtacagcaac aagtgccaga ccccctgggc atggcctct       4200
ggccacatca gggacttcca gatcactgcc tctggccagt atggccagtg ggcccccaag      4260
ctggccaggc tgcactactc tggcagcatc aatgcctgga gcaccaagga gcccttcagc      4320
tggatcaagg tggacctgct ggccccccatg atcatccatg gcatcaagac caggggggcc    4380
aggcagaagt tcagcagcct gtacatcagc cagttcatca tcatgtacag cctggatggc     4440
aagaagtggg agacctacag gggcaacagc actggcaccc tgatggtgtt ctttggcaat     4500
gtggacagct ctggcatcaa gcacaacatc ttcaaccccc ccatcattgc cagatacatc     4560
aggctgcacc ccacccacta cagcatcagg agcaccctga ggatggagct gatgggctgt    4620
gacctgaaca gctgcagcat gcccctgggc atggagagca aggccatctc tgatgcccag     4680
atcactgcca gcagctactt caccaacatg tttgccacct ggagcccag caaggccagg      4740
ctgcacctgc agggcaggag caatgcctgg aggcccagg tcaacaaccc caaggagtgg      4800
ctgcaggtgg acttccagaa gaccatgaag gtgactgggg tgaccaccca gggggtgaag     4860
agcctgctga ccagcatgta tgtgaaggag ttcctgatca gcagcagcca ggatggccac     4920
cagtggaccc tgttcttcca gaatggcaag gtgaaggtgt tccagggcaa ccaggacagc     4980
```

```
ttcacccctg tggtgaacag cctggacccc ccctgctga ccagatacct gaggattcac     5040
ccccagagct gggtgcacca gattgccctg aggatggagg tgctgggctg tgaggcccag     5100
gacctgtact gacctcgagg tgtgccttct agttgccagc catctgttgt tgcccctcc      5160 cccgtgcctt ccttgaccct ggaaggtgcc actcccactg tcctttccta ataaaatgag     5220
gaaattgcat cgcattgtct gagtaggtgt cattctattc tggggggtgg ggtggggcag     5280
gacagcaagg gggaggattg gaagacaat agcaggcatg ctggggatgc ggtgggctct      5340
atgggcacgt ggcggccgca ggaacccta gtgatggagt tggccactcc ctctctgcgc      5400
gctcgctcgc tcactgaggc cgggcgacca aggtcgccc gacgcccggg ctttgcccgg      5460
gcggcctcag tgagcgagcg agcgcgcaga gagggagtgg ccaa                      5504

<210> SEQ ID NO 32
<211> LENGTH: 5507
<212> TYPE: DNA
<213> ORGANISM: Adeno-Associated Virus 2

<400> SEQUENCE: 32
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaact cctgtgtgcc     480
tctgagcctg cagacgcgaa acgtcgacga tcttgctacc agtggaacag ccactaagga    540
ttctgcagtg agagcagagg gccagctaag tggtactctc ccagagactg tctgactcac    600
gccaccccct ccaccttgga cacaggacgc tgtggtttct gagccaggta caatgactcc    660
tttcggtaag tgcagtggaa gctgtacact gcccaggcaa agcgtccggg cagcgtaggc    720
gggcgactca gatcccagcc agtggactta gcccctgttt gctcctccga taactggggt    780
gaccttggtt aatattcacc agcagcctcc ccgttgccc ctctggatcc actgcttaaa    840
tacggacgag gacagggccc tgtctcctca gcttcaggca ccaccactga cctgggacag    900
tgaatcgcga tcgccaccat gcagattgag ctgagcacct gcttcttcct gtgcctgctg    960
aggttctgct tctctgccac caggagatac tacctggggg ctgtggagct gagctgggac   1020
tacatgcagt ctgacctggg ggagctgcct gtggatgcca ggttcccccc cagagtgccc   1080
aagagcttcc ccttcaacac ctctgtggtg tacaagaaga cctgtttgt ggagttcact    1140 gaccacctgt tcaacattgc caagccagg ccccctgga tgggcctgct gggccccacc     1200
atccaggctg aggtgtatga cactgtggtg atcccctga gaacatggc cagccaccct     1260 gtgagcctgc atgctgtggg ggtgagctac tggaaggcct ctgaggggc tgagtatgat    1320 gaccagacca gccagaggga aaggaggat acaaggtgt tccctggggg cagccacacc     1380
tatgtgtggc aggtgctgaa ggagaatggc cccatggcct ctgacccct gtgcctgacc    1440 tacagctacc tgagccatgt ggacctggtg aaggacctga actctggcct gattggggcc    1500
ctgctggtgt gcagggaggg cagcctgccc aaggagaaga cccagaccct gcacaagttc    1560
atcctgctgt ttgctgtgtt tgatgagggc aagagctggc actctgaaac caagaacagc    1620
```

```
ctgatgcagg acagggatgc tgcctctgcc agggcctggc ccaagatgca cactgtgaat  1680
ggctatgtga acaggagcct gcctggcctg attggctgcc acaggaagtc tgtgtactgg  1740
catgtgattg gcatgggcac caccectgag gtgcacagca tcttcctgga gggccacacc  1800
ttcctggtca ggaaccacag gcaggccagc ctggagatca gccccatcac cttcctgact  1860
gcccagaccc tgctgatgga cctgggccag ttcctgctgt tctgccacat cagcagccac  1920
cagcatgatg gcatggaggc ctatgtgaag gtggacagct gccctgagga gccccagctg  1980
aggatgaaga acaatgagga ggctgaggac tatgatgatg acctgactga ctctgagatg  2040
gatgtggtga ggtttgatga tgacaacagc cccagcttca tccagatcag gtctgtggcc  2100
aagaagcacc ccaagacctg ggtgcactac attgctgctg aggaggagga ctgggactat  2160
gcccccctgg tgctggcccc tgatgacagg agctacaaga ccagtacct gaacaatggc  2220
ccccagagga ttggcaggaa gtacaagaag gtcaggttca tggcctacac tgatgaaacc  2280
ttcaagacca gggaggccat ccagcatgag tctggcatcc tgggccccct gctgtatggg  2340
gaggtggggg acaccctgct gatcatcttc aagaaccagg ccagcaggcc ctacaacatc  2400
taccccatg gcatcactga tgtgaggccc ctgtacagca ggaggctgcc caagggggtg  2460
aagcacctga aggacttccc catcctgcct ggggagatct tcaagtacaa gtggactgtg  2520
actgtggagg atggccccca caagtctgac cccaggtgcc tgaccagata ctacagcagc  2580
tttgtgaaca tggagaggga cctggcctct ggcctgattg cccctgct gatctgctac  2640
aaggagtctg tggaccagag gggcaaccag atcatgtctg acaagaggaa tgtgatcctg  2700
ttctctgtgt ttgatgagaa caggagctgg tacctgactg agaacatcca gaggttcctg  2760
cccaaccctg ctggggtgca gctggaggac cctgagttcc aggccagcaa catcatgcac  2820
agcatcaatg gctatgtgtt tgacagcctg cagctgtctg tgtgcctgca tgaggtggcc  2880
tactggtaca tcctgagcat tgggccccag actgacttcc tgtctgtgtt ctttctctggc  2940
tacaccttca agcacaagat ggtgtatgag acaccctga ccctgttccc cttctctggg  3000
gagactgtgt tcatgagcat ggagaaccct ggcctgtgga ttctgggctg ccacaactct  3060
gacttcagga acagggcat gactgccctg ctgaaagtct ccagctgtga caagaacact  3120
ggggactact atgaggacag ctatgaggac atctctgcct acctgctgag caagaacaat  3180
gccattgagc caggagcttc agccagaac cccccagtgc tgaagaggca ccagagggag  3240
atcaccagga ccaccctgca gtctgaccag gaggagattg actatgatga caccatctct  3300
gtggagatga agaaggagga ctttgacatc tacgacgagg acgagaacca gagccccagg  3360
agcttccaga agaaccagg cactacttc attgctgctg tggagaggct gtgggactat  3420
ggcatgagca gcagccccca tgtgctgagg aacagggccc agtctggctc tgtgccccag  3480
ttcaagaagg tggtgttcca ggagttcact gatggcagct tcacccagcc cctgtacaga  3540
ggggagctga atgagcacct gggcctgctg ggccccctaca tcagggctga ggtggaggac  3600
aacatcatgg tgaccttcag gaaccaggcc agcaggccct acagcttcta cagcagcctg  3660
atcagctatg aggaggacca gaggcagggg gctgagccca ggaagaactt tgtgaagccc  3720
aatgaaacca agacctactt ctggaaggtg cagcaccaca tggcccccac caaggatgag  3780
tttgactgca aggcctgggc ctacttctct gatgtggacc tggagaagga tgtgcactct  3840
ggcctgattg ccccctgct ggtgtgccac accaacaccc tgaaccctgc ccatggcagg  3900
caggtgactg tgcaggagtt tgccctgttc ttcaccatct ttgatgaaac caagagctgg  3960
```

```
tacttcactg agaacatgga gaggaactgc agggccccct gcaacatcca gatggaggac    4020
cccaccttca aggagaacta caggttccat gccatcaatg ctacatcat ggacaccctg     4080
cctggcctgg tgatggccca ggaccagagg atcaggtggt acctgctgag catgggcagc    4140
aatgagaaca tccacagcat ccacttctct ggccatgtgt tcactgtgag gaagaaggag    4200
gagtacaaga tggccctgta caacctgtac cctggggtgt ttgagactgt ggagatgctg    4260
cccagcaagg ctggcatctg gagggtggag tgcctgattg gggagcacct gcatgctggc    4320
atgagcaccc tgttcctggt gtacagcaac aagtgccaga ccccctggg catggcctct     4380
ggccacatca gggacttcca gatcactgcc tctggccagt atggccagtg ggccccaag     4440
ctggccaggc tgcactactc tggcagcatc aatgcctgga gcaccaagga gcccttcagc    4500
tggatcaagg tggacctgct ggcccccatg atcatccatg catcaagac caggggggcc     4560
aggcagaagt tcagcagcct gtacatcagc cagttcatca tcatgtacag cctggatggc    4620
aagaagtggc agacctacag gggcaacagc actggcaccc tgatggtgtt ctttggcaat    4680
gtggacagct ctggcatcaa gcacaacatc ttcaaccccc ccatcattgc cagatacatc    4740
aggctgcacc ccaccccacta cagcatcagg agcaccctga ggatggagct gatgggctgt    4800
gacctgaaca gctgcagcat gccctgggc atggagagca aggccatctc tgatgcccag    4860
atcactgcca gcagctactt caccaacatg tttgccacct ggagcccag caaggccagg    4920
ctgcacctgc agggcaggag caatgcctgg aggcccagg tcaacaaccc caaggagtgg    4980
ctgcaggtgg acttccagaa gaccatgaag gtgactgggg tgaccaccca gggggtgaag    5040
agcctgctga ccagcatgta tgtgaaggag ttcctgatca gcagcagcca ggatggccac    5100
cagtggaccc tgttcttcca gaatggcaag gtgaaggtgt tccagggcaa ccaggacagc    5160
ttcacccctg tggtgaacag cctggacccc cccctgctga ccagatacct gaggattcac    5220
ccccagagct gggtgcacca gattgccctg aggatggagg tgctgggctg tgaggcccag    5280
gacctgtact gacctcgagg aataaaggaa atttattttc attgcaatag tgtgttggtt    5340
ttttgtgtca cgtggcggcc gcaggaaccc ctagtgatgg agttggccac tccctctctg    5400
cgcgctcgct cgctcactga ggccgggcga ccaaaggtcg cccgacgccc gggctttgcc    5460
cgggcggcct cagtgagcga gcgagcgcgc agagagggag tggccaa                  5507

<210> SEQ ID NO 33
<211> LENGTH: 5311
<212> TYPE: DNA
<213> ORGANISM: Adeno-Associated Virus 2

<400> SEQUENCE: 33
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgacgc agagaggtct    180
ctgacctctg ccccagctcc aaggtcagca ggcagggagg gctgtgtgtt tgctgtttgc    240
tgcttgcaat gttttgcccat tttagggaca tgagtaggct gaagtttgtt cagtgtggac    300
ttcagaggca gcacacaaac agccagagag gtctctgacc tctgccccag ctccaaggtc    360
agcaggcagg gagggctgtg tgtttgctgt ttgctgcttg caatgtttgc ccattttagg    420
gacatgagta ggctgaagtt tgttcagtgt ggacttcaga ggcagcacac aaacagcacg    480
cgaaacgtcg actggacaca ggacgctgtg gtttctgagc caggggggcga ctcagatccc    540
agccagtgga cttagccccct gtttgctcct ccgataactg gggtgacctt ggttaatatt    600
```

```
caccagcagc ctcccccgtt gcccctctgg atccactgct taaatacgga cgaggacagg    660
gccctgtctc ctcagcttca ggcaccacca ctgacctggg acagtgaatc gcgatcgcca    720
ccatgcagat tgagctgagc acctgcttct tcctgtgcct gctgaggttc tgcttctctg    780
ccaccaggag atactacctg ggggctgtgg agctgagctg ggactacatg cagtctgacc    840
tgggggagct gcctgtggat gccaggttcc cccccagagt gcccaagagc ttccccttca    900
acacctctgt ggtgtacaag aagaccctgt ttgtggagtt cactgaccac ctgttcaaca    960
ttgccaagcc caggcccccc tggatgggcc tgctgggccc caccatccag gctgaggtgt   1020
atgacactgt ggtgatcacc ctgaagaaca tggccagcca ccctgtgagc ctgcatgctg   1080
tgggggtgag ctactggaag gcctctgagg ggctgagta tgatgaccag accagccaga   1140
gggagaagga ggatgacaag gtgttccctg ggggcagcca cacctatgtg tggcaggtgc   1200
tgaaggagaa tggccccatg gcctctgacc ccctgtgcct gacctacagc tacctgagcc   1260
atgtggacct ggtgaaggac ctgaactctg gcctgattgg ggccctgctg gtgtgcaggg   1320
agggcagcct ggccaaggag aagacccaga ccctgcacaa gttcatcctg ctgtttgctg   1380
tgtttgatga gggcaagagc tggcactctg aaaccaagaa cagcctgatg caggacaggg   1440
atgctgcctc tgccagggcc tggcccaaga tgcacactgt gaatggctat gtgaacagga   1500
gcctgcctgg cctgattggc tgccacagga agtctgtgta ctggcatgtg attggcatgg   1560
gcaccacccc tgaggtgcac agcatcttcc tggagggcca caccttcctg gtcaggaacc   1620
acaggcaggc cagcctggag atcagcccca tcaccttcct gactgcccag accctgctga   1680
tggacctggg ccagttcctg ctgttctgcc acatcagcag ccaccagcat gatggcatgg   1740
aggcctatgt gaaggtggac agctgccctg aggagcccca gctgaggatg aagaacaatg   1800
aggaggctga ggactatgat gatgacctga ctgactctga gatggatgtg gtgaggtttg   1860
atgatgacaa cagcccccag cttcatccaga tcaggtctgt ggccaagaag caccccaaga   1920
cctgggtgca ctacattgct gctgaggagg aggactggga ctatgccccc ctggtgctgg   1980
cccctgatga caggagctac aagagccagt acctgaacaa tggcccccag aggattggca   2040
ggaagtacaa gaaggtcagg ttcatggcct acactgatga aaccttcaag accagggagg   2100
ccatccagca tgagtctggg atcctgggcc cctgctgta tggggaggtg ggggacaccc   2160
tgctgatcat cttcaagaac caggccagca ggccctacaa catctacccc catggcatca   2220
ctgatgtgag gccctgtac agcaggaggc tgcccaaggg ggtgaagcac ctgaaggact   2280
tccccatcct gcctggggag atcttcaagt acaagtggac tgtgactgtg gaggatggcc   2340
ccaccaagtc tgaccccagg tgcctgacca gatactacag cagctttgtg aacatggaga   2400
gggacctggc ctctggcctg attggccccc tgctgatctg ctacaaggag tctgtggacc   2460
agagggggcaa ccagatcatg tctgacaaga ggaatgtgat cctgttctct gtgtttgatg   2520
agaacaggag ctggtacctg actgagaaca tccagaggtt cctgcccaac cctgctgggg   2580
tgcagctgga ggaccctgag ttccaggcca gcaacatcat gcacagcatc aatggctatg   2640
tgtttgacag cctgcagctg tctgtgtgcc tgcatgaggt ggcctactgg tacatcctga   2700
gcattggggc ccagactgac ttcctgtctg tgttcttctc tggctacacc ttcaagcaca   2760
agatggtgta tgaggacacc ctgaccctgt tccccttctc tggggagact gtgttcatga   2820
gcatggagaa ccctggcctg tggattctgg gctgccacaa ctctgacttc aggaacaggg   2880
gcatgactgc cctgctgaaa gtctccagct gtgacaagaa cactggggac tactatgagg   2940
```

```
acagctatga ggacatctct gcctacctgc tgagcaagaa caatgccatt gagcccagga    3000
gcttcagcca gaaccccca gtgctgaaga ggcaccagag ggagatcacc aggaccaccc     3060
tgcagtctga ccaggaggag attgactatg atgacaccat ctctgtggag atgaagaagg    3120
aggactttga catctacgac gaggacgaga accagagccc caggagcttc cagaagaaga    3180
ccaggcacta cttcattgct gctgtggaga ggctgtggga ctatggcatg agcagcagcc    3240
cccatgtgct gaggaacagg gcccagtctg gctctgtgcc ccagttcaag aaggtggtgt    3300
tccaggagtt cactgatggc agcttcaccc agcccctgta cagaggggag ctgaatgagc    3360
acctgggcct gctgggcccc tacatcaggg ctgaggtgga ggacaacatc atggtgacct    3420
tcaggaacca ggccagcagg ccctacagct tctacagcag cctgatcagc tatgaggagg    3480
accagaggca gggggctgag cccaggaaga actttgtgaa gcccaatgaa accaagacct    3540
acttctggaa ggtgcagcac cacatggccc ccaccaagga tgagtttgac tgcaaggcct    3600
gggcctactt ctctgatgtg gacctggaga aggatgtgca ctctggcctg attggccccc    3660
tgctggtgtg ccacaccaac accctgaacc ctgcccatgg caggcaggtg actgtgcagg    3720
agtttgccct gttcttcacc atctttgatg aaaccaagag ctggtacttc actgagaaca    3780
tggagaggaa ctgcagggcc ccctgcaaca tccagatgga ggaccccacc ttcaaggaga    3840
actacaggtt ccatgccatc aatggctaca tcatggacac cctgcctggc ctggtgatgg    3900
cccaggacca gaggatcagg tggtacctgc tgagcatggg cagcaatgag aacatccaca    3960
gcatccactt ctctggccat gtgttcactg tgaggaagaa ggaggagtac aagatggccc    4020
tgtacaacct gtaccctggg gtgtttgaga ctgtggagat gctgcccagc aaggctggca    4080
tctggagggt ggagtgcctg attggggagc acctgcatgc tggcatgagc accctgttcc    4140
tggtgtacag caacaagtgc cagaccccc tgggcatggc ctctggccac atcagggact    4200
tccagatcac tgcctctggc cagtatggcc agtgggcccc caagctggcc aggctgcact    4260
actctggcag catcaatgcc tggagcacca aggagccctt cagctggatc aaggtggacc    4320
tgctggcccc catgatcatc catggcatca agacccaggg ggccaggcag aagttcagca    4380
gcctgtacat cagccagttc atcatcatgt acagcctgga tggcaagaag tggcagacct    4440
acaggggcaa cagcactggc acctgatgg tgttctttgg caatgtggac agctctggca    4500
tcaagcacaa catcttcaac ccccccatca ttgccagata catcaggctg cacccaccc    4560 actacagcat caggagcacc ctgaggatgg agctgatggg ctgtgacctg aacagctgca    4620
gcatgcccct gggcatggag agcaaggcca tctctgatgc ccagatcact gccagcagct    4680
acttcaccaa catgtttgcc acctggagcc ccagcaaggc caggctgcac ctgcagggca    4740
ggagcaatgc ctggaggccc caggtcaaca ccccaaggga gtggctgcag gtggacttcc    4800
agaagaccat gaaggtgact ggggtgacca cccaggggt gaagagcctg ctgaccagca    4860
tgtatgtgaa ggagttcctg atcagcagca gccaggatgg ccaccagtgg acccctgttct    4920 tccagaatgg caaggtgaag gtgttccagg caaccagga cagcttcacc cctgtggtga    4980
```

<210> SEQ ID NO 34
<211> LENGTH: 5156
<212> TYPE: DNA
<213> ORGANISM: Adeno-Associated Virus 2

<400> SEQUENCE: 34

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgcggc | cgcacgcgtg | ttttcgacca | gagaggtctc | 180 |
| tgacctctgc | cccagctcca | aggtcagcag | gcagggaggg | ctgtgtgttt | gctgtttgct | 240 |
| gcttgcaatg | tttgcccatt | ttagggacat | gagtaggctg | aagtttgttc | agtgtggact | 300 |
| tcagaggcag | cacacaaaca | gcacgcgaaa | cgtcgactgg | acacaggacg | ctgtggtttc | 360 |
| tgagccaggg | ggcgactcag | atcccagcca | gtggacttag | cccctgtttg | ctcctccgat | 420 |
| aactggggtg | accttggtta | atattcacca | gcagcctccc | ccgttgcccc | tctggatcca | 480 |
| ctgcttaaat | acggacgagg | acagggccct | gtctcctcag | cttcaggcac | caccactgac | 540 |
| ctgggacagt | gaatcgcgat | cgccaccatg | cagattgagc | tgagcacctg | cttcttcctg | 600 |
| tgcctgctga | ggttctgctt | ctctgccacc | aggagatact | acctgggggc | tgtggagctg | 660 |
| agctgggact | acatgcagtc | tgacctgggg | gagctgcctg | tggatgccag | gttcccccc | 720 |
| agagtgccca | agagcttccc | cttcaacacc | tctgtggtgt | acaagaagac | cctgtttgtg | 780 |
| gagttcactg | accacctgtt | caacattgcc | aagcccaggc | cccctggat | gggcctgctg | 840 |
| ggccccacca | tccaggctga | ggtgtatgac | actgtggtga | tcaccctgaa | gaacatggcc | 900 |
| agccaccctg | tgagcctgca | tgctgtgggg | gtgagctact | ggaaggcctc | tgagggggct | 960 |
| gagtatgatg | accagaccag | ccagagggag | aaggaggatg | acaaggtgtt | ccctgggggc | 1020 |
| agccacacct | atgtgtggca | ggtgctgaag | gagaatggcc | ccatggcctc | tgacccctg | 1080 |
| tgcctgacct | acagctacct | gagccatgtg | gacctggtga | aggacctgaa | ctctggcctg | 1140 |
| attgggcccc | tgctggtgtg | cagggagggc | agcctggcca | aggagaagac | ccagaccctg | 1200 |
| cacaagttca | tcctgctgtt | tgctgtgttt | gatgagggca | gagctggca | ctctgaaacc | 1260 |
| aagaacagcc | tgatgcagga | cagggatgct | gcctctgcca | gggcctggcc | aagatgcac | 1320 |
| actgtgaatg | gctatgtgaa | caggagcctg | cctggcctga | ttggctgcca | caggaagtct | 1380 |
| gtgtactggc | atgtgattgg | catgggcacc | acccctgagg | tgcacagcat | cttcctggag | 1440 |
| ggccacacct | tcctggtcag | gaaccacagg | caggccagcc | tggagatcag | ccccatcacc | 1500 |
| ttcctgactg | cccagaccct | gctgatggac | ctgggccagt | tcctgctgtt | ctgccacatc | 1560 |
| agcagccacc | agcatgatgg | catggaggcc | tatgtgaagg | tggacagctg | ccctgaggag | 1620 |
| ccccagctga | ggatgaagaa | caatgaggag | gctgaggact | atgatgatga | cctgactgac | 1680 |
| tctgagatgg | atgtggtgag | gtttgatgat | gacaacagcc | cagcttcat | ccagatcagg | 1740 |
| tctgtggcca | agaagcaccc | caagacctgg | gtgcactaca | ttgctgctga | ggaggaggac | 1800 |
| tgggactatg | ccccctggt | gctggcccct | gatgacagga | gctacaagag | ccagtacctg | 1860 |
| aacaatggcc | cccagaggat | tggcaggaag | tacaagaagg | tcaggttcat | ggcctacact | 1920 |
| gatgaaacct | tcaagaccag | ggaggccatc | cagcatgagt | ctggcatcct | gggcccctg | 1980 |
| ctgtatgggg | aggtggggga | cacctgctg | atcatcttca | agaaccaggc | cagcaggccc | 2040 |
| tacaacatct | acccccatgg | catcactgat | gtgaggccc | tgtacagcag | gaggctgccc | 2100 |

```
aaggggtga agcacctgaa ggacttcccc atcctgcctg ggagatcttc aagtacaag    2160
tggactgtga ctgtggagga tggccccacc aagtctgacc ccaggtgcct gaccagatac    2220
tacagcagct ttgtgaacat ggagagggac ctggcctctg gcctgattgg cccctgctg    2280
atctgctaca aggagtctgt ggaccagagg ggcaaccaga tcatgtctga caagaggaat    2340
gtgatcctgt tctctgtgtt tgatgagaac aggagctggt acctgactga gaacatccag    2400
aggttcctgc ccaaccctgc tggggtgcag ctggaggacc ctgagttcca ggccagcaac    2460
atcatgcaca gcatcaatgg ctatgtgttt gacagcctgc agctgtctgt gtgcctgcat    2520
gaggtggcct actggtacat cctgagcatt ggggcccaga ctgacttcct gtctgtgttc    2580
ttctctggct acaccttcaa gcacaagatg gtgtatgagg acaccctgac cctgttcccc    2640
ttctctgggg agactgtgtt catgagcatg gagaaccctg gcctgtggat tctgggctgc    2700
cacaactctg acttcaggaa caggggcatg actgccctgc tgaaagtctc cagctgtgac    2760
aagaacactg ggactactac tgaggacagc tatgaggaca tctctgccta cctgctgagc    2820
aagaacaatg ccattgagcc caggagcttc agccagaacc ccccagtgct gaagaggcac    2880
cagagggaga tcaccaggac caccctgcag tctgaccagg aggagattga ctatgatgac    2940
accatctctg tggagatgaa gaaggaggac tttgacatct acgacgagga cgagaaccag    3000
agccccagga gcttccagaa gaagaccagg cactacttca ttgctgctgt ggagaggctg    3060
tgggactatg gcatgagcag cagcccccat gtgctgagga cagggcccag tctggctctg    3120
gtgccccagt tcaagaaggt ggtgttccag gagttcactg atggcagctt cacccagccc    3180
ctgtacagag gggagctgaa tgagcacctg ggcctgctgg gccctacat cagggctgag    3240
gtggaggaca acatcatggt gaccttcagg aaccaggcca gcaggcccta cagcttctac    3300
agcagcctga tcagctatga ggaggaccag aggcaggggg ctgagcccag gaagaacttt    3360
gtgaagccca atgaaaccaa gacctacttc tggaaggtgc agcaccacat ggccccacc    3420
aaggatgagt ttgactgcaa ggcctgggcc tacttctctg atgtggacct ggagaaggat    3480
gtgcactctg gcctgattgg cccctgctg gtgtgccaca ccaacaccct gaaccctgcc    3540
catggcaggc aggtgactgt gcaggagttt gccctgttct tcaccatctt tgatgaaacc    3600
aagagctggt acttcactga gaacatggag aggaactgca gggccccctg caacatccag    3660
atggaggacc ccaccttcaa ggagaactac aggttccatg ccatcaatgg ctacatcatg    3720
gacaccctgc ctggcctggt gatggcccag gaccagagga tcaggtggta cctgctgagc    3780
atgggcagca atgagaacat ccacagcatc cacttctctg gccatgtgtt cactgtgagg    3840
aagaaggagg agtacaagat ggccctgtac aacctgtacc ctgggtgtt tgagactgtg    3900
gagatgctgc ccagcaaggc tggcatctgg agggtggagt gcctgattgg ggagcacctg    3960
catgctggca tgagcaccct gttcctggtg tacagcaaca agtgccagac ccccctgggc    4020
atggcctctg ccacatcag ggacttccag atcactgcct ctggccagta tggccagtgg    4080
gccccaagc tggccaggct gcactactct ggcagcatca atgcctggag caccaaggag    4140
ccttcagct ggatcaaggt ggacctgctg gcccccatga tcatccatgg catcaagacc    4200
caggggccca ggcagaagtt cagcagcctg tacatcagcc agttcatcat catgtacagc    4260
ctggatggca agaagtggca gacctacagg ggcaacagca ctggcacccct gatggtgttc    4320
tttggcaatg tggacagctc tggcatcaag cacaacatct tcaaccccc catcattgcc    4380
agatacatca ggctgcaccc cacccactac agcatcagga gcacctgag gatggagctg    4440
atggctgtg acctgaacag ctgcagcatg ccctgggca tggagagcaa ggccatctct    4500
```

```
gatgcccaga tcactgccag cagctacttc accaacatgt ttgccacctg gagcccagc    4560 aaggccaggc tgcacctgca gggcaggagc aatgcctgga ggcccaggt caacaacccc    4620 aaggagtggc tgcaggtgga cttccagaag accatgaagg tgactggggt gaccacccag    4680
ggggtgaaga gcctgctgac cagcatgtat gtgaaggagt tcctgatcag cagcagccag    4740
gatggccacc agtggaccct gttcttccag aatggcaagg tgaaggtgtt ccagggcaac    4800
caggacagct tcaccctgt ggtgaacagc ctggaccccc cctgctgac cagataccctg    4860 aggattcacc cccagagctg ggtgcaccag attgccctga ggatggaggt gctgggctgt    4920
gaggcccagg acctgtactg acctcgagga ataaaggaaa tttattttca ttgcaatagt    4980
gtgttggttt tttgtgtcac gtggcggccg caggaacccc tagtgatgga gttggccact    5040
ccctctctgc gcgctcgctc gctcactgag gccgggcgac caaaggtcgc ccgacgcccg    5100
ggctttgccc gggcggcctc agtgagcgag cgagcgcgca gagagggagt ggccaa       5156
```

<210> SEQ ID NO 35
<211> LENGTH: 5178
<212> TYPE: DNA
<213> ORGANISM: Adeno-Associated Virus 2

<400> SEQUENCE: 35

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc atttaggga catgtttgct gtttgctgct tgcaatgttt    240
gcccatttta gggacatgtt tgctgtttgc tgcttgcaat gtttgcccat tttaggaca    300 tgtttgctgt ttgctgcttg caatgtttgc ccattttagg acaacgcga aacgtcgact    360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacgacga ggacagggcc ctgtctcctc    540
agcttcaggc accaccactg acctgggaca gtgaatcgcg atcgccacca tgcagattga    600
gctgagcacc tgcttcttcc tgtgcctgct gaggttctgc ttctctgcca ccaggagata    660
ctacctgggg gctgtggagc tgagctggga ctacatgcag tctgacctgg gggagctgcc    720
tgtggatgcc aggttccccc ccagagtgcc caagagcttc ccttcaaca cctctgtggt    780 gtacaagaag accctgtttg tggagttcac tgaccacctg ttcaacattg ccaagcccag    840
gcccccctgg atgggcctgc tgggccccac catccaggct gaggtgtatg acactgtggt    900
gatcacccta aagaacatgg ccagccaccc tgtgagcctg catgctgtgg gggtgagcta    960
ctggaaggcc tctgaggggg ctgagtatga tgaccagacc agccagaggg agaaggagga   1020
tgacaaggtg ttccctgggg gcagccacac ctatgtgtgg caggtgctga aggagaatgg   1080
ccccatggcc tctgaccccc tgtgcctgac ctacagctac ctgagccatg tggacctggt   1140
gaaggacctg aactctggcc tgattggggc cctgctggtg tgcagggagg cagcctggc    1200 caaggagaag acccagaccc tgcacaagtt catcctgctg tttgctgtgt ttgatgaggg   1260
caagagctgg cactctgaaa ccaagaacag cctgatgcag gacagggatg ctgcctctgc   1320
cagggcctgg cccaagatgc acactgtgaa tggctatgtg aacaggagcc tgcctggcct   1380
gattggctgc cacaggaagt ctgtgtactg gcatgtgatt ggcatgggca ccacccctga   1440
```

```
ggtgcacagc atcttcctgg agggccacac cttcctggtc aggaaccaca ggcaggccag    1500
cctggagatc agccccatca ccttcctgac tgcccagacc ctgctgatgg acctgggcca    1560
gttcctgctg ttctgccaca tcagcagcca ccagcatgat ggcatggagg cctatgtgaa    1620
ggtggacagc tgccctgagg agccccagct gaggatgaag aacaatgagg aggctgagga    1680
ctatgatgat gacctgactg actctgagat ggatgtggtg aggtttgatg atgacaacag    1740
ccccagcttc atccagatca ggtctgtggc caagaagcac cccaagacct gggtgcacta    1800
cattgctgct gaggaggagg actgggacta tgcccccctg gtgctggccc ctgatgacag    1860
gagctacaag agccagtacc tgaacaatgg ccccccagagg attggcagga agtacaagaa    1920
```

```
tggccatgtg ttcactgtga ggaagaagga ggagtacaag atggccctgt acaacctgta    3900
ccctggggtg tttgagactg tggagatgct gcccagcaag gctggcatct ggagggtgga    3960
gtgcctgatt ggggagcacc tgcatgctgg catgagcacc ctgttcctgg tgtacagcaa    4020
caagtgccag accccctgg gcatggcctc tggccacatc agggacttcc agatcactgc     4080
ctctggccag tatggccagt gggcccccaa gctggccagg ctgcactact ctggcagcat    4140
caatgcctgg agcaccaagg agcccttcag ctggatcaag gtggacctgc tggcccccat    4200
gatcatccat ggcatcaaga cccagggggc caggcagaag ttcagcagcc tgtacatcag    4260
ccagttcatc atcatgtaca gcctggatgg caagaagtgg cagacctaca ggggcaacag    4320
cactggcacc ctgatggtgt tctttggcaa tgtggacagc tctggcatca agcacaacat    4380
cttcaacccc cccatcattg ccagatacat caggctgcac cccacccact acagcatcag    4440
gagcaccctg aggatggagc tgatgggctg tgacctgaac agctgcagca tgccccctggg   4500 catggagagc aaggccatct ctgatgccca gatcactgcc agcagctact tcaccaacat    4560
gtttgccacc tggagcccca gcaaggccag gctgcacctg cagggcagga gcaatgcctg    4620
gaggccccag gtcaacaacc ccaaggagtg gctgcaggtg gacttccaga agaccatgaa    4680
ggtgactggg gtgaccaccc agggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca accaggacag cttcaccct gtggtgaaca gcctggaccc     4860
ccccctgctg accagatacc tgaggattca ccccagagc tgggtgcacc agattgccct     4920
gaggatggag gtgctgggct gtgaggccca ggacctgtac tgacctcgag gaataaagga   4980
aatttatttt cattgcaata gtgtgttggt tttttgtgtc acgtggcggc cgcaggaacc    5040
cctagtgatg gagttggcca ctccctctct gcgcgctcgc tcgctcactg aggccgggcg    5100
accaaaggtc gcccgacgcc cgggctttgc ccgggcggcc tcagtgagcg agcgagcgcg    5160
cagagaggga gtggccaa                                                  5178

<210> SEQ ID NO 36
<211> LENGTH: 5160
<212> TYPE: DNA
<213> ORGANISM: Adeno-Associated Virus 2

<400> SEQUENCE: 36
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtt gtccctaaaa tgggcaaaca    180
ttgcaagcag caaacagcaa acatgtccct aaaatgggca acattgcaa gcagcaaaca    240 gcaaacatgt ccctaaaatg gcaaacatt gcaagcagca acagcaaac atgtccctaa    300 aatgggcaaa cattgcaagc agcaaacagc aaacagtcga ctggacacag gacgctgtgg    360
tttctgagcc agggggcgac tcagatccca gccagtggac ttagcccctg tttgctcctc    420
cgataactgg ggtgaccttg gttaatattc accagcagcc tccccgttg ccctctgga    480 tccactgctt aaatacggac gaggacaggg ccctgtctcc tcagcttcag gcaccaccac    540
tgacctggga cagtgaatcg cgatcgccac catgcagatt gagctgagca cctgcttctt    600
cctgtgcctg ctgaggttct gcttctctgc caccaggaga tactacctgg gggctgtgga    660
gctgagctgg gactacatgc agtctgacct gggggagctg cctgtggatg ccaggttccc    720
```

```
ccccagagtg cccaagagct tccccttcaa cacctctgtg gtgtacaaga agaccctgtt    780
tgtggagttc actgaccacc tgttcaacat tgccaagccc aggccccccct ggatgggcct    840
gctgggcccc accatccagg ctgaggtgta tgacactgtg gtgatcaccc tgaagaacat    900
ggccagccac cctgtgagcc tgcatgctgt gggggtgagc tactggaagg cctctgaggg    960
ggctgagtat gatgaccaga ccagccagag ggagaaggag gatgacaagg tgttccctgg   1020
gggcagccac acctatgtgt ggcaggtgct gaaggagaat ggccccatgg cctctgaccc   1080
cctgtgcctg acctacagct acctgagcca tgtggacctg gtgaaggacc tgaactctgg   1140
cctgattggg gccctgctgg tgtgcaggga gggcagcctg gccaaggaga gacccagac   1200
cctgcacaag ttcatcctgc tgtttgctgt gtttgatgag ggcaagagct ggcactctga   1260
aaccaagaac agcctgatgc aggacaggga tgctgcctct gccagggcct ggcccaagat   1320
gcacactgtg aatggctatg tgaacaggag cctgcctggc ctgattggct gccacaggaa   1380
gtctgtgtac tggcatgtga ttggcatggg caccaccect gaggtgcaca gcatcttcct   1440
ggagggccac accttcctgg tcaggaacca caggcaggcc agcctggaga tcagccccat   1500
caccttcctg actgcccaga ccctgctgat ggacctgggc cagttcctgc tgttctgcca   1560
catcagcagc caccagcatg atggcatgga ggcctatgtg aaggtggaca gctgccctga   1620
ggagccccag ctgaggatga agaacaatga ggaggctgag gactatgatg atgacctgac   1680
tgactctgag atggatgtgg tgaggtttga tgatgacaac agcccagct tcatccagat   1740
caggtctgtg gccaagaagc accccaagac ctgggtgcac tacattgctg ctgaggagga   1800
ggactgggac tatgcccccc tggtgctggc ccctgatgac aggagctaca agagccagta   1860
cctgaacaat ggcccccaga ggattggcag gaagtacaag aaggtcaggt tcatggccta   1920
cactgatgaa accttcaaga ccagggaggc catccagcat gagtctggca tcctgggccc   1980
cctgctgtat ggggaggtgg gggacaccct gctgatcatc ttcaagaacc aggccagcag   2040
gccctacaac atctaccccc atggcatcac tgatgtgagg cccctgtaca gcaggaggct   2100
gcccaagggg gtgaagcacc tgaaggactt ccccatcctg cctggggaga tcttcaagta   2160
caagtggact gtgactgtgg aggatggccc caccaagtct gaccccaggt gcctgaccag   2220
atactacagc agctttgtga acatggagag ggacctggcc tctggcctga ttggcccct   2280
gctgatctgc tacaaggagt ctgtggacca gaggggcaac cagatcatgt ctgacaagag   2340
gaatgtgatc ctgttctctg tgtttgatga aaacaggagc tggtacctga ctgagaacat   2400
ccagaggttc ctgcccaacc tgctgggggt gcagctggag gacctgagt tccaggccag   2460
caacatcatg cacagcatca atggctatgt gtttgacagc ctgcagctgt ctgtgtgcct   2520
gcatgaggtg gcctactggt acatcctgag cattgggggcc cagactgact tcctgtctgt   2580
gttcttctct ggctacacct tcaagcacaa gatggtgtat gaggacaccc tgaccctgtt   2640
cccctttctct ggggagactg tgttcatgag catggagaac cctggccttgt ggattctggg   2700
ctgccacaac tctgacttca ggaacagggg catgactgcc ctgctgaaag tctccagctg   2760
tgacaagaac actgggggact actatgagga cagctatgag gacatctctg cctacctgct   2820
gagcaagaac aatgccattg agcccaggag cttcagccag aaccccccag tgctgaagag   2880
gcaccagagg gagatcacca ggaccacccct gcagtctgac caggaggaga ttgactatga   2940
tgacaccatc tctgtggaga tgaagaagga ggactttgac atctacgacg aggacgagaa   3000
ccagagcccc aggagcttcc agaagaagac caggcactac ttcattgctg ctgtggagag   3060
gctgtgggac tatggcatga gcagcagccc ccatgtgctg aggaacaggg cccagtctgg   3120
```

```
ctctgtgccc cagttcaaga aggtggtgtt ccaggagttc actgatggca gcttcaccca    3180 gccccctgtac agaggggagc tgaatgagca cctgggcctg ctgggcccct acatcagggc    3240
tgaggtggag acaacatca tggtgacctt caggaaccag gccagcaggc cctacagctt     3300
ctacagcagc ctgatcagct atgaggagga ccagaggcag ggggctgagc ccaggaagaa    3360
ctttgtgaag cccaatgaaa ccaagaccta cttctggaag gtgcagcacc acatggcccc    3420
caccaaggat gagtttgact gcaaggcctg ggcctacttc tctgatgtgg acctggagaa    3480
ggatgtgcac tctggcctga ttggccccct gctggtgtgc cacaccaaca ccctgaaccc    3540
tgcccatggc aggcaggtga ctgtgcagga gtttgccctg ttcttcacca tctttgatga    3600
aaccaagagc tggtacttca ctgagaacat ggagaggaac tgcagggccc cctgcaacat    3660
ccagatggag accccacct tcaaggagaa ctacaggttc catgccatca atggctacat    3720
catggacacc ctgcctggcc tggtgatggc ccaggaccag aggatcaggt ggtacctgct    3780
gagcatgggc agcaatgaga acatccacag catccacttc tctggccatg tgttcactgt    3840
gaggaagaag gaggagtaca agatggccct gtacaacctg taccctgggg tgtttgagac    3900
tgtggagatg ctgcccagca aggctggcat ctggagggtg gagtgcctga ttggggagca    3960
cctgcatgct ggcatgagca ccctgttcct ggtgtacagc aacaagtgcc agaccccct     4020 gggcatggcc tctggccaca tcagggactt ccagatcact gcctctggcc agtatggcca    4080
gtgggccccc aagctggcca ggctgcacta ctctggcagc atcaatgcct ggagcaccaa    4140
ggagcccttc agctggatca aggtggacct gctggccccc atgatcatcc atggcatcaa    4200
gacccagggg gccaggcaga agttcagcag cctgtacatc agccagttca tcatcatgta    4260
cagcctggat ggcaagaagt ggcagaccta caggggcaac agcactgca ccctgatggt     4320 gttctttggc aatgtggaca gctctggcat caagcacaac atcttcaacc ccccatcat    4380 tgccagatac atcaggctgc accccacca ctacagcatc aggagcaccc tgaggatgga    4440
gctgatgggc tgtgacctga acagctgcag catgcccctg ggcatggaga gcaaggccat    4500
ctctgatgcc cagatcactg ccagcagcta cttcaccaac atgtttgcca cctggagccc    4560
cagcaaggcc aggctgcacc tgcagggcag gagcaatgcc tggaggcccc aggtcaacaa    4620 cccccaaggag tggctgcagg tggacttcca gaagaccatg aaggtgactg gggtgaccac    4680
ccagggggtg aagagcctgc tgaccagcat gtatgtgaag gagttcctga tcagcagcag    4740
ccaggatggc caccagtgga cccctgttctt ccagaatggc aaggtgaagg tgttccaggg    4800
caaccaggac agcttcaccc ctgtggtgaa cagcctggac ccccccctgc tgaccagata    4860
cctgaggatt caccccccaga gctgggtgca ccagattgcc ctgaggatgg aggtgctggg    4920
ctgtgaggcc caggacctgt actgacctcg aggaataaag gaaatttatt ttcattgcaa    4980
tagtgtgttg gtttttttgtg tcacgtggcg gccgcaggaa ccccctagtga tggagttggc    5040 cactccctct ctgcgcgctc gctcgctcac tgaggccggg cgaccaaagg tcgcccgacg    5100
cccgggcttt gcccgggcgg cctcagtgag cgagcgagcg cgcagagagg gagtggccaa    5160
```

<210> SEQ ID NO 37
<211> LENGTH: 5383
<212> TYPE: DNA
<213> ORGANISM: Adeno-Associated Virus 2

<400> SEQUENCE: 37

```
ttggccactc cctctctgcg cgctcgctcg ctcactgagg ccgcccgggc aaagcccggg    60
```

-continued

```
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttagggaca    300
tgtttgctgt tgctgcttg caatgtttgc ccattttagg acaacgcga aacgtcgact     360
ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtatgcctt tcactgcgag    600
aggtctgga gaggcttctg agctccccat ggcccaggca ggcagcaggt ctggggcagg     660
agggggttg tggagtgcct tgactcgggg cctggcccc ccatctctgt cttgcaggac      720
aattgccgtc ttctgtctcg tggggcatcc tcctgctggc aggcctgtgc tgcctggtcc    780
ctgcgatcgc caccatgcag attgagctga gcacctgctt cttcctgtgc ctgctgaggt    840
tctgcttctc tgccaccagg agatactacc tgggggctgt ggagctgagc tgggactaca    900
tgcagtctga cctgggggag ctgcctgtgg atgccaggtt cccccccaga gtgcccaaga    960
gcttccccct caacacctct gtggtgtaca agaagaccct gtttgtggag ttcactgacc    1020
acctgttcaa cattgccaag cccaggcccc cctggatggg cctgctgggc ccaccatcc     1080
aggctgaggt gtatgacact gtggtgatca ccctgaagaa catggccagc caccctgtga    1140
gcctgcatgc tgtgggggtg agctactgga aggcctctga gggggctgag tatgatgacc    1200
agaccagcca gagggagaag gaggatgaca aggtgttccc tgggggcagc cacacctatg    1260
tgtggcaggt gctgaaggag aatggccca tggcctctga ccccctgtgc ctgacctaca    1320
gctacctgag ccatgtggac ctggtgaagg acctgaactc tggcctgatt ggggccctgc    1380
tggtgtgcag ggagggcagc ctggccaagg agaagaccca gacctgcac aagttcatcc     1440
tgctgttgc tgtgtttgat gagggcaaga gctggcactc tgaaaccaag aacagcctga    1500
tgcaggacag ggatgctgcc tctgccaggg cctggcccaa gatgcacact gtgaatggct    1560
atgtgaacag gagcctgcct ggcctgattg ctgccacag gaagtctgtg tactggcatg     1620
tgattggcat gggcaccacc cctgaggtgc acagcatctt cctggagggc acacccttcc    1680
tggtcaggaa ccacaggcag gccagcctgg agatcagccc catcaccttc ctgactgccc    1740
agacctgct gatggacctg gccagttcc tgctgttctg ccacatcagc agccaccagc     1800
atgatggcat ggaggcctat gtgaaggtgg acagctgccc tgaggagccc cagctgagga    1860
tgaagaacaa tgaggaggct gaggactatg atgatgacct gactgactct gagatggatg    1920
tggtgaggtt tgatgatgac aacagcccca gcttcatcca gatcaggtct gtggccaaga    1980
agcaccccaa gacctgggtg cactacattg ctgctgagga ggaggactgg gactatgccc    2040
ccctggtgct ggcccctgat gacaggagct acaagagcca gtacctgaac aatggccccc    2100
agaggattgg caggaagtac aagaaggtca ggttcatggc ctacactgat gaaaccttca    2160
agaccaggga ggccatccag catgagtctg gcatcctggg ccccctgctg tatggggagg    2220
tgggggacac cctgctgatc atcttcaaga accaggccag caggccctac aacatctacc    2280
cccatgcat cactgatgtg aggcccctgt acagcaggag gctgcccaag ggggtgaagc     2340
acctgaagga cttcccccatc ctgcctgggg agatcttcaa gtacaagtgg actgtgactg    2400
tggaggatgg ccccaccaag tctgaccccc ggtgcctgac cagatactac agcagctttg    2460
```

```
tgaacatgga gagggacctg gcctctggcc tgattggccc cctgctgatc tgctacaagg    2520
agtctgtgga ccagaggggc aaccagatca tgtctgacaa gaggaatgtg atcctgttct    2580
ctgtgtttga tgagaacagg agctggtacc tgactgagaa catccagagg ttcctgccca    2640
accctgctgg ggtgcagctg gaggaccctg agttccaggc cagcaacatc atgcacagca    2700
tcaatggcta tgtgtttgac agcctgcagc tgtctgtgtg cctgcatgag gtggcctact    2760
ggtacatcct gagcattggg gcccagactg acttcctgtc tgtgttcttc tctggctaca    2820
ccttcaagca caagatggtg tatgaggaca ccctgaccct gttccccttc tctggggaga    2880
ctgtgttcat gagcatggag aaccctgccc tgtggattct gggctgccac aactctgact    2940
tcaggaacag gggcatgact gccctgctga agtctccag ctgtgacaag aacactgggg    3000
actactatga ggacagctat gaggacatct ctgcctacct gctgagcaag aacaatgcca    3060
ttgagcccag gagcttcagc cagaaccccc cagtgctgaa gaggcaccag agggagatca    3120
ccaggaccac cctgcagtct gaccaggagg agattgacta tgatgacacc atctctgtgg    3180
agatgaagaa ggaggacttt gacatctacg acgaggacga gaaccagagc ccaggagct    3240 tccagaagaa gaccaggcac tacttcattg ctgctgtgga gaggctgtgg gactatggca    3300
tgagcagcag ccccatgtg ctgaggaaca gggcccagtc tggctctgtg ccccagttca    3360
agaaggtggt gttccaggag ttcactgatg gcagcttcac ccagcccctg tacagagggg    3420
agctgaatga gcacctgggc ctgctgggcc cctacatcag ggctgaggtg gaggacaaca    3480
tcatggtgac cttcaggaac caggccagca ggcctacag cttctacagc agcctgatca    3540
gctatgagga ggaccagagg caggggctg agcccaggaa gaactttgtg aagcccaatg    3600
aaaccaagac ctacttctgg aaggtgcagc accacatggc ccccaccaag gatgagtttg    3660
actgcaaggc ctgggcctac ttctctgatg tggacctgga aaggatgtg cactctggcc    3720 tgattggccc cctgctggtg tgccacacca acacctgaa ccctgcccat ggcaggcagg    3780
tgactgtgca ggagtttgcc ctgttcttca ccatctttga tgaaaccaag agctggtact    3840
tcactgagaa catggagagg aactgcaggg cccctgcaa catccagatg gaggacccca    3900
ccttcaagga gaactacagg ttccatgcca tcaatggcta catcatggac accctgcctg    3960
gcctggtgat ggcccaggac cagaggatca ggtggtacct gctgagcatg ggcagcaatg    4020
agaacatcca cagcatccac ttctctggcc atgtgttcac tgtgaggaag aaggaggagt    4080
acaagatggc cctgtacaac ctgtaccctg gggtgtttga gactgtggag atgctgccca    4140
gcaaggctgg catctggagg gtggagtgcc tgattgggga gcacctgcat gctggcatga    4200
gcaccctgtt cctggtgtac agcaacaagt gccagacccc cctgggcatg gcctctggcc    4260
acatcaggga cttccagatc actgcctctg ccagtatgg ccagtgggcc ccaagctgg    4320 ccaggctgca ctactctggc agcatcaatg cctggagcac caaggagccc ttcagctgga    4380
tcaaggtgga cctgctggcc cccatgatca tccatggcat caagacccag ggggccaggc    4440
agaagttcag cagcctgtac atcagccagt tcatcatcat gtacagcctg gatggcaaga    4500
agtggcagac ctacaggggc aacagcactg gcacccgat ggtgttcttt ggcaatgtgg    4560
acagctctgg catcaagcac aacatcttca acccccccat cattgccaga tacatcaggc    4620 tgcacccca ccactacagc atcaggagca cctgaggat ggagctgatg ggctgtgacc    4680
tgaacagctg cagcatgccc ctgggcatgg agagcaaggc catctctgat gcccagatca    4740
ctgccagcag ctacttcacc aacatgtttg ccacctggag ccccagcaag gccaggctgc    4800
```

| | |
|---|---:|
| acctgcaggg caggagcaat gcctggaggc cccaggtcaa caaccccaag gagtggctgc | 4860 |
| aggtggactt ccagaagacc atgaaggtga ctggggtgac cacccagggg gtgaagagcc | 4920 |
| tgctgaccag catgtatgtg aaggagttcc tgatcagcag cagccaggat ggccaccagt | 4980 |
| ggaccctgtt cttccagaat ggcaaggtga aggtgttcca gggcaaccag acagcttca | 5040 |
| cccctgtggt gaacagcctg accccccccc tgctgaccag atacctgagg attcaccccc | 5100 |
| agagctgggt gcaccagatt gccctgagga tggaggtgct gggctgtgag gcccaggacc | 5160 |
| tgtactgacc tcgaggaata aggaaattt attttcattg caatagtgtg ttggtttttt | 5220 |
| gtgtcacgtg gcggccgcag gaaccccctag tgatggagtt ggccactccc tctctgcgcg | 5280 |
| ctcgctcgct cactgaggcc gggcgaccaa aggtcgcccg acgcccgggc tttgcccggg | 5340 |
| cggcctcagt gagcgagcga gcgcgcagag agggagtggc caa | 5383 |

<210> SEQ ID NO 38
<211> LENGTH: 5728
<212> TYPE: DNA
<213> ORGANISM: Adeno-Associated Virus 2

<400> SEQUENCE: 38

| | |
|---|---:|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgactg tttgctgttt | 180 |
| gctgcttgca atgtttgccc attttaggga catgtttgct gtttgctgct tgcaatgttt | 240 |
| gcccattttta gggacatgtt tgctgtttgc tgcttgcaat gtttgcccat tttagggaca | 300 |
| tgtttgctgt ttgctgcttg caatgtttgc cattttaggg acaacgcga acgtcgaca | 360 |
| ggttaatttt taaaaagcag tcaaaagtcc aagtggccct tggcagcatt tactctctct | 420 |
| gtttgctctg gttaataatc tcaggagcac aaacattcct ggaggcagga agaaaatca | 480 |
| acatcctgga cttatcctct gggcctctcc ccaccccccag gagaggctca ggttaattt | 540 |
| taaaaagcag tcaaaagtcc aagtggccct tggcagcatt tactctctct gtttgctctg | 600 |
| gttaataatc tcaggagcac aaacattcct ggaggcagga agaaaatca acatcctgga | 660 |
| cttatcctct gggcctctcc ccaccccccag gagaggctgt cgactggaca caggacgctg | 720 |
| tggtttctga gccaggggggc gactcagatc ccagccagtg gacttagccc ctgtttgctc | 780 |
| ctccgataac tggggtgacc ttggttaata ttcaccagca gcctccccccg ttgccctct | 840 |
| ggatccactg cttaaatacg gacgaggaca gggccctgtc tcctcagctt caggcaccac | 900 |
| cactgacctg ggacagtgaa tcgtaagtat gcctttcact gcgagaggtt ctggagaggc | 960 |
| ttctgagctc cccatggccc aggcaggcag caggtctggg gcaggagggg ggttgtggag | 1020 |
| tgccttgact cggggcctgg cccccccatc tctgtcttgc aggacaattg ccgtcttctg | 1080 |
| tctcgtgggg catcctcctg ctggcaggcc tgtgctgcct ggtccctgcg atcgccacca | 1140 |
| tgcagattga gctgagcacc tgcttcttcc tgtgcctgct gaggttctgc ttctctgcca | 1200 |
| ccaggagata ctacctgggg gctgtggagc tgagctggga ctacatgcag tctgacctgg | 1260 |
| gggagctgcc tgtggatgcc aggttccccc ccagagtgcc caagagcttc ccttcaaca | 1320 |
| cctctgtggt gtacaagaag accctgtttg tggagttcac tgaccacctg ttcaacattg | 1380 |
| ccaagcccag gccccctgg atgggcctgc tgggccccac catccaggct gaggtgtatg | 1440 |
| acactgtggt gatcaccctg aagaacatgg ccagccaccc tgtgagcctg catgctgtgg | 1500 |
| gggtgagcta ctggaaggcc tctgagggggg ctgagtatga tgaccagacc agccagaggg | 1560 |

```
agaaggagga tgacaaggtg ttccctgggg gcagccacac ctatgtgtgg caggtgctga   1620
aggagaatgg ccccatggcc tctgacccce tgtgcctgac ctacagctac ctgagccatg   1680
tggacctggt gaaggacctg aactctggcc tgattggggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc acaggaagt ctgtgtactg gcatgtgatt ggcatgggca    1980 ccaccectga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgcccccctg gtgctggccc   2400
ctgatgacag gagctacaag agccagtacc tgaacaatgg ccccagagg attggcagga    2460 agtacaagaa ggtcaggttc atggcctaca ctgatgaaac cttcaagacc agggaggcca   2520
tccagcatga gtctggcatc ctgggccccc tgctgtatgg ggaggtgggg gacaccctgc   2580
tgatcatctt caagaaccag gccagcaggc cctacaacat ctaccccat ggcatcactg    2640 atgtgaggcc cctgtacagc aggaggctgc caagggggt gaagcacctg aaggacttcc    2700
ccatcctgcc tgggagatc ttcaagtaca agtggactgt gactgtggag atggcccca    2760 ccaagtctga ccccaggtgc ctgaccagat actacagcag ctttgtgaac atggagaggg   2820
acctggcctc tggcctgatt ggcccctgc tgatctgcta caaggagtct gtggaccaga    2880
ggggcaacca gatcatgtct gacaagagga atgtgatcct gttctctgtg tttgatgaga   2940
acaggagctg gtacctgact gagaacatcc agaggttcct gcccaaccct gctggggtgc   3000
agctggagga ccctgagttc caggccagca acatcatgca cagcatcaat ggctatgtgt   3060
ttgacagcct gcagctgtct gtgtgcctgc atgaggtggc ctactggtac atcctgagca   3120
ttggggccca gactgacttc ctgtctgtgt cttctctgg ctacaccttc aagcacaaga    3180
tggtgtatga ggacacctg accctgttcc ccttctctgg ggagactgtg ttcatgagca   3240
tggagaaccc tggcctgtgg attctgggct gccacaactc tgacttcagg aacaggggca   3300
tgactgccct gctgaaagtc tccagctgtg acaagaacac tggggactac tatgaggaca   3360
gctatgagga catctctgcc tacctgctga gcaagaacaa tgccattgag cccaggagct   3420
tcagccagaa ccccccagtg ctgaagaggc accagaggga gatcaccagg accaccctgc   3480
agtctgacca ggaggagatt gactatgatg acaccatctc tgtggagatg aagaaggagg   3540
actttgacat ctacgacgag gacgagaacc agagcccag gagcttccag aagaagacca    3600
ggcactactt cattgctgct gtggagaggc tgtgggacta tggcatgagc agcagccccc   3660
atgtgctgag gaacagggcc cagtctggct ctgtgcccca gttcaagaag gtggtgttcc   3720
aggagttcac tgatggcagc ttcacccagc ccctgtacag aggggagctg aatgagcacc   3780
tgggcctgct gggcccctac atcagggctg aggtggagga caacatcatg gtgaccttca   3840
ggaaccaggc cagcaggccc tacagcttct acagcagcct gatcagctat gaggaggacc   3900
```

-continued

```
agaggcaggg ggctgagccc aggaagaact ttgtgaagcc caatgaaacc aagacctact    3960
tctggaaggt gcagcaccac atggccccca ccaaggatga gtttgactgc aaggcctggg    4020
cctacttctc tgatgtggac ctggagaagg atgtgcactc tggcctgatt ggcccctgc     4080 tggtgtgcca caccaacacc ctgaaccctg cccatggcag gcaggtgact gtgcaggagt    4140
ttgccctgtt cttcaccatc tttgatgaaa ccaagagctg gtacttcact gagaacatgg    4200
agaggaactg cagggccccc tgcaacatcc agatggagga ccccaccttc aaggagaact    4260
acaggttcca tgccatcaat ggctacatca tggacaccct gcctggcctg gtgatggccc    4320
aggaccagag gatcaggtgg tacctgctga gcatgggcag caatgagaac atccacagca    4380
tccacttctc tggccatgtg ttcactgtga ggaagaagga ggagtacaag atggccctgt    4440
acaacctgta ccctggggtg tttgagactg tggagatgct gcccagcaag gctggcatct    4500 ggaggtgga gtgcctgatt ggggagcacc tgcatgctgg catgagcacc ctgttcctgg    4560
tgtacagcaa caagtgccag acccccctgg gcatggcctc tggccacatc agggacttcc    4620
agatcactgc ctctggccag tatggccagt gggcccccaa gctggccagg ctgcactact    4680
ctggcagcat caatgcctgg agcaccaagg agcccttcag ctggatcaag gtggacctgc    4740 tggccccat gatcatccat ggcatcaaga cccagggggc caggcagaag ttcagcagcc    4800
tgtacatcag ccagttcatc atcatgtaca gcctggatgg caagaagtgg cagacctaca    4860
ggggcaacag cactggcacc ctgatggtgt tctttggcaa tgtggacagc tctggcatca    4920
agcacaacat cttcaacccc cccatcattg ccagatacat caggctgcac cccacccact    4980
acagcatcag gagcacctg aggatggagc tgatgggctg tgacctgaac agctgcagca    5040 tgccctggg catggagagc aaggccatct ctgatgccca gatcactgcc agcagctact    5100
tcaccaacat gtttgccacc tggagcccca gcaaggccag gctgcacctg cagggcagga    5160
gcaatgcctg gaggcccag gtcaacaacc caaggagtg gctgcaggtg gacttccaga    5220
agaccatgaa ggtgactggg gtgaccaccc aggggggtgaa gagcctgctg accagcatgt    5280
atgtgaagga gttcctgatc agcagcagcc aggatggcca ccagtggacc ctgttcttcc    5340
agaatggcaa ggtgaaggtg ttccagggca accaggacac cttcaccccct gtggtgaaca    5400 gcctggaccc cccctgctg accagatacc tgaggattca ccccagagc tgggtgcacc    5460 agattgccct gaggatggag gtgctgggct gtgaggccca ggacctgtac tgacctcgag    5520
gaataaagga aatttatttt cattgcaata gtgtgttggt ttttgtgtc acgtggcggc    5580 cgcaggaacc cctagtgatg gagttggcca ctccctctct gcgcgctcgc tcgctcactg    5640
aggccgggcg accaaaggtc gcccgacgcc cgggctttgc ccgggcggcc tcagtgagcg    5700
agcgagcgcg cagagaggga gtggccaa                                       5728
```

<210> SEQ ID NO 39
<211> LENGTH: 5905
<212> TYPE: DNA
<213> ORGANISM: Adeno-Associated Virus 2

<400> SEQUENCE: 39

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc attttaggga catgttgct gtttgctgct tgcaatgttt     240 gcccattta gggacatgtt tgctgtttgc tgcttgcaat gtttgcccat tttagggaca     300
```

```
tgtttgctgt tgctgcttg caatgtttgc ccatttagg gacaacgcga aacgtcgaca      360
ggttaatttt taaaaagcag tcaaaagtcc aagtggccct tggcagcatt tactctctct      420
gtttgctctg gttaataatc tcaggagcac aaacattcct ggaggcagga aagaaatca       480
acatcctgga cttatcctct gggcctctcc cacccccag gagaggctca ggttaatttt       540
taaaaagcag tcaaaagtcc aagtggccct tggcagcatt tactctctct gtttgctctg      600
gttaataatc tcaggagcac aaacattcct ggaggcagga aagaaatca acatcctgga       660
cttatcctct gggcctctcc cacccccag gagaggctgt cgactggaca caggacgctg       720
tggtttctga gccaggggc gactcagatc ccagccagtg gacttagccc ctgtttgctc       780
ctccgataac tggggtgacc ttggttaata ttcaccagca gcctcccccg ttgccctct       840
ggatccactg cttaaatacg gacgaggaca gggccctgtc tcctcagctt caggcaccac      900
cactgacctg gacagtgaa tcgtaagtat gcctttcact gcgagaggtt ctggagaggc       960
ttctgagctc cccatggccc aggcaggcag caggtctggg gcaggagggg ggttgtggag     1020
tgccttgact cggggcctgg ccccccatc tctgtcttgc aggacaattg ccgtcttctg       1080
tctcgtgggg catcctcctg ctggcaggcc tgtgctgcct ggtccctgcg atcgccacca      1140
tgcagattga gctgagcacc tgcttcttcc tgtgcctgct gaggttctgc ttctctgcca      1200
ccaggagata ctacctgggg gctgtggagc tgagctggga ctacatgcag tctgacctgg      1260
gggagctgcc tgtggatgcc aggttccccc ccagagtgcc caagagcttc cccttcaaca     1320
cctctgtggt gtacaagaag accctgtttg tggagttcac tgaccacctg ttcaacattg      1380
ccaagcccag gccccctgg atgggcctgc tgggccccac catccaggct gaggtgtatg      1440
acactgtggt gatcaccctg aagaacatgg ccagccaccc tgtgagcctg catgctgtgg     1500
gggtgagcta ctggaaggcc tctgagggg ctgagtatga tgaccagacc agccagaggg      1560
agaaggagga tgacaaggtg ttccctgggg gcagccacac ctatgtgtgg caggtgctga     1620
aggagaatgg ccccatggcc tctgacccc tgtgcctgac ctacagctac ctgagccatg     1680
tggacctggt gaaggacctg aactctggcc tgattgggc cctgctggtg tgcagggagg      1740
gcagcctggc caaggagaag acccagaccc tgcacaagtt catcctgctg tttgctgtgt    1800
ttgatgaggg caagagctgg cactctgaaa ccaagaacag cctgatgcag gacaggatg     1860
ctgcctctgc cagggcctgg ccaagatgc acactgtgaa tggctatgtg aacaggagcc     1920
tgcctggcct gattggctgc acaggaagt ctgtgtactg gcatgtgatt ggcatgggca      1980
ccacccctga ggtgcacagc atcttcctgg agggccacac cttcctggtc aggaaccaca     2040
ggcaggccag cctggagatc agccccatca ccttcctgac tgcccagacc ctgctgatgg     2100
acctgggcca gttcctgctg ttctgccaca tcagcagcca ccagcatgat ggcatggagg    2160
cctatgtgaa ggtggacagc tgccctgagg agccccagct gaggatgaag aacaatgagg     2220
aggctgagga ctatgatgat gacctgactg actctgagat ggatgtggtg aggtttgatg    2280
atgacaacag ccccagcttc atccagatca ggtctgtggc caagaagcac cccaagacct    2340
gggtgcacta cattgctgct gaggaggagg actgggacta tgccccctg gtgctggccc    2400
ctgatgcaca gagctacaag agccagtacc tgaacaatgg ccccagagg attggcagga    2460
agtacaagaa ggtcaggttc atggcctaca ctgatgaaac cttcaagacc agggaggcca    2520
tccagcatga gtctggcatc ctgggccccc tgctgtatgg ggaggtgggg gacacccgc     2580
tgatcatctt caagaaccag gccagcaggc cctacaacat ctaccccat ggcatcactg     2640
```

```
atgtgaggcc cctgtacagc aggaggctgc ccaaggggt gaagcacctg aaggacttcc      2700
ccatcctgcc tggggagatc ttcaagtaca agtggactgt gactgtggag gatggcccca      2760
ccaagtctga ccccaggtgc ctgaccagat actacagcag ctttgtgaac atggagaggg      2820
acctggcctc tggcctgatt ggccccctgc tgatctgcta caaggagtct gtggaccaga      2880
ggggcaacca gatcatgtct gacaagagga atgtgatcct gttctctgtg tttgatgaga      2940
acaggagctg gtacctgact gagaacatcc agaggttcct gcccaaccct gctgggtgc       3000
agctggagga ccctgagttc caggccagca acatcatgca cagcatcaat ggctatgtgt      3060
ttgacagcct gcagctgtct gtgtgcctgc atgaggtggc ctactggtac atcctgagca      3120
ttggggccca gactgacttc ctgtctgtgt cttctctgg ctacaccttc aagcacaaga       3180
tggtgtatga ggacaccctg accctgttcc ccttctctgg ggagactgtg ttcatgagca      3240
tggagaaccc tggcctgtgg attctgggct gccacaactc tgacttcagg aacagggca      3300
tgactgccct gctgaaagtc tccagctgtg acaagaacac tggggactac tatgaggaca      3360
gctatgagga catctctgcc tacctgctga gcaagaacaa tgccattgag cccaggagct      3420
tcagccagaa ccccccagtg ctgaagaggc accagaggga gatcaccagg accaccctgc      3480
agtctgacca ggaggagatt gactatgatg acaccatctc tgtggagatg aagaaggagg      3540
actttgacat ctacgacgag gacgagaacc agagccccag gagcttccag aagaagacca      3600
ggcactactt cattgctgct gtggagaggc tgtgggacta tggcatgagc agcagccccc      3660
atgtgctgag gaacagggcc cagtctggct ctgtgcccca gttcaagaag gtggtgttcc      3720
aggagttcac tgatggcagc ttcacccagc ccctgtacag aggggagctg aatgagcacc      3780
tgggcctgct gggcccctac atcagggctg aggtggagga caacatcatg gtgaccttca      3840
ggaaccaggc cagcaggccc tacagcttct acagcagcct gatcagctat gaggaggacc      3900
agaggcaggg ggctgagccc aggaagaact tgtgaagcc caatgaaacc aagacctact      3960
tctgaaggt gcagcaccac atggcccca ccaaggatga gtttgactgc aaggcctggg       4020
cctacttctc tgatgtggac ctggagaagg atgtgcactc tggcctgatt ggccccctgc      4080
tggtgtgcca caccaacacc ctgaaccctg cccatggcag gcaggtgact gtgcaggagt      4140
ttgccctgtt cttcaccatc tttgatgaaa ccaagagctg gtacttcact gagaacatgg      4200
agaggaactg cagggccccc tgcaacatcc agatggagga ccccaccttc aaggagaact      4260
acaggttcca tgccatcaat ggctacatca tggacaccct gcctggcctg gtgatggccc      4320
aggaccagag gatcaggtgg tacctgctga gcatgggcag caatgagaac atccacagca      4380
tccacttctc tggccatgtg ttcactgtga ggaagaagga ggagtacaag atggcctgt      4440
acaacctgta ccctgggggtg tttgagactg tggagatgct gcccagcaag gctggcatct      4500
ggagggtgga gtgcctgatt ggggagcacc tgcatgctgg catgagcacc ctgttcctgg      4560
tgtacagcaa caagtgccag accccctgg gcatggcctc tggccacatc agggacttcc       4620
agatcactgc ctctggccag tatggccagt gggccccca gctggccagg ctgcactact       4680
ctggcagcat caatgcctgg agcaccaagg agcccttcag ctggatcaag gtggacctgc      4740
tggcccccat gatcatccat ggcatcaaga cccgagggggc caggcagaag ttcagcagcc      4800
tgtacatcag ccagttcatc atcatgtaca gcctggatgg caagaagtgg cagacctaca      4860
ggggcaacag cactggcacc ctgatggtgt tctttggcaa tgtggacagc tctggcatca      4920
agcacaacat cttcaacccc cccatcattg ccagatacat caggctgcac cccaccccact      4980
acagcatcag gagcaccctg aggatggagc tgatgggctg tgacctgaac agctgcagca      5040
```

```
tgcccctggg catggagagc aaggccatct ctgatgccca gatcactgcc agcagctact      5100
tcaccaacat gtttgccacc tggagcccca gcaaggccag gctgcacctg cagggcagga      5160
gcaatgcctg gaggcccag gtcaacaacc caaggagtg gctgcaggtg gacttccaga       5220
agaccatgaa ggtgactggg gtgaccaccc aggggtgaa gagcctgctg accagcatgt      5280
atgtgaagga gttcctgatc agcagcagcc aggatggcca ccagtggacc ctgttcttcc     5340
agaatggcaa ggtgaaggtg ttccagggca accaggacac cttcaccct gtggtgaaca      5400 gcctggaccc cccctgctg accagatacc tgaggattca ccccagagc tgggtgcacc       5460 agattgccct gaggatggag gtgctgggct gtgaggccca ggacctgtac tgacctcgag     5520
gtgtgccttc tagttgccag ccatctgttg tttgcccctc cccgtgcct tccttgaccc      5580 tggaaggtgc cactcccact gtcctttcct aataaaatga ggaaattgca tcgcattgtc     5640
tgagtaggtg tcattctatt ctggggggtg gggtggggca ggacagcaag ggggaggatt     5700
gggaagacaa tagcaggcat gctggggatg cggtgggctc tatgggcacg tggcggccgc     5760 aggaaccct agtgatggag ttggccactc cctctctgcg cgctcgctcg ctcactgagg      5820
ccgggcgacc aaaggtcgcc cgacgcccgg gctttgcccg gcggcctca gtgagcgagc      5880 gagcgcgcag agagggagtg gccaa                                           5905
```

<210> SEQ ID NO 40
<211> LENGTH: 5355
<212> TYPE: DNA
<213> ORGANISM: Adeno-Associated Virus 2

<400> SEQUENCE: 40

```
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgactg tttgctgttt      180
gctgcttgca atgtttgccc attttaggga catgtttgct gtttgctgct tgcaatgttt      240
gcccatttta gggacatgtt tgctgtttgc tgcttgcaat gtttgcccat tttaggaca      300 tgtttgctgt ttgctgcttg caatgtttgc ccatttagg acaacgcgaa acgtcgact       360 ggacacagga cgctgtggtt tctgagccag ggggcgactc agatcccagc cagtggactt      420 agccccctgtt tgctcctccg ataactgggg tgaccttggt taatattcac cagcagcctc     480
ccccgttgcc cctctggatc cactgcttaa atacggacga ggacagggcc ctgtctcctc     540
agcttcaggc accaccactg acctgggaca gtgaatcgcg atcgccacca tgcagattga     600
gctgagcacc tgcttcttcc tgtgcctgct gaggttctgc ttctctgcca ccaggagata     660
ctacctgggg gctgtggagc tgagctggga ctacatgcag tctgacctgg ggagctgcc     720 tgtggatgcc aggttccccc ccagagtgcc caagagcttc cccttcaaca cctctgtggt     780
gtacaagaag accctgtttg tggagttcac tgaccacctg ttcaacattg ccaagcccag     840 gccccctgg atgggcctgc tgggccccac catccaggct gaggtgtatg acactgtggt     900
gatcaccctg aagaacatgg ccagccaccc tgtgagcctg catgctgtgg gggtgagcta     960
ctggaaggcc tctgagggg ctgagtatga tgaccagacc agccagaggg agaaggagga    1020
tgacaaggtg ttccctgggg gcagccacac ctatgtgtgg caggtgctga aggagaatgg    1080
ccccatggcc tctgaccccc tgtgcctgac ctacagctac ctgagccatg tggacctggt    1140
gaaggacctg aactctggcc tgattggggc cctgctggtg tgcagggagg gcagcctggc    1200
```

-continued

```
caaggagaag acccagaccc tgcacaagtt catcctgctg tttgctgtgt tgatgaggg      1260 caagagctgg cactctgaaa ccaagaacag cctgatgcag acagggatg ctgcctctgc      1320 cagggcctgg cccaagatgc acactgtgaa tggctatgtg aacaggagcc tgcctggcct     1380
gattggctgc cacaggaagt ctgtgtactg catgtgatt ggcatgggca ccacccctga      1440
ggtgcacagc atcttcctgg agggccacac cttcctggtc aggaaccaca ggcaggccag     1500
cctggagatc agccccatca ccttcctgac tgcccagacc ctgctgatgg acctgggcca     1560
gttcctgctg ttctgccaca tcagcagcca ccagcatgat ggcatggagg cctatgtgaa     1620
ggtggacagc tgccctgagg agccccagct gaggatgaag aacaatgagg aggctgagga     1680
ctatgatgat gacctgactg actctgagat ggatgtggtg aggtttgatg atgacaacag     1740
ccccagcttc atccagatca ggtctgtggc caagaagcac cccaagacct gggtgcacta     1800
cattgctgct gaggaggagg actgggacta tgcccccctg gtgctggccc ctgatgacag     1860
gagctacaag agccagtacc tgaacaatgg cccccagagg attggcagga agtacaagaa     1920
ggtcaggttc atggcctaca ctgatgaaac cttcaagacc agggaggcca tccagcatga     1980
gtctggcatc ctgggccccc tgctgtatgg ggaggtgggg gacaccctgc tgatcatctt     2040
caagaaccag gccagcaggc cctacaacat ctaccccat ggcatcactg atgtgaggcc      2100
cctgtacagc aggaggctgc ccaaggggt gaagcacctg aaggacttcc ccatcctgcc      2160
tggggagatc ttcaagtaca gtggactgt gactgtggag gatggcccca ccaagtctga     2220
ccccaggtgc ctgaccagat actacagcag ctttgtgaac atggagaggg acctggcctc     2280
tggcctgatt ggcccctgc tgatctgcta caaggagtct gtggaccaga ggggcaacca      2340
gatcatgtct gacaagagga atgtgatcct gttctctgtg tttgatgaga caggagctg      2400 gtacctgact gagaacatcc agaggttcct gcccaacct gctggggtgc agctggagga     2460
ccctgagttc caggccagca acatcatgca cagcatcaat ggctatgtgt tgacagcct      2520 gcagctgtct gtgtgcctgc atgaggtggc ctactggtac atcctgagca ttggggccca     2580
gactgacttc ctgtctgtgt tcttctctgg ctacaccttc aagcacaaga tggtgtatga     2640
ggacaccctg accctgttcc ccttctctgg ggagactgtg ttcatgagca tggagaaccc     2700
tggcctgtgg attctgggct gccacaactc tgacttcagg aacaggggca tgactgccct     2760
gctgaaagtc tccagctgtg acaagaacac tggggactac tatgaggaca gctatgagga     2820
catctctgcc tacctgctga gcaagaacaa tgccattgag cccaggagct tcagccagaa     2880 cccccagtg ctgaagaggc accagaggga gatcaccagg accaccctgc agtctgacca      2940
ggaggagatt gactatgatg acaccatctc tgtggagatg aagaaggagg acttttgacat    3000 ctacgacgag gacgagaacc agagccccag gagcttccag aagaagacca ggcactactt     3060
cattgctgct gtggagaggc tgtgggacta tggcatgagc agcagccccc atgtgctgag     3120
gaacagggcc cagtctggct ctgtgcccca gttcaagaag gtggtgttcc aggagttcac     3180
tgatggcagc ttcacccagc ccctgtacag aggggagctg aatgagcacc tgggcctgct     3240
gggcccctac atcagggctg aggtggagga caacatcatg gtgaccttca ggaaccaggc     3300 cagcaggcc tacagcttct acagcagcct gatcagctat gaggaggacc agaggcaggg     3360
ggctgagccc aggaagaact tgtgaagcc caatgaaacc aagacctact tctggaaggt     3420
gcagcaccac atggccccca ccaaggatga gtttgactgc aaggcctggg cctacttctc     3480
tgatgtggac ctggagaagg atgtgcactc tggcctgatt ggcccctgc tggtgtgcca     3540 caccaacacc ctgaaccctg cccatggcag gcaggtgact gtgcaggagt ttgccctgtt     3600
```

```
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tccacttctc    3840
tggccatgtg ttcactgtga ggaagaagga ggagtacaag atggccctgt acaacctgta    3900
ccctggggtg tttgagactg tggagatgct gcccagcaag gctggcatct ggagggtgga    3960
gtgcctgatt ggggagcacc tgcatgctgg catgagcacc ctgttcctgg tgtacagcaa    4020
caagtgccag acccccctgg gcatggcctc tggccacatc agggacttcc agatcactgc    4080
ctctggccag tatggccagt gggccccaa gctggccagg ctgcactact ctggcagcat    4140
caatgcctgg agcaccaagg agcccttcag ctggatcaag gtggacctgc tggccccat    4200
gatcatccat ggcatcaaga cccagggggc caggcagaag ttcagcagcc tgtacatcag    4260
ccagttcatc atcatgtaca gcctggatgg caagaagtgg cagacctaca ggggcaacag    4320
cactggcacc ctgatggtgt tctttggcaa tgtggacagc tctggcatca agcacaacat    4380
cttcaacccc cccatcattg ccagatacat caggctgcac cccacccact acagcatcag    4440
gagcaccctg aggatggagc tgatgggctg tgacctgaac agctgcagca tgccctggg    4500
catggagagc aaggccatct ctgatgccca gatcactgcc agcagctact tcaccaacat    4560
gtttgccacc tggagcccca gcaaggccag gctgcacctg cagggcagga gcaatgcctg    4620
gaggcccag gtcaacaacc caaggagtg gctgcaggtg gacttccaga gaccatgaa    4680
ggtgactggg gtgaccaccc aggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca accaggacag cttcacccct gtggtgaaca gcctggaccc    4860
cccctgctg accagatacc tgaggattca ccccagagc tgggtgcacc agattgccct    4920
gaggatggag gtgctgggct gtgaggccca ggacctgtac tgacctcgag gtgtgccttc    4980
tagttgccag ccatctgttg tttgccccte ccccgtgcct tccttgaccc tggaaggtgc    5040
cactcccact gtccttttcct aataaaatga ggaaattgca tcgcattgtc tgagtaggtg    5100
tcattctatt ctggggggtg gggtggggca ggacagcaag ggggaggatt gggaagacaa    5160
tagcaggcat gctgggatg cggtgggctc tatgggcacg tggcggccgc aggaacccct    5220
agtgatggag ttggccactc cctctctgcg cgctcgctcg ctcactgagg ccgggcgacc    5280
aaaggtcgcc cgacgcccgg gctttgcccg ggcggcctca gtgagcgagc gagcgcgcag    5340
agagggagtg gccaa                                                    5355
```

<210> SEQ ID NO 41
<211> LENGTH: 5618
<212> TYPE: DNA
<213> ORGANISM: Adeno-Associated Virus 2

<400> SEQUENCE: 41

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgacca gagaggtctc    180
tgacctctgc cccagctcca aggtcagcag gcagggaggg ctgtgtgttt gctgtttgct    240
gcttgcaatg tttgcccatt ttagggacat gagtaggctg aagtttgttc agtgtggact    300
```

```
tcagaggcag cacacaaaca gccagagagg tctctgacct ctgccccagc tccaaggtca    360
gcaggcaggg agggctgtgt gtttgctgtt tgctgcttgc aatgtttgcc cattttaggg    420
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gcccagctc     660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga acgtcgact ggacacagga cgctgtggtt tctgagccag ggggcgactc     840
agatcccagc cagtgactt agcccctgtt tgctcctccg ataactgggg tgaccttggt     900
taatattcac cagcagcctc cccgttgcc cctctggatc cactgcttaa atacggacga     960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gccccctggg atgggcctgc tgggcccac catccaggct    1320
gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg cagcctggc caaggagaag acccagaccc tgcacaagtt catcctgctg    1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccacccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agccccagct gaggatgaag   2100
aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgccccctg    2280
gtgctggccc ctgatgacag gagctacaag agccagtacc tgaacaatgg cccccagagg   2340
attggcagga agtacaagaa ggtcaggttc atggcctaca ctgatgaaac cttcaagacc   2400
agggaggcca tccagcatga gtctggcatc ctgggccccc tgctgtatgg ggaggtgggg   2460
gacaccctgc tgatcatctt caagaaccag gccagcaggc cctacaacat ctaccccat    2520
ggcatcactg atgtgaggcc cctgtacagc aggaggctgc caaggggggt gaagcacctg   2580
aaggacttcc ccatcctgcc tgggagatc ttcaagtaca agtggactgt gactgtggag   2640
gatggcccca ccaagtctga ccccaggtgc ctgaccagat actacagcag ctttgtgaac   2700
```

```
atggagaggg acctggcctc tggcctgatt ggcccctgc tgatctgcta caaggagtct    2760
gtggaccaga ggggcaacca gatcatgtct gacaagagga atgtgatcct gttctctgtg    2820
tttgatgaga acaggagctg gtacctgact gagaacatcc agaggttcct gcccaaccct    2880
gctggggtgc agctggagga ccctgagttc caggccagca acatcatgca cagcatcaat    2940
ggctatgtgt ttgacagcct gcagctgtct gtgtgcctgc atgaggtggc ctactggtac    3000
atcctgagca ttggggccca gactgacttc ctgtctgtgt tcttctctgg ctacaccttc    3060
aagcacaaga tggtgtatga ggacaccctg accctgttcc ccttctctgg ggagactgtg    3120
ttcatgagca tggagaaccc tggcctgtgg attctgggct gccacaactc tgacttcagg    3180
aacaggggca tgactgccct gctgaaagtc tccagctgtg acaagaacac tggggactac    3240
tatgaggaca gctatgagga catctctgcc tacctgctga gcaagaacaa tgccattgag    3300
cccaggagct tcagccagaa ccccccagtg ctgaagaggc accagaggga gatcaccagg    3360
accaccctgc agtctgacca ggaggagatt gactatgatg acaccatctc tgtggagatg    3420
aagaaggagg actttgacat ctacgacgag gacgagaacc agagcccag gagcttccag    3480 aagaagacca ggcactactt cattgctgct gtggagaggc tgtgggacta tggcatgagc    3540
agcagccccc atgtgctgag gaacagggcc cagtctggct ctgtgcccca gttcaagaag    3600
gtggtgttcc aggagttcac tgatggcagc ttcacccagc ccctgtacag aggggagctg    3660
aatgagcacc tgggcctgct gggcccctac atcagggctg aggtggagga caacatcatg    3720
gtgaccttca ggaaccaggc cagcaggccc tacagcttct acagcagcct gatcagctat    3780
gaggaggacc agaggcaggg ggctgagccc aggaagaact ttgtgaagcc caatgaaacc    3840
aagacctact tctggaaggt gcagcaccac atggcccca ccaaggatga gtttgactgc    3900
aaggcctggg cctacttctc tgatgtggac ctggagaagg atgtgcactc tggcctgatt    3960 ggcccctgc tggtgtgcca caccaacacc ctgaaccctg ccatggcag gcaggtgact    4020 gtgcaggagt ttgccctgtt cttcaccatc tttgatgaaa ccaagagctg gtacttcact    4080
gagaacatgg agaggaactg cagggccccc tgcaacatcc agatggagga ccccacctcc    4140
aaggagaact acaggttcca tgccatcaat ggctacatca tggacaccct gcctggcctg    4200
gtgatggccc aggaccagag gatcaggtgg tacctgctga gcatgggcag caatgagaac    4260
atccacagca tccacttctc tggccatgtg ttcactgtga ggaagaagga ggagtacaag    4320 atggcccctgt acaacctgta ccctgggggtg tttgagactg tggagatgct gcccagcaag    4380
gctggcatct ggagggtgga gtgcctgatt ggggagcacc tgcatgctgg catgagcacc    4440
ctgttcctgg tgtacagcaa caagtgccag accccctgg gcatggcctc tggccacatc    4500
agggacttcc agatcactgc ctctggccag tatggccagt gggccccaa gctggccagg    4560 ctgcactact ctggcagcat caatgcctgg agcaccaagg agcccttcag ctggatcaag    4620
gtggacctgc tggccccat gatcatccat ggcatcaaga cccagggggc caggcagaag    4680
ttcagcagcc tgtacatcag ccagttcatc atcatgtaca gcctggatgg caagaagtgg    4740
cagacctaca gggcaacag cactggcacc ctgatggtgt tctttggcaa tgtggacagc    4800
tctggcatca gcacaacat cttcaacccc cccatcattg ccagatacat caggctgcac    4860
cccacccact acagcatcag gagcaccctg aggatggagc tgatgggctg tgacctgaac    4920
agctgcagca tgcccctggg catggagagc aaggccatct ctgatgccca gatcactgcc    4980
agcagctact tcaccaacat gtttgccacc tggagcccca gcaaggccag gctgcacctg    5040
```

| | |
|---|---|
| cagggcagga gcaatgcctg gaggccccag gtcaacaacc ccaaggagtg gctgcaggtg | 5100 |
| gacttccaga agaccatgaa ggtgactggg gtgaccaccc aggggggtgaa gagcctgctg | 5160 |
| accagcatgt atgtgaagga gttcctgatc agcagcagcc aggatggcca ccagtggacc | 5220 |
| ctgttcttcc agaatggcaa ggtgaaggtg ttccagggca accaggacag cttcaccct | 5280 |
| gtggtgaaca gcctggaccc cccctgctg accagatacc tgaggattca ccccagagc | 5340 |
| tgggtgcacc agattgccct gaggatggag gtgctgggct gtgaggccca ggacctgtac | 5400 |
| tgacctcgag gaataaagga aatttatttt cattgcaata gtgtgttggt tttttgtgtc | 5460 |
| acgtggcggc cgcaggaacc cctagtgatg gagttggcca ctccctctct gcgcgctcgc | 5520 |
| tcgctcactg aggccgggcg accaaaggtc gcccgacgcc cgggctttgc ccgggcggcc | 5580 |
| tcagtgagcg agcgagcgcg cagagaggga gtggccaa | 5618 |

<210> SEQ ID NO 42
<211> LENGTH: 5993
<212> TYPE: DNA
<213> ORGANISM: Adeno-Associated Virus 2

<400> SEQUENCE: 42

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtt tttaaacgtc gacaggttaa | 180 |
| ttttttaaaaa gcagtcaaaa gtccaagtgg ccccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc caggagagg ctcaggttaa ttttaaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc caggagagg ctgtcgactg acacaggac gctgtggttt | 540 |
| ctgagccagg gggcgactca gatcccagcc agtggactta gccctgtttt gctcctccga | 600 |
| taactggggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgcga tcgccaccat gcagattgag ctgagcacct gcttcttcct | 780 |
| gtgcctgctg aggttctgct tctctgccac caggagatac tacctggggg ctgtggagct | 840 |
| gagctgggac tacatgcagt ctgacctggg ggagctgcct gtggatgcca ggttcccccc | 900 |
| cagagtgccc aagagcttcc ccttcaacac ctctgtggtg tacaagaaga cctgtttgt | 960 |
| ggagttcact gaccacctgt tcaacattgc caagcccagg ccccctgga tgggcctgct | 1020 |
| gggcccccac catccaggctg aggtgtatga cactgtggtg atcaccctga gaacatggc | 1080 |
| cagccaccct gtgagcctgc atgctgtggg ggtgagctac tggaaggcct gaggggc | 1140 |
| tgagtatgat gaccagacca gccagaggga aaggaggat gacaaggtgt ccctggggg | 1200 |
| cagccacacc tatgtgtggc aggtgctgaa ggagaatggc cccatggcct ctgaccccct | 1260 |
| gtgcctgacc tacagctacc tgagccatgt ggacctggtg aaggacctga actctggcct | 1320 |
| gattggggcc ctgctggtgt gcaggagg cagcctggcc aaggagaaga cccagaccct | 1380 |
| gcacaagttc atcctgctgt ttgctgtgtt tgatgagggc aagagctggc actctgaaac | 1440 |
| caagaacagc ctgatgcagg acagggatgc tgcctctgcc agggcctggc caagatgca | 1500 |
| cactgtgaat ggctatgtga acaggagcct gcctggcctg attggctgcc acaggaagtc | 1560 |

```
tgtgtactgg catgtgattg gcatgggcac caccectgag gtgcacagca tcttcctgga    1620
gggccacacc ttcctggtca ggaaccacag gcaggccagc ctggagatca gccccatcac    1680
cttcctgact gcccagaccc tgctgatgga cctgggccag ttcctgctgt tctgccacat    1740
cagcagccac cagcatgatg gcatggaggc ctatgtgaag gtggacagct gccctgagga    1800
gccccagctg aggatgaaga acaatgagga ggctgaggac tatgatgatg acctgactga    1860
ctctgagatg gatgtggtga ggtttgatga tgacaacagc cccagcttca tccagatcag    1920
gtctgtggcc aagaagcacc ccaagacctg ggtgcactac attgctgctg aggaggagga    1980
ctgggactat gccccctgg tgctggcccc tgatgacagg agctacaaga gccagtacct    2040
gaacaatggc ccccagagga ttggcaggaa gtacaagaag gtcaggttca tggcctacac    2100
tgatgaaacc ttcaagacca gggaggccat ccagcatgag tctggcatcc tgggcccct    2160
gctgtatggg gaggtggggg acaccctgct gatcatcttc aagaaccagg ccagcaggcc    2220
ctacaacatc tacccccatg gcatcactga tgtgaggccc ctgtacagca ggaggctgcc    2280
caaggggtg aagcacctga aggacttccc catcctgcct ggggagatct tcaagtacaa    2340
gtggactgtg actgtggagg atggcccac caagtctgac cccaggtgcc tgaccagata    2400
ctacagcagc tttgtgaaca tggagaggga cctggcctct ggcctgattg ccccctgct    2460
gatctgctac aaggagtctg tggaccagag gggcaaccag atcatgtctg acaagaggaa    2520
tgtgatcctg ttctctgtgt ttgatgagaa caggagctgg tacctgactg agaacatcca    2580
gaggttcctg cccaacctg ctgggtgca gctggaggac cctgagttcc aggccagcaa    2640
catcatgcac agcatcaatg gctatgtgtt tgacagcctg cagctgtctg tgtgcctgca    2700
tgaggtggcc tactggtaca tcctgagcat tggggcccag actgacttcc tgtctgtgtt    2760
cttctctggc tacaccttca gcacaagat ggtgtatgag gacaccctga ccctgttccc    2820
cttctctggg gagactgtgt tcatgagcat ggagaaccct ggcctgtgga ttctgggctg    2880
ccacaactct gacttcagga acaggggcat gactgccctg ctgaaagtct ccagctgtga    2940
caagaacact ggggactact atgaggacag ctatgaggac atctctgcct acctgctgag    3000
caagaacaat gccattgagc ccaggagctt cagccagaac cccccagtgc tgaagaggca    3060
ccagagggag atcaccagga ccacectgca gtctgaccag gaggagattg actatgatga    3120
caccatctct gtggagatga agaaggagga cttgacatc tacgacgagg acgagaacca    3180
gagccccagg agcttccaga agaagaccag gcactacttc attgctgctg tggagaggct    3240
gtgggactat ggcatgagca gcagccccca tgtgctgagg aacagggccc agtctggctc    3300
tgtgccccag ttcaagaagg tggtgttcca ggagttcact gatggcagct cacccagcc    3360
cctgtacaga ggggagctga atgagcacct gggcctgctg gcccctaca tcagggctga    3420
ggtggaggac aacatcatgg tgaccttcag gaaccaggcc agcaggccct acagcttcta    3480
cagcagcctg atcagctatg aggaggacca gaggcagggg gctgagccca ggaagaactt    3540
tgtgaagccc aatgaaacca agacctactt ctggaaggtg cagcaccaca tggccccac    3600
caaggatgag tttgactgca aggcctgggc ctacttctct gatgtggacc tggagaagga    3660
tgtgcactct ggcctgattg ccccctgct ggtgtgccac accaacaccc tgaaccctgc    3720
ccatggcagg caggtgactg tgcaggagtt tgccctgttc ttcaccatct ttgatgaaac    3780
caagagctgg tacttcactg agaacatgga gagaactgc agggcccct gcaacatcca    3840
gatggaggac cccaccttca aggagaacta caggttccat gccatcaatg gctacatcat    3900
```

| | |
|---|---|
| ggacaccctg cctggcctgg tgatggccca ggaccagagg atcaggtggt acctgctgag | 3960 |
| catgggcagc aatgagaaca tccacagcat ccacttctct ggccatgtgt tcactgtgag | 4020 |
| gaagaaggag gagtacaaga tggccctgta caacctgtac cctggggtgt ttgagactgt | 4080 |
| ggagatgctg cccagcaagg ctggcatctg gagggtggag tgcctgattg gggagcacct | 4140 |
| gcatgctggc atgagcaccc tgttcctggt gtacagcaac aagtgccaga ccccctggg | 4200 |
| catggcctct ggccacatca gggacttcca gatcactgcc tctggccagt atggccagtg | 4260 |
| ggcccccaag ctggccaggc tgcactactc tggcagcatc aatgcctgga gcaccaagga | 4320 |
| gcccttcagc tggatcaagg tggacctgct ggccccatg atcatccatg catcaagac | 4380 |
| ccaggggggcc aggcagaagt tcagcagcct gtacatcagc cagttcatca tcatgtacag | 4440 |
| cctggatggc aagaagtggc agacctacag gggcaacagc actggcaccc tgatggtgtt | 4500 |
| ctttggcaat gtggacagct ctggcatcaa gcacaacatc ttcaaccccc ccatcattgc | 4560 |
| cagatacatc aggctgcacc ccacccacta cagcatcagg agcaccctga ggatggagct | 4620 |
| gatgggctgt gacctgaaca gctgcagcat gcccctgggc atggagagca aggccatctc | 4680 |
| tgatgcccag atcactgcca gcagctactt caccaacatg tttgccacct ggagccccag | 4740 |
| caaggccagg ctgcacctgc agggcaggag caatgcctgg aggccccagg tcaacaaccc | 4800 |
| caaggagtgg ctgcaggtgg acttccagaa gaccatgaag gtgactgggg tgaccaccca | 4860 |
| gggggtgaag agcctgctga ccagcatgta tgtgaaggag ttcctgatca gcagcagcca | 4920 |
| ggatggccac cagtggacccc tgttcttcca gaatggcaag gtgaaggtgt tccagggcaa | 4980 |
| ccaggacagc ttcaccctg tggtgaacag cctggacccc cctgctga ccagataccc | 5040 |
| gaggattcac ccccagagct gggtgcacca gattgccctg aggatggagg tgctgggctg | 5100 |
| tgaggcccag gacctgtact gacctcgagg aataaaggaa atttatttc attgcaatag | 5160 |
| tgtgttggtt ttttgtgtca cgtgccctct cacactacct aaaccacgcc aggacaacct | 5220 |
| ctgctcctct ccaccgaaat tccaagggt cgagtggatg ttggaggtgg catgggccca | 5280 |
| gagaggtctc tgacctctgc cccagctcca aggtcagcag gcagggaggg ctgtgtgttt | 5340 |
| gctgtttgct gcttgcaatg tttgcccatt ttagggacat gagtaggctg aagtttgttc | 5400 |
| agtgtggact tcagaggcag cacacaaaca gctgctggag gatgggaact gaggggttgg | 5460 |
| aagggggcag ggtgagccca gaaactcctg tgtgcctctg agcctgcagc cctctcacac | 5520 |
| tacctaaacc acgccaggac aacctctgct cctctccacc gaaattccaa ggggtcgagt | 5580 |
| ggatgttgga ggtggcatgg gcccagagag gtctctgacc tctgccccag ctccaaggtc | 5640 |
| agcaggcagg gagggctgtg tgtttgctgt ttgctgcttg caatgtttgc ccattttagg | 5700 |
| gacatgagta ggctgaagtt tgttcagtgt ggacttcaga ggcagcacac aaacagctgc | 5760 |
| tggaggatgg gaactgaggg gttggaaggg ggcagggtga gcccagaaac tcctgtgtgc | 5820 |
| ctctgagcct gcagcacgtg gcggccgcag gaaccctag tgatggagtt ggccactccc | 5880 |
| tctctgcgcg ctcgctcgct cactgaggcc gggcgaccaa aggtcgcccg acgcccgggc | 5940 |
| tttgcccggg cggcctcagt gagcgagcga gcgcgcagag agggagtggc caa | 5993 |

<210> SEQ ID NO 43
<211> LENGTH: 5337
<212> TYPE: DNA
<213> ORGANISM: Adeno-Associated Virus 2

<400> SEQUENCE: 43

| | |
|---|---|
| ttggccactc cctctctgcg cgctcgctcg ctcactgagg ccgcccgggc aaagcccggg | 60 |

-continued

| | |
|---|---|
| cgtcgggcga cctttggtcg cccggcctca gtgagcgagc gagcgcgcag agagggagtg | 120 |
| gccaactcca tcactagggg ttcctgcggc cgcacgcgtg tttaaacgtc gacaggttaa | 180 |
| ttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa ttttaaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg gacacaggac gctgtggttt | 540 |
| ctgagccagg gggcgactca gatcccagcc agtggactta gccctgtttt gctcctccga | 600 |
| taactggggt gaccttggtt aatattcacc agcagcctcc cccgttgccc ctctggatcc | 660 |
| actgcttaaa tacgacgag acagggccc tgtctcctca gcttcaggca ccaccactga | 720 |
| cctgggacag tgaatcgcga tcgccaccat gcagattgag ctgagcacct gcttcttcct | 780 |
| gtgcctgctg aggttctgct tctctgccac caggagatac tacctggggg ctgtggagct | 840 |
| gagctgggac tacatgcagt ctgacctggg ggagctgcct gtggatgcca ggttccccc | 900 |
| cagagtgccc aagagcttcc ccttcaacac ctctgtggtg tacaagaaga ccctgtttgt | 960 |
| ggagttcact gaccacctgt tcaacattgc caagcccagg ccccctggaa tgggcctgct | 1020 |
| gggcccccacc atccaggctg aggtgtatga cactgtggtg atcaccctga gaacatggc | 1080 |
| cagccaccct gtgagcctgc atgctgtggg ggtgagctac tggaaggcct ctgaggggc | 1140 |
| tgagtatgat gaccagacca gccagaggga aaggaggat gacaaggtgt tccctggggg | 1200 |
| cagccacacc tatgtgtggc aggtgctgaa ggagaatggc cccatggcct ctgacccct | 1260 |
| gtgcctgacc tacagctacc tgagccatgt ggacctggtg aaggacctga actctggcct | 1320 |
| gattggggcc ctgctggtgt gcagggaggg cagcctggcc aaggagaaga cccagaccct | 1380 |
| gcacaagttc atcctgctgt ttgctgtgtt tgatgagggc aagagctggc actctgaaac | 1440 |
| caagaacagc ctgatgcagg acagggatgc tgcctctgcc agggcctggc caagatgca | 1500 |
| cactgtgaat ggctatgtga acaggagcct gcctggcctg attggctgcc acaggaagtc | 1560 |
| tgtgtactgg catgtgattg gcatgggcac cacccctgag gtgcacagca tcttcctgga | 1620 |
| gggccacacc ttcctggtca ggaaccacag gcaggccagc ctggagatca gccccatcac | 1680 |
| cttcctgact gcccagaccc tgctgatgga cctgggccag ttcctgctgt tctgccacat | 1740 |
| cagcagccac cagcatgatg gcatggaggc ctatgtgaag gtggacagct gccctgagga | 1800 |
| gccccagctg aggatgaaga acaatgagga ggctgaggac tatgatgatg acctgactga | 1860 |
| ctctgagatg gatgtggtga ggtttgatga tgacaacagc cccagcttca tccagatcag | 1920 |
| gtctgtggcc aagaagcacc ccaagacctg ggtgcactac attgctgctg aggaggagga | 1980 |
| ctgggactat gccccctggt gctggcccc tgatgacagg agctacaaga gccagtacct | 2040 |
| gaacaatggc ccccagagga ttggcaggaa gtacaagaag gtcaggttca tggcctacac | 2100 |
| tgatgaaacc ttcaagacca gggaggccat ccagcatgag tctggcatcc tgggcccct | 2160 |
| gctgtatggg gaggtggggg acaccctgct gatcatcttc aagaaccagg ccagcaggcc | 2220 |
| ctacaacatc taccccatg gcatcactga tgtgaggccc ctgtacagca ggaggctgcc | 2280 |
| caaggggtga agcacctga aggacttccc catcctgcct ggggagatct tcaagtacaa | 2340 |
| gtggactgtg actgtggagg atggcccac caagtctgac cccaggtgcc tgaccagata | 2400 |

```
ctacagcagc tttgtgaaca tggagaggga cctggcctct ggcctgattg cccccctgct    2460
gatctgctac aaggagtctg tggaccagag gggcaaccag atcatgtctg acaagaggaa    2520
tgtgatcctg ttctctgtgt ttgatgagaa caggagctgg tacctgactg agaacatcca    2580
gaggttcctg cccaaccctg ctggggtgca gctggaggac cctgagttcc aggccagcaa    2640
catcatgcac agcatcaatg ctatgtgtt tgacagcctg cagctgtctg tgtgcctgca     2700
tgaggtggcc tactggtaca tcctgagcat tggggcccag actgacttcc tgtctgtgtt    2760
cttctctggc tacaccttca agcacaagat ggtgtatgag gacaccctga ccctgttccc    2820
cttctctggg gagactgtgt tcatgagcat ggagaaccct ggcctgtgga ttctgggctg    2880
ccacaactct gacttcagga cagggggcat gactgccctg ctgaaagtct ccagctgtga    2940
caagaacact ggggactact atgaggacag ctatgaggac atctctgcct acctgctgag    3000
caagaacaat gccattgagc ccaggagctt cagccagaac cccccagtgc tgaagaggca    3060
ccagagggag atcaccagga ccaccctgca gtctgaccag gaggagattg actatgatga    3120
caccatctct gtggagatga agaaggagga ctttgacatc tacgacgagg acgagaacca    3180
gagccccagg agcttccaga agaagaccag gcactacttc attgctgctg tggagaggct    3240
gtgggactat ggcatgagca gcagccccca tgtgctgagg aacagggccc agtctggctc    3300
tgtgccccag ttcaagaagg tggtgttcca ggagttcact gatggcagct tcacccagcc    3360
cctgtacaga ggggagctga atgagcacct gggcctgctg gcccctaca tcagggctga     3420 ggtggaggac aacatcatgg tgaccttcag gaaccaggcc agcaggccct acagcttcta    3480
cagcagcctg atcagctatg aggaggacca gaggcagggg gctgagccca ggaagaactt    3540
tgtgaagccc aatgaaacca agacctactt ctggaaggtg cagcaccaca tggcccccac    3600
caaggatgag tttgactgca aggcctgggc ctacttctct gatgtggacc tggagaagga    3660
tgtgcactct ggcctgattg cccccctgct ggtgtgccac accaacaccc tgaaccctgc    3720
ccatggcagg caggtgactg tgcaggagtt tgccctgttc ttcaccatct ttgatgaaac    3780
caagagctgg tacttcactg agaacatgga gaggaactgc agggcccct gcaacatcca     3840 gatggaggac cccaccttca ggagaactac aggttccat gccatcaatg ctacatcat      3900 ggacaccctg cctggcctgg tgatggccca ggaccagagg atcaggtggt acctgctgag    3960
catgggcagc aatgagaaca tccacagcat ccacttctct ggccatgtgt tcactgtgag    4020
gaagaaggag gagtacaaga tggcctgta caacctgtac cctggggtgt ttgagactgt     4080
ggagatgctg cccagcaagg ctggcatctg gagggtggag tgcctgattg gggagcacct    4140
gcatgctggc atgagcaccc tgttcctggt gtacagcaac aagtgccaga cccccctggg    4200 catgcctct ggccacatca gggacttcca gatcactgcc tctggccagt atggccagtg     4260 ggccccaag ctggccaggc tgcactactc tggcagcatc aatgcctgga gcaccaagga    4320
gcccttcagc tggatcaagg tggacctgct ggcccccatg atcatccatg gcatcaagac    4380 ccaggggggcc aggcagaagt tcagcagcct gtacatcagc cagttcatca tcatgtacag   4440
cctggatggc aagaagtggc agacctacag gggcaacagc actggcaccc tgatggtgtt    4500
ctttggcaat gtggacagct ctggcatcaa gcacaacatc ttcaaccccc ccatcattgc    4560
cagatacatc aggctgcacc ccacccacta gcagcatcagg agcaccctga ggatggagct    4620
gatgggctgt gacctgaaca gctgcagcat gccctgggc atggagagca aggccatctc    4680
tgatgcccag atcactgcca gcagctactt caccaacatg tttgccacct ggagcccag     4740 caaggccagg ctgcacctgc agggcaggag caatgcctgg aggccccagg tcaacaaccc    4800
```

```
caaggagtgg ctgcaggtgg acttccagaa gaccatgaag gtgactgggg tgaccaccca    4860
gggggtgaag agcctgctga ccagcatgta tgtgaaggag ttcctgatca gcagcagcca    4920
ggatggccac cagtggaccc tgttcttcca gaatggcaag gtgaaggtgt tccagggcaa    4980
ccaggacagc ttcaccctg tggtgaacag cctggacccc ccctgctga ccagatacct     5040 gaggattcac ccccagagct gggtgcacca gattgccctg aggatggagg tgctgggctg    5100
tgaggcccag gacctgtact gacctcgagg aataaaggaa atttattttc attgcaatag    5160
tgtgttggtt ttttgtgtca cgtggcggcc gcaggaaccc ctagtgatgg agttggccac    5220
tccctctctg cgcgctcgct cgctcactga ggccgggcga ccaaaggtcg cccgacgccc    5280
gggctttgcc cggcggcct cagtgagcga gcgagcgcgc agagagggag tggccaa       5337

<210> SEQ ID NO 44
<211> LENGTH: 5542
<212> TYPE: DNA
<213> ORGANISM: Adeno-Associated Virus 2

<400> SEQUENCE: 44
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa ttttttaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg acacaggac gctgtggttt    540 ctgagccagg gggcgactca gatcccagcc agtggactta gccctgtttt gctcctccga    600
taactggggt gaccttggtt aatattcacc agcagcctcc cccgttgccc tctggatcc    660 actgcttaaa tacggacgag gacagggccc tgtctcctca gcttcaggca ccaccactga    720
cctgggacag tgaatcgtaa gtatgccttt cactgcgaga ggttctggag aggcttctga    780
gctccccatg gccaggcag gcagcaggtc tggggcagga gggggggttgt ggagtgcctt    840 gactcggggc ctggccccc catctctgtc ttgcaggaca attgccgtct tctgtctcgt    900
ggggcatcct cctgctggca ggcctgtgct gcctggtccc tgcgatcgcc accatgcaga    960
ttgagctgag cacctgcttc ttcctgtgcc tgctgaggtt ctgcttctct gccaccagga   1020
gatactacct gggggctgtg agctgagct gggactacat gcagtctgac ctgggggagc   1080
tgcctgtgga tgccaggttc cccccagag tgcccaagag cttccccttc aacacctctg   1140
tggtgtacaa gaagaccctg tttgtggagt tcactgacca cctgttcaac attgccaagc   1200
ccaggccccc ctggatgggc ctgctggccc caccatcca ggctgaggtg tatgacactg   1260
tggtgatcac cctgaagaac atggccagcc accctgtgag cctgcatgct gtggggtga   1320 gctactggaa ggcctctgag ggggctgagt atgatgacca gaccagccag agggagaagg   1380
aggatgacaa ggtgttccct ggggcagcc acacctatgt gtggcaggtg ctgaaggaga   1440
atggccccat ggcctctgac cccctgtgcc tgacctacag ctacctgagc catgtggacc   1500
tggtgaagga cctgaactct ggcctgattg gggccctgct ggtgtgcagg gagggcagcc   1560
```

```
tggccaagga gaagacccag accctgcaca agttcatcct gctgtttgct gtgtttgatg    1620
agggcaagag ctggcactct gaaaccaaga acagcctgat gcaggacagg gatgctgcct    1680
ctgccagggc ctggcccaag atgcacactg tgaatggcta tgtgaacagg agcctgcctg    1740
gcctgattgg ctgccacagg aagtctgtgt actggcatgt gattggcatg ggcaccaccc    1800
ctgaggtgca cagcatcttc ctggagggcc acaccttcct ggtcaggaac acaggcagg    1860 ccagcctgga gatcagcccc atcaccttcc tgactgccca gaccctgctg atggacctgg    1920
gccagttcct gctgttctgc cacatcagca gccaccagca tgatggcatg gaggcctatg    1980
tgaaggtgga cagctgccct gaggagcccc agctgaggat gaagaacaat gaggaggctg    2040
aggactatga tgatgacctg actgactctg agatggatgt ggtgaggttt gatgatgaca    2100
acagccccag cttcatccag atcaggtctg tggccaagaa gcaccccaag acctgggtgc    2160
actacattgc tgctgaggag gaggactggg actatgcccc cctggtgctg gcccctgatg    2220
acaggagcta caagagccag tacctgaaca atggccccca gaggattggc aggaagtaca    2280
agaaggtcag gttcatggcc tacactgatg aaaccttcaa gaccagggag gccatccagc    2340
atgagtctgg catcctgggc cccctgctgt atggggaggt ggggacacc ctgctgatca    2400 tcttcaagaa ccaggccagc aggccctaca acatctaccc ccatggcatc actgatgtga    2460
ggcccctgta cagcaggagg ctgcccaagg gggtgaagca cctgaaggac ttccccatcc    2520
tgcctgggga gatcttcaag tacaagtgga ctgtgactgt ggaggatggc cccaccaagt    2580
ctgaccccag gtgcctgacc agatactaca gcagctttgt gaacatggag agggacctgg    2640
cctctggcct gattggcccc ctgctgatct gctacaagga gtctgtggac cagggggca    2700 accagatcat gtctgacaag aggaatgtga tcctgttctc tgtgtttgat gagaacagga    2760
gctggtacct gactgagaac atccagaggt tcctgcccaa ccctgctggg gtgcagctgg    2820
aggaccctga gttccaggcc agcaacatca tgcacagcat caatggctat gtgtttgaca    2880
gcctgcagct gtctgtgtgc ctgcatgagg tggcctactg gtacatcctg agcattgggg    2940
cccagactga cttcctgtct gtgttcttct ctggctacac cttcaagcac aagatggtgt    3000
atgaggacac cctgaccctg ttcccctttct ctggggagac tgtgttcatg agcatggaga    3060
accctggcct gtggattctg ggctgccaca actctgactt caggaacagg ggcatgactg    3120
ccctgctgaa agtctccagc tgtgacaaga cactgggga ctactatgag acagctatg    3180 aggacatctc tgcctacctg ctgagcaaga acaatgccat tgagcccagg agcttcagcc    3240
agaacccccc agtgctgaag aggcaccaga gggagatcac caggaccacc ctgcagtctg    3300
accaggagga gattgactat gatgacacca tctctgtgga gatgaagaag gaggactttg    3360
acatctacga cgaggacgag aaccagagcc caggagctt ccagaagaag accaggcact    3420
acttcattgc tgctgtggag aggctgtggg actatggcat gagcagcagc ccccatgtgc    3480
tgaggaacag ggcccagtct ggctctgtgc cccagttcaa gaaggtggtg ttccaggagt    3540
tcactgatgg cagcttcacc cagccccctgt acagagggga gctgaatgag cacctgggcc    3600
tgctgggccc ctacatcagg gctgaggtgg aggacaacat catggtgacc ttcaggaacc    3660
aggccagcag gccctacagc ttctacagca gcctgatcag ctatgaggag gaccagaggc    3720 aggggctga gccaggaag aactttgtga agcccaatga aaccaagacc tacttctgga    3780
aggtgcagca ccacatggcc cccaccaagg atgagtttga ctgcaaggcc tgggcctact    3840
tctctgatgt ggacctggag aaggatgtgc actctggcct gattggcccc ctgctggtgt    3900
gccacaccaa caccctgaac cctgcccatg gcaggcaggt gactgtgcag gagtttgccc    3960
```

```
tgttcttcac catctttgat gaaaccaaga gctggtactt cactgagaac atggagagga    4020
actgcagggc cccctgcaac atccagatgg aggacccccac cttcaaggag aactacaggt    4080
tccatgccat caatggctac atcatggaca ccctgcctgg cctggtgatg gcccaggacc    4140
agaggatcag gtggtacctg ctgagcatgg gcagcaatga aacatccac agcatccact     4200 tctctggcca tgtgttcact gtgaggaaga aggaggagta caagatggcc ctgtacaacc    4260
tgtaccctgg ggtgtttgag actgtggaga tgctgcccag caaggctggc atctggaggg   4320
tggagtgcct gattggggag cacctgcatg ctggcatgag cacctgttc ctggtgtaca    4380 gcaacaagtg ccagacccccc ctgggcatgg cctctggcca catcagggac ttccagatca    4440
ctgcctctgg ccagtatggc cagtgggccc ccaagctggc caggctgcac tactctggca    4500
gcatcaatgc ctggagcacc aaggagccct tcagctggat caaggtggac ctgctggccc    4560
ccatgatcat ccatggcatc aagacccagg gggccaggca gaagttcagc agcctgtaca    4620
tcagccagtt catcatcatg tacagcctgg atggcaagaa gtggcagacc tacaggggca    4680
acagcactgg caccctgatg gtgttctttg gcaatgtgga cagctctggc atcaagcaca    4740
acatcttcaa cccccccatc attgccagat acatcaggct gcacccccacc cactacagca    4800 tcaggagcac cctgaggatg gagctgatgg gctgtgacct gaacagctgc agcatgcccc    4860
tgggcatgga gagcaaggcc atctctgatg cccagatcac tgccagcagc tacttccacc    4920
acatgtttgc cacctggagc cccagcaagg ccaggctgca cctgcagggc aggagcaatg    4980
cctggaggcc ccaggtcaac aaccccaagg agtggctgca ggtggacttc cagaagacca    5040
tgaaggtgac tgggggtgacc acccagggggg tgaagagcct gctgaccagc atgtatgtga    5100
aggagttcct gatcagcagc agccaggatg gccaccagtg gaccctgttc ttccagaatg    5160
gcaaggtgaa ggtgttccag ggcaaccagg acagcttcac ccctgtggtg aacagcctgg    5220
acccccccct gctgaccaga tacctgagga ttcaccccca gagctgggtg caccagattg    5280
ccctgaggat ggaggtgctg ggctgtgagg cccaggacct gtactgacct cgaggaataa    5340
aggaaattta ttttcattgc aatagtgtgt tggtttttttg tgtcacgtgg cggccgcagg    5400
aacccctagt gatggagttg gccactccct ctctgcgcgc tcgctcgctc actgaggccg    5460
ggcgaccaaa ggtcgcccga cgcccgggct ttgcccgggc ggcctcagtg agcgagcgag    5520
cgcgcagaga gggagtggcc aa                                             5542
```

ADENO-ASSOCIATED VIRUS FACTOR VIII VECTORS, ASSOCIATED VIRAL PARTICLES AND THERAPEUTIC FORMULATIONS COMPRISING THE SAME

This application claims priority benefit of U.S. Provisional Patent Application No. 62/232,242 filed Sep. 24, 2015, U.S. Provisional Patent Application No. 62/323,182, filed Apr. 15, 2016 and U.S. Provisional Application No. 62/365,544 filed Jul. 22, 2016, which are incorporated herein by reference in their entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII protein. The invention also relates to methods of making the herein described AAV FVIII vectors, recombinant AAV FVIII virus particles comprising or expressing such vectors, associated pharmaceutical formulations comprising the same and therapeutic uses thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., *New Engl. J. Med.* 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., *Blood* 117:798-807, 2011, and McIntosh et al., *Blood* 121:3335-3344, 2013).

While AAV vectors have been reported in the literature having AAV genomes of >5.0 kb, in many of these cases the 5' or 3' ends of the encoded genes appear to be truncated (see Hirsch et al., *Molec. Ther.* 18:6-8, 2010 and Ghosh et al., *Biotech. Genet. Engin. Rev.* 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein, and recombinant AAV virus particles comprising the same, useful in gene therapy approaches for the treatment of hemophilia A. As such, the present invention relates to AAV vectors that encode functionally active FVIII such that either the recombinant AAV virus encapsidates the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. This invention also relates to the production of AAV FVIII vectors having high FVIII expression activity. Finally, the present invention relates to pharmaceutical formulations comprising AAV Factor VIII vectors and/or recombinant Factor VIII AAV particles/viruses comprising any of the herein described AAV FVIII vectors, associated pharmaceutical formulations, and associated methods of administration for the treatment of hemophilia A in subjects suffering therefrom.

SUMMARY OF INVENTION

The present invention provides AAV vectors encoding functionally active FVIII (referred to herein as "AAV FVIII vectors"). The recombinant AAV vectors of the present invention include non-naturally occurring derivatives of the AAV virus into which nucleic acid sequences encoding a functional FVIII protein have been introduced. The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, functionally contributing in the blood coagulation cascade and/or reducing the time that it takes for blood to clot in a subject suffering from hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa. One example of a functionally active FVIII protein is a FVIII SQ protein as described in WO 2015/038625, herein incorporated by reference.

As used herein, an "AAV vector" refers to nucleic acids, either single-stranded or double-stranded, having an AAV 5' inverted terminal repeat (ITR) sequence and an AAV 3' ITR flanking a protein-coding sequence (preferably a functional Factor VIII-encoding sequence) operably linked to transcription regulatory elements that are heterologous to the AAV viral genome, i.e., one or more promoters and/or enhancers and, optionally, a polyadenylation sequence and/or one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., *J. Virol.* 79(1):364-379 (2005) which is herein incorporated by reference in its entirety. ITR sequences that find use herein may be full length, wild-type AAV ITRs or fragments thereof that retain functional capability, or may be sequence variants of full-length, wild-type AAV ITRs that are capable of functioning in cis as origins of replication. AAV ITRs useful in the recombinant AAV FVIII vectors of the present invention may derive from any known AAV serotype and, in certain preferred embodiments, derive from the AAV2 or AAV5 serotype.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII protein having the B domain replaced by the 14 amino acid SQ sequence. The SQ sequence is disclosed in Ward et al., *Blood,* 117:798-807, 2011, McIntosh et al., *Blood* 121:3335-3344, 2013, WO 2013/186563 and WO 2015/038625. The FVIII coding region sequence may be a codon-optimized FVIII-encoding sequence (see, e.g., WO 2011/005968, published Jan. 13, 2011, WO 2015/038625, published Mar. 19, 2015, and McIntosh et al., *Blood* 121:3335-3344, 2013, which are incorporated herein by reference in their entirety). In a preferred embodiment, the nucleic acid encoding the functionally active human FVIII protein of the AAV vector or recombinant AAV virus particle consists of nucleotides 403 to 4776 of SEQ ID NO:1. This sequence is herein referred to as "FVIII-SQ".

In a first aspect, the recombinant AAV vector of the invention comprises Proto 1, which is depicted schematically in FIG. 2A, and comprises the nucleic acid sequence set forth in SEQ ID NO:1.

In a second aspect, the recombinant AAV vector of the invention comprises Proto 1S, which is depicted schematically in FIG. 2B, and comprises the nucleic acid sequence set forth in SEQ ID NO:2.

In a third aspect, the recombinant AAV vector of the invention comprises Proto 2S, which is depicted schematically in FIG. 2C, and comprises the nucleic acid sequence set forth in SEQ ID NO:3.

In a fourth aspect, the recombinant AAV vector of the invention comprises Proto 3S, which is depicted schematically in FIG. 2D, and comprises the nucleic acid sequence set forth in SEQ ID NO:4.

In another embodiment, the recombinant AAV vector of the invention comprises a nucleic acid encoding functional FVIII lacking the entire B domain, including the SQ sequence, and the a3 domain, which is located just N-terminal to the light chain or C domain. The FVIII coding region sequence may be a codon-optimized sequence (see, e.g., WO 2011/005968, published Jan. 13, 2011, WO 2015/038625, published Mar. 19, 2015, and McIntosh et al., *Blood* 121:3335-3344, 2013).

In a first aspect, the recombinant AAV vector of the invention comprises Proto 4, which is depicted schematically in FIG. 3A, and comprises the nucleic acid sequence set forth in SEQ ID NO:5.

In a second aspect, the recombinant AAV vector of the invention comprises Proto 5, which is depicted schematically in FIG. 3B, and comprises the nucleic acid sequence set forth in SEQ ID NO:6.

In a third aspect, the recombinant AAV vector of the invention comprises Proto 6, which is depicted schematically in FIG. 3C, and comprises the nucleic acid sequence set forth in SEQ ID NO:7.

In a fourth aspect, the recombinant AAV vector of the invention comprises Proto 7, which is depicted schematically in FIG. 3D, and comprises the nucleic acid sequence set forth in SEQ ID NO:8.

In other embodiments, the recombinant AAV vector of the invention comprises a nucleic acid comprising an AAV2 5' inverted terminal repeat (ITR) (which may or may not be modified as known in the art), a liver-specific transcription regulatory region, a codon-optimized functionally active FVIII coding region, optionally one or more introns, a polyadenylation sequence, and an AAV2 3' ITR (which may or may not be modified as known in the art). In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding region encoding the FVIII-SQ variant. In another preferred embodiment, the liver specific transcription regulatory region comprises an a1-microglobulin enhancer sequence and the 186 base human alpha anti-trypsin (AAT) proximal promoter.

In a first aspect, the recombinant AAV vector of the invention comprises Construct 100ATG comprising the nucleic acid sequence forth in SEQ ID NO:9.

In a second aspect, the recombinant AAV vector of the invention comprises Construct 100ATG bGH poly A comprising the nucleic acid sequence set forth in SEQ ID NO:10.

In a third aspect, the recombinant AAV vector of the invention comprises Construct 100ATG short bGH polyA sequence set forth in SEQ ID NO:11.

In a fourth aspect, the recombinant AAV vector of the invention comprises Construct 103ATG comprising the nucleic acid sequence forth in SEQ ID NO:12.

In a fifth aspect, the recombinant AAV vector of the invention comprises Construct 103ATG short bGH poly A comprising the nucleic acid sequence set forth in SEQ ID NO:13.

In a sixth aspect, the recombinant AAV vector of the invention comprises Construct 105ATG bGH poly A comprising the nucleic acid sequence set forth in SEQ ID NO:14.

In a seventh aspect, the recombinant AAV vector of the invention comprises Construct DC172ATG FVIII comprising the nucleic acid sequence set forth in SEQ ID NO:15.

In an eighth aspect, the recombinant AAV vector of the invention comprises Construct DC172ATG FVIII hAAT comprising the nucleic acid sequence set forth in SEQ ID NO:16.

In a ninth aspect, the recombinant AAV vector of the invention comprises Construct DC172 2xHCR ATG FVIII comprising the nucleic acid sequence set forth in SEQ ID NO:17.

In a tenth aspect, the recombinant AAV vector of the invention comprises Construct DC172 2xHCR ATG FVIII hAAT comprising the nucleic acid sequence set forth in SEQ ID NO:18.

In an eleventh aspect, the recombinant AAV vector of the invention comprises Construct 2xSerpinA hAAT ATG FVIII comprising the nucleic acid sequence set forth in SEQ ID NO:19.

In a twelfth aspect, the recombinant AAV vector of the invention comprises Construct 2xSerpinA hAAT ATG FVIII 2xµ-globulin enhancer comprising the nucleic acid sequence set forth in SEQ ID NO:20.

In a thirteenth aspect, the recombinant AAV vector of the invention Construct 100ATG short polyA 2xµ-globulin enhancer comprising the nucleic acid sequence set forth in SEQ ID NO:21.

In a fourteenth aspect, the recombinant AAV vector of the invention comprises Construct Factor VIII-BMN001 comprising the nucleic acid sequence set forth in SEQ ID NO:22.

In a fifteenth aspect, the recombinant AAV vector of the invention comprises Construct Factor VIII-BMN002 sequence set forth in SEQ ID NO:23.

In a sixteenth aspect, the recombinant AAV vector of the invention comprises Construct 99 comprising the nucleic acid sequence set forth in SEQ ID NO:24.

In a seventeenth aspect, the recombinant AAV vector of the invention comprises Construct 100 comprising the nucleic acid sequence set forth in SEQ ID NO:25.

In an eighteenth aspect, the recombinant AAV vector of the invention comprises Construct 100 reverse orientation comprising the nucleic acid sequence set forth in SEQ ID NO:26.

In a nineteenth aspect, the recombinant AAV vector of the invention Construct 100AT comprising the nucleic acid sequence set forth in SEQ ID NO:27.

In a twentieth aspect, the recombinant AAV vector of the invention Construct 100AT 2xMG comprising the nucleic acid sequence set forth in SEQ ID NO:28.

In a twenty-first aspect, the recombinant AAV vector of the invention comprises Construct 100AT 2xMG bGH polyA comprising the nucleic acid sequence set forth in SEQ ID NO:29.

In a twenty-second aspect, the recombinant AAV vector of the invention comprises Construct 100AT 2xMG (reverse) bGH polyA comprising the nucleic acid sequence set forth in SEQ ID NO:30.

In a twenty-third aspect, the recombinant AAV vector of the invention comprises Construct 100 bGH polyA comprising the nucleic acid sequence set forth in SEQ ID NO:31.

In a twenty-fourth aspect, the recombinant AAV vector of the invention comprises Construct 100-400 comprising the nucleic acid sequence set forth in SEQ ID NO:32.

In a twenty-fifth aspect, the recombinant AAV vector of the invention comprises Construct 101 comprising the nucleic acid sequence set forth in SEQ ID NO:33.

In a twenty-sixth aspect, the recombinant AAV vector of the invention comprises Construct 102 sequence comprising the nucleic acid sequence set forth in SEQ ID NO:34.

In a twenty-seventh aspect, the recombinant AAV vector of the invention comprises Construct 103 comprising the nucleic acid sequence set forth in SEQ ID NO:35.

In a twenty-ninth aspect, the recombinant AAV vector of the invention comprises Construct 103 reverse orientation comprising the nucleic acid sequence set forth in SEQ ID NO:36.

In a thirtieth aspect, the recombinant AAV vector of the invention comprises Construct 103AT comprising the nucleic acid sequence set forth in SEQ ID NO:37.

In a thirty-first aspect, the recombinant AAV vector of the invention comprises Construct 103AT 2xMG comprising the nucleic acid sequence set forth in SEQ ID NO:38.

In a thirty-second aspect, the recombinant AAV vector of the invention comprises Construct 103AT 2xMG bGH polyA comprising the nucleic acid sequence set forth in SEQ ID NO:39.

In a thirty-third aspect, the recombinant AAV vector of the invention comprises the Construct 103 bGH polyA comprising the nucleic acid sequence set forth in SEQ ID NO:40.

In a thirty-fourth aspect, the recombinant AAV vector of the invention comprises Construct 104 comprising the nucleic acid comprising the nucleic acid sequence set forth in SEQ ID NO:41.

In a thirty-fifth aspect, the recombinant AAV vector of the invention comprises Construct 105 comprising the nucleic acid sequence set forth in SEQ ID NO:42.

In a thirty-sixth aspect, the recombinant AAV vector of the invention comprises Construct 106 comprising the nucleic acid sequence set forth in SEQ ID NO:43.

In a thirty-seventh aspect, the recombinant AAV vector of the invention comprises Construct 106AT comprising the nucleic acid sequence set forth in SEQ ID NO:44.

In a thirty-eighth aspect, the recombinant AAV vector of the invention comprises p-100 ATGB, which comprises the nucleic acid sequence set forth in SEQ ID NO:45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation. The present invention is also directed to recombinant AAV virus particles comprising the herein described AAV FVIII vectors and their use for the treatment of hemophilia A.

The AAV vectors of the invention in single strand form are less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand form range from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particles comprising any of the AAV vectors of the invention. The methods comprise the steps of culturing a cell that has been transfected with any of the AAV vectors of the invention (in association with various AAV cap and rep genes) and recovering recombinant AAV FVIII virus particles from the supernatant of the transfected cell.

The cells of the invention useful for recombinant AAV production are any cell type susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NSO, SP2/0, PER.C6, Vero, RD, BHK, HT 1080, A549, Cos-7, ARPE-19 and MRC-5.

The invention also provides for a recombinant viral particle comprising any of the AAV vectors of the invention or any viral particle produced by the forgoing methods of the invention.

An "AAV virion" or "AAV viral particle" or "AAV vector particle" or "AAV virus" refers to a viral particle composed of at least one AAV capsid protein and an encapsidated polynucleotide AAV vector as described herein. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particles necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient a therapeutically effective amount of any of the AAV vectors of the invention, or a viral particle of the invention or a viral particle produced by a method of the invention.

In another embodiment, the invention provides for methods of increasing circulating FVIII protein levels in a subject in need thereof comprising administering to the subject any of the AAV vectors of the invention, or a viral particle of the invention or a viral particle produced by a method of the invention.

In another embodiment, the invention provides for methods for inducing the expression of FVIII protein in a subject in need thereof comprising administering to the subject any of the AAV vectors of the invention, or viral particles of the invention or a viral particle produced by a method of the invention.

In another embodiment, the invention provides for methods for increasing FVIII protein expression in a subject in need thereof comprising administering to the subject any of the AAV vectors of the invention, or viral particles of the invention or a viral particle produced by a method of the invention.

The invention also provides for any of the methods of the invention further comprising the step of determining the absence or presence of anti-AAV capsid antibodies in the serum of said subject after administration of said therapeutically effective amount of said recombinant AAV FVIII virus. In addition, the invention provides for any of the methods of the invention further comprising the step of administering an effective amount of a corticosteroid to said subject after a determination of the presence of anti-AAV capsid antibodies in the serum of said subject is made.

In a further embodiment, the invention provides for a use of any of the AAV vectors of the invention or recombinant AAV virus particles of the invention for preparation of a medicament for the treatment of hemophilia A. In one aspect, the medicament comprises an amount of AAV vector or recombinant AAV FVIII virus particle that expresses human FVIII in an amount effective to treat hemophilia A. The invention also provides for any of the uses of the invention wherein after administration of the medicament, the absence or presence of anti-AAV capsid antibodies in the serum of the subject is determined. If the subject is determined to have anti-AAV capsid antibodies in the serum, use of an effective amount of a corticosteroid for the preparation of a medicament for the administration to the subject having anti-AAV capsid antibodies in the serum.

In another embodiment, the invention provides for a composition comprising any of the AAV vectors or recombinant AAV virus particles of the invention for the treatment of hemophilia A. In one aspect, the composition comprises an amount of AAV vector or recombinant AAV virus particles that expresses human FVIII in an amount effective to treat hemophilia A. In addition, any of the compositions of the invention are administered with an effective amount of a corticosteroid in a subject determined to have anti-AAV capsid antibodies in the serum after administration of the composition.

In another embodiment, the AAV vectors of the invention are used to produce AAV viral particles that are useful for treating a patient suffering from hemophilia A.

In another embodiment, the invention provides for pharmaceutical formulations comprising recombinant FVIII-encoding AAV virus particles as described herein. More specifically, in certain aspects, the present invention is directed to pharmaceutical formulations that comprise a recombinant AAV FVIII-encoding virus, a buffering agent, an isotonicity agent, a bulking agent and a surfactant. In particularly preferred embodiments, the pharmaceutical formulations of the present invention comprise AAV5-FVIII-SQ, p-100 ATGB or any of the other herein described vectors and/or are stable during storage at ≤65° C. for at least 2 weeks. In yet other embodiments of the present invention, the pharmaceutical formulation comprises sodium phosphate, dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml. In a particularly preferred embodiment, the pharmaceutical formulation of the present invention comprises sodium phosphate, dibasic at a concentration of about 1.42 mg/ml, sodium phosphate monobasic monohydrate at a concentration of about 1.38 mg/ml, sodium chloride at a concentration of about 8.18 mg/ml, mannitol at a concentration of about 20 mg/ml, and poloxamer 188 at a concentration of about 2 mg/ml. The pharmaceutical formulations of the present invention may be in liquid form and may comprise the AAV FVIII virus particle at a concentration of from about 1E12 vg/ml to about 2E14 vg/ml, more preferably at a concentration of about 2E13 vg/ml. In one embodiment, the pharmaceutical formulations of the invention are useful for intravenous administration to a human suffering from hemophilia A.

The present invention is also directed to methods for treating a subject suffering from hemophilia A which comprise the step of administering to the subject a therapeutically effective amount of a recombinant AAV FVIII virus, which optionally may be formulated as described above. In a preferred embodiment, the subject suffering from hemophilia A is a human. In one embodiment, the recombinant AAV FVIII virus is AAV5-FVIII-SQ. In one embodiment, the step of administering is accomplished by intravenous (IV) administration. In certain aspects of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, the therapeutically effective amount of AAV FVIII virus administered to the subject is least 2E13 vg/kg of body weight, sometimes at least 6E13 vg/kg of body weight. In certain embodiments, in addition to administration of a therapeutically effective amount of AAV FVIII virus, the subject is treated either prophylactically, therapeutically, or both with a corticosteroid to prevent and/or treat any hepatotoxicity associated with administration of the AAV FVIII virus. In one embodiment, associated hepatotoxicity is measured by comparing baseline (i.e., pre-dosing with FVIII AAV) alanine transaminase (ALT) levels to post-treatment ALT levels, wherein an increase in ALT levels post-dosing is evidence of associated hepatotoxicity. Prophylactic corticosteroid treatment refers to the administration of a corticosteroid to prevent hepatotoxicity and/or to prevent an increase in measured ALT levels in the subject. Therapeutic corticosteroid treatment refers to the administration of a corticosteroid to reduce hepatotoxicity caused by administration of an AVV FVIII virus and/or to reduce an elevated ALT concentration in the bloodstream of the subject caused by administration of an AAV FVIII virus. In certain embodiments, prophylactic or therapeutic corticosteroid treatment may comprise administration of at least 5, 10, 15, 20, 25, 30, 35, 40, 45, 50, 55, 60, or more mg/day of the corticosteroid to the subject. In certain embodiments, prophylactic or therapeutic corticosteroid treatment of a subject may occur over a continuous period of at least about 3, 4, 5, 6, 7, 8, 9, 10 weeks, or more.

The present invention is also directed to a composition comprising a therapeutically effective amount of a recombinant AAV FVIII virus for use in treating a subject suffering from hemophilia A. In one embodiment, the AAV FVIII virus is AAV5-FVIII-SQ. In another embodiment, the AAV FVIII virus comprises the p-100 ATGB vector. The composition optionally may be formulated as described above. In certain embodiments, compositions comprising a therapeutically effective amount of AAV FVIII virus are administered with a composition comprising a prophylactic and/or therapeutic corticosteroid for use in preventing and/or treating any hepatotoxicity associated with administration of the AAV FVIII virus. The composition comprising a prophylactic or therapeutic corticosteroid treatment may comprise at least 5, 10, 15, 20, 25, 30, 35, 40, 45, 50, 55, 60, or more mg/day of the corticosteroid. In certain embodiments, compositions comprising a prophylactic or therapeutic corticosteroid may be administered over a continuous period of at least about 3, 4, 5, 6, 7, 8, 9, 10 weeks, or more.

The present invention is also directed to use of a therapeutically effective amount of recombinant AAV FVIII virus for the preparation of a medicament for the treatment of a subject suffering from hemophilia A. In certain embodiments, the AAVFVIII virus is AAV5-FVIII-SQ or a virus comprising the p-100 ATGB vector. The medicament optionally may be formulated as described above. In a preferred embodiment, the subject suffering from hemophilia A is a human. In one embodiment, the medicament is administered by intravenous (IV) administration. In one aspect of the present invention, administration of the medicament results in expression of at least about 5 IU/dl of Factor VIII protein in the bloodstream of the subject, preferably at least about 5 IU/dl of Factor VIII protein in the bloodstream of the subject 16 weeks or more after administration. In certain embodiments, the medicament also comprises a prophylactic and/or therapeutic corticosteroid for the prevention and/or treatment of any hepatotoxicity associated with administration of the AAV FVIII virus. The medicament comprising a prophylactic or therapeutic corticosteroid treatment may comprise at least 5, 10, 15, 20, 25, 30, 35, 40, 45, 50, 55, 60, or more mg/day of the corticosteroid. In certain embodiments, the medicament comprising a prophylactic or therapeutic corticosteroid may be administered over a continuous period of at least about 3, 4, 5, 6, 7, 8, 9, 10 weeks, or more.

The present invention is also directed to methods for reducing bleeding time during a bleeding episode in a subject suffering from hemophilia A which comprise the step of administering to the subject a therapeutically effective amount of a recombinant AAV FVIII virus as described herein, which optionally may be formulated as described above. In a preferred embodiment, the subject suffering from hemophilia A is a human. In one embodiment, the step of administering is accomplished by intravenous (IV) administration. In certain embodiments, the step of administering occurs at least about 3, 4, 5, 6, 7, 8, 9, 10, 15, 20, 25, 30, 35, 40, 45, 50 weeks, or more, prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of a therapeutically effective amount of AAV FVIII virus, the subject is treated either prophylactically, therapeutically, or both with a corticosteroid to prevent and/or treat any hepatotoxicity associated with administration of the AAV FVIII virus, as described above.

The present invention is also directed to a composition comprising a therapeutically effective amount of a recombinant AAV FVIII virus for use in reducing bleeding time of a bleeding episode in a subject suffering from hemophilia A. In one embodiment, the AAVFVIII virus is AAV5-FVIII-SQ. The composition optionally may be formulated as described above. In a preferred embodiment, the subject suffering from hemophilia A is a human. The composition may be administered prior to the bleeding episode. In one embodiment, the composition is administered by intravenous (IV) administration prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, compositions comprising a therapeutically effective amount of AAV FVIII virus for use in reducing bleeding time are administered with a composition comprising a prophylactic and/or therapeutic corticosteroid for use in preventing and/or treating any hepatotoxicity associated with administration of the AAV FVIII virus, as described above.

The invention also provides for any of the methods of reducing bleeding time further comprising the step of determining the absence or presence of anti-AAV capsid antibodies in the serum of said subject after administration of said therapeutically effective amount of said recombinant AAV FVIII virus. In addition, the invention provides for any of the methods of reducing bleeding time further comprising the step of administering an effective amount of a corticosteroid to said subject after a determination of the presence of anti-AAV capsid antibodies in the serum of said subject is made.

The present invention is also directed to use of a therapeutically effective amount of recombinant AAV FVIII virus for the preparation of a medicament for reducing bleeding time of a bleeding episode in a subject suffering from hemophilia A. In one embodiment, the AAVFVIII virus is AAV5-FVIII-SQ. The medicament optionally may be formulated as described above. In a preferred embodiment, the subject suffering from hemophilia A is a human. The medicament may be administered prior to the bleeding episode. In one embodiment, the medicament is administered by intravenous (IV) administration prior to the bleeding episode. In one aspect of the present invention, administration of the medicament results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, administration of the medicament results in expression of at least about 1, 2, 3, 4, 5, 6, 7, 8, 9, 10, or more IU/di of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, medicaments comprising a therapeutically effective amount of AAV FVIII virus for reducing bleeding time also comprise a prophylactic and/or therapeutic corticosteroid for preventing and/or treating any hepatotoxicity associated with administration of the AAV FVIII virus, as described above. In addition, any of the compositions of the invention for use in reducing bleeding time are administered with an effective amount of a corticosteroid in a subject determined to have anti-AAV capsid antibodies in the serum after administration of the composition.

The present invention is also directed to methods for inducing expression of a functional FVIII protein in a subject in need thereof which comprise the step of administering to the subject a recombinant AAV FVIII virus as described herein, which optionally may be formulated as described above, wherein such administration results in increased expression of functional FVIII protein or increased concentrations of functional FVIII protein in the bloodstream of the subject. In a preferred embodiment, the subject in need is a human. In one embodiment, the step of administering is accomplished by intravenous (IV) administration. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of an AAV FVIII virus, the subject is treated either prophylactically, therapeutically, or both with a corticosteroid to prevent and/or treat any hepatotoxicity associated with administration of the AAV FVIII virus, as described above. In addition, in any of the uses of the invention after administration of the medicament to reduce bleeding time, the absence or presence of anti-AAV capsid antibodies in the serum of the subject is determined. If the subject is determined to have anti-AAV capsid antibodies in the serum, use of an effective amount of a corticosteroid for the preparation of a medicament for the administration to the subject having anti-AAV capsid antibodies in the serum is contemplated.

The present invention is also directed to methods for increasing expression of FVIII protein in a subject in need thereof which comprise the step of administering to the subject a recombinant AAV FVIII virus as described herein, which optionally may be formulated as described above, wherein such administration results in increased expression of functional FVIII protein or increased concentrations of functional FVIII protein in the bloodstream of the subject. In a preferred embodiment, the subject in need is a human. In one embodiment, the step of administering is accomplished by intravenous (IV) administration. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, in addition to administration of an AAV FVIII virus, the subject is treated either prophylactically, therapeutically, or both with a corticosteroid to prevent and/or treat any hepatotoxicity associated with administration of the AAV FVIII virus, as described above.

The present invention is also directed to a composition comprising a therapeutically effective amount of a recombinant AAV FVIII virus for use in increasing or inducing expression of FVIII protein in a subject in need thereof. In one embodiment, the AAVFVIII virus is AAV5-FVIII-SQ. The composition optionally may be formulated as described above. In a preferred embodiment, the subject in need is a human suffering from hemophilia A. The composition may be administered prior to the bleeding episode. In one embodiment, the composition is administered by intravenous (IV) administration prior to the bleeding episode. In one aspect of the present invention, the step of administration results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, the step of administration results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, compositions comprising a therapeutically effective amount of AAV FVIII virus for use in increasing or inducing expression of FVIII protein are administered with a composition comprising a prophylactic and/or therapeutic corticosteroid for use in preventing and/or treating any hepatotoxicity associated with administration of the AAV FVIII virus, as described above.

The present invention is also directed to use of a therapeutically effective amount of recombinant AAV FVIII virus for the preparation of a medicament for increasing or inducing expression of FVIII protein in a subject in need. In one embodiment, the subject in need is a human suffering from hemophilia A. In one embodiment, the AAVFVIII virus is AAV5-FVIII-SQ. The medicament optionally may be formulated as described above. The medicament may be administered prior to the bleeding episode. In one embodiment, the medicament is administered by intravenous (IV) administration prior to the bleeding episode. In one aspect of the present invention, administration of the medicament results in expression of at least about 1, 2, 3, 4, 5, 6, 7, 8, 9, 10, or more IU/dl of Factor VIII protein in the bloodstream of the subject, preferably at least about 5 IU/dl of Factor VIII protein in the bloodstream of the subject. In certain embodiments, administration of the medicament results in expression of at least about 1, 2, 3, 4, 5, 6, 7, 8, 9, 10, or more IU/dl of Factor VIII protein in the bloodstream of the subject 1, 2, 3, 4, 5, 6, 7, 8, 9, 10, 11, 12, 13, 14, 15, 16, 17, 18, 19, 20, or more weeks after administration. In certain embodiments, medicaments comprising a therapeutically effective amount of AAV FVIII virus for increasing or inducing expression of FVIII protein also comprise a prophylactic and/or therapeutic corticosteroid for preventing and/or treating any hepatotoxicity associated with administration of the AAV FVIII virus, as described above.

The present invention is also directed to a method of treating a subject suffering from hemophilia A comprising the steps of (i) determining the absence of anti-AAV capsid antibodies in the serum of said subject, and (ii) administering to said subject a therapeutically effective amount of a recombinant AAV FVIII virus.

The present invention is also directed to use of a therapeutically effective amount of a recombinant AAV FVIII virus for the preparation of a medicament for the treatment of a subject suffering from hemophilia A, wherein anti-AAV capsid antibodies are absent from the serum of the subject.

The present invention is also directed to a composition comprising a therapeutically effective amount of a recombinant AAV FVIII virus for use in treating a subject suffering from hemophilia A, wherein anti-AAV capsid antibodies are absent from the subject's serum.

The present invention is also directed to a method of treating a subject suffering from hemophilia A comprising the steps of (i) administering to said subject a therapeutically effective amount of a recombinant AAV FVIII virus, and (ii) after administration of said therapeutically effective amount of said recombinant AAV FVIII virus, determining the absence or presence of anti-AAV capsid antibodies in the serum of said subject. In one embodiment, the method further comprises the step of administering an effective amount of a corticosteroid to the subject after a determination of the presence of anti-AAV capsid antibodies in the serum of said subject is made.

The present invention is directed to use of a therapeutically effective amount of a recombinant AAV FVIII virus for the preparation of a medicament for the treatment of hemophilia A wherein after administration of the medicament, the absence or presence of anti-AAV capsid antibodies in the serum of the subject is determined. If the subject is determined to have anti-AAV capsid antibodies in the serum, use of an effective amount of a corticosteroid for the preparation of a medicament for administration to the subject having anti-AAV capsid antibodies in the serum. The present invention is also directed to a composition comprising an effective amount of recombinant AAV FVIII for treatment of hemophilia A, wherein this composition is administered with an effective amount of a corticosteroid in a subject determined to have anti-AAV capsid antibodies in the serum after administration of the composition.

Other embodiments of the present invention will be evident to one skilled in the art upon reading the present patent specification.

DETAILED DESCRIPTION

The present invention provides for AAV vectors encoding functionally active FVIII, e.g., completely packaged AAV FVIII vectors or AAV FVIII vectors with high expression activity. The recombinant AAV FVIII vectors of the invention have improved transgene expression, as well as improved AAV virus production yield and simplified purification. Introducing one or more introns into the FVIII protein-coding region enhances expression. Reconfiguring the number and positioning of enhancers also enhances expression.

Exemplary AAV FVIII Vector

Figure 1:
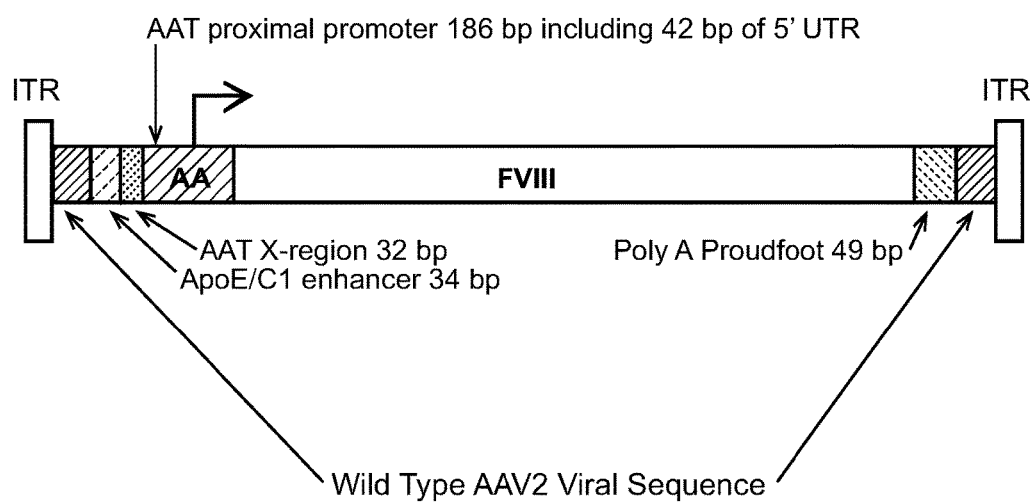
FIG. 1 provides a schematic of an exemplary FVIII-encoding recombinant AAV vector. From left to right, the vector comprises an AAV2 5' ITR sequence, wild-type AAV2 viral sequence, a 34 base human ApoE/C1 enhancer sequence, a 32 base human AAT promoter distal X region sequence, a 186 base human AAT promoter sequence that includes 42 bases of 5' UTR sequence, a codon-optimized human FVIII SQ sequence, a 49 base synthetic Proudfoot polyadenylation sequence, wild-type AAV2 viral sequence, and an AAV2 3'ITR sequence (see WO 2011/005968, published Jan. 13, 2011, which is incorporated herein by reference in its entirety, and McIntosh et al., *Blood* 121:3335-3344, 2013). This vector is 5081 bases in length.

The exemplary recombinant AAV FVIII vector shown in FIG. 1, which is described in detail in WO 2011/005968, published Jan. 13, 2011, which is incorporated herein by reference in its entirety, and McIntosh et al., *Blood* 121: 3335-3344, 2013, is an oversized, i.e., greater than 5.0 kb, AAV FVIII vector. As shown in FIG. 1, this AAV FVIII vector comprises, from left to right, the AAV serotype 2 (AAV2) 5' ITR, wild-type AAV2-derived viral sequence, a 34 base human apolipoprotein E (ApoE)/C1 enhancer element, a 32 base human alpha anti-trypsin (AAT) promoter distal X region, a 186 base human AAT (hAAT) promoter, including 42 bases of 5' untranslated region (UTR) sequence, a codon-optimized human FVIII sequence in which the FVIII B domain is replaced with the 14 amino acid SQ sequence, a 49 bases synthetic Proudfoot polyadenylation sequence, wild-type AAV2-derived viral sequence, and the AAV2 3' ITR. This vector is 5081 bases in length and, as shown in WO 2011/005968, expresses functionally active FVIII both in vitro and in vivo.

Proto 1, Proto 1S, Proto 2S and Proto 3S Vectors

To avoid problems associated with over-sized AAV vectors and/or to increase the expression of a FVIII transgene from AAV vectors, the present invention provides completely packaged, smaller, i.e., less than 5.0 kb, AAV vectors encoding a functional FVIII protein. The 4970 bp nucleotide sequence of the recombinant AAV Proto 1 construct is provided in SEQ ID NO:1.

To generate the recombinant AAV FVIII vector Proto 1, sequences that were determined to be unnecessary for production of functionally active FVIII were deleted from the vector shown in FIG. 1. As shown in Example 1, 111 bases of extraneous DNA were removed, including 53 bases of wild-type AAV2 viral sequence 3' to the AAV2 5' ITR, 46 bases of AAV2 viral sequence 5' to the AAV2 3' ITR, and 12 bases adjacent to the codon-optimized FVIII protein coding region. The codon-optimized FVIII SQ sequence of the vector shown in FIG. 1 was also replaced by a novel, codon-optimized FVIII SQ sequence referred to herein as "FVIII-SQ". The FVIII-SQ coding sequence (bases 403-4776 of SEQ ID NO:1) was then introduced into the Proto 1 vector. The resultant Proto 1 vector is 4970 bases in length and comprises, from left to right, a modified AAV serotype 2 (AAV2) 5' ITR, a 34 base human apolipoprotein E (ApoE)/C1 enhancer element, a 32 base human alpha anti-trypsin (AAT) promoter distal X region, a 186 base hAAT promoter, including 42 bases of 5' untranslated region (UTR) sequence, a novel codon-optimized human FVIII sequence in which the FVIII B domain is replaced with the 14 amino acid SQ sequence, a 49 bases synthetic Proudfoot polyadenylation sequence, and a modified AAV2 3' ITR. When designed, it was unknown whether the Proto 1 vector would be capable of expressing functional FVIII polypeptide, either in vitro or in vivo.

To generate the AAV vector Proto 1S, 10 bases at the 3' end of the AAV2 5' ITR, and 10 bases at the 5' end of the AAV2 3'ITR, were removed from the Proto 1 vector. The resultant Proto 1S vector is 4950 bases in length. The nucleotide sequence of sequence of Proto 1S is set forth in SEQ ID NO:2.

To generate the AAV vector Proto 2S, a synthetic 100 base intron was inserted between exons 1 and 2 of the FVIII-SQ sequence in the Proto 1S vector. The 34 base ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO:3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO:4.

Proto 4, Proto S, Proto 6 and Proto 7 Vectors

In an attempt to further reduce the size of the AAV FVIII vectors and/or increase the expression of the FVIII transgene from the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO:5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO:6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO:7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO:8.

Additional Recombinant AAV FVIII Vectors with Improved Promoter/Enhancer Sequences Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the μ-globulin enhancer or fragments thereof, the human alpha 1 antitrypsin promoter (hAAT) or fragments thereof, Serpin A enhancer or fragments thereof, the LP1 promoter enhancer or fragments thereof or macroglobulin enhancer or fragment thereof. These constructs comprise a polyadenylation sequence such as the bGH poly A sequence or the synthetic rabbit β-globin poly A sequence. In some embodiment, the constructs comprise an intron or fragments of an intron such as a hAAT intron or a human β-globin intron. In some embodiments, the recombinant AAV FVIII vectors comprise the novel codon-optimized FVIII-SQ coding sequence.

Figure 4A:
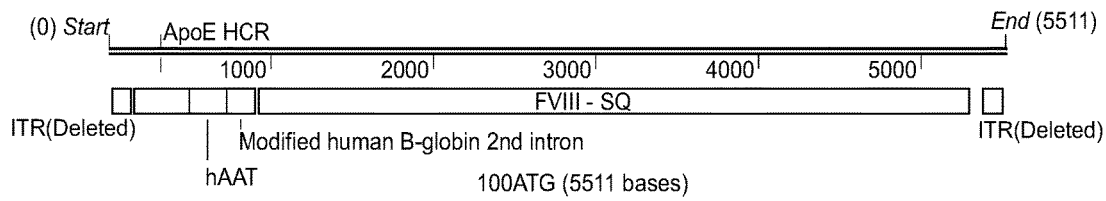
FIG. 4A-FIG. 4JJ provide schematic representations of certain recombinant AAV FVIII vectors of the present invention. (A) Construct 100ATG, (B) Construct 100ATG bGH polyA, (C) Construct 100ATG short bGH poly A, (D) Construct 103ATG, (E) Construct 103ATG short bGH poly A, (F) Construct 105ATG bGH polyA, (G) Construct DC172ATG FVIII, (H) Construct DC172ATG FVIII hAAT, (I) Construct DC172 2×HCR ATG FVIII, (J) Construct DC172 2×HCR ATG FVIII hAAT, (K) Construct 2×SerpinA hAAT ATG FVIII, (L) Construct 2×SerpinA hAAT ATG FVIII 2×μ-globulin enhancer, (M) Construct 100ATG short bGH poly A 2×μ-globulin enhancer, (N) Construct Factor VIII-BMN001, (O) Construct Factor VIII-BMN002, (P) Construct 99, (Q) Construct 100, (R) Construct 100 reverse orientation, (S) Construct 100AT, (T) Construct 100AT 2×MG, (U) Construct 100AT 2×MG bGH polyA, (V) Construct 100AT 2×MG (reverse) bGH poly A, (W) Construct 100 bGH poly A, (X) Construct 100-400, (Y) Construct 101, (Z) Construct 102, (AA) Construct 103, (BB) Construct 103 reverse orientation, (CC) Construct 103AT, (DD) Construct 103AT 2×MG, (EE) Construct 103AT 2×MG bGH poly A, (FF) Construct 103 bGH poly A, (GG) Construct 104, (HH) Construct 105, (II) Construct 106 and (JJ) Construct 106AT.

Construct 100ATG (FIG. 4A) is 5511 bases in length. The nucleotide sequence of this construct is set forth in SEQ ID NO:9 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5352 are a synthetic rabbit β-globin poly A and bases 5367-5511 are a 3' AAV2 ITR.

Figure 4B:
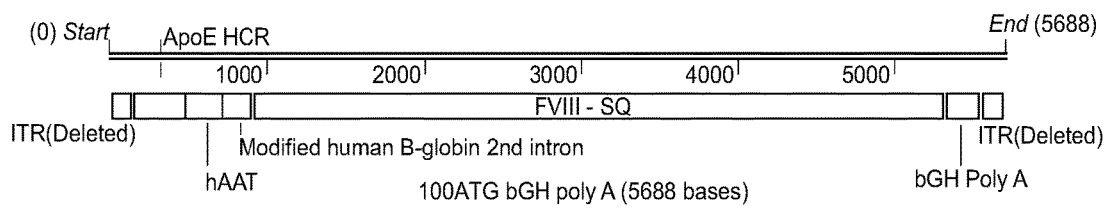

Construct 100ATG bGH poly A (FIG. 4B) is 5688 bases in length. The nucleotide sequence of this construct is set forth in SEQ ID NO:10 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5529 are a bGH poly A and bases 5544-5688 are a 3' AAV2 ITR.

Figure 4C:
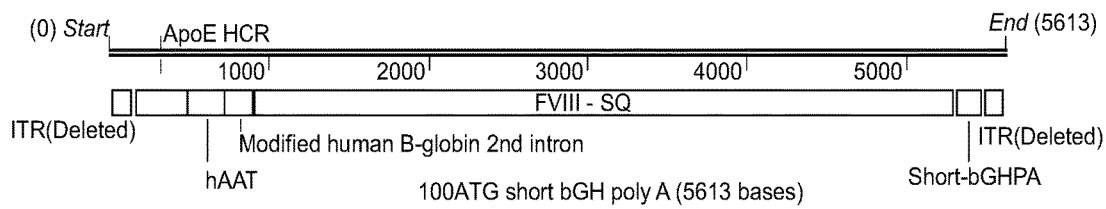

Construct 100ATG short bGH poly A (FIG. 4C) is 5613 bases in length. The nucleotide sequence of this construct is set forth in SEQ ID NO:11 in which bases 1-145 are a 5' AAV2 ITR, bases 160-502 are an ApoE HCR, bases 509-726 are a hAAT promoter, bases 727-910 are a modified human β-globin 2nd intron, bases 923-5296 are FVIII-SQ, bases 5305-5454 are a short bGH poly A and bases 5469-5613 are a 3' AAV2 ITR.

Figure 4D:
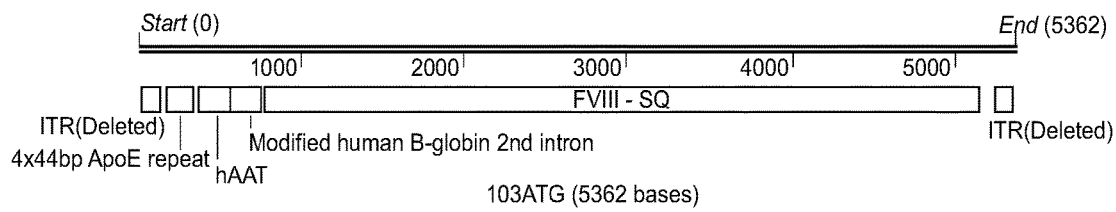

Construct 103ATG (FIG. 4D) is 5362 bases in length. The nucleotide sequence of this construct is set forth in SEQ ID NO:12 in which bases 1-145 are a 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are FVIII-SQ, bases 5156-5203 are a synthetic rabbit β-globin poly A and bases 5218-5362 are a 3' AAV2 ITR.

Figure 4E:
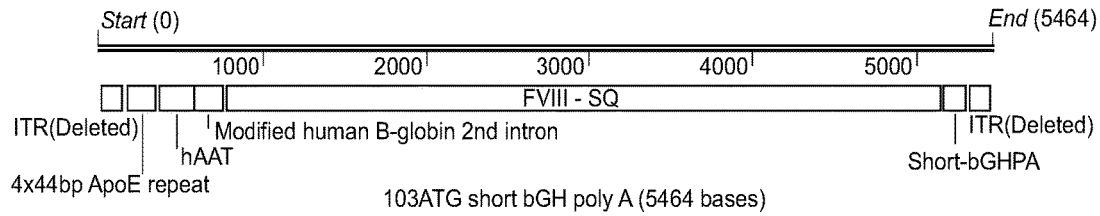

Construct 103ATG short bGH poly A (FIG. 4E) is 5464 bases in length. The nucleotide sequence of this construct is set forth in SEQ ID NO:13 in which bases 1-145 are a 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are FVIII-SQ, bases 5156-5305 are a bGH short poly A and bases 5320-5464 are a 3' AAV2 ITR.

Figure 4F:
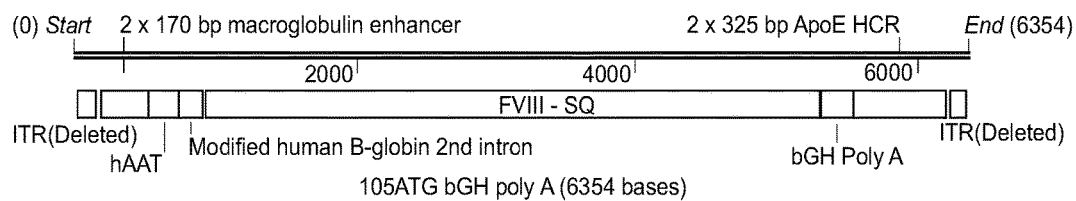

Construct 105ATG bGH polyA (FIG. 4F) is 6354 bases in length. The nucleotide sequence of this construct is set forth in SEQ ID NO:14 in which bases 1-145 are a 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are FVIII-SQ, bases 5315-5539 are a bGH poly A, bases 5546-6195 are two copies (2×) of a 325 bp ApoE HCR and bases 6210-6354 are a 3' AAV2 ITR.

Figure 4G:
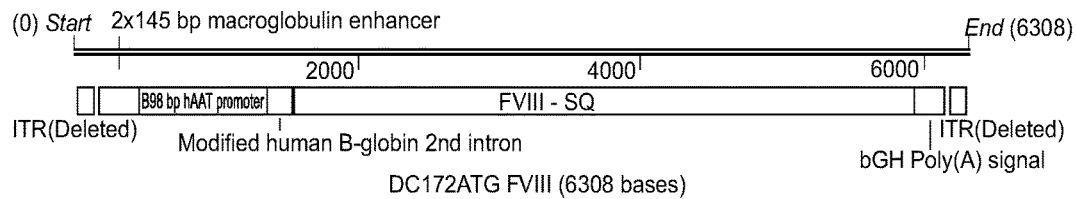

Construct DC172ATG FVIII (FIG. 4G) is 6308 bases in length. The nucleotide sequence of this construct is set forth in SEQ ID NO:15 in which bases 1-145 are a 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are FVIII-SQ, bases 5926-6149 are a bGH poly A and bases 6164-6308 are a 3' AAV2 ITR.

Figure 4H:
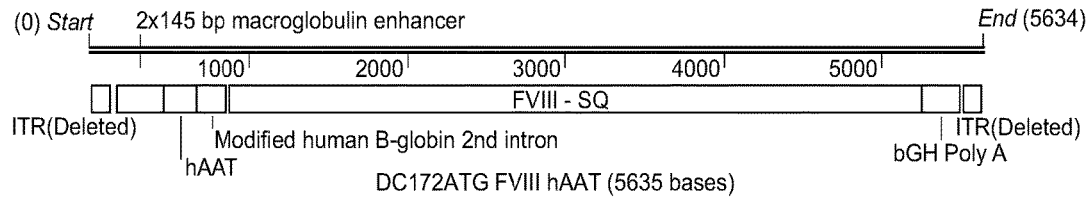

Construct DC172ATG FVIII hAAT (FIG. 4H) is 5635 bases in length, This construct is set forth as SEQ ID NO:16 in which bases 1-145 are a 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are FVIII-SQ, bases 5253-5476 are a bGH poly A and bases 5490-5635 are a 3' AAV2 ITR.

Figure 4I:
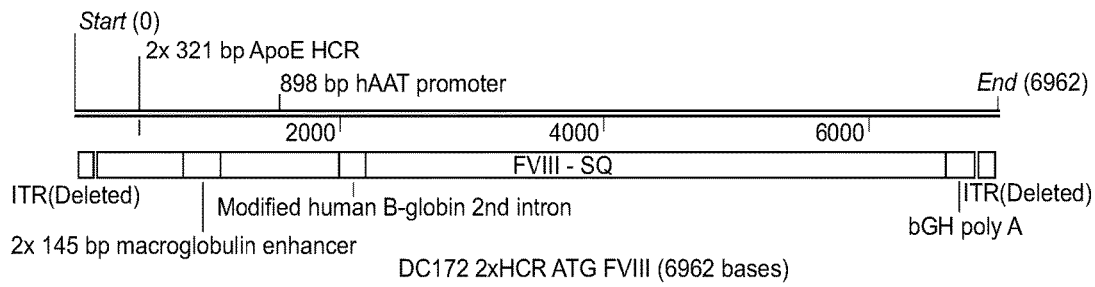

Construct DC172 2×HCR ATG FVIII (FIG. 4I) is 6962 bases in length. The nucleotide sequence of this construct is set forth in SEQ ID NO:17 in which bases 1-145 are a 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are FVIII-SQ, bases 6580-6803 are a bGH poly A and bases 6818-6962 are a 3' AAV2 ITR.

Figure 4J:
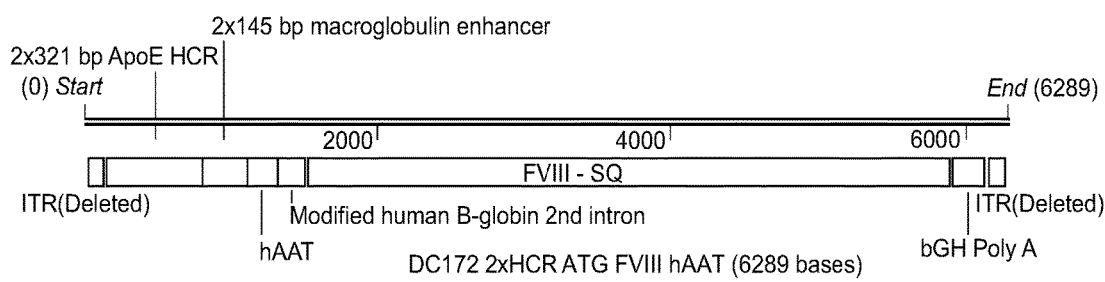

Construct DC172 2×HCR ATG FVIII hAAT (FIG. 4J) is 6289 bases in length. The nucleotide sequence of this construct is set forth in SEQ ID NO:18 in which bases 1-145 are a 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are FVIII-SQ, bases 5907-6130 are a bGH poly A and bases 6245-6289 are a 3' AAV2 ITR.

Figure 4K:
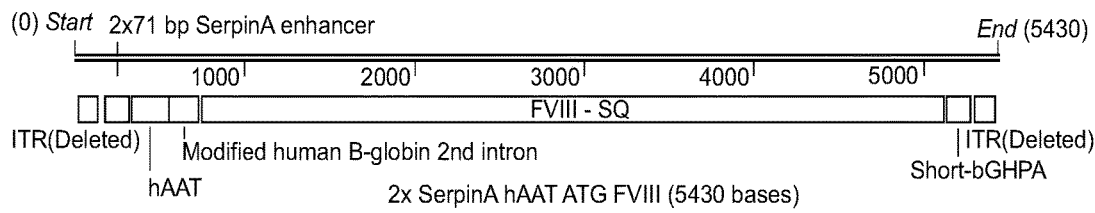

Construct 2×SerpinA hAAT ATG FVIII (FIG. 4K) is 5430 bases in length. The nucleotide sequence of this construct is set forth in SEQ ID NO:19 in which bases 1-145 are a 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are FVIII-SQ, bases 5122-5271 are a short bGH poly A, and bases 5286-5430 are a 3'AAV2 ITR.

Figure 4L:
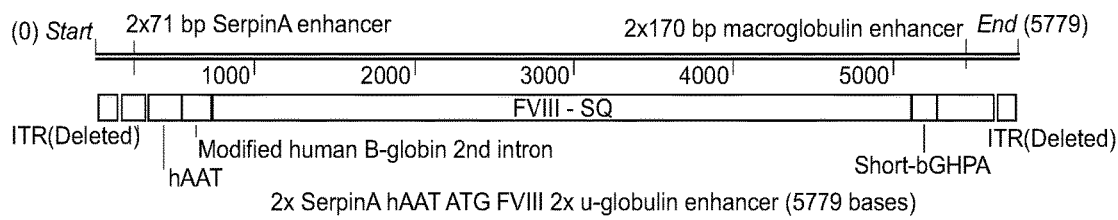

Construct 2×SerpinA hAAT ATG FVIII 2×µ-globulin enhancer (FIG. 4L) is 5779 bases in length. The nucleotide sequence of this construct is set forth in SEQ ID NO:20 in which bases 1-145 are a 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are FVIII-SQ, bases 5122-5271 are a short bGH poly A, bases 5279-5618 are two copies (2×) of a 170 bp µ-globulin enhancer and bases 5635-5779 are a 3' AAV2 ITR.

Figure 4M:
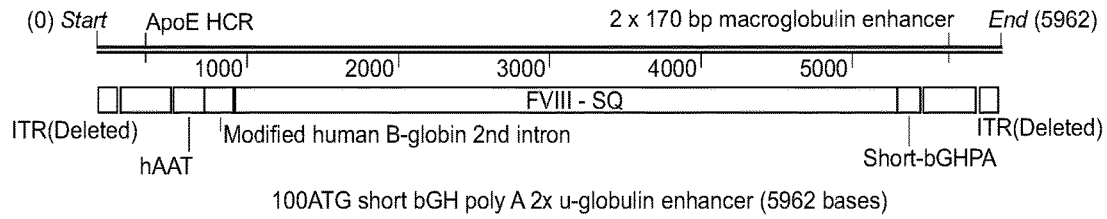

Construct 100ATG short bGH poly A 2×µ-globulin enhancer (FIG. 4M) is 5962 bases in length. The nucleotide sequence of this construct is set forth in SEQ ID NO:21 in which bases 1-145 are a 5' AAV2 ITR, bases 160-502 are an ApoE HCR, bases 509-726 are a hAAT promoter, bases 727-910 are a modified human β-globin $2^{nd}$ intron, bases 923-5296 are FVIII-SQ, bases 5305-5454 are a short bGH poly A, bases 5462-5801 are two copies (2×) of a 170 bp microglobulin enhancer and bases 5818-5962 are a 3' AAV2 ITR.

Figure 4N:
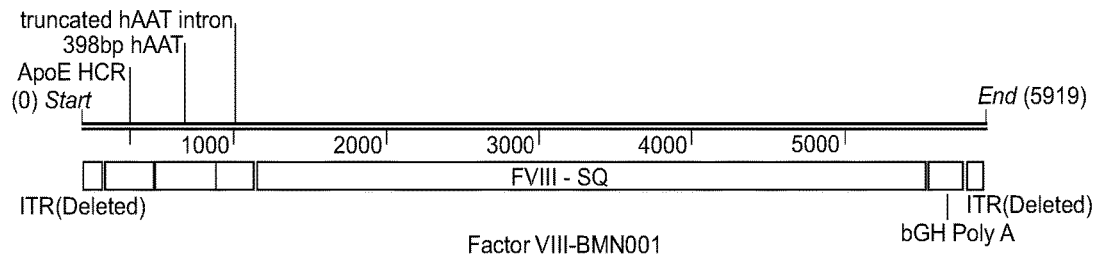

Construct Factor VIII-BMN001 (FIG. 4N) is 5919 bases in length. The nucleotide sequence of this construct is set forth in SEQ ID NO:22 in which bases 1-145 are a 5' AAV2 ITR, bases 160-480 are an ApoE HCR, bases 487-884 are a 398 bp hAAT promoter, bases 885-1145 are a truncated hAAT intron, bases 1155-5528 are FVIII-SQ, bases 5537-5760 are a bGH poly A and bases 5775-5919 are a 3' AAV2 ITR.

Figure 4O:
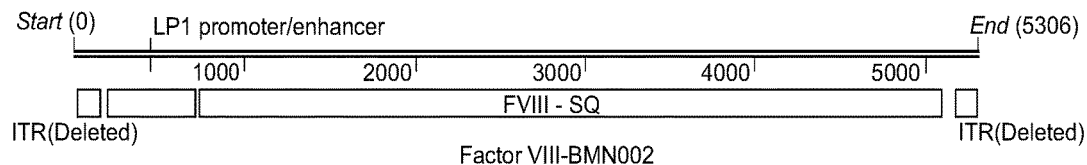

Construct Factor VIII-BMN002 (FIG. 4O) is 5306 bases in length. The nucleotide sequence of this construct is set forth in SEQ ID N0:23 in which bases 1-145 are a 5' AAV2 ITR, bases 175-705 are an LP1 promoter/enhancer, bases 718-5091 are FVIII-SQ, bases 5100-5147 are a synthetic rabbit β-globin poly A and bases 5162-5306 are a 3' AAV2 ITR.

Figure 4P:
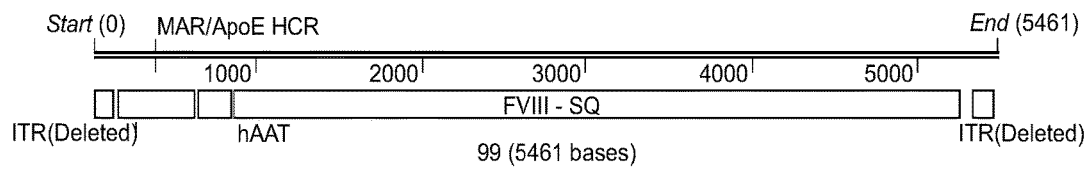

Construct 99 (FIG. 4P) is 5461 bases in length. The nucleotide sequence of this construct is set forth in SEQ ID NO:24 in which bases 1-145 are a 5' AAV2 ITR, bases 169-627 are an ApoE HCR/MAR, bases 634-866 are a hAAT promoter, bases 873-5246 are FVIII-SQ, bases 5255-5302 are a synthetic rabbit β-globin poly A and bases 5317-5461 are a 3' AAV2 ITR.

Figure 4Q:
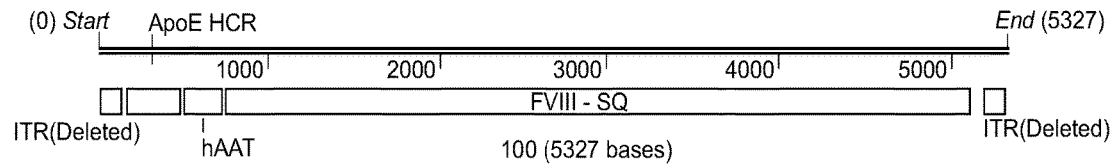

Construct 100 (FIG. 4Q) is 5327 bases in length. The nucleotide sequence of this construct is set forth in SEQ ID NO:25 in which bases 1-145 are a 5' AAV2 ITR, bases 169-493 are an ApoE HCR, bases 509-726 are a hAAT promoter, bases 739-5112 are FVIII-SQ, bases 5121-5168 are a synthetic rabbit β-globin poly A and bases 5183-5327 are a 3' AAV2 ITR.

Figure 4R:
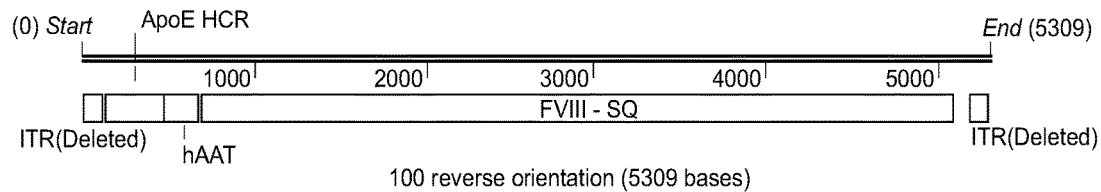

Construct 100 reverse orientation (FIG. 4R) is 5309 bases in length. The nucleotide sequence of this construct is set forth in SEQ ID NO:26 in which bases 1-145 are a 5' AAV2 ITR, bases 160-484 are an ApoE HCR in reverse orientation, bases 491-708 are a hAAT promoter, bases 721-5094 are FVIII-SQ, bases 5103-5150 are a synthetic rabbit β-globin poly A and bases 5165-5309 are a 3' AAV2 ITR.

Figure 4S:
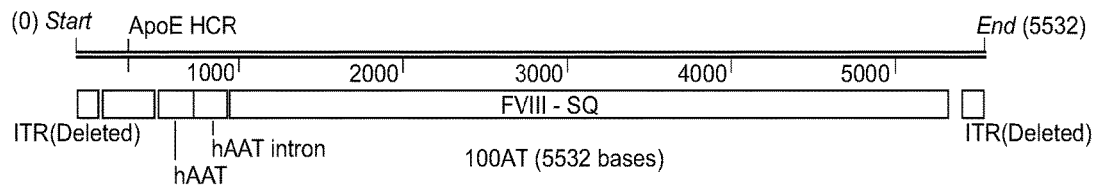

Construct 100AT (FIG. 4S) is 5532 bases in length. The nucleotide sequence of this construct is set forth in SEQ ID NO:27 in which bases 1-145 are a 5' AAV2 ITR, bases 169-493 are an ApoE HCR, bases 509-726 are a hAAT promoter, bases 727-931 are a hAAT intron, bases 944-5317 are FVIII-SQ, bases 5326-5373 are a synthetic rabbit β-globin poly A and bases 5388-5532 are a 3' AAV2 ITR.

Figure 4T:
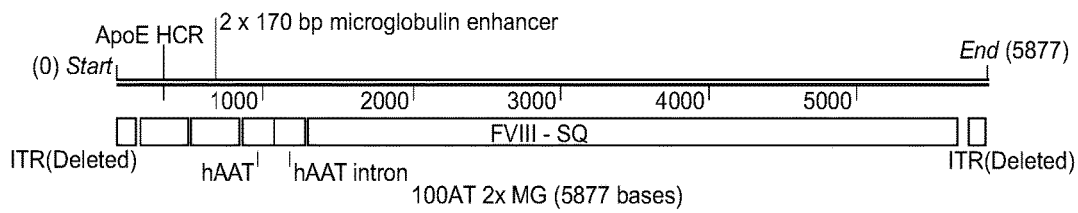

Construct 100AT 2×MG (FIG. 4T) is 5877 bases in length. The nucleotide sequence of this construct is set forth in SEQ ID NO:28 in which bases 1-145 are a 5' AAV2 ITR, bases 169-493 are an ApoE HCR, bases 508-847 are two copies (2×) of a 170 bp µ-globulin enhancer, bases 854-1071 are a hAAT promoter, bases 1072-1276 are a hAAT intron, bases 1289-5662 are FVIII-SQ, bases 5671-5718 are a synthetic rabbit β-globin poly A and bases 5733-5877 are a 3' AAV2 ITR.

Figure 4U:
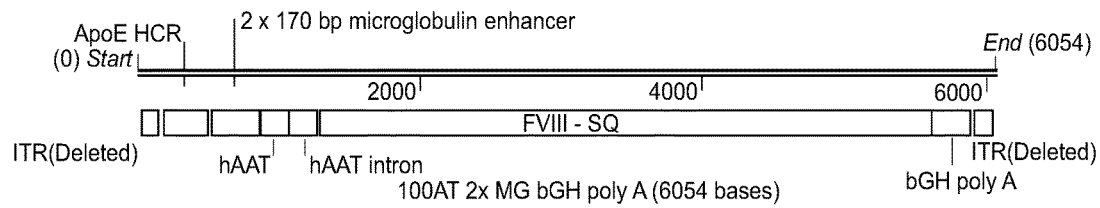

Construct 100AT 2×MG bGH poly A (FIG. 4U) is 6054 bases in length. The nucleotide sequence of this construct is set forth in SEQ ID NO:29 in which bases 1-145 are a 5' AAV2 ITR, bases 169-493 are an ApoE HCR, bases 508-847 are two copies (2×) of a 170 bp µ-globulin enhancer, bases 854-1071 are a hAAT promoter, bases 1072-1276 are a hAAT intron, bases 1289-5662 are FVIII-SQ, bases 5671-5895 are a bGH poly A and bases 5910-6054 are a 3' AAV2 ITR.

Figure 4V:
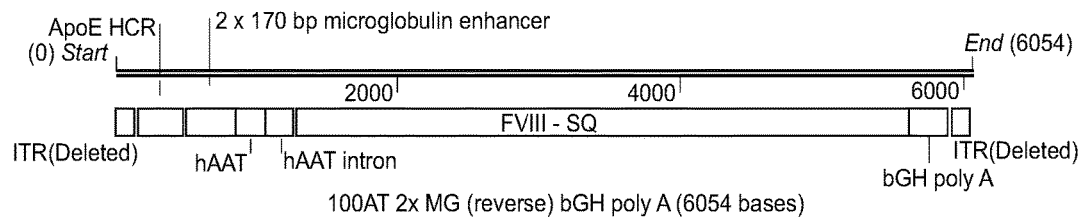

Construct 100AT 2×MG (reverse) bGH poly A (FIG. 4V) is 6054 bases in length. The nucleotide sequence of this construct is set forth in SEQ ID NO:30 in which bases 1-145 are a 5' AAV2 ITR, bases 169-493 are an ApoE HCR, bases 508-847 are two copies (2×) of a 170 bp µ-globulin enhancer in reverse orientation, bases 854-1071 are a hAAT promoter, bases 1072-1276 are a hAAT intron, bases 1289-5662 are FVIII-SQ, bases 5671-5895 are a bGH poly A and bases 5910-6054 are a 3' AAV2 ITR.

Figure 4W:
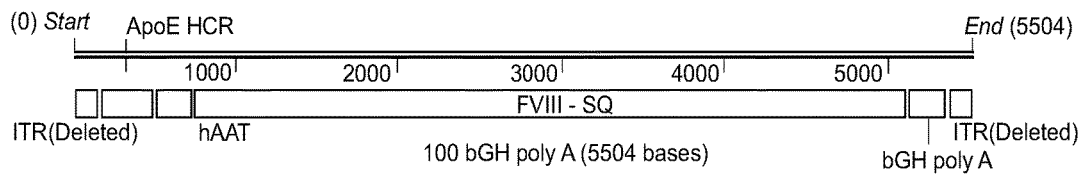

Construct 100 bGH poly A (FIG. 4W) is 5504 bases in length. The nucleotide sequence of this construct is set forth in SEQ ID NO:31 in which bases 1-145 are a 5' AAV2 ITR, bases 169-493 are an ApoE HCR, bases 509-726 are a hAAT promoter, bases 739-5112 are FVIII-SQ, base pairs 5121-5345 are a bGH poly A and bases 5360-5504 are a 3' AAV2 ITR.

Figure 4X:
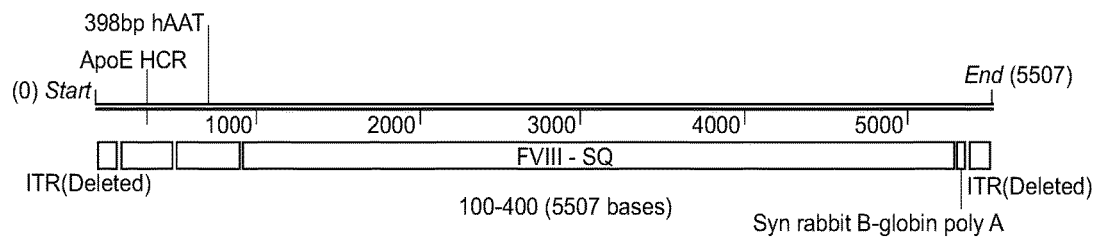

Construct 100-400 (FIG. 4X) is 5507 bases in length. The nucleotide sequence of this construct is set forth in SEQ ID NO:32 in which bases 1-145 are a 5' AAV2 ITR, bases 169-493 are an ApoE HCR, bases 512-906 are a 398 bp hAAT promoter, bases 919-5292 are FVIII-SQ, bases 5301-5348 are a synthetic rabbit β-globin poly A and bases 5363-5507 are a 3' AAV2 ITR.

Figure 4Y:
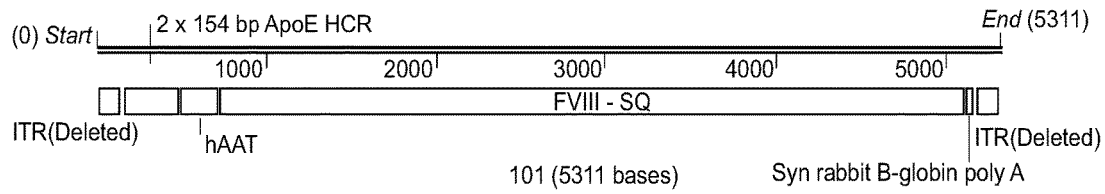

Construct 101 (FIG. 4Y) is 5311 base in length. The nucleotide sequence of this construct is set forth in SEQ ID NO:33 in which bases 1-145 are a 5' AAV2 ITR, bases 170-477 are two copies (2×) of a 154 bp ApoE HCR, bases 493-710 are a hAAT promoter, bases 723-5096 are FVIII-SQ, bases 5105-5152 are a synthetic rabbit β-globin poly A and bases 5167-5311 are a 3' AAV2 ITR.

Figure 4Z:
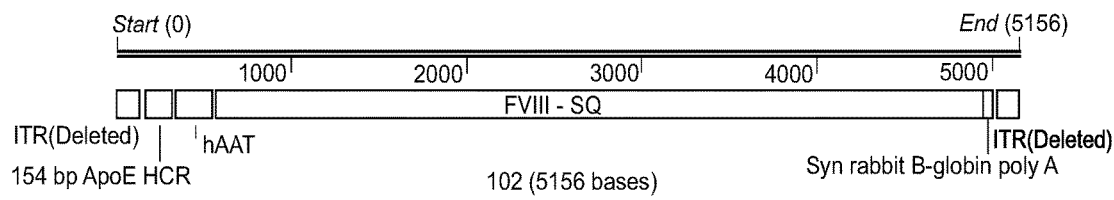
Figure 4A:
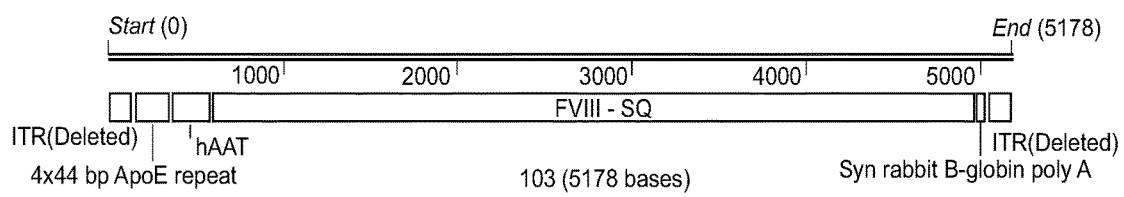
Figure 4B:
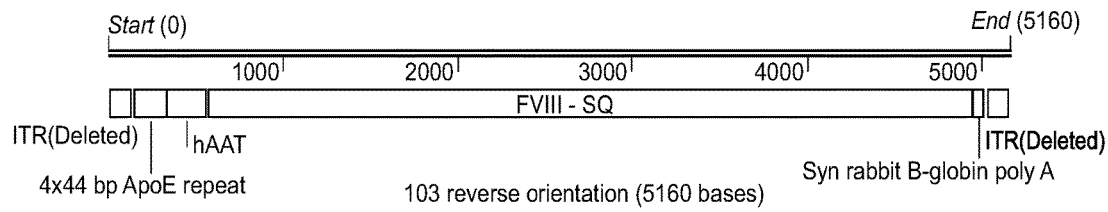
Figure 4C:
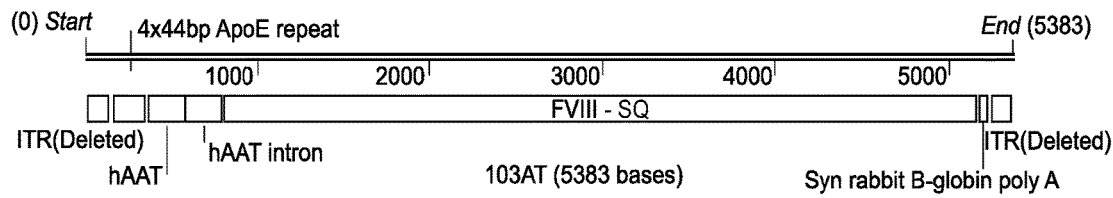
Figure 4D:
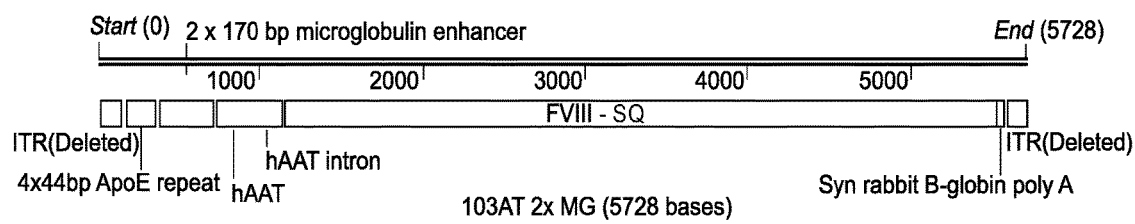
Figure 4E:
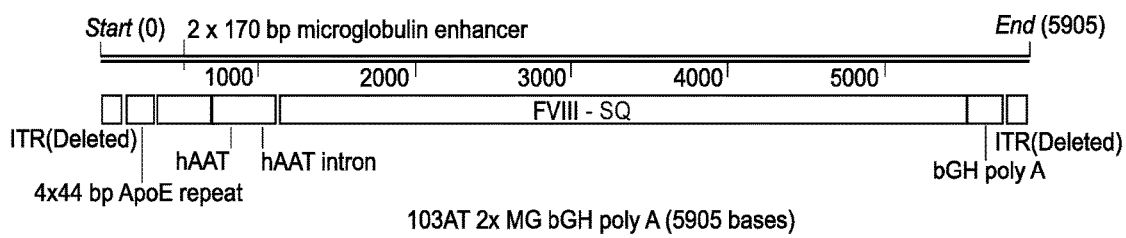
Figure 4F:
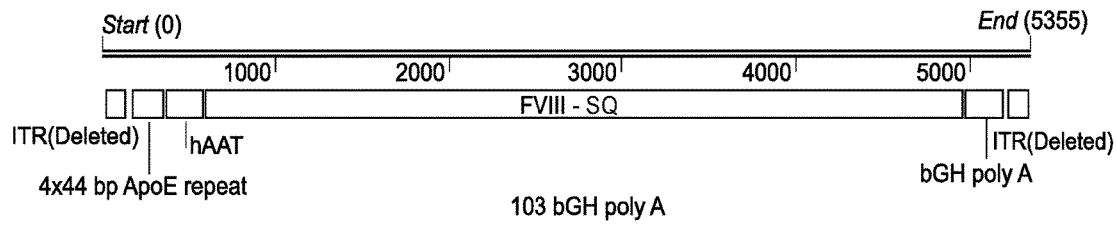
Figure 4G:
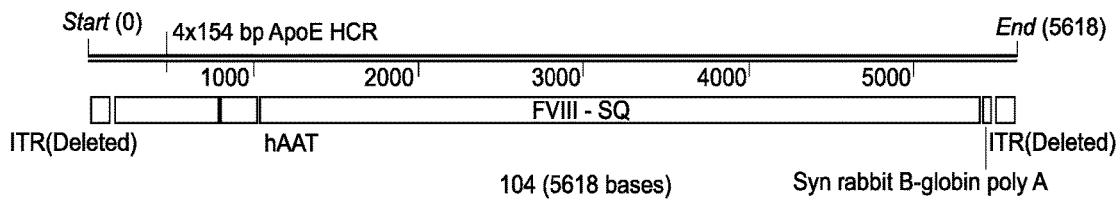
Figure 4H:
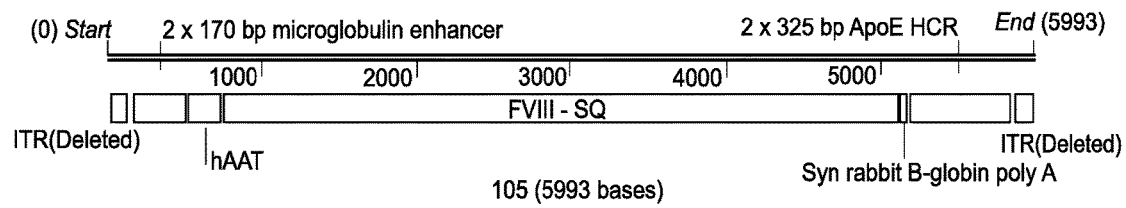
Figure 4I:
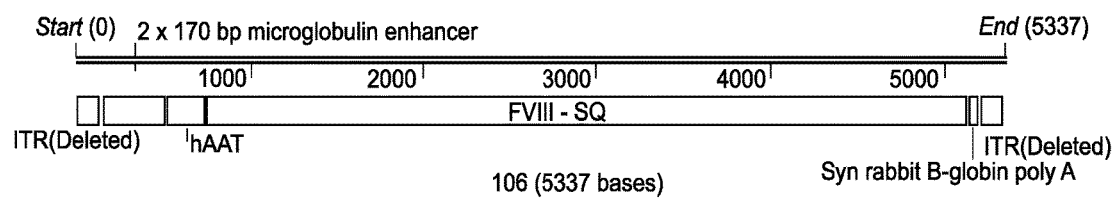
Figure 4J:
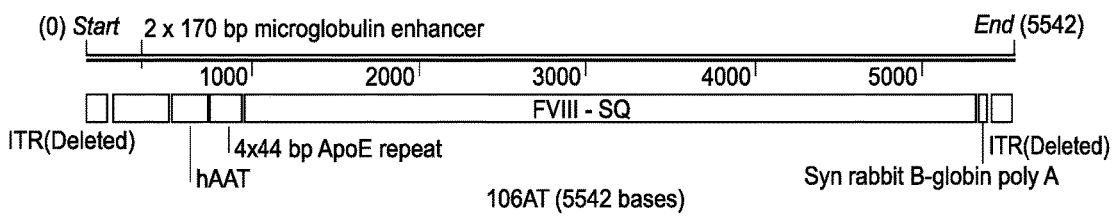

Construct 102 (FIG. 4Z) is 5156 bases in length. The nucleotide sequence of this construct is set forth in SEQ ID NO:34 in which bases 1-145 are a 5' AAV2 ITR, bases 169-322 are a 154 bp ApoE HCR, bases 338-555 are a hAAT promoter, bases 568-4941 are FVIII-SQ, bases 4950-4997 are a synthetic rabbit β-globin poly A and bases 5012-5156 are a 3' AAV2 ITR.

Construct 103 (FIG. 4AA) is 5178 bases in length. The nucleotide sequence of this construct is set forth in SEQ ID NO:35 in which bases 1-145 are a 5' AAV2 ITR, bases 169-344 are four copies (4×) of a 44 bp ApoE HCR, bases 360-577 are a hAAT promoter, bases 590-4963 are FVIII-SQ, bases 4972-5019 are a synthetic rabbit β-globin poly A and bases 5034-5178 are a 3' AAV2 ITR.

Construct 103 reverse orientation (FIG. 4BB) is 5160 bases in length. The nucleotide sequence of this construct is set forth in SEQ ID NO:36 in which bases 1-145 are a 5' AAV2 ITR, bases 160-335 are four copies (4×) of a 44 bp ApoE HCR in reverse orientation, bases 342-559 are a hAAT promoter, bases 572-4945 are FVIII-SQ, bases 4954-

5001 are a synthetic rabbit β-globin poly A and bases 5016-5160 are a 3' AAV2 ITR.

Construct 103AT (FIG. 4CC) is 5383 bases in length. The nucleotide sequence of this construct is set forth in SEQ ID NO:37 in which bases 1-145 are a 5' AAV2 ITR, bases 169-344 are four copies (4×) of a 44 bp ApoE HCR, bases 360-577 are a hAAT promoter, bases 578-782 are a hAAT intron, bases 795-4374 are FVIII-SQ, bases 5177-5224 are a synthetic rabbit β-globin poly A and bases 5239-5383 are a 3' AAV2 ITR.

Construct 103AT 2×MG (FIG. 4DD) is 5728 bases in length. The nucleotide sequence of this construct is set forth in SEQ ID NO:38 in which bases 1-145 are a 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are FVIII-SQ, bases 5522-5569 are a synthetic rabbit β-globin poly A and bases 5584-5728 are a 3' AAV2 ITR.

Construct 103AT 2×MG bGH poly A (FIG. 4EE) is 5905 bases in length. The nucleotide sequence of this construct is set forth in SEQ ID NO:39 in which bases 1-145 are a 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are FVIII-SQ, bases 5522-5746 are a synthetic rabbit β-globin poly A and bases 5761-5905 are a 5' AAV2 ITR.

Construct 103 bGH poly A (FIG. 4FF) is 5355 bases in length. The nucleotide sequence of this construct is set forth in SEQ ID NO:40 in which bases 1-145 are a 5' AAV2 ITR, bases 169-344 are four copies (4×) of a 44 bp ApoE HCR, bases 360-577 are a hAAT promoter, bases 590-4963 are FVIII-SQ, bases 4972-5196 are a synthetic rabbit β-globin poly A and bases 5211-5355 are a 3' AAV2 ITR.

Construct 104 (FIG. 4GG) is 5618 bases in length. The nucleotide sequence of this construct is set forth in SEQ ID NO:41 in which bases 1-145 are a 5' AAV2 ITR, bases 169-784 are four copies (4×) of a 154 bp ApoE HCR, bases 800-1017 are a hAAT promoter, bases 1030-5403 are FVIII-SQ, bases 5412-5459 are a synthetic rabbit β-globin poly A and bases 5474-5618 are a 3' AAV2 ITR.

Construct 105 (FIG. 4HH) is 5993 bases in length. The nucleotide sequence of this construct is set forth in SEQ ID NO:42 in which bases 1-145 are a 5' AAV2 ITR, bases 173-512 are two copies (2×) of a 170 bp μ-globulin enhancer, bases 519-736 are a hAAT promoter, bases 749-5122 are FVIII-SQ, bases 5131-5178 are a synthetic rabbit β-globin poly A, bases 5185-5834 are two copies (2×) of an ApoE HCR and bases 5849-5993 are a 3' AAV2 ITR.

Construct 106 (FIG. 4II) is 5337 bases in length. The nucleotide sequence of this construct is set forth in SEQ ID NO:43 in which bases 1-145 are a 5' AAV2 ITR, bases 173-512 are two copies (2×) of a 170 bp μ-globulin enhancer, bases 519-736 are a hAAT promoter, bases 749-5122 are FVIII-SQ, bases 5131-5178 are a synthetic rabbit β-globin poly A and bases 5193-5337 are a 3' AAV2 ITR.

Construct 106AT (FIG. 4JJ) is 5542 bases in length. The nucleotide sequence of this construct is set forth in SEQ ID NO:44 in which bases 1-145 are a 5' AAV2 ITR, bases 173-512 are two copies (2×) of a 170 bp μ-globulin enhancer, bases 519-736 are a hAAT promoter, bases 737-941 are a hAAT intron, bases 954-5327 are FVIII-SQ, bases 5336-5383 are a synthetic rabbit β-globin poly A and bases 5398-5542 are a 3' AAV2 ITR.

Construct p-100 ATGB is 5640 bases in length. The nucleotide sequence of this construct is set forth in SEQ ID NO:45 and comprises a 5' AAV2 ITR, an ApoE HCR, a hAAT promoter, a modified human β-globin 2nd intron, an FVIII-SQ encoding sequence, a bGH poly A sequence and a 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, *Handbook of Parvoviruses*, Vol. 1, pp. 169-228, and Berns, 1990, *Virology*, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, *Comprehensive Virology* 3:1-61 (1974)). For example, all AAV serotypes apparently exhibit very similar replication properties mediated by homologous rep genes; and all bear three related capsid proteins. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs) and operably linked to one or more expression control elements. Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap genes in accordance with the present invention encode Cap proteins which are capable of packaging AAV vectors in the presence of rep and adeno helper function and are capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
|---|---|
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chiorini et al., J. Vir. 71: 6823-33(1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter. The ITRs employed in the vectors of the present invention may correspond to the same serotype as the associated cap genes, or may differ. In a particularly preferred embodiment, the ITRs employed in the vectors of the present invention correspond to an AAV2 serotype and the cap genes correspond to an AAV5 serotype.

In some embodiments, a nucleic acid sequence encoding an AAV capsid protein is operably linked to expression control sequences for expression in a specific cell type, such as Sf9 or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. *A Manual of Methods for Baculovirus Vectors and Insect Culture Procedures*, Texas Agricultural Experimental Station Bull. No. 7555, College Station, Tex.; Luckow. 1991. In Prokop et al., *Cloning and Expression of Heterologous Genes in Insect Cells with Baculovirus Vectors' Recombinant DNA Technology and Applications*, 97-152; King, L. A. and R. D. Possee, 1992, *The baculovirus expression system*, Chapman and Hall, United Kingdom; O'Reilly, D. R., L. K. Miller, V. A. Luckow, 1992, *Baculovirus Expression Vectors: A Laboratory Manual*, New York; W.H. Freeman and Richardson, C. D., 1995, *Baculovirus Expression Protocols, Methods in Molecular Biology*, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, *METHODS IN MOLECULAR BIOLOGY*, ed. Richard, Humana Press, N J (1995); O'Reilly et al., *BACULOVIRUS EXPRESSION VECTORS, A LABORATORY MANUAL*, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kirnbauer et al., *Vir.* 219:37-44 (1996); Zhao et al., *Vir.* 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene which may or may not correspond to the same serotype as the cap genes. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be produced using any invertebrate cell type which allows for production of AAV or biologic products and which can be maintained in culture. For example, the insect cell line used can be from *Spodoptera frugiperda*, such as SF9, SF21, SF900+, *drosophila* cell lines, mosquito cell lines, e.g., *Aedes albopictus* derived cell lines, domestic silkworm cell lines, e.g. *Bombyx mori* cell lines, *Trichoplusia ni* cell lines such as High Five cells or *Lepidoptera* cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm-NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NSO, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in HEK293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the representative vector shown in FIG. 1, and preferably 1.5-fold, 2-fold, 3-fold, 4-fold, or 5-fold or more expression and/or activity as compared to the vector shown in FIG. 1.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the vector shown in FIG. 1.

Pharmaceutical Formulations

In other embodiments, the present invention is directed to pharmaceutical formulations of FVIII AAV vectors/virions useful for administration to subjects suffering from hemophilia A. In certain aspects, the pharmaceutical formulations of the present invention are liquid formulations that comprise recombinant AAV FVIII virions produced from the vectors disclosed herein, wherein the concentration of recombinant AAV FVIII virions in the formulation may vary widely. In certain embodiments, the concentration of recombinant AAV FVIII virion in the formulation may range from 1E12 vg/ml to 2E14 vg/ml. In a particularly preferred embodiment, the concentration of recombinant AAV FVIII virion in the formulation is about 2E13 vg/ml. In another preferred embodiment, the recombinant AAV FVIII virion present in the formulation is AAV5-FVIII-SQ derived from encapsidation of the Proto 1 vector shown schematically in FIG. 2A in an AAV5 capsid.

In other aspects, the AAV FVIII pharmaceutical formulation of the invention comprises one or more pharmaceutically acceptable excipients to provide the formulation with advantageous properties for storage and/or administration to subjects for the treatment of hemophilia A. In certain embodiments, the pharmaceutical formulations of the present invention are capable of being stored at ≤65° C. for a period of at least 2 weeks, preferably at least 4 weeks, more preferably at least 6 weeks and yet more preferably at least about 8 weeks, without detectable change in stability. In this regard, the term "stable" means that the recombinant AAV FVIII virus present in the formulation essentially retains its physical stability, chemical stability and/or biological activity during storage. In certain embodiments of the present invention, the recombinant AAV FVIII virus present in the pharmaceutical formulation retains at least about 80% of its biological activity in a human patient during storage for a determined period of time at −65° C., more preferably at least about 85%, 90%, 95%, 98% or 99% of its biological activity in a human patient.

In certain aspects, the formulation comprising recombinant AAV FVIII virions further comprises one or more buffering agents. For example, in various aspects, the formulation of the present invention comprises sodium phosphate dibasic at a concentration of about 0.1 mg/ml to about 3 mg/ml, about 0.5 mg/ml to about 2.5 mg/ml, about 1 mg/ml to about 2 mg/ml, or about 1.4 mg/ml to about 1.6 mg/ml. In a particularly preferred embodiment, the AAV FVIII formulation of the present invention comprises about 1.42 mg/ml of sodium phosphate, dibasic (dried). Another buffering agent that may find use in the recombinant AAV FVIII formulations of the present invention is sodium phosphate, monobasic monohydrate which, in some embodiments, finds use at a concentration of from about 0.1 mg/ml to about 3 mg/ml, about 0.5 mg/ml to about 2.5 mg/ml, about 1 mg/ml to about 2 mg/ml, or about 1.3 mg/ml to about 1.5 mg/ml. In a particularly preferred embodiment, the AAV FVIII formulation of the present invention comprises about 1.38 mg/ml of sodium phosphate, monobasic monohydrate. In a yet more particularly preferred embodiment of the present invention, the recombinant AAV FVIII formulation of the present invention comprises about 1.42 mg/ml of sodium phosphate, dibasic and about 1.38 mg/ml of sodium phosphate, monobasic monohydrate.

In another aspect, the recombinant AAV FVIII formulation of the present invention may comprise one or more isotonicity agents, such as sodium chloride, preferably at a concentration of about 1 mg/ml to about 20 mg/ml, for example, about 1 mg/ml to about 10 mg/ml, about 5 mg/ml to about 15 mg/ml, or about 8 mg/ml to about 20 mg/ml. In a particularly preferred embodiment, the formulation of the present invention comprises about 8.18 mg/ml sodium chloride. Other buffering agents and isotonicity agents known in the art are suitable and may be routinely employed for use in the formulations of the present disclosure.

In another aspect, the recombinant AAV FVIII formulations of the present invention may comprise one or more bulking agents. Exemplary bulking agents include without limitation mannitol, sucrose, dextran, lactose, trehalose, and povidone (PVP K24). In certain preferred embodiments, the formulations of the present invention comprise mannitol, which may be present in an amount from about 5 mg/ml to about 40 mg/ml, or from about 10 mg/ml to about 30 mg/ml, or from about 15 mg/ml to about 25 mg/ml. In a particularly preferred embodiment, mannitol is present at a concentration of about 20 mg/ml.

In yet another aspect, the recombinant AAV FVIII formulations of the present invention may comprise one or more surfactants, which may be non-ionic surfactants. Exemplary surfactants include ionic surfactants, non-ionic surfactants, and combinations thereof. For example, the surfactant can be, without limitation, TWEEN 80 (also known as polysorbate 80, or its chemical name polyoxyethylene sorbitan monooleate), sodium dodecylsulfate, sodium stearate, ammonium lauryl sulfate, TRITON AG 98 (Rhone-Poulenc), poloxamer 407, poloxamer 188 and the like, and combinations thereof. In a particularly preferred embodiment, the formulation of the present invention comprises poloxamer 188, which may be present at a concentration of from about 0.1 mg/ml to about 4 mg/ml, or from about 0.5 mg/ml to about 3 mg/ml, from about 1 mg/ml to about 3 mg/ml, about 1.5 mg/ml to about 2.5 mg/ml, or from about 1.8 mg/ml to about 2.2 mg/ml. In a particularly preferred embodiment, poloxamer 188 is present at a concentration of about 2.0 mg/ml.

In a particular preferred embodiment of the present invention, the pharmaceutical formulation of the present invention comprises AAV5-FVIII-SQ formulated in a liquid solution that comprises about 1.42 mg/ml of sodium phosphate, dibasic, about 1.38 mg/ml of sodium phosphate, monobasic monohydrate, about 8.18 mg/ml sodium chloride, about 20 mg/ml mannitol and about 2 mg/ml poloxamer 188.

The recombinant AAV FVIII virus-containing formulations of the present disclosure are stable and can be stored for extended periods of time without an unacceptable change in quality, potency, or purity. In one aspect, the formulation is stable at a temperature of about 5° C. (e.g., 2° C. to 8° C.) for at least 1 month, for example, at least 1 month, at least 3 months, at least 6 months, at least 12 months, at least 18 months, at least 24 months, or more. In another aspect, the formulation is stable at a temperature of less than or equal to about −20° C. for at least 6 months, for example, at least 6 months, at least 12 months, at least 18 months, at least 24 months, at least 36 months, or more. In another aspect, the formulation is stable at a temperature of less than or equal to about −40° C. for at least 6 months, for example, at least 6 months, at least 12 months, at least 18 months, at least 24 months, at least 36 months, or more. In another aspect, the formulation is stable at a temperature of less than or equal to about −60° C. for at least 6 months, for example, at least 6 months, at least 12 months, at least 18 months, at least 24 months, at least 36 months, or more.

Methods of Treatment

In certain embodiments, the present invention is directed to methods for treating a subject suffering from hemophilia A comprising administering to that subject a therapeutically effective amount of an AAV FVIII vector, recombinant AAV FVIII virus or a pharmaceutical composition comprising the same. In yet other embodiments, the present invention is directed to methods for reducing bleeding time during a bleeding episode in a subject suffering from hemophilia A comprising administering to that subject a therapeutically effective amount of an AAV FVIII vector, recombinant AAV FVIII virus or a pharmaceutical composition comprising the same. In this regard, a "therapeutically effective amount", in reference to the treatment of hemophilia A or for use in a method for reducing bleeding time during a bleeding episode in a subject suffering from hemophilia A, refers to an amount capable of invoking one or more of the following effects: (1) reduction, inhibition, or prevention, to some extent, of one or more of the physiological symptoms of hemophilia A including, for example, bruising, joint pain or swelling, prolonged headache, vomiting or fatigue, (2) improvement in the capability to clot blood, (3) reduction of overall bleeding time during a bleeding episode, (4) administration resulting in a measurable increase in the concentration or activity of functional FVIII protein in the plasma of a subject, and/or (5) relief, to some extent, of one or more symptoms associated with the disorder. A "therapeutically effective amount" of an AAV FVIII vector or virus or a pharmaceutical composition comprising the same for purposes of treatment as described herein may be determined empirically and in a routine manner. In certain embodiments, however, a "therapeutically effective amount" of recombinant AAV FVIII virus ranges from about 1E12 vg/kg body weight to about 1E14 vg/kg body weight, preferably from about 6E12 vg/kg body weight to about 6E13 vg/kg body weight. In a particularly preferred embodiment, a therapeutically effective amount of recombinant AAV FVIII virus is about 2E13 vg/kg body weight. In another particularly preferred embodiment, a therapeutically effective amount of recombinant AAV FVIII virus is about 6E13 vg/kg body weight.

Recombinant AAV FVIII vectors/virus of the present invention may be administered to a subject, preferably a mammalian subject, more preferably a human subject, through a variety of known administration techniques. In a preferred embodiment, the recombinant AAV FVIII gene therapy virus is administered by intravenous injection either as a single bolus or over a prolonged time period, which may be at least about 1, 5, 10, 15, 30, 45, 60, 75, 90, 120, 150, 180, 210 or 240 minutes, or more. In a particularly preferred embodiment of the present invention, the recombinant AAV FVIII virus administered is AAV5-FVIII-SQ.

Administration of a recombinant AAV FVIII vector/virus, or pharmaceutical formulation comprising the same, of the present invention preferably results in an increase in functional FVIII protein activity in the plasma of the subject of at least 1, 2, 3, 4, 5, 6, 7, 8, 9, 10, 11, 12, 13, 14, 15, or more IU/dl as compared to the amount of functional FVIII protein activity present in the plasma in the subject prior to administration. In certain embodiments, administration of a recombinant AAV FVIII vector/virus, or pharmaceutical formulation comprising the same, of the present invention results in the expression of at least about 1, 2, 3, 4, 5, 6, 7, 8, 9, 10 or more IU/dl of functional FVIII protein activity in the plasma of the subject. In this regard, the term "IU" or "international unit" in regards to FVIII activity is a well understood and accepted term, wherein 1 IU of FVIII activity is equivalent to the quantity of FVIII in one ml of normal human plasma. FVIII activity in the plasma may be quantitatively determined by a number of well-known and accepted assays including, for example, the activated partial thromboplastin time (APPT) method (see, e.g., Miletich JP: Activated partial thromboplastin time. In Williams Hematology. Fifth edition. Edited by E Beutler, M A Lichtman, B A Coller, T J Kipps. New York, McGraw-Hill, 1995, pp L85-86, Greaves and Preston, Approach to the bleeding patient. In Hemostasis and Thrombosis: Basic Principles and Clinical Practice. Fourth edition. Edited by R W Colman, J Hirsh, V J Marder, et al. Philadelphia, JB Lippincott Co, 2001, pp 1197-1234 and Olson et al, *Arch. Pathol. Lab. Med.* 122: 782-798 (1998)) or chromogenic FXa assay (Harris et al., Thromb. Res. 128(6):125-129 (2011)).

In other embodiments of the present invention, bleeding time in a subject may be measured by well-known and accepted techniques including, for example, the Ivy method (see, e.g., Ivy et al., *Surg. Gynec. Obstet.* 60:781 (1935) and Ivy et al., *J. Lab. Clin. Med.* 26:1812 (1941)) or the Duke method (see, e.g., Duke et al., *JAMA* 55:1185 (1910)). A "bleeding episode" in a subject refers to an injury that results in bleeding in the subject, either externally or internally, and generally comprises the time period from injury to formation of a blood clot.

Administration of an AAV FVIII virus of the present invention may, in some cases, result in an observable degree of hepatotoxicity. Hepatotoxicity may be measured by a variety of well-known and routinely used techniques for example, measuring concentrations of certain liver-associated enzyme(s) (e.g., alanine transaminase, ALT) in the bloodstream of a subject both prior to AAV FVIII administration (i.e., baseline) and after AAV FVIII administration. An observable increase in ALT concentration after AAV FVIII administration (as compared to prior to administration) is indicative of drug-induced hepatotoxicity. In certain embodiments of the present invention, in addition to administration of a therapeutically effective amount of AAV FVIII virus, the subject may be treated either prophylactically, therapeutically, or both with a corticosteroid to prevent and/or treat any hepatotoxicity associated with administration of the AAV FVIII virus. "Prophylactic" corticosteroid treatment refers to the administration of a corticosteroid to prevent hepatotoxicity and/or to prevent an increase in measured ALT levels in the subject. "Therapeutic" corticosteroid treatment refers to the administration of a corticosteroid to reduce hepatotoxicity caused by administration of an AVV FVIII virus and/or to reduce an elevated ALT concentration in the bloodstream of the subject caused by administration of an AAV FVIII virus. In certain embodiments, prophylactic or therapeutic corticosteroid treatment may comprise administration of at least 5, 10, 15, 20, 25, 30, 35, 40, 45, 50, 55, 60, or more mg/day of the corticosteroid to the subject. In certain embodiments, prophylactic or therapeutic corticosteroid treatment of a subject may occur over a continuous period of at least about 3, 4, 5, 6, 7, 8, 9, 10 weeks, or more. Corticosteroids that find use in the methods described herein include any known or routinely-employed corticosteroid including, for example, dexamethasone, prednisone, fludrocortisone, hydrocortisone, and the like.

Detection of Anti-AAV Antibodies

To maximize the likelihood of successful liver transduction with systemic AAV-mediated Factor VIII gene transfer, prior to administration of an AAV vector in a therapeutic regimen to a human patient as described above, the prospective patient may be assessed for the presence of anti-AAV capsid antibodies that are capable of blocking cell transduction or otherwise reduce the overall efficiency of the therapeutic regimen. Such antibodies may be present in the serum of the prospective patient and may be directed against an AAV capsid of any serotype. In one embodiment, the serotype against which pre-existing antibodies are directed is AAV5.

Methods to detect pre-existing AAV immunity are well known and routinely employed in the art and include cell-based in vitro transduction inhibition (TI) assays, in vivo (e.g., in mice) TI assays, and ELISA-based detection of total anti-capsid antibodies (TAb) (see, e.g., Masat et al., *Discov. Med.* 15:379-389 (2013) and Boutin et al., *Hum. Gene Ther.* 21:704-712 (2010)). TI assays may employ host cells into which an AAV-inducible reporter vector has been previously introduced. The reporter vector may comprise an inducible reporter gene such as GFP, etc. whose expression is induced upon transduction of the host cell by an AAV virus. Anti-AAV capsid antibodies present in human serum that are capable of preventing/reducing host cell transduction would thereby reduce overall expression of the reporter gene in the system. Therefore, such assays may be employed to detect the presence of anti-AAV capsid antibodies in human serum that are capable of preventing/reducing cell transduction by the therapeutic FVIII AAV virus.

TAb assays to detect anti-AAV capsid antibodies may employ solid-phase-bound AAV capsid as a "capture agent" over which human serum is passed, thereby allowing anti-capsid antibodies present in the serum to bind to the solid-phase-bound capsid "capture agent". Once washed to remove non-specific binding, a "detection agent" may be employed to detect the presence of anti-capsid antibodies bound to the capture agent. The detection agent may be an antibody, an AAV capsid, or the like, and may be detectably-labeled to aid in detection and quantitation of bound anti-capsid antibody. In one embodiment, the detection agent is labeled with ruthenium or a ruthenium-complex that may be detected using electrochemiluminescence techniques and equipment.

The same above-described methodology may be employed to assess and detect the generation of an anti-AAV capsid immune response in a patient previously treated with a therapeutic AAV virus of interest. As such, not only may these techniques be employed to assess the presence of anti-AAV capsid antibodies prior to treatment with a therapeutic FVIII AAV virus, they may also be employed to assess and measure the induction of an immune response against the administered therapeutic FVIII AAV virus after administration. As such, the present invention contemplates methods that combine techniques for detecting anti-AAV capsid antibodies in human serum and administration of a therapeutic FVIII AAV virus for the treatment of hemophilia A, wherein the techniques for detecting anti-AAV capsid antibodies in human serum may be performed either prior to or after administration of the therapeutic FVIII AAV virus.

Other aspects and advantages of the present invention will be understood upon consideration of the following illustrative examples.

EXAMPLES

Example 1

Generation of Proto 1, Proto 1S, Proto 2S and Proto 3S Vectors

The recombinant AAV FVIII vector schematically shown in FIG. 1, which is described in detail in WO 2011/005968, published Jan. 13, 2011, which is incorporated herein by reference in its entirety, and McIntosh et al., *Blood* 121: 3335-3344, 2013, is an oversized, i.e., greater than 5.0 kb, AAV vector. As shown in FIG. 1, this vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3' ITR. This vector is 5081 bases in length.

To obtain a vector that is smaller than the FVIII vector shown in FIG. 1, DNA sequences believed by the inventors herein to be unnecessary for FVIII expression and/or activity, or for AAV virion production, were removed from the original vector sequence. Extraneous DNA sequence was removed, including 53 bases of AAV2 viral sequence 3' to the AAV2 5' ITR, 46 bases of AAV2 viral sequence 5' to the AAV2 3' ITR, and 11 bases adjacent to the codon-optimized FVIII SQ coding region. A novel codon-optimized, B-domain-deleted FVIII-encoding sequence possessing an SQ linker was also produced and introduced into new recombinant AAV FVIII vectors. Certain sequence changes were made to the AAV2 5' and 3' ITRs. The resultant Proto 1 vector, which is 4970 bases in length, is shown in schematic form in FIG. 2A, and the complete nucleotide sequence is set forth in SEQ ID NO:1. The inventors herein have demonstrated that Proto 1 produced infectious recombinant AAV virus and encodes a functional Factor VIII polypeptide.

Sequences adjacent to the hairpin loop in the AAV2 ITR may also be dispensable in recombinant AAV vectors (see Srivastava et al., U.S. Pat. No. 6,521,225; Wang et al., *J. Virol.* 70:1668-1677, 1996; and Wang et al., *J. Virol.* 71:3077-3082, 1997). To further reduce the size of the Proto 1 vector, 10 bases of AAV2 sequence was removed directly 3' to the hairpin loop in the AAV2 5' ITR and 10 bases of AAV2 sequence was removed directly 5' to the hairpin loop in the AAV2 3' ITR. The resultant Proto 1S vector, which is 4950 bases in length, is shown in schematic form in FIG. 2B, and the sequence is set forth in SEQ ID NO:2.

In an effort to increase the expression of the FVIII SQ variant in the Proto 1S vector, a 100 base synthetic intron was inserted between exons 1 and 2 in the codon-optimized FVIII sequence. It is known that insertion of an intron possibly can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in U.S. Pat. No. 8,030,065 (FIX expression) and in WO 2011/005968 (FVIII expression), both of which are incorporated herein by reference in their entirety. The 32 base human AAT promoter distal X region, described in Di Simone et al., *EMBO J.* 6:2759-2766, 1987, is located within a regulatory domain that enhances expression of a heterologous promoter.

In another attempt to further increase the expression of the FVIII SQ variant in the Proto 1S vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 1S. The resultant Proto 2S vector, which is 4983 bases in length, is shown in schematic form in FIG. 2C, and the sequence set forth in SEQ ID NO:3.

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO:4.

The Proto 1, Proto 1S, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
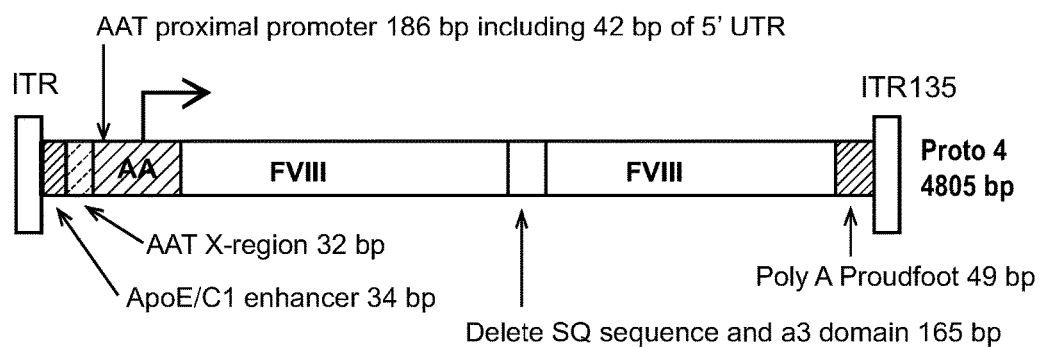
FIG. 3A-FIG. 3D provide schematic representations of certain recombinant AAV FVIII vectors of the present invention. (A) Proto 4, (B) Proto 5, (C) Proto 6 and (D) Proto 7.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO:5.

Figure 3B:
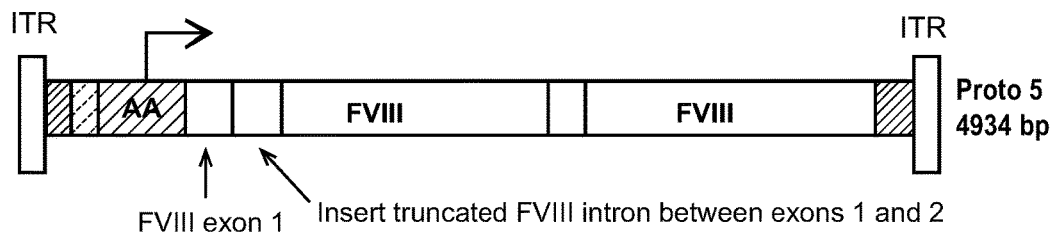

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO:6.

Figure 3C:
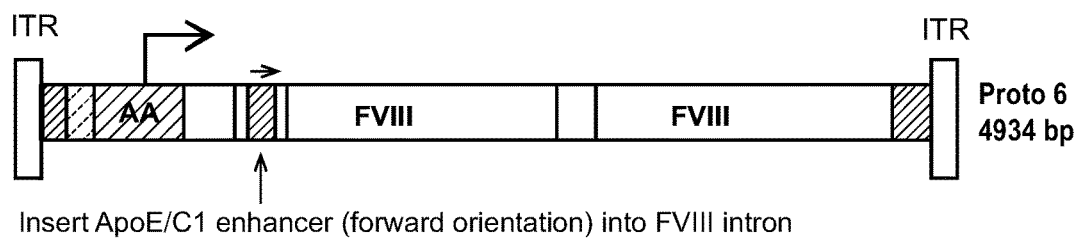

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO:7.

Figure 3D:
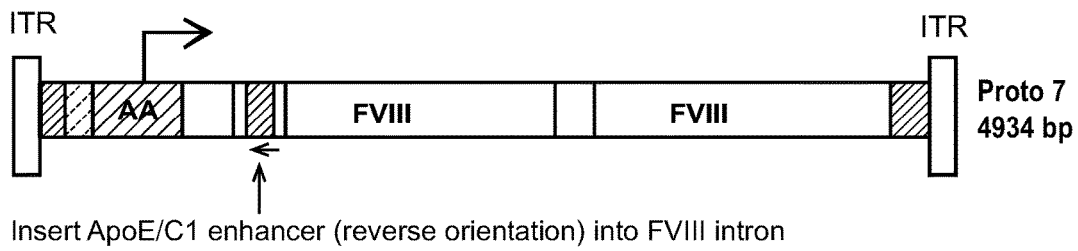

The resultant Proto 7 vector, which is 4934 bases in length and has the intronic ApoE/C1 enhancer in the reverse orientation, is shown in schematic form in FIG. 3D, and the sequence is set forth in SEQ ID NO:8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the recombinant AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays

A preliminary in vitro assay is performed to compare the FVIII expression and activity from the AAV FVIII vectors of the present invention with that from the FVIII-expressing vector shown in FIG. 1. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the FVIII vector of FIG. 1, demonstrating that the Proto 1, Proto 1S and Proto 2S vectors were capable of expressing functional Factor VIII protein.

Production of AAV FVIII Virions in 293 Cells and Baculovirus-Infected Insect Cells To demonstrate that the recombinant AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5' ITR (sense strand) or 3' ITR (anti-sense strand).

Alternatively, a PCR assay is used to determine whether the AAV FVIII vectors nucleic acids have complete ends, i.e., terminate at the 5' end of the hairpin loop in the AAV2 5' ITR (sense strand) or 3' ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, administered intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional recombinant AAV vectors with strong promoters that increase expression of functional FVIII, constructs were generated with modified enhancer and/or promoter sequences. In some embodiments, the constructs comprised shortened versions of the ApoE or the µ-globulin enhancers. These constructs were generated using standard DNA cloning techniques and the sequences thereof are shown in SEQ ID NOS:9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described above. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1 \times 10^6$ cells/well in a 6-well plate (or $6 \times 10^6$ cells in a 10-cm plate or $1.7 \times 10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30-45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+ antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of Baculovirus (P1)

Sf9 cells were grown to approximately $4 \times 10^6$ cells/mL and diluted to approximately $2 \times 10^6$ cells/mL with fresh medium in shaking flasks. An amount of the Sf9 cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV Using P1 Recombinant Baculoviruses

Sf9 cells were grown to about 1×10$^7$ cells/mL and diluted to about 5×10$^6$ cells/mL. An amount of the diluted Sf9 cells were infected with Bac-vector (5Moi) and Bac-helper (15Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding/Purification Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV virions which comprise a codon-optimized SQ FVIII-encoding gene sequence were generated using baculovirus and 293 cells using the FVIII vector of FIG. 1, Proto 1, Proto 1S, Proto 2S and Proto 3S constructs. The packaging limits are about 4800 bp for baculovirus and about 4950 bp for 293 cells.

Figure 5:
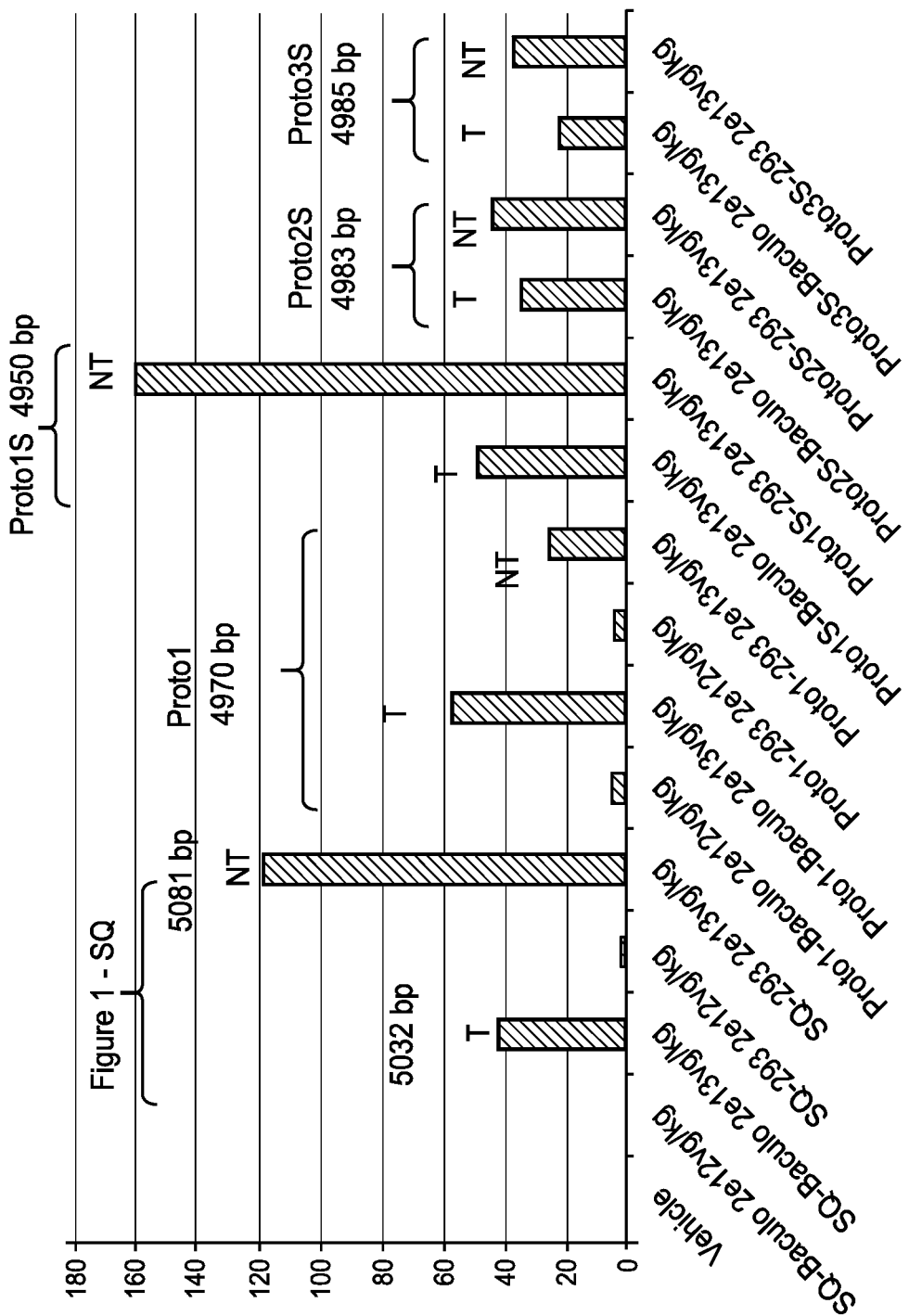
FIG. 5 provides the results of the evaluation of the recombinant AAV FVIII Proto constructs in Rag2 mice, and demonstrates that the Proto viral constructs transduce FVIII similarly to the vector shown in FIG. 1, wherein the y-axis represents ng/ml of FVIII protein determined by ELISA analysis.

As shown in FIG. 5, all constructs tested with truncated (T) or non-truncated (NT) genomes are capable of inducing FVIII expression. Expression of FVIII from Proto 1 was similar to the FVIII construct of FIG. 1 when these AAV were made by the baculovirus system. Inclusion of the intron in Proto 2S and Proto 3S did not result in improved FVIII expression as compared to Proto 1. The FVIII vector of FIG. 1 containing the AAV flanking sequences made in 293 cells were more potent than the same vector lacking the AAV sequence made in baculovirus. As a result, additional enhancers were added to Proto 1, e.g. Constructs 101, 102, 102 and 104, in an attempt to increase potency and associated FVIII expression.

Example 6

Expression and Activity of AAV FVIII Vectors with Improved Promoters/Enhancer Sequences The expression and activity of additional recombinant AAV FVIII vectors were tested using a hydrodynamic injection protocol. Hydrodynamic delivery is a rapid method to screen the efficiency of various recombinant AAV FVIII vectors in vivo. Specifically, AAV FVIII plasmid DNA was generated as described above and then diluted in TransIT-QR Hydrodynamic Delivery Solution. The plasmid DNA was injected into the tail vein of 5-6 week old C57Bl/6 mice (18-25 g) at a volume determined by (mouse weight (g)/10)= 0.1 ml delivery solution). The injection time was less than 5 seconds. Plasma from each mouse was then collected 48 hours after injection and the amount of FVIII protein expressed was measured using an ELISA assay. The amount of FVIII in the plasma of the injected mouse was measured using an ELISA test and recombinant FVIII (Xyntha SQ equivalents) was used as a standard for comparison.

Figure 6:
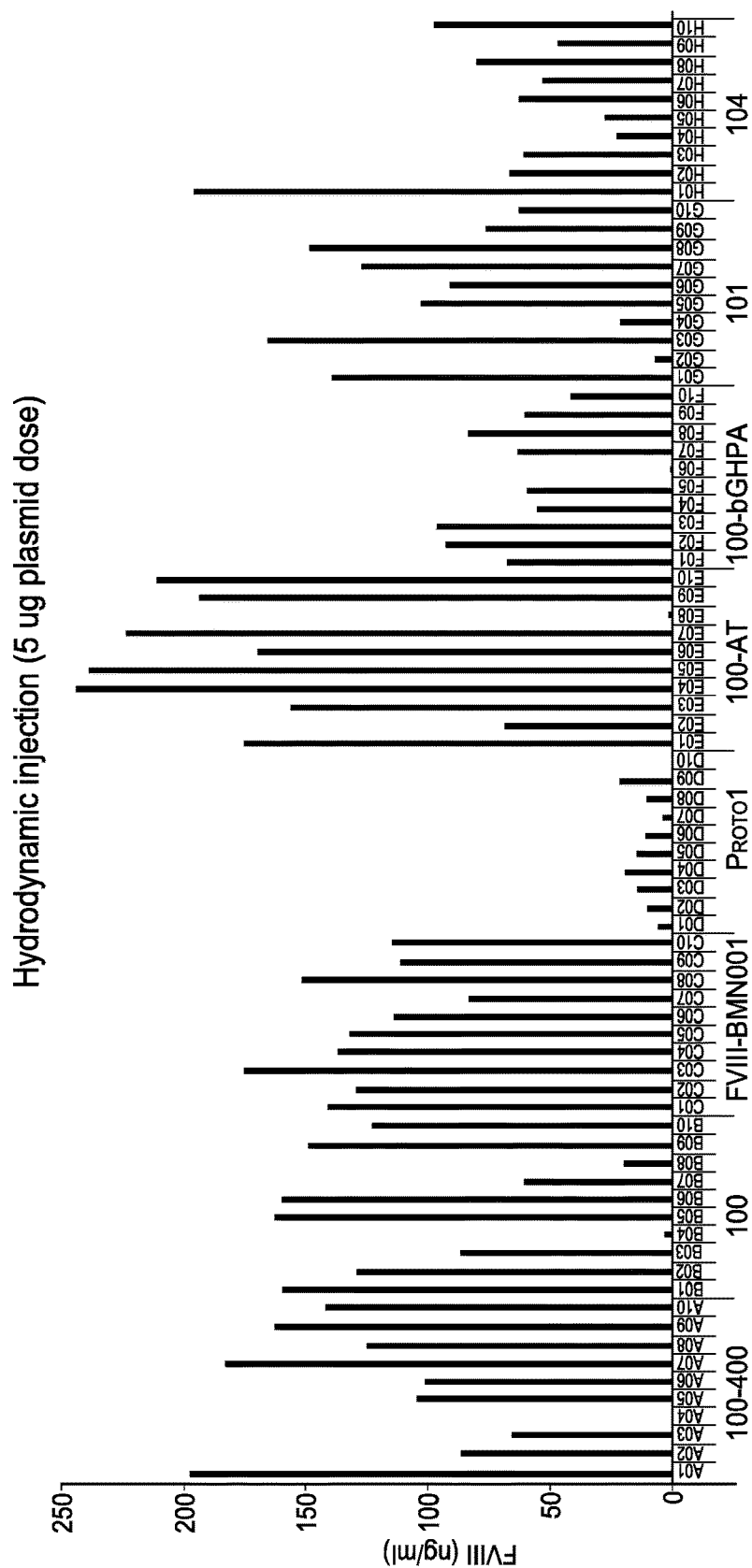
FIG. 6 demonstrates that various recombinant AAV FVIII constructs of the present invention induce in vivo expression of FVIII protein as measured in a mouse tail vein hydrodynamic injection assay.

To investigate FVIII expression, certain recombinant AAV FVIII constructs of the present invention were tested in the hydrodynamic injection protocol to measure their ability to result in expression of functional FVIII protein in vivo. As shown in FIG. 6, all constructs tested at a 5 μg of plasmid dose produced functional FVIII at varying levels of efficiency.

Figure 7:
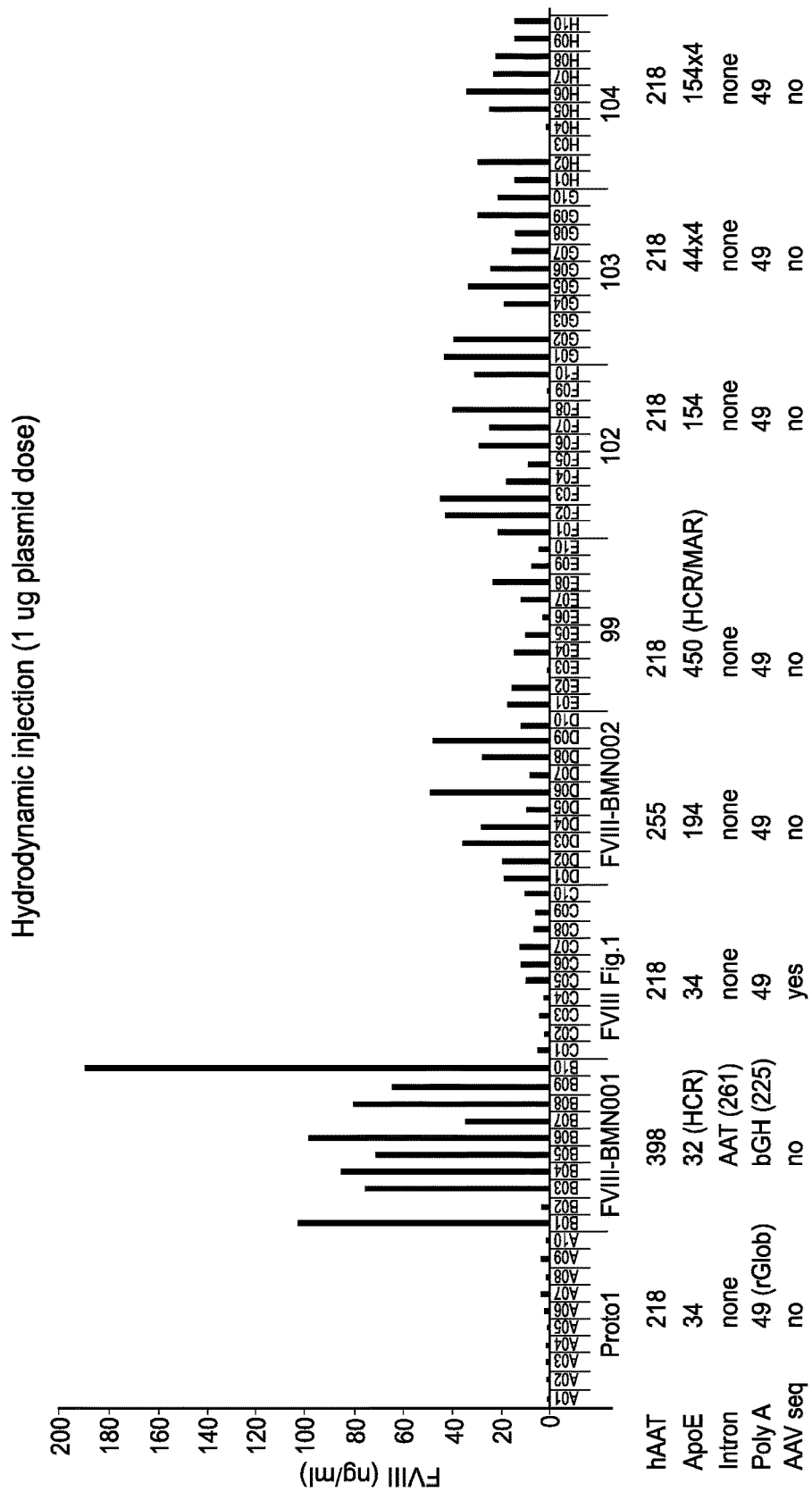
FIG. 7 demonstrates that various recombinant AAV FVIII constructs of the present invention induce in vivo expression of FVIII protein as measured in a mouse tail vein hydrodynamic injection assay.
Figure 8:
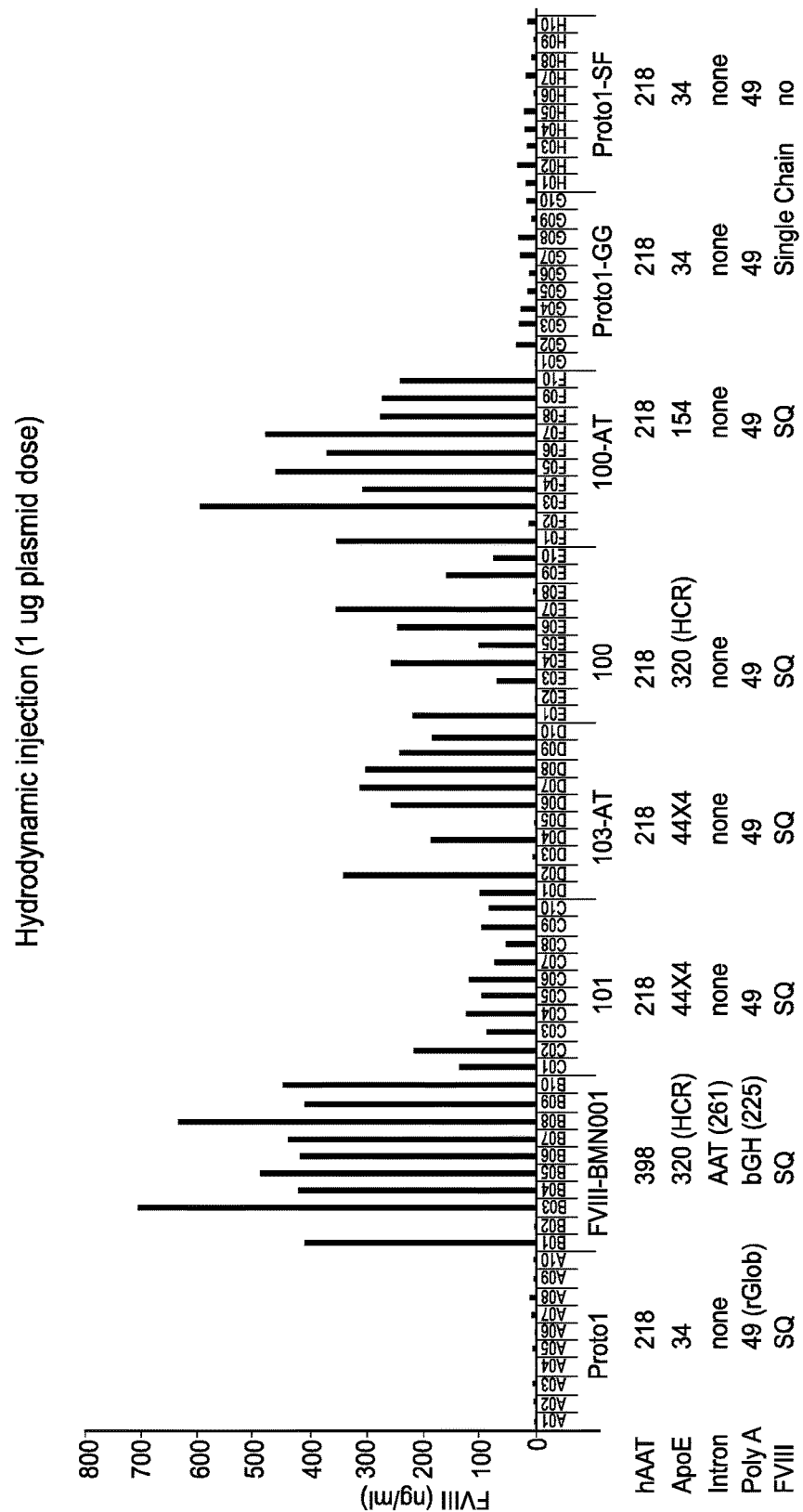
FIG. 8 demonstrates that various recombinant AAV FVIII constructs of the present invention induce in vivo expression of FVIII protein as measured in a mouse tail vein hydrodynamic injection assay.

FIGS. 7 and 8 provide data for hydrodynamic injection for a dose of 1 μg of plasmid of various recombinant AAV FVIII constructs of the present invention. As shown in FIGS. 7 and 8, injection of the various constructs tested all resulted in the in vivo expression of FVIII protein with varying levels of efficiency.

Example 7

Analysis of AAV Virus Comprising p-100 ATGB Vector

AAV virus comprising the FVIII-SQ-encoding vector p-100 ATGB shown herein as SEQ ID NO:45 ("AAV5-p100ATGB-FVIII") were produced and evaluated for the ability to express functional FVIII-SQ protein in Rag2 mice as described in Example 5 above. More specifically, Rag2 mice were administered a single dose of either AAV5-FVIII-SQ virus or AAV5-p100ATGB-FVIII virus at a dose of either 6E12 vg/kg, 2E13 vg·kg or 6E13 vg/kg and FVIII protein concentrations were subsequently determined in the bloodstream of the mice. The results of these analyses demonstrated that administration of the AAV5-p100ATGB-FVIII virus produced approximately a 3-fold higher level of circulating functional FVIII protein than did the AAV5-FVIII-SQ virus at the two lower doses tested. The observed difference in expression was somewhat attenuated at the highest dose tested, although even at the highest dose tested, the AAV5-p100ATGB-FVIII virus produced a higher level of circulating functional FVIII protein than did the AAV5-FVIII-SQ virus. These results demonstrate that the AAV5-p100ATGB-FVIII virus effectively transduces liver cells in vivo and provides for expression of high levels of functional FVIII protein.

Example 8

Studies of a Specific Recombinant FVIII AAV Vector/Virus for Hemophilia a

Hemophilia A (HA) is an X-linked recessive bleeding disorder that affects approximately 1 in 5,000 males. It is caused by deficiency in the activity of coagulation factor VIII (FVIII), an essential cofactor in the intrinsic coagulation cascade. This disorder can be either inherited, due to a new mutation or an acquired immunologic process, leading to insufficient quantities of FVIII or a dysfunctional FVIII, but all are characterized by a defective coagulation process. The clinical phenotype of HA patients is largely governed by the level of residual expression. Severe HA is classified as FVIII activity less than 1% of wild type (<1 IU/dL), moderate disease comprises 1-5% of wild type activity (1 IU/dl-5 IU/dl) and the mild form is 5-40% activity (5 IU/dl-40 IU/dl). The clinical manifestations of severe HA remain frequent spontaneous bleeding episodes, predominantly in joints and soft tissues, with a substantially increased risk of death from hemorrhage when the brain is involved.

Treatment of severe HA presently consists of intravenous injection of plasma-derived or recombinant FVIII protein (rhFVIII) concentrates, both as prophylaxis 2-3 times per week, and at the time of a bleed, to prevent or control bleeding episodes, respectively. The half-life for rhFVIII (under 24 hours for most approved products) necessitates frequent infusions, and although a major advance in the treatment of HA, it remains common for severe HA patients to continue to have multiple bleeding events on treatment (mean of 1 to 7 episodes/year with prophylaxis up to 30 to 50 for on demand treatment). The consequence of multiple bleeding events is the development of an underlying pathology that contributes to debilitating multiple-joint arthropathy and substantially increased risk of death. Chemical modification (e.g. direct conjugation of polyethylene glycol (PEG) polymers) and bioengineering of FVIII (e.g. FVIII-Fc fusion proteins) improve half-life by approximately 50%, and thus, show promise in reduced dosing and maintaining activity levels above 1% trough. However, these longer acting FVIIIs remain dependent on multiple infusions to maintain critical levels of FVIII activity in severe HA patients. There is therefore a strong unmet need for a fully preventive treatment of HA to give patients a FVIII level compatible with a normal and hemorrhage-free life.

Gene therapy offers the potential of disease-modifying therapy by continuous endogenous production of active FVIII following a single intravenous administration of a vector with the appropriate gene sequence. Hemophilia A is well suited for a gene replacement approach because clinical manifestations are attributable to the lack of a single gene product (FVIII) that circulates in minute amounts (200 ng/ml) in the plasma. Tightly regulated control of gene expression is not essential, and modest increases in the level of FVIII (any increase of the plasma level by 2 ng/ml induces an increase in activity of 1%) can ameliorate the severe form of the disease. Thus, relatively small changes in endogenous FVIII activity results in clinically relevant improvements in disease phenotype. Finally, the response to gene transduction can be assessed using validated quantitative rather than qualitative endpoints that are easily assayed using established laboratory techniques.

Several different gene transfer strategies for FVIII replacement have been evaluated, but adeno-associated viral (AAV) vectors show the greatest promise. They have an excellent and well-defined safety profile, and can direct long term transgene expression with tropism for specific tissues such as the liver (for serotypes 2, 5 and 8, among others). Indeed, an ongoing gene therapy clinical trial for a related disorder, hemophilia B, has established that stable (>36 months) expression of human factor IX at levels that are sufficient for conversion of their bleeding phenotype from severe to moderate or mild is achievable following a single peripheral vein administration of recombinant FIX AAV-8 vector. Several participants in this trial have been able to discontinue factor prophylaxis without suffering spontaneous hemorrhages, even when they undertook activities that previously resulted in bleeding. Thus, gene therapy treatment has resulted in a substantial improvement in their quality of life.

Additional Preclinical Studies

The recombinant FVIII-SQ-encoding vector Proto1 (shown herein in FIG. 2A and SEQ ID NO:1) was used to produce recombinant AAV5 FVIII-SQ-encoding virus using a baculovirus/Sf9-based expression system as described above. The virus generated (herein referred to as "AAV5-FVIII-SQ") was purified and formulated for pre-clinical animal studies in Dulbecco's phosphate buffered saline (DPBS) containing 0.001% Poloxamer 188.

The AAV5-FVIII-SQ nonclinical program was designed to elucidate the transduction, relative expression and activity of the FVIII-SQ protein and the overall safety profile of the AAV5 capsid and FVIII-SQ transgene product components of AAV5-FVIII-SQ to support a single IV administration of the recombinant virus in human patients. The nonclinical profile of AAV5-FVIII-SQ was assessed across one in vitro study and ten single dose studies in mice, normal wild type (WT), Rag2−/− (B6.129S6-Rag2tm1Fwa N12) and Factor VIII−/− (B6; 129S-F8tm1Kaz/J) crossed with Rag2−/− mouse (Rag2−/−×FVIII−/−), and cynomolgus and rhesus monkeys.

Pharmacodynamics (PD) assessment demonstrated that AAV5-FVIII-SQ gene therapy results in (i) plasma expression of the correctly sized FVIII-SQ (light and heavy chains) compared to ReFacto® (rhFVIII-SQ; marketed as ReFacto® in the EU and Xyntha® in the US) in mice, (ii) administration of AAV5-FVIII-SQ corrected the coagulopathy in a mouse model of hemophilia A, in a dose dependent fashion, similar to exogenously administered ReFacto® and (iii) the proposed clinical route of administration via IV infusion is likely to be similar to or better than bolus administration when plasma FVIII-SQ protein and activity or corresponding liver RNA and DNA levels are compared in mice.

The transient FVIII-SQ expression in non-human primates is suspected to be species-specific and not expected to occur in the clinic, as was seen in other clinical studies that have achieved stable transgene expression in human patients. Immunogenicity will be closely monitored in the clinic and the relationship to protein expression will be evaluated.

The overall nonclinical program considered the potential for toxicity due to AAV5-FVIII-SQ and its major components, AAV5 capsid and the transgene product, FVIII-SQ. FVIII-SQ has the same amino acid sequence as the marketed recombinant factor replacement treatment, ReFacto®. The design of the toxicology program was intended to characterize the toxicological profile of AAV5-FVIII-SQ including the identification of target organs, relative plasma FVIII-SQ protein and relative activity, immunogenicity and liver DNA genomes and RNA. One GLP single-dose study in normal CD-1 mice with a 4- and 13-week follow up period was conducted with AAV5-FVIII-SQ. PD studies in Rag2−/−× FVIII−/− mice and normal monkeys included additional toxicity parameters of histology and clinical pathology.

The nonclinical safety profile of AAV5-FVIII-SQ included expected observations of immunogenicity: (i) detection of anti-AAV5 antibodies in the plasma of all AAV5 vector treated immuno-competent animals (CD1 mouse and monkeys) and (ii) detection of anti-FVIII-SQ antibodies in immune-competent animals was observed in one mouse and several monkeys that did not correlate with FVIII expression or activity but may be a contributor in slight APTT prolongation in four monkeys given 6E12 or 6E13 vg/kg AAV5-FVIII-SQ. Antibody levels were not determined in the Rag2−/− derived mice because they lack mature B and T lymphocytes, and are incapable of generating antibody responses. However interspecies cross reactivity of anti-FVIII-SQ antibody with monkey FVIII was not assessed, precluding firm conclusions regarding the impact of antibody on coagulation. Non-dose dependent minimal to mild kidney inflammation was observed in Rag2−/−xFVIII−/− mice after 8-weeks with no corresponding changes in kidney clinical chemistry parameters indicating kidney dysfunction. Kidney findings were not observed in CD-1 mice after 13-weeks suggesting a strain specific response to a heterologous protein. No AAV5-FVIII-SQ-related changes in liver clinical chemistry was observed in monkey that would indicate liver dysfunction or cytotoxicity. One unscheduled euthanasia in rhesus monkey given 6E12 vg/kg on Day 14 due to body weight loss throughout the acclimation and study period, and morbidity was deemed not related to AAV5-FVIII-SQ due to persistent body weight loss and on-going colon findings. No other AAV5-FVIII-SQ-related findings, including changes in liver clinical chemistry parameters were noted in monkeys, cynomolgus or rhesus, given AAV5-FVIII-SQ.

No specific findings were associated with the FVIII-SQ transgene product other than expected immunogenicity. Because the FVIII-SQ transgene product has a final sequence that is the same as the marketed enzyme treatment, ReFacto®, no unique FVIII-specific target organs toxicity were identified.

No unique AAV5 capsid related toxicities, in addition to expected immunogenicity, were observed in the nonclinical program. Immunogenicity of the AAV capsid will be monitored in the nonclinical and clinical programs.

Both normal and disease model mice and a limited number of monkeys were utilized to establish proof of concept, evaluate potential species scaling and dose response in order to select the FIH dose of 6E12 vg/kg. The starting dose took into consideration the overall data from the pre-clinical studies conducted in mice (normal and disease model, Rag2−/−xFVIII−/−) and monkey. A detectable pharmacological response based on activity was observed at 6E12 vg/kg in mice and two species of monkeys. No consistent interspecies scaling was noted between the mouse and cynomolgus and rhesus monkeys that could ascertain a more precise dose recommendation. A 10-fold safety margin was based on a NOAEL of 6E13 vg/kg AAV5-FVIII-SQ in the GLP 13-week study in normal mouse at the highest dose administered. No AAV5-FVIII-SQ-related changes in clinical observations or chemistry was observed in the monkey at doses up to 6E13 vg/kg, a 10-fold safety margin after 8-weeks. Overall, no AAV5-FVIII-SQ-related findings, except expected formation of anti-AAV5 antibodies in all animals and limited formation of low titers of anti-FVIII-SQ antibodies in immune-competent animals were observed at the highest administered doses of 6E13 vg/kg in the normal mouse and monkey, respectively.

One in vitro and nine in vivo studies were conducted to evaluate the primary pharmacodynamics (PD) of AAV5-FVIII-SQ (six non-GLP mouse studies and three non-GLP monkey studies). All studies were single dose and used the intravenous (IV) route of administration. The proposed clinical route of administration is IV infusion up to 60 minutes. The majority of animals in this program were administered AAV5-FVIII-SQ via IV bolus injection, so an evaluation of the duration of administration (IV bolus versus infusion for 30 minutes) on FVIII-SQ expression was evaluated one mouse study. Two dose response studies in mouse given 2E10 to 2E14 vg/kg AAV5-FVIII-SQ established the PD relationship of FVIII-SQ protein and activity plasma concentrations including DNA and RNA expression in the liver after 8-weeks. One mouse study supported the selection of the baculovirus-infected cell line for manufacturing. One mouse study assessed plasma FVIII protein and activity along with liver DNA and RNA over 4- and 13-weeks. One mouse study evaluated bleeding time as a functional assessment of coagulation. Two monkey studies supported the selection of the vector AAV5 and the baculovirus-infected cell line for manufacturing. A third monkey study compared the PD effect of AAV5-FVIII-SQ in cynomolgus and rhesus monkey.

The PD endpoints (plasma FVIII-SQ protein and activity, liver DNA vector genomes and RNA transcription copies) were evaluated in the mouse and monkey studies. Liver DNA vector genomes and RNA transcription copies were assessed to confirm liver transduction by AAV5-FVIII-SQ. Plasma FVIII-SQ protein and activity were used as biomarkers of liver expression of the FVIII-SQ transgene. Several toxicity endpoints were combined into one mouse study (histology) and three monkey studies (clinical pathology) to assess dose relationship across the two species.

Pharmacodynamic Assessment of AAV5-FVIII-SQ in Rag2−/−xFVIII−/− Mice

The objective of this study was to evaluate the primary PD of AAV5-FVIII-SQ over 4- and 13-weeks following a single IV administration in male Rag2−/−xFVIII−/− mice given 6E12 or 6E13 vg/kg AAV5-FVIII-SQ. PD endpoints included plasma FVIII-SQ protein and activity levels and presence of liver FVIII-SQ RNA and DNA. Sixty male Rag2−/−xFVIII−/− mice were 8-weeks of age at study initiation. Animals were randomly assigned to six groups (10/group) and were given a single IV injection via the tail vein of either vehicle, 6E12 or 6E13 vg/kg AAV5-FVIII-SQ.

Appropriate monoclonal antibodies were coated onto plates overnight at a final concentration of 2 µg/ml, GMA8023 for FVIII heavy chain, and GMA8001 for FVIII light chain. The following day, wells were blocked with green diluent, and mouse plasma samples (50 ul) from Group 4 and Group 6, or normal mouse plasma samples spiked with Xyntha® (500 ng/ml), were diluted with equal volume of green diluent and 100 µl mixture was added to individual wells for enrichment of FVIII heavy or light chains. Enriched plasma samples were resolved by denaturing reducing polyacrylamide gels and transferred to nitrocellulose membrane for western analysis. FVIII heavy chain was detected by sequential incubation with biotin conjugated anti-FVIII polyclonal (SAFC-APBIO, 0.5 µg/ml) and Streptavidin conjugated alkaline phosphatase (0.25 µg/ml). FVIII-SQ light chain was detected by sequential incubation with anti-FVIII monoclonal (GMA8025, 1.0 µg/ml) and Donkey anti-mouse conjugated alkaline phosphatase (0.25 µg/ml). Membranes were developed using colorimetric precipitating alkaline phosphatase substrate (WesternBlue) and imaged.

The assessment of molecular weight of AAV transgene-derived FVIII-SQ heavy and light chains of serum from animals given 6E13 vg/kg AAV5-FVIII-SQ by western blot established that that the expressed plasma FVIII-SQ heavy and light chains were of similar molecular size as rhFVIII-SQ protein. This indicates that despite a potentially truncated genome, expression of the both the heavy and light chain of FVIII-SQ was the correct size. Efficient and functional expression of dysferlin and hemophilia A factor VIII from vectors with such truncated genomes have been demonstrated previously. The molecular weight of both chains of plasma FVIII-SQ protein were the correct size and the corresponding mice had FVIII-SQ activity.

IV Bolus and Infusion Study in Rag2–/– Mice

The objective of this study was to compare the effect of a single IV bolus or 30-minute IV infusion of 6.0E12 and 2.0E13 vg/kg on FVIII-SQ DNA and RNA in liver tissue and plasma FVIII-SQ protein and activity levels in Rag2–/– mice at 5 weeks post-dose. Sixty male Rag2–/– mice were approximately 8-weeks old at study initiation. Animals were randomly distributed into 6 groups (10 animals/group). Groups 1-3 and 4-6 were administered a single IV bolus or 30-minute IV infusion (vehicle, 6.0E12, or 2.0E13 vg/kg AAV5-FVIII-SQ) via the tail vein, respectively.

In animals given 6.0E12 vg/kg AAV5-FVIII-SQ, hFVIII-SQ vector genomes/liver cell were 5.06E-2 and 3.50E-2 in the IV infusion and slow bolus group, respectively. FVIII-SQ expression copies/µg RNA in the liver were 3.76E4 and 1.87E4 in the IV infusion and bolus groups, respectively. In animals given 2.0E13 vg/kg AAV5-FVIII-SQ, DNA values were 0.342 vector genomes/cell for the infusion group and 0.316 vector genomes/cell for the bolus group. FVIII-SQ expression copies/µg RNA in the liver were 2.35E5 for the infusion group and 1.53E5 for the bolus group.

In animals given 6.0E12 vg/kg AAV5-FVIII-SQ (low dose) there was little difference in liver RNA and DNA levels or plasma FVIII-SQ protein and activity when administered IV either by bolus or 30-minute infusion. In animals given 2.0E13 vg/kg AAV5-FVIII-SQ, administration by IV infusion over 30 minutes resulted in roughly twice the FVIII-SQ protein and activity in plasma, while liver RNA and DNA levels remained similar. Based on these data, the proposed clinical administration of AAV5-FVIII-SQ via IV infusion is likely to be similar to or better than bolus administration.

Bleeding Time Evaluation in Rag2–/–xFVIII–/– Mice

The objective this study was to evaluate the functional coagulation endpoint of bleeding time 8 weeks after a single dose of AAV5-FVIII-SQ in male Rag2–/–xFVIII–/– mice, compared to wild-type mice (C57BL/6J). Additionally, the changes in bleeding time 8 weeks after AAV5-FVIII-SQ treatment were compared to results achieved in Rag2–/–x FVIII–/– mice treated with ReFacto®. One hundred male Rag2–/–xFVIII–/– mice and twenty male age-matched C57BL/6J mice were approximately 8 weeks old at study initiation. Animals were randomly distributed into four groups (20 animals/dose) and administered a single IV injection of AAV5-FVIII-SQ via the tail vein (C57BL/6J: vehicle; Rag2–/–xFVIII–/–: vehicle, 2.0E13 or 1E14 vg/kg AAV5-FVIII-SQ).

Rag2–/–xFVIII–/– animals given ReFacto® had dose related decrease in bleeding time and volume. In Rag2–/–x FVIII–/– animals given 50 U/kg of ReFacto® a mean blood loss of 0.49±0.30 g and a mean bleeding time of 18.1±9.39 min was observed. Rag2–/–xFVIII–/– mice given 200 U/kg of ReFacto® had a mean blood loss and bleeding time of 0.134±0.19 g and 4.29±6.16 min.

Plasma levels of ReFacto® and FVIII-SQ were similar in mice given 50 U/kg ReFacto® and 2E13 vg/kg AAV5-FVIII-SQ, respectively.

Administration of AAV5-FVIII-SQ to Rag2–/–xFVIII–/– mice resulted in a dose dependent reduction in blood loss volume and bleeding time at 8 weeks post-dose. A dose dependent reduction in blood volume loss and bleeding time was observed at 8-weeks, postdose. In animals given 1E14 vg/kg AAV5-FVIII-SQ blood loss and bleeding time was corrected to wild-type levels, comparable to the correction achieved with ReFacto® treatment. Administration of AAV5-FVIII-SQ can correct the coagulopathy in the mouse model of hemophilia A, in a dose dependent fashion, similar to exogenously administered ReFacto®.

Dose Response in Rag2–/–xFVIII–/– Mice

In Rag2–/–xFVIII–/– mice given 2E11 through 2E12 vg/kg AAV5-FVIII-SQ, no plasma FVIII-SQ protein or activity levels were detected.

In the present study, sixty male Rag2–/–xFVIII–/– mice were approximately 8 weeks old at study initiation. Animals were randomly distributed into six groups (10 animals/dose) and administered a single IV injection of AAV5-FVIII-SQ via the tail vein (vehicle, 2E12, 6E12, 2E13, 6E13 and 2E14 vg/kg AAV5-FVIII-SQ).

FVIII-SQ plasma protein levels were generally dose related in animals given ≥1.5E12 vg/kg AAV5-FVIII-SQ. FVIII-SQ protein levels were below the level of quantitation in animals given ≤1.7E11 vg/kg AAV5-FVIII-SQ. PD activity generally increased with dose and was correlated with activity. In animals given ≤1.8E13 vg/kg AAV5-FVIII-SQ, inter-animal variability was observed and only a subset of animals had detectable levels of plasma FVIII-SQ and activity.

Consistent with the FVIII-SQ protein and activity levels, vector genome copies and expression copies (RNA) were observed in animals given ≥1.5E12 vg/kg AAV5-FVIII-SQ. Vector genome DNA copies and expression copies RNA/µg RNA generally increased with dose.

FVIII-SQ plasma protein levels, activity levels and vector genome and RNA levels were generally dose related in Rag2–/–xFVIII–/– animals given ≥1.5E12 vg/kg AAV5-FVIII-SQ. In a subset of animals given 1.5E12 (two animals) or 1.8E13 vg/kg AAV5-FVIII-SQ (eight of ten animals), doses which bracket the proposed FIH clinical dose of 6.0E12 vg/kg AAV5-FVIII-SQ, activity ranged from 2.8 through 66.4% of normal. This indicates that PD activity in the clinic may be achieved at the 6.0E12 dose level because the resulting plasma FVIII-SQ protein and activity levels will likely give a more consistent response in animals.

Capsid Selection in Cynomolgus Monkeys

The objective of this study was to assess the relative activity of two capsids (AAV5.2 FVIII-SQ and AAV8.2 FVIII-SQ, i.e., AAV5 and AAV8 capsid protein, respectively, and AAV2 ITRs) with FVIII-SQ transgenes over 8 weeks when given as a single IV bolus to cynomolgous monkey. Eight male cynomolgus monkeys were 2.8 to 4.1 years old and weighed between 2.6 and 3.6 kg at the time of study initiation. All animals were prescreened for anti-AAV5 or anti-AAV8 transduction inhibition activities in comparison to immune-depleted cynomolgus monkey serum. Animals were assigned to four groups and were given either 2.0E12 or 2.0E13 vg/kg of AAV5.2-hFVIII-SQ or AAV8.2-hFVIII-SQ as a single slow bolus intravenous administration (0.5 and 5.0 mL/kg, respectively).

Administration of a single injection of AAV5.2 hFVIII-SQ and AAV8.2 hFVIII-SQ resulted in detectable levels of plasma FVIII-SQ protein levels that was well tolerated in cynomolgus monkeys given 2.0E13 vector/kg. No AAV5-FVIII-SQ related changes in liver clinical chemistry was observed, indicating no liver dysfunction was observed. The AAV5 capsid was selected for continued development.

Single Dose IV Study in Cynomolgus Monkeys

The objective of this study was to assess the relative activity of AAV5-FVIII-SQ of two manufacturing lots produced in two cell lines (Baculovirus infected sf9 insect and human 293 cells) over 8 weeks when given as a single IV administration to cynomolgous monkey. Eight naive male monkeys were 3.9 to 4.3 years of age and weighed 2.8 to 4.3 kg at treatment initiation. All animals were prescreened for anti-AAV5 antibodies and AAV5 transduction inhibition activities prior to assignment to the study. Each monkey (2/dose group) received a single slow bolus IV injection (2E13 and 6E13 vg/kg AAV5-FVIII-SQ) and was observed for eight weeks.

Relative plasma FVIII-SQ protein levels were assessed over 8-weeks. Possible AAV5-FVIII-SQ-related APTT prolongation was observed in animals with anti-FVIII antibody formation. This is a known potential immunogenicity outcome for exogenous factor replacement. No AAV5-FVIII-SQ-related changes in liver clinical chemistry was observed, indicating no liver dysfunction was observed. Plasma FVIII-SQ levels increased over three to six weeks but declined thereafter.

All animals given AAV5-FVIII-SQ expressed levels of FVIII-SQ in the plasma after Week 2 post administration. In general, FVIII-SQ levels increased over time and then decreased by Week 8. Peak levels of plasma FVIII-SQ ranged from 4.8 ng to 67.4 ng FVIII-SQ/ml.

Single Dose IV Study in Cynomolgus and Rhesus Monkeys

In cynomolgus and rhesus monkey given 6E12 and 2E13 vg/kg AAV5-FVIII-SQ, relative expression of FVIII-SQ was assessed over 6 weeks. No AAV5-FVIII-SQ-related changes in liver clinical chemistry were observed, indicating no liver dysfunction. Plasma FVIII-SQ protein levels were greater in cynomolgus monkey compared to rhesus. Plasma FVIII-SQ levels increased over four to five weeks but declined thereafter. Liver vector genome DNA was detected in all animals given AAV5-FVIII-SQ, which implied that levels of AAV5-FVIII-SQ transduction occurred in all animals. Liver FVIII-SQ RNA copies were observed in animals that expressed plasma FVIII-SQ protein. No AAV5-FVIII-SQ-related changes in liver clinical chemistry was observed in surviving monkeys, indicating no liver dysfunction was observed.

Conclusions

Overall in multiple Rag2−/−xFVIII−/− mouse studies, plasma FVIII-SQ protein and % of normal human activity appear generally proportional with dose; similarly for DNA and RNA in liver. FVIII-SQ activity and protein levels generally increased with time after a single dose of AAV5-FVIII-SQ in mouse, while RNA increased in the liver with time. Plasma FVIII-SQ protein expression and activity tended to correlate in these studies. There was high inter-animal and inter-study variability in animals given ≤6E12 vg/kg AAV5-FVIII-SQ as evidenced by plasma FVIII-SQ levels and activity. Consistent expression of plasma FVIII-SQ protein levels was observed in animals given ≥6E12 vg/kg AAV5-FVIII-SQ.

In the limited number of monkeys given 2E12 to 6E13 vg/kg AAV5-FVIII-SQ, plasma FVIII-SQ levels were detected in animals given ≥6E12 vg/mL with no detectable plasma levels observed in animals given 2E12 vg/kg.

In studies conducted in cynomolgus monkeys, expression of FVIII-SQ peaked between 3 and 5 weeks post dosing, and declined toward study end to levels that were in some cases below the limit of detection. In some instances, anti-FVIII antibodies were detected in animals prior to, or following peak FVIII-SQ levels in the plasma. However, antibody was not detected in all animals with diminished expression of FVIII-SQ, suggesting other potential mechanisms are inhibiting expression, such as cytotoxic T-Lymphocyte (CTL) mediated clearance of transduced cells, or possibly other non-specified inhibitors of expression. The transient FVIII-SQ expression in non-human primates is suspected to be species-specific and not expected to occur in the clinic.

A single IV bolus of AAV5-FVIII-SQ in the monkey resulted in measurable FVIII-SQ protein levels in plasma at the proposed clinical starting dose 6E12 vg/kg and up to 6E13 vg/kg AAV5-FVIII-SQ; administration of AAV5-FVIII-SQ in the mouse has resulted in plasma FVIII-SQ protein and activity levels consistently observed in studies over a comparable dose range. The proposed starting dose of a Phase 1/2 human clinical trial, 6E12 vg/kg AAV5-FVIII-SQ, was selected based on a 10-fold safety factor that also had a detectable plasma FVIII-SQ protein and activity level in both monkey and mice reducing the possibility of a sub-therapeutic outcome.

Figure 2A:
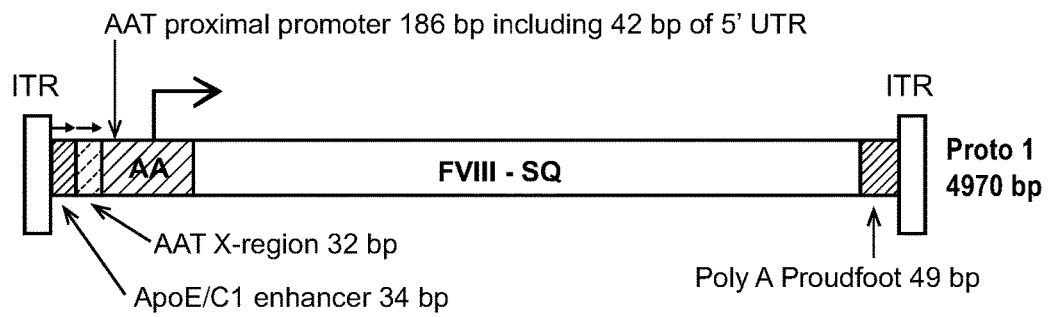
FIG. 2A-FIG. 2D provide schematic representations of certain recombinant AAV FVIII vectors of the present invention. (A) Proto 1, (B) Proto 1S, (C) Proto 2S and (D) Proto 3S.
Figure 2B:
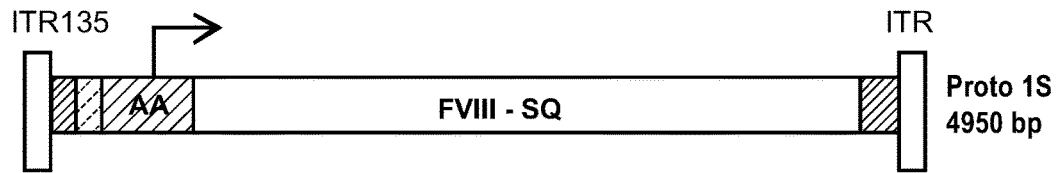
Figure 2C:
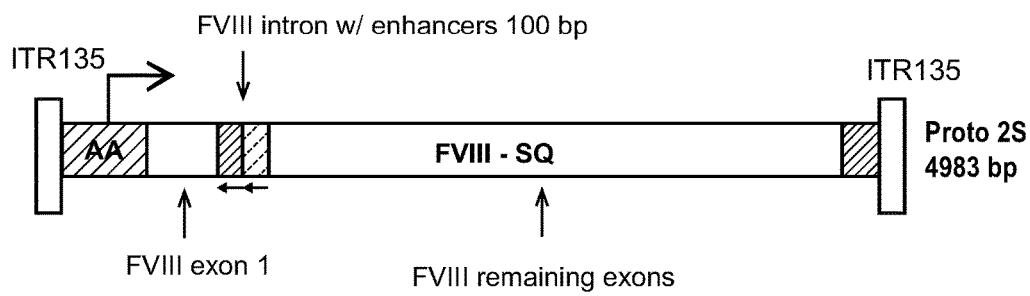
Figure 2D:
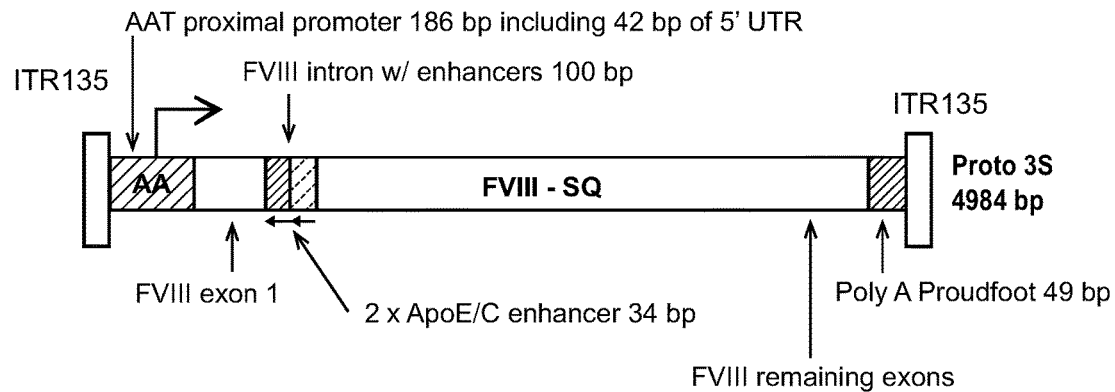

Dose Escalation Safety, Tolerability and Efficacy Study of AAV5-FVIII-SQ in Human Patients with Severe Hemophilia A In the present study, recombinant FVIII AAV virions comprising the Proto1 FVIII-SQ vector of FIG. 2A (SEQ ID NO:1) will be delivered to human patients by single intravenous dose. The study is designed to achieve stable, potentially life-long expression of active hFVIII in the plasma, synthesized from vector-transduced liver tissue. This clinical study is a first-in-human study designed to assess the relationship of vector dose to the augmentation of residual FVIII activity, and whether these levels are sufficient to alter the clinical phenotype. The relationship of dose to safety will be correlated to the activity of hFVIII in patients with severe HA.

The primary objectives of this study are (i) to assess the safety of a single intravenous administration of a recombinant AAV encoding human FVIII-SQ and (ii) to determine the dose of recombinant AAV encoding FVIII-SQ required to achieve expression of FVIII at or above 5% of normal activity (>5 IU/dL) at 16 weeks after infusion. The kinetics, duration and magnitude of AAV-mediated FVIII activity in individuals with hemophilia A will be determined and correlated to an appropriate dose.

Secondary objectives of this study are (i) to describe the immune response to the FVIII transgene and/or AAV capsid proteins following systemic administration of the recombinant FVIII AAV virus, (ii) to assess the impact of FVIII AAV dosing on the frequency of FVIII replacement therapy during the study and (iii) to assess the impact of dosing on the number of bleeding episodes requiring treatment during the study.

The recombinant FVIII-SQ-encoding vector Proto1 (shown herein in FIG. 2A and SEQ ID NO:1) was used to produce recombinant AAV5-FVIII-SQ virus using a baculovirus/Sf9-based expression system. The AAV5-FVIII-SQ process consists of batch cell culture, harvest, purification, and formulation, resulting in formulated bulk drug substance (FBDS). The FBDS is filtered through tandem 0.2 μm sterilizing filters and collected into sterile bioprocess collection bags prior to filling. AAV5-FVIII-SQ is then aseptically prepared by filling 1.1 ml of the sterile FBDS into 2 ml cryovials and closed with sterile caps. The filled vials are then visually inspected prior to labeling, packaging and freezing at ≤−65° C.

Clinical AAV5-FVIII-SQ Liquid Formulation

As the AAV5-FVIII-SQ liquid formulation described above and employed for the non-/pre-clinical studies exhibited significant adsorption of the recombinant AAV to glass and plastic surfaces, work was conducted herein to develop a novel AAV5-FVIII-SQ formulation with advantageous properties for use in human clinical studies. Purified AAV5-FVIII-SQ was formulated for human clinical studies as follows.

Purified recombinant AAV5-FVIII-SQ virus was formulated at various concentrations in a liquid formulation useful for IV administration to human patients comprising 1.38 mg/ml sodium phosphate, monobasic monohydrate, 1.42 mg/ml sodium phosphate, dibasic (dried), 8.18 mg/ml sodium chloride, 20 mg/ml mannitol and 2.0 mg/ml Poloxamer 188 (Pluronic F-68), pH 7.4. In one embodiment, the concentration of recombinant AAV5-FVIII-SQ virus in the above described formulation was 2E13 vg/ml. The resulting liquid formulation is a sterile clear/colorless to pale yellow solution useful for IV infusion and, as compared to the formulation employed for the non-/pre-clinical studies described above, reduced viral adsorptive losses to binding to glass and plastic to acceptable levels. This liquid formulation proved to be stable for extended periods during storage at ≤−65° C. and is employed for the human clinical studies described below.

Human Clinical Study Design

Participants in this first-in-man, dose-escalation study with severe hemophilia A will be enrolled sequentially into one of up to three cohorts according to dose level, (i) 6E12 vector genomes [vg] per kilogram of body weight, given as a single intravenous dose (iv), (ii) 2E13 vg per kilogram, iv, or (iii) 6E13 vg per kilogram, iv, followed by a 16 week post-infusion follow-up period during which safety and efficacy assessments will be taken. After the primary endpoint analysis at 16 weeks, safety and efficacy will then be assessed for approximately 5 years.

Patients will be enrolled sequentially every 3 weeks or more between cohorts. Dose escalation may occur after a single patient has been safely dosed if the resulting FVIII activity at Week 3 is <5 IU/dL. Three weeks is expected to be the time the expression will be close to the maximum. This escalation paradigm is intended to minimize the patient numbers exposed to sub-therapeutic doses.

The starting dose was based on the expression and safety of FVIII observed in nonclinical studies of mice and monkeys. The starting dose has a significant safety margin (10-fold) from no observed adverse effect level (NOAEL) in non-human primates.

Approximately three weeks after an injection, the decision to escalate to the next dose level will be made based on the review of safety parameters and FVIII activity. If the FVIII activity is ≥5 IU/dL, then the other patients of the dose group will be enrolled without waiting for 3 weeks between patients.

Patient 1 will be dosed by intravenous perfusion with 6E12 vector genomes [vg] per kilogram of body weight. If the activity level does not reach ≥5 IU/dL at 21 days, then a higher dose (2E13 vg per kilogram) will be used for the next patient.

If the activity level does not reach ≥5 IU/dL after Patient 2, then the highest dose (6E13 vg per kilogram) will be used for the next patient.

For each dose, if the activity level reaches 5 IU/dL and if no safety issue is found, then up to four patients will receive this dose. If at any time activity levels reach 10 IU/dL or higher, no further dose escalation will take place, but additional patients will then be dosed at this dose level for a total of 6 patients per dose.

Frequent monitoring of liver enzymes will be performed on all patients in the trial. Baseline (i.e., prior to FVIII vector administration) alanine transaminase (ALT) concentrations will be determined and post-administration ALT elevations of 1.5-fold or greater will trigger therapeutic corticosteroid use. Patients may also be treated prophylactically (i.e., prior to FVIII vector administration) with corticosteroids to protect against hepatotoxicity.

Results—Patient One

Patient One was dosed by single intravenous perfusion with 6E12 vector genomes [vg] of AAV5-FVIII-SQ per kilogram of body weight as described above. At the time of dosing, Patient One had a circulating blood Factor VIII level of ≤0.5 IU/dl. Seven days after dosing, Patient One's circulating blood Factor VIII level had increased to 5.4 IU/dl and had further increased to 19.2 IU/dl 14 days post-dosing. At 21 days post-dosing, however, Patient One's circulating Factor VIII level had decreased to ≤0.5 IU/dl and held consistently at that level thereafter.

Results—Patient Two

As the Factor VIII activity level of Patient One was not at least 5 IU/dl on day 21 post-dosing, Patient Two was escalated to a dose by single intravenous perfusion of 2E13 vector genomes [vg] of AAV5-FVIII-SQ per kilogram of body weight as described above. At the time of dosing, Patient Two had a circulating blood Factor VIII level of ≤0.1 IU/dl. Twenty-one days after dosing, Patient Two's circulating blood Factor VIII level had increased to 0.7 IU/dl, 2.1 IU/dl at 10 weeks post-dosing, 2.4 IU/dl at 12 weeks post-dosing, 1.9 IU/dl at 16 weeks post-dosing and 2.4 IU/dl at 28 weeks post-dosing, the latter representing an at least 24-fold increase as compared to pre-dosing levels. ALT levels measured in Patient Two did not increase to 1.5-fold or greater above baseline at any point during the 28 week observation period and, as such, no corticosteroid treatment was initiated.

Results—Patient Three

Patient Three was escalated to a dose by single intravenous perfusion of 6E13 vector genomes [vg] of AAV5-FVIII-SQ per kilogram of body weight as described above. At the time of dosing, Patient Three had a circulating blood Factor VIII level of <1.0 UL/dl. Twenty-one days after dosing, Patient Three's circulating blood Factor VIII level had increased to 3.1 IU/dl, 20.8 IU/dl at 10 weeks post-dosing, 34.7 IU/dl at 12 weeks post-dosing, 56.6 IU/dl at 16 weeks post-dosing and 89.3 IU/dl at 28 weeks post-dosing, well above the concentration of Factor VIII required for satisfactory blood coagulation in humans and decrease in bleeding time during a bleeding event in the patient.

As ALT levels in Patient Three were observed to increase 1.5-fold above baseline after FVIII vector administration, the subject was treated therapeutically with corticosteroid at concentrations ranging from 5 mg/day to 60 mg/day over the continued period of observation. Therapeutic corticosteroid treatment reduced hepatotoxicity-related ALT concentration to acceptable levels without concomitant decrease in Factor VIII levels or any associated serious adverse events.

Results—Patient Four

Patient Four was dosed by single intravenous perfusion of 6E13 vector genomes [vg] of AAV5-FVIII-SQ per kilogram of body weight as described above. At the time of dosing, Patient Four had a circulating blood Factor VIII level of <1.0 UL/dl. Twenty-one days after dosing, Patient Four's circulating blood Factor VIII level had increased to 5.6 IU/dl, 67.8 IU/dl at 10 weeks post-dosing, 89 IU/dl at 12 weeks post-dosing, >170 IU/dl at 16 weeks post-dosing and 219.2 IU/dl at 20 weeks post-dosing, well above the concentration of Factor VIII required for satisfactory blood coagulation in humans and decrease in bleeding time during a bleeding event in the patient.

Patient Four was treated prophylactically with corticosteroid at concentrations ranging from 5 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Five

Patient Five was dosed by single intravenous perfusion of 6E13 vector genomes [vg] of AAV5-FVIII-SQ per kilogram of body weight as described above. At the time of dosing, Patient Five had a circulating blood Factor VIII level of <1.0 UL/dl. Twenty-one days after dosing, Patient Five's circulating blood Factor VIII level had increased to 2.2 IU/dl, 24.4 IU/dl at 10 weeks post-dosing, 59.4 IU/dl at 12 weeks post-dosing, 126.5 IU/dl at 16 weeks post-dosing and 271.2 IU/dl at 19 weeks post-dosing, well above the concentration of Factor VIII required for satisfactory blood coagulation in humans and decrease in bleeding time during a bleeding event in the patient.

Patient Five was treated both prophylactically and therapeutically with corticosteroid at concentrations ranging from 5 mg/day to 40 mg/day over the continued period of observation. Prophylactic and therapeutic corticosteroid treatment maintained hepatotoxicity-related ALT concentrations at acceptable levels without concomitant decrease in Factor VIII levels or any associated serious adverse events.

Results—Patient Six

Patient Six was dosed by single intravenous perfusion of 6E13 vector genomes [vg] of AAV5-FVIII-SQ per kilogram of body weight as described above. At the time of dosing, Patient Six had a circulating blood Factor VIII level of <1.0 UL/dl. Twenty-one days after dosing, Patient Six's circulating blood Factor VIII level was <1.0 IU/dl, 6.2 IU/dl at 10 weeks post-dosing, 19.6 IU/dl at 12 weeks post-dosing, 13 IU/dl at 16 weeks post-dosing and 13 IU/dl at 19 weeks post-dosing, well above the concentration of Factor VIII required for satisfactory blood coagulation in humans and decrease in bleeding time during a bleeding event in the patient.

Patient Six was treated therapeutically with corticosteroid at concentrations ranging from 5 mg/day to 60 mg/day over the continued period of observation. Therapeutic corticosteroid treatment maintained hepatotoxicity-related ALT concentrations at acceptable levels without concomitant decrease in Factor VIII levels or any associated serious adverse events.

Results—Patient Seven

Patient Seven was dosed by single intravenous perfusion of 6E13 vector genomes [vg] of AAV5-FVIII-SQ per kilogram of body weight as described above. At the time of dosing, Patient Seven had a circulating blood Factor VIII level of <1.0 UL/dl. Twenty-one days after dosing, Patient Seven's circulating blood Factor VIII level had increased to 10.4 IU/dl, 56.4 IU/dl at 10 weeks post-dosing, 58 IU/dl at 12 weeks post-dosing, 93.1 IU/dl at 16 weeks post-dosing and 135.8 IU/dl at 18 weeks post-dosing, well above the concentration of Factor VIII required for satisfactory blood coagulation in humans and decrease in bleeding time during a bleeding event in the patient.

Patient Seven was treated prophylactically with corticosteroid at concentrations ranging from 5 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Eight

Patient Eight was dosed by single intravenous perfusion of 6E13 vector genomes [vg] of AAV5-FVIII-SQ per kilogram of body weight as described above. At the time of dosing, Patient Eight had a circulating blood Factor VIII level of <1.0 UL/dl. Twenty-one days after dosing, Patient Eight's circulating blood Factor VIII level had increased to 5.1 IU/dl, 35.2 IU/dl at 10 weeks post-dosing, 42.7 IU/dl at 12 weeks post-dosing, 49.7 IU/dl at 16 weeks post-dosing and 68.8 IU/dl at 17 weeks post-dosing, well above the concentration of Factor VIII required for satisfactory blood coagulation in humans and decrease in bleeding time during a bleeding event in the patient.

Patient Eight was treated prophylactically with corticosteroid at concentrations ranging from 10 mg/day to 40 mg/day over the continued period of observation. Prophylactic corticosteroid treatment maintained hepatotoxicity-related ALT concentrations at acceptable levels without concomitant decrease in Factor VIII levels or any associated serious adverse events.

Results—Patient Nine

Patient Nine was dosed by single intravenous perfusion of 6E13 vector genomes [vg] of AAV5-FVIII-SQ per kilogram of body weight as described above. At the time of dosing, Patient Nine had a circulating blood Factor VIII level of <1.0 UL/dl. Twelve weeks after dosing, Patient Nine's circulating blood Factor VIII level had increased to 78.7 IU/dl, well above the concentration of Factor VIII required for satisfactory blood coagulation in humans and decrease in bleeding time during a bleeding event in the patient.

Patient Nine was treated therapeutically with corticosteroid at concentrations ranging from 10 mg/day to 40 mg/day over the continued period of observation. Therapeutic corticosteroid treatment maintained hepatotoxicity-related ALT concentrations at acceptable levels without concomitant decrease in Factor VIII levels or any associated serious adverse events.

Summary

The results presented in this Example 8 demonstrate that successful therapy of hemophilia A in human patients can be achieved using the compositions and methods of the present invention. More specifically, demonstrated herein is that treatment of humans suffering from hemophilia A with at least 2E13 vector genomes [vg] of AAV5-FVIII-SQ per kilogram of body weight results in stable FVIII activity of ≥2 IU/dl over at least 26 weeks post-dosing and that treatment of humans suffering from hemophilia A with at least 6E13 vector genomes [vg] of AAV5-FVIII-SQ per kilogram of body weight results in high, sustained FVIII activity of >10 IU/dl in all patients treated. Moreover, the data provided herein demonstrates that treatment with AAV5-FVIII-SQ is well-tolerated and results in no clinically-relevant sustained rises in ALT levels or other markers of hepatotoxicity. Prophylactic and/or therapeutic corticosteroid treatment of patients is capable of maintaining hepatotoxicity-related ALT concentrations at acceptable levels without concomitant decrease in Factor VIII levels or any associated serious adverse events. Finally, initial data demonstrates that patients treated either prophylactically or therapeutically with corticosteroids can be successfully tapered off steroid treatment with no adverse impact on FVIII expression or ALT concentration levels.

What is claimed:

1. A method of treating a subject suffering from hemophilia A comprising administering a pharmaceutical formulation to said subject by intravenous administration,
    wherein the pharmaceutical formulation comprises a recombinant AAV-FVIII virus, sodium phosphate dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml,
    wherein the recombinant AAV-FVIII virus comprises a vector comprising an AAV2 5' inverted terminal repeat (ITR), a liver specific transcriptional regulatory region, a FVIII nucleic acid sequence that encodes a functionally active FVIII protein, a polyadenylation sequence, an AAV2 3' ITR, and optionally one or more introns inserted into the FVIII coding sequence or between the promoter and the FVIII coding sequence, wherein the functionally active FVIII coding region nucleic acid sequence comprises nucleotides 403-4776 of SEQ ID NO: 1 wherein expression of the FVIII from the recombinant AAV-FVIII in the subject treats the hemophilia A.

2. The method of claim 1, wherein said recombinant AAV FVIII virus comprises an AAV5 capsid protein.

3. The method of claim 1, wherein the pharmaceutical formulation comprises from about 1E12 vg/kg to about 1E14 vg/kg of the recombinant AAV FVIII virus from about 6E12 vg/kg to about 6E13 vg/kg of the recombinant AAV FVIII virus.

4. The method of claim 1, wherein the treated subject expresses at least about 5 IU/dl of functional Factor VIII protein after administration of the pharmaceutical formulation.

5. The method of claim 1, wherein the treated subject expresses at least about 1 IU/dl functional Factor VIII protein after administration of the pharmaceutical formulation.

6. The method of claim 1, wherein said subject is treated prophylactically with a corticosteroid at a concentration ranging from 5 mg/day to 60 mg/day before or after administration of the pharmaceutical formulation.

7. The method of claim 1, wherein said subject is treated therapeutically with a corticosteroid at a concentration ranging from 5 mg/day to 60 mg/day after administration of the pharmaceutical formulation.

8. The method of claim 1 further comprising the step of determining the absence or the presence of anti-AAV capsid antibodies in the serum of said subject after administration of said pharmaceutical formulation.

9. The method of claim 8 further comprising the step of administering an effective amount of a corticosteroid to said subject after a determination of the presence of anti-AAV capsid antibodies in the serum of said subject is made.

10. A method of increasing Factor VIII protein levels in a subject in need thereof comprising administering a pharmaceutical formulation to said subject by intravenous administration,
wherein the pharmaceutical formulation comprises a recombinant AAV-FVIII virus, sodium phosphate dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml,
wherein the recombinant AAV-FVIII virus comprises a vector comprising an AAV2 5' ITR, a liver specific transcriptional regulatory region, a functionally active FVIII coding region FVIII nucleic acid sequence that encodes a functionally active FVIII protein, a polyadenylation sequence, an AAV2 3' ITR, and optionally one or more introns inserted into the FVIII coding sequence or between the promoter and the FVIII coding sequence, wherein the functionally active FVIII coding region comprises nucleotides 403-4776 of SEQ ID NO: 1 wherein expression of the FVIII from the recombinant AAV-FVIII in the subject increases the level of FVIII in the subject.

11. The method of claim 10, wherein said recombinant AAV FVIII virus comprises an AAV5 capsid protein.

12. The method of claim 10, wherein the pharmaceutical formulation comprises from about 1E12 vg/kg to about 1E14 vg/kg of the recombinant AAV FVIII virus or from about 6E12 vg/kg to about 6E13 vg/kg of the recombinant AAV FVIII virus.

13. The method of claim 10, wherein the administration of the pharmaceutical formulation results in expression of at least about 5 IU/dl of functional Factor VIII protein in said subject.

14. The method of claim 10, wherein the treated subject has increased expression of at least about 5 IU/dl of functional Factor VIII protein after administration of the pharmaceutical composition.

15. The method of claim 10, wherein the treated subject has increased expression of of at least about 1 IU/dl of functional Factor VII protein after administration of the pharmaceutical formulation.

16. The method of claim 10, wherein said subject is treated with a corticosteroid at a concentration ranging from 5 mg/day to 60 mg/day before or after administration of the pharmaceutical formulation.

17. The method of claim 16, wherein the corticosteroid treatment is performed prophylactically.

18. The method of claim 16, wherein the corticosteroid treatment is performed therapeutically.

19. The method of claim 10, wherein said subject is treated with a corticosteroid at a concentration ranging from 5 mg/day to 60 mg/day over a continuous period of at least 3, 4, 5, 6, 7, 8, 9 or 10 weeks or greater after administration of the pharmaceutical formulation.

20. The method of claim 10 further comprising a step of determining the absence or the presence of anti-AAV capsid antibodies in the serum of said subject after administration of said pharmaceutical formulation.

21. The method of claim 20 further comprising the step of administering an effective amount of a corticosteroid to said subject after a determination of the presence of anti-AAV capsid antibodies in the serum of said subject is made.

22. A method of treating a subject suffering from hemophilia A comprising the steps of (i) determining the absence of anti-AAV capsid antibodies in the serum of said subject, and (ii) administering to said subject a pharmaceutical formulation by intravenous administration,
wherein the pharmaceutical formulation comprises a recombinant AAV-FVIII virus, sodium phosphate dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml,
wherein the recombinant AAV-FVIII virus comprises a vector comprising an AAV2 5' ITR, a liver specific transcriptional regulatory region, a functionally active FVIII coding region FVIII nucleic acid sequence that encodes a functionally active FVIII protein, a polyadenylation sequence, an AAV2 3' ITR, and optionally one or more introns inserted into the FVIII coding sequence or between the promoter and the FVIII coding sequence, wherein the functionally active FVIII coding region comprises nucleotides 403-4776 of SEQ ID NO: 1 wherein expression of the FVIII from the recombinant AAV-FVIII in the subject treats the hemophilia A.

23. A method of treating a subject suffering from hemophilia A comprising the steps of (i) administering to said subject a pharmaceutical formulation by intravenous administration,
wherein the pharmaceutical formulation comprises a recombinant AAV-FVIII virus, sodium phosphate dibasic at a concentration of from about 0.1 mg/ml to about 3 mg/ml, sodium phosphate monobasic monohydrate at a concentration of from about 0.1 mg/ml to about 3 mg/ml, sodium chloride at a concentration of from about 1 mg/ml to about 20 mg/ml, mannitol at a concentration of from about 5 mg/ml to about 40 mg/ml, and poloxamer 188 at a concentration of from about 0.1 mg/ml to about 4 mg/ml,
wherein the recombinant AAV-FVIII virus comprises a vector comprising an AAV2 5' ITR, a liver specific transcriptional regulatory region, a functionally active FVIII coding region FVIII nucleic acid sequence that encodes a functionally active FVIII protein, a polyadenylation sequence, an AAV2 3' ITR, and optionally one or more introns inserted into the FVIII coding sequence or between the promoter and the FVIII coding sequence, wherein the functionally active FVIII coding region comprises nucleotides 403-4776 of SEQ ID NO: 1, (ii) after administration of said recombinant AAV FVIII virus, determining the absence or the presence of anti-AAV capsid antibodies in the serum of said subject wherein expression of the FVIII from the recombinant AAV-FVIII in the subject treats the hemophilia A.

24. The method of claim 23 which further comprises the step of administering an effective amount of a corticosteroid to said subject after a determination of the presence of anti-AAV capsid antibodies in the serum of said subject is made.

25. The method of any one of claim 1, 10, 22 or 23 wherein the pharmaceutical formulation comprises 1.38 mg/ml of the sodium phosphate monobasic monohydrate, 1.42 mg/nil of the sodium phosphate dibasic, 8.18 mg/ml of the sodium chloride, 20 mg/ml of the mannitol and 2.0 mg/ml of the Poloxamer 188 wherein the formulation is stable during storage at <65° C. for at least 2 weeks.

* * * * *